US009018381B2

(12) United States Patent
Diebold et al.

(10) Patent No.: US 9,018,381 B2
(45) Date of Patent: Apr. 28, 2015

(54) CHEMICAL COMPOUNDS

(75) Inventors: Robert Bruce Diebold, Waltham, MA (US); Thomas Gero, Waltham, MA (US); Paul Grover, Waltham, MA (US); Shan Huang, Waltham, MA (US); Stephanos Ioannidis, Waltham, MA (US); Claude Afona Ogoe, Waltham, MA (US); Jamal Carlos Saeh, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 501 days.

(21) Appl. No.: 13/198,764

(22) Filed: Aug. 5, 2011

(65) Prior Publication Data

US 2012/0035134 A1    Feb. 9, 2012

Related U.S. Application Data

(60) Provisional application No. 61/371,648, filed on Aug. 6, 2010, provisional application No. 61/384,170, filed on Sep. 17, 2010.

(51) Int. Cl.
| | |
|---|---|
| *C07D 211/30* | (2006.01) |
| *A61K 31/445* | (2006.01) |
| *C07D 211/34* | (2006.01) |
| *C07F 9/59* | (2006.01) |
| *C07D 413/12* | (2006.01) |
| *C07D 211/22* | (2006.01) |

(52) U.S. Cl.
CPC ............... *C07D 211/34* (2013.01); *C07F 9/59* (2013.01); *C07D 413/12* (2013.01); *C07D 211/22* (2013.01)

(58) Field of Classification Search
CPC ........................... C07D 295/13; A61K 31/445
USPC .......................................... 546/247; 514/315
See application file for complete search history.

(56) References Cited

U.S. PATENT DOCUMENTS

| | | | |
|---|---|---|---|
| 7,642,260 | B2 | 1/2010 | Bruncko et al. |
| 7,767,684 | B2 | 8/2010 | Bruncko et al. |
| 7,973,161 | B2 | 7/2011 | Bruncko et al. |
| 8,084,607 | B2 | 12/2011 | Bruncko et al. |
| 8,173,811 | B2 | 5/2012 | Bruncko et al. |
| 8,546,399 | B2 | 10/2013 | Bruncko et al. |
| 8,580,794 | B2 | 11/2013 | Doherty et al. |
| 8,614,318 | B2 | 12/2013 | Bruncko et al. |
| 2002/0086887 | A1 | 7/2002 | Augeri et al. |
| 2005/0159427 | A1 | 7/2005 | Bruncko et al. |
| 2006/0128706 | A1 | 6/2006 | Bruncko et al. |
| 2006/0258657 | A1 | 11/2006 | Bruncko et al. |
| 2007/0015787 | A1 | 1/2007 | Bruncko et al. |
| 2007/0072860 | A1 | 3/2007 | Bruncko et al. |
| 2010/0022773 | A1 | 1/2010 | Bruncko et al. |
| 2010/0240715 | A1 | 9/2010 | Bruncko et al. |
| 2010/0305122 | A1 | 12/2010 | Bruncko et al. |
| 2011/0124628 | A1 | 5/2011 | Bruncko et al. |

FOREIGN PATENT DOCUMENTS

| | | |
|---|---|---|
| CN | 1906183 A | 1/2007 |
| CN | 101175738 A | 5/2008 |
| WO | WO 97/22596 A1 | 6/1997 |
| WO | WO 97/30035 A1 | 8/1997 |
| WO | WO 97/32856 A1 | 9/1997 |
| WO | WO 98/13354 A1 | 4/1998 |

(Continued)

OTHER PUBLICATIONS

Bruncko et al. "Studies Leading to Potent, Dual Inhibitors of Bcl-2 and Bcl-xL" Journal of Medicinal Chemistry (2007); vol. 50; pp. 641-662; XP002661692.
International Search Report for PCT/GB2011/051484, mailed Dec. 16, 2011.
Wendt et al. "Discovery and Structure—Activity Relationship of Antagonists of B-Cell Lymphoma 2 Family Proteins with Chemopotentiation Activity in Vitro and in Vivo" Journal of Medicinal Chemistry (2006); vol. 49; pp. 1165-1181.
Written Opinion for PCT/GB2011/051484, mailed Dec. 16, 2011.
Aalto et al., 'Distinct Gene Expression Profiling in Chronic Lymphocytic Leukemia with 11q23', Leukemia (Nov. 2001); vol. 15; No. 11; 1721-1728.
Altman et al., 'Pd-Catalyzed Suzuki-Miyaura Reactions of Aryl Halides Using Bulky Biarylmonophosphine Ligands', Nature Protocols (2007); vol. 2; No. 12; 3115-3121.
Barder et al., 'Catalysts for Suzuki—Miyaura Coupling Processes: Scope and Studies of the Effect of Ligand Structure', Journal of American Chem. Soc. (2005); vol. 127; 4685-4696.
Beroukhim et al., 'The Landscape of Somatic Copy-Number Alteration Across Human Cancers', Nature (Feb. 18, 2010); vol. 463; No. 7283; 899-905.
Calin et al., 'MiR-15a and miR-16-1 Cluster Functions in Human Leukemia', Proc. Natl. Acad. Sci. (Apr. 1, 2008); vol. 105; No. 13; 5166-5171.
Chipuk et al., 'The BCL-2 Family Reunion', Molecular Cell (Feb. 12, 2010); vol. 37; No. 3; 299-310.

(Continued)

*Primary Examiner* — John Mabry

(57) ABSTRACT

The present invention relates to compounds of Formula (I):

Formula (I)

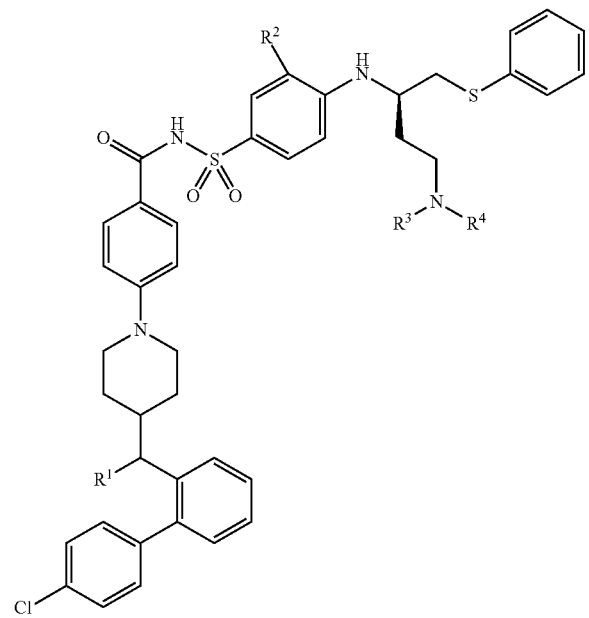

and to their salts, pharmaceutical compositions, methods of use, and methods for their preparation. These compounds inhibit Bcl-2 and/or Bcl-$X_L$ activities and may be used for the treatment of cancer.

8 Claims, No Drawings

(56) References Cited

FOREIGN PATENT DOCUMENTS

| WO | WO 99/02166 A1 | 1/1999 |
|---|---|---|
| WO | WO 00/40529 A1 | 7/2000 |
| WO | WO 00/41669 A2 | 7/2000 |
| WO | WO 00/47212 A1 | 8/2000 |
| WO | WO 01/92224 A1 | 12/2001 |
| WO | WO 01/94341 A1 | 12/2001 |
| WO | WO 02/04434 A1 | 1/2002 |
| WO | WO 02/08213 A1 | 1/2002 |
| WO | 02/24636 A2 | 3/2002 |
| WO | 2005/049593 A2 | 6/2005 |
| WO | 2005/049594 A1 | 6/2005 |
| WO | 2007/040650 A2 | 4/2007 |
| WO | 2008/061208 A2 | 5/2008 |
| WO | 2009/036035 A1 | 3/2009 |
| WO | 2010/065865 A2 | 6/2010 |
| WO | 2010/138588 A9 | 12/2010 |
| WO | 2010/143074 A2 | 12/2010 |
| WO | 2011/149492 A1 | 12/2011 |

OTHER PUBLICATIONS

Dierlamm et al., 'Gain of chromosome region 18q21 including the MALT1 gene is associated with the activated B-cell-like gene expression subtype and increased BCL2 gene dosage and protein expression in diffuse large B-cell lymphoma', Haematologica (May 2008); vol. 93; No. 5; 688-696.

Ellman et al., 'N-tert-Butanesulfinyl lmines: Versatile Intermediates for the Asymmetric Synthesis of Amines', Acc. Chem. Res. (2002); vol. 35; No. 11, 984-995.

Faderl et al., 'Expression profile of 11 proteins and their prognostic significance in patients with chronic lymphocytic leukemia (CLL)', Leukemia (Jun. 2002); vol. 16; No. 6; 1045-1052.

Gascoyne et al., 'Prognostic Significance of Bcl-2 Protein Expression and Bcl-2 Gene Rearrangement in Diffuse Aggressive Non-Hodgkin's Lymphoma', Blood (Jul. 1, 1997); vol. 90; No. 1; 244-251.

Hauck et al., Alterations in the Noxa-Mcl-1 Axis Determine Sensitvity of Small Cell Lung Cancer to the BH3 Mimetic ABT-737, Mol. Cancer Ther. (Apr. 2009); vol. 8; No. 4; 883-892.

Ilievska et al., 'Bcl-2 As A Prognostic Factor for Survival in Small-Cell Lung Cancer', Makedonska Akademija Na Naukite I Umetnostite Oddelenie Za Bioloshki I Meditsinki Nauki Prilozi (Dec. 2008); vol. 29; No. 2; 281-293.

Iqbal et al., 'BCL2 Expression is A Prognostic Marker for the Activated B-Cell-Like Type of Diffuse Large B-Cell Lymphoma', Journal of Clinical Oncology (Feb. 20, 2006); vol. 24; No. 6; 961-968.

Kramer et al., 'Clinical Relevance of BCL2, BCL6, and MYC Rearrangements in Diffuse Large B-Cell Lympohoma', Blood (Nov. 1, 1998); vol. 92; No. 9; 3152-3162.

Krasovskiy et al., 'A LiCl-Mediated Br/Mg Exchange Reaction for the Preparation of Functionalized Aryl-and Heteroarylmagnesium Compounds from Organic Bromides', Angew. Chem. Int. Ed (2004); vol. 43; 3333-3336.

Largo et al., 'Identification of Overexpressed Genes in Frequently Gained/Amplified Chromosome Regions in Multiple Myeloma', Haematologica: The Hematology Journal (Feb. 1, 2006); vol. 92; No. 2; 184-191.

Legartova et al., 'Nuclear Topography of the 1q21 Genomic Region and Mcl-1 Protein Levels Associated With Pathophysiology of Multiple Myeloma', Neoplasma (2009); vol. 56; No. 5; 404-413.

Lin et al., 'Seed' Analysis of Off-Target siRNAs Reveals an Essential Role of Mcl-1 in Resistance to the Small-Molecule Bcl-2/Bcl-$X_L$ Inhibitor ABT-737, Oncogene (Jun. 7, 2007); vol. 26; No. 27; 3972-3979.

Lombardi et al., 'Molecular Characterization of Human Multiple Myeloma Cell Lines by Integrative Genomics: Insights into the Biology of the Disease', Genes, Chromosomes and Cancer (2007); vol. 46; No. 3; 226-238.

Lombardo et al., 'Discovery of N-(2-Chloro-6-methylpheny1)-2-(6-(4-(2-hydroxyethyl)-piperazin-1-y1)-2-methylpyrimidin-4-ylamino)thiazole-5-carboxamide(BMS-354825), a Dual Src/Abl Kinase Inhibitor with Potent Antitumor Activity in Preclinical Assays', J Med. Chem. (2004); vol. 47; 6658-6661.

Majid et al., 'BCL2 Expression in Chronic Lymphocytic Leukemia: Lack of Association with the BCL2—938A>C Promoter Single Nucleotide Polymorphism', Blood (Jan. 15, 2008); vol. 111; No. 2; 874-877.

March, Advanced Organic Chemistry, 3rd Edition; (1985); 104-107.

Mauger et al., 'Synthetic applications of Buchwald's phosphines in palladium-catalyzed aromatic-bond-forming reactions', Aldrichimica ACTA (2006); vol. 39; 17.

Miller et al., 'BH3 Mimetic ABT-737 and a Proteasome Inhibitor Synergistically Kill Melanomas Through Noxa-Dependent Apoptosis', Journal of Investigative Dermatology (Apr. 2009); vol. 129; No. 4; 964-971.

Nagy et al., 'Abnormal Expression of Apoptosis-related Genes in Haematological Malignancies: Overexpression of MYC is Poor Prognostic Sign in Mantle Cell Lymphoma', British Journal of Haematology (Feb. 2003); vol. 120; No. 3; 434-441.

Nardonet et al., 'Expression of COX-2, mPGE-Synthase$_f$, MDR-I (P-gp__, and Bcl-$x_L$: A Molecular Pathway of H pylori-related Gastric Carcinogenesis', Journal of Pathology (Mar. 2004); vol. 202; No. 3; 305-312.

Office Action, Non-final; Issued against U.S. Appl. No. 13/814,318; mailed Jul. 30, 2014.

Otake et al., 'Overexpression of Nucleolin in Chronic Lymphocytic Leukemia Cells Induces Stabilization of bcl2 mRNA', Blood (Apr. 1, 2007); vol. 109; No. 7; 3069-3075.

Robertson et al., 'Bcl-2 Expression in Chronic Lymphocytic Leukemia and its Correlation with the Induction of Apoptosis and Clinical Outcome', Leukemia (Mar. 1, 1996); vol. 10; No. 3; 456-459.

Shigemasa et al., 'Increased MCL-1 Expression is Associated with Poor Prognosis in Ovarian Carcinomas', Jpn. J. Cancer. Res. (May 2002); vol. 93; No. 5; 542-550.

Stern et al., 'Overview of Monoclonal Antibodies in Cacner Therapy: Present and Promise', Critical Reviews in Oncology/Hematology (2005); vol. 54; No. 1; 11-29.

Surry et al., 'Dialkylbiaryl Phosphines in Pd-catalyzed Amination: A User's Guide', Chem. Sci. (2011); vol. 2; No. 1; 27-50.

Szende et al., 'Apoptosis, Mitosis, p53, bcl$_2$, Ki-67 and Clinical Outcome in Prostate Carcinoma Treated by Androgen Ablation', Urol. Int. (1999); vol. 63; No. 2; 115-119.

Tahir et al., 'Influence of Bcl-2 Family Members on the Cellular Response of Small-Cell Lung Cancer Cell Lines to ABT-737', Cancer Research (Feb. 1, 2007); vol. 67; No. 3; 1176-1183.

Wacheck et al., 'Mcl-1 is A Relevant Molecular Target for Antisense Oligonucleotide Strategies in Gastric Cancer Cells', Cancer Biology & Therapy (Oct. 2006); vol. 5; No. 10; 1348-1354.

Zhang et al., 'Significance of Bcl-xL in human colon carcinoma', World Journal of Gastroenterology (May 21, 2008); vol. 14; No. 19; 3069-3073.

CHEMICAL COMPOUNDS

RELATED APPLICATIONS

This application claims priority to U.S. provisional patent application Ser. No. 61/371,648, filed Aug. 6, 2010; and to to U.S. provisional patent application Ser. No. 61/384,170, filed Sep. 17, 2010, the entire disclosure of each of which is incorporated herein by reference.

FIELD OF THE INVENTION

The present invention relates to novel compounds, their pharmaceutical compositions, and their methods of use. In addition, the present invention relates to therapeutic methods for the treatment and prevention of cancers and to use of such compounds in the manufacture of medicaments for use in the treatment and prevention of cancers.

BACKGROUND OF THE INVENTION

Apoptosis is the process by which a cell undergoes programmed cell death in response to nutrient deprivation, stress signals, death receptor signaling, DNA damage, treatment with novel targeted or cytotoxic agents or other insults from the external environment. Two forms of apoptosis have been identified: the intrinsic or mitochondrial pathway involving members of the BCL2 family of proteins and BH3 only proteins, and the extrinsic pathway where signals from death domain containing receptors trigger the activation of the caspase cascade via regulation of members of the inhibitor of apoptosis (IAP) family of proteins.

The BCL2 family of BH-3 containing proteins, comprising Bcl-2, Bcl-$X_L$, Mcl-1, Bcl-w and Bcl-A1 (also known as Bfl-1), is a family of adaptor molecules involved in regulating the control of mitochondrial apoptosis in a variety of different cell types (reviewed in (1)). BCL2 family members are generally considered to be anti-apoptotic because they bind to and counteract the activity of pro-apoptotic members of the BH3-only family, including Bim, tBid, and Puma, and the multidomain effector proteins Bak and Bax. Bim and tBid in turn facilitate the oligomerization and activation of Bak and Bax to form a pore in the outer mitochondrial membrane through which Smac and cytochrome c are released into the cytosol. The release of cytochrome c triggers activation of the caspase cascade via formation of a complex with Apaf-1, termed the apoptosome, ultimately leading to apoptotic cell death. Another group of BH3-only proteins, the "sentinels" are upregulated by a variety of transcriptional and post-translational mechanisms in response to the pro-apoptotic triggers mentioned above. These proteins, including Noxa, Bmf, Bad, Bik, and Hrk bind selectively to certain BCL2 family members and alter the balance of free and bound pro-apoptotic members, through a process of sensitization (binding to anti-apoptotic BCL2 family members) and depression (displacing bound Bim, tBid, Bak and Bax), permitting permeabilization of the outer mitochondrial membrane (MOMP) to occur. In healthy cells, the balance of pro- and anti-apoptotic proteins ensures that apoptosis is held in check until needed.

The anti-apoptotic BCL2 family members are often found to be up-regulated in cancers and have been associated both with stage of disease and prognosis. Over-expression of Bcl-2, Bcl-$X_L$ and Mcl-1 has been linked to resistance to common therapeutic agents and strategies that target BCL2 family members can restore sensitivity to cytotoxic agents by reinstating the ability of the tumor cell to undergo apoptosis. A translocation, t(14;18)(q32;q31) involving Bcl2 and IGH leads to over-expression of the Bcl-2 protein and is commonly found in tumors of hematological origin including non Hodgkin's Lymphomas (2-4). Even in the absence of a translocation, BCL2 family expression is often de-regulated (2,3, 5-8). Amplifications of Bcl-$X_L$ and Mcl-1 are also commonly seen in many tumor types (9-11) for example by activation of NFkB or by suppression of certain microRNAs (12).

In a number of tumors, including chronic lymphocytic leukemia (CLL) (4,13-15), small cell lung cancer (SCLC) (16), and prostate cancer (17), Bcl-2 expression is an independent indicator of poor prognosis. In other tumor types such as colorectal cancer Bcl-$X_L$ expression is linked to grade and stage (18) and in hepatocellular cancer Bcl-$X_L$ expression is an independent marker of poorer overall and disease-free survival (19). Mcl-1 expression has also been linked to stage in CLL and to prognosis, for example in myeloma, melanoma, ovarian and gastric tumors (20-22).

Redundancy has been seen among members of the BCL2 family and is believed to account at least in part for resistance to the BH3-mimetic compounds that target Bcl-2, Bcl-$X_L$, Bcl-w, and Bcl-A1, but not Mcl-1 (23-26). Hence, for many cancers, a combination of a selective BH-3 mimetic with another agent that targets the Bim/Noxa/Mcl-1 axis may be desirable to ensure apoptosis induction and tumor regression. Examples of such agents include but are not limited to cytotoxic chemotherapeutics, proteasome inhibitors, EGFR inhibitors, and MEk/ERK pathway inhibitors.

(1) Chipuk J E, Moldoveanu T, Llambi F, Parsons M J, Green D R. The BCL-2 family reunion. Mol.Cell 2010 Feb. 12; 37(3):299-310.

(2) Majid A, Tsoulakis O, Walewska R, Gesk S, Siebert R, Kennedy D B, et al. BCL2 expression in chronic lymphocytic leukemia: lack of association with the BCL2 938A>C promoter single nucleotide polymorphism. Blood 2008 Jan. 15; 111(2):874-877.

(3) Otake Y, Soundararajan S, Sengupta T K, Kio E A, Smith J C, Pineda-Roman M, et al. Overexpression of nucleolin in chronic lymphocytic leukemia cells induces stabilization of bcl2 mRNA. Blood 2007 Apr. 1; 109(7):3069-3075.

(4) Nagy B, Lundan T, Larramendy M L, Aalto Y, Zhu Y, Niini T, et al. Abnormal expression of apoptosis-related genes in haematological malignancies: overexpression of MYC is poor prognostic sign in mantle cell lymphoma. Br.J. Haematol. 2003 February; 120(3):434-441.

(5) Dierlamm J. Murga Penas E M. Bentink S. Wessendorf S. Berger H. Hummel M. Klapper W. Lenze D. Rosenwald A. Haralambieva E. Ott G. Cogliatti S B. Moller P. Schwaenen C. Stein H. Loffler M. Spang R. Trumper L. Siebert R. Deutsche Krebshilfe Network Project "Molecular Mechanisms in Malignant Lymphomas". Gain of chromosome region 18q21 including the MALT1 gene is associated with the activated B-cell-like gene expression subtype and increased BCL2 gene dosage and protein expression in diffuse large B-cell lymphoma. Haematologica 2008 May; 93(5):688-696.

(6) Gascoyne R D, Adomat S A, Krajewski S, Krajewska M, Horsman D E, Tolcher A W, et al. Prognostic significance of Bcl-2 protein expression and Bcl-2 gene rearrangement in diffuse aggressive non-Hodgkin's lymphoma. Blood 1997 Jul. 1; 90(1):244-251.

(7) Iqbal J, Neppalli V T, Wright G, Dave B J, Horsman D E, Rosenwald A, et al. BCL2 expression is a prognostic marker for the activated B-cell-like type of diffuse large B-cell lymphoma. Journal of Clinical Oncology 2006 Feb. 20; 24(6):961-968.

(8) Kramer M H, Hermans J, Wijburg E, Philippo K, Geelen E, van Krieken J H, et al. Clinical relevance of BCL2, BCL6, and MYC rearrangements in diffuse large B-cell lymphoma. Blood 1998 Nov. 1; 92(9):3152-3162.

(9) Largo C, Alvarez S, Saez B, Blesa D, Martin-Subero J, Gonzalez-Garcia I, et al. Identification of overexpressed genes in frequently gained/amplified chromosome regions in multiple myeloma. Haematologica 2006 February 1; 91(2): 184-191.

(10) Lombardi L, Poretti G, Mattioli M, Fabris S, Agnelli L, Bicciato S, et al. Molecular characterization of human multiple myeloma cell lines by integrative genomics: Insights into the biology of the disease. Genes, Chromosomes and Cancer 2007; 46(3):226-238.

(11) Beroukhim R, Mermel C H, Porter D, Wei G, Raychaudhuri S, Donovan J, et al. The landscape of somatic copy-number alteration across human cancers. Nature 2010 Feb. 18; 463(7283):899-905.

(12) Calin G A, Cimmino A, Fabbri M, Ferracin M, Wojcik S E, Shimizu M, et al. MiR-15a and miR-16-1 cluster functions in human leukemia. Proc.Natl.Acad.Sci.U.S.A. 2008 Apr. 1; 105(13):5166-5171.

(13) Aalto Y, El-Rifa W, Vilpo L, Ollila J, Nagy B, Vihinen M, et al. Distinct gene expression profiling in chronic lymphocytic leukemia with 11q23 deletion. Leukemia 2001 November; 15(11):1721-1728.

(14) Faderl S, Keating M J, Do K A, Liang S Y, Kantarjian H M, O'Brien S, et al. Expression profile of 11 proteins and their prognostic significance in patients with chronic lymphocytic leukemia (CLL). Leukemia 2002 June; 16(6):1045-1052.

(15) Robertson L E, Plunkett W, McConnell K, Keating M J, McDonnell T J. Bcl-2 expression in chronic lymphocytic leukemia and its correlation with the induction of apoptosis and clinical outcome. Leukemia 1996 March; 10(3):456-459.

(16) Ilievska Poposka B, Smickova S, Jovanovska Crvenkovska S, Zafirovska Ivanovska B, Stefanovski T, Petrusevska G. Bcl-2 as a prognostic factor for survival in small-cell lung cancer. Makedonska Akademija na Naukite i Umetnostite Oddelenie Za Bioloshki i Meditsinski Nauki Prilozi 2008 December; 29(2):281-293.

(17) Szende B, Romics I, Torda I, Bely M, Szegedi Z, Lovasz S. Apoptosis, mitosis, p53, bcl(2), Ki-67 and clinical outcome in prostate carcinoma treated by androgen ablation. Urol.Int. 1999; 63(2):115-119.

(18) Zhang Y L, Pang L Q, Wu Y, Wang X Y, Wang C Q, Fan Y. Significance of Bcl-xL in human colon carcinoma. World J. Gastroenterol. 2008 May 21; 14(19):3069-3073.

(19) Nardone G, Rocco A, Vaira D, Staibano S, Budillon A, Tatangelo F, et al. Expression of COX-2, mPGE-synthasel, MDR-1 (P-gp), and Bcl-xL: a molecular pathway of H pylori-related gastric carcinogenesis. J. Pathol. 2004 March; 202(3): 305-312.

(20) Wacheck V, Cejka D, Sieghart W, Losert D, Strommer S, Crevenna R, et al. Mcl-1 is a relevant molecular target for antisense oligonucleotide strategies in gastric cancer cells. Cancer Biology & Therapy 2006 October; 5(10):1348-1354.

(21) Legartova S, Krejci J, Harnicarova A, Hajek R, Kozubek S, Bartova E. Nuclear topography of the 1q21 genomic region and Mcl-1 protein levels associated with pathophysiology of multiple myeloma. Neoplasma 2009; 56(5):404-413.

(22) Shigemasa K, Katoh O, Shiroyama Y, Mihara S, Mukai K, Nagai N, et al. Increased MCL-1 expression is associated with poor prognosis in ovarian carcinomas. Jap. J. Cancer Res. 2002 May; 93(5):542-550.

(23) Hauck P, Chao B H, Litz J, Krystal G W. Alterations in the Noxa/Mcl-1 axis determine sensitivity of small cell lung cancer to the BH3 mimetic ABT-737. Molecular Cancer Therapeutics 2009 April; 8(4):883-892.

(24) Miller L A, Goldstein N B, Johannes W U, Walton C H, Fujita M, Norris D A, et al. BH3 mimetic ABT-737 and a proteasome inhibitor synergistically kill melanomas through Noxa-dependent apoptosis. J. Invest.Dermatol. 2009 April; 129(4):964-971.

(25) Lin X, Morgan-Lappe S, Huang X, Li L, Zakula D M, Vernetti L A, et al. 'Seed' analysis of off-target siRNAs reveals an essential role of Mcl-1 in resistance to the small-molecule Bcl-2/Bcl-XL inhibitor ABT-737. Oncogene 2007 Jun. 7; 26(27):3972-3979.

(26) Tahir S K, Yang X, Anderson M G, Morgan-Lappe S E, Sarthy A V, Chen J, et al. Influence of Bcl-2 family members on the cellular response of small-cell lung cancer cell lines to ABT-737. Cancer Res. 2007 Feb. 1; 67(3):1176-1183.

SUMMARY OF THE INVENTION

The present invention relates to compounds of Formula (I):

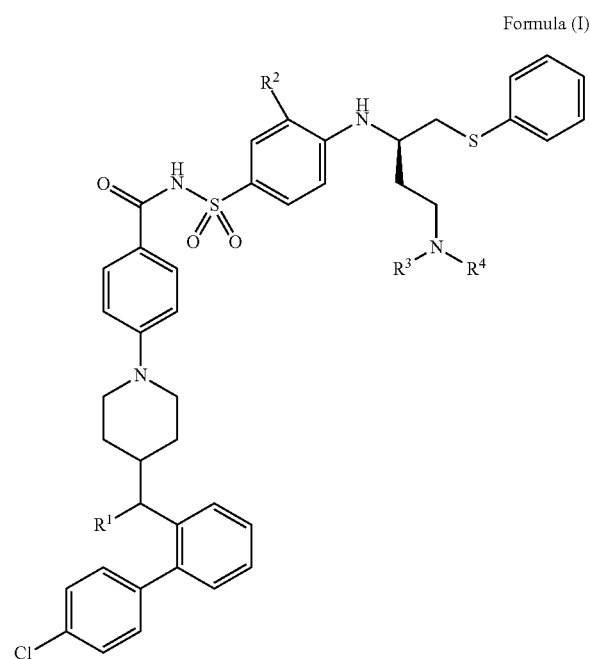

Formula (I)

and/or to pharmaceutically acceptable salts thereof.

In certain embodiments, compounds provided by the present invention have the structure set forth in Formulae (I-a) and/or (I-b):

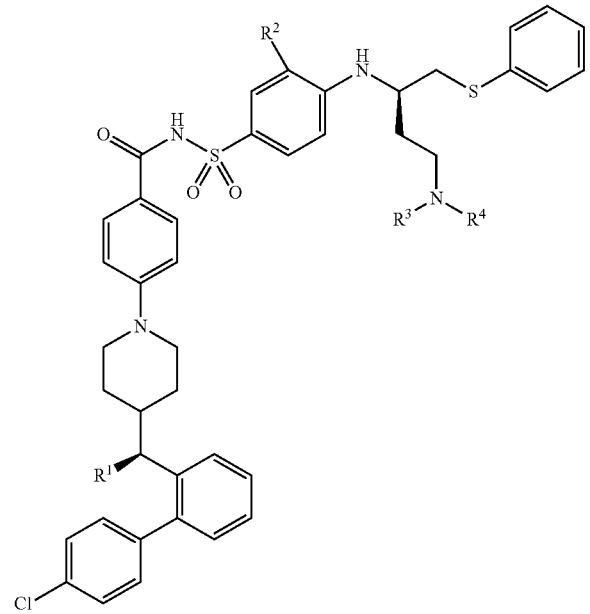

(I-a)

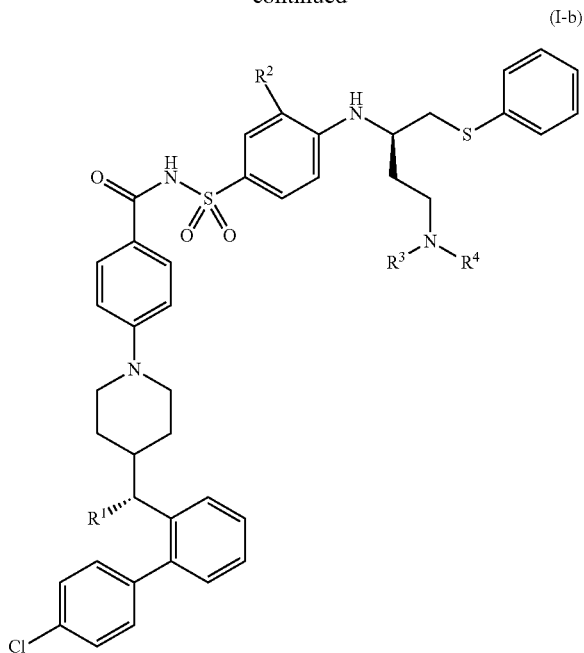

(I-b)

and/or a pharmaceutically acceptable salt thereof, wherein each of $R^1$, $R^2$, $R^3$, and $R^4$ are as defined for compounds of formula (I) and in classes and subclasses described herein.

In some embodiments, the present invention provides a compound of formula (I-a), as depicted above, or a pharmaceutically acceptable salt thereof, wherein each $R^1$, $R^2$, $R^3$, and $R^4$ are as defined for compounds of formula (I) and in classes and subclasses described herein.

In some embodiments, the present invention provides a compound of formula (I-b), as depicted above, or a pharmaceutically acceptable salt thereof, wherein each $R^1$, $R^2$, $R^3$, and $R^4$ are as defined for compounds of formula (I) and in classes and subclasses described herein.

Compounds of Formulae (I), (I-a), (I-b), (I-c), (I-d) and/or (I-e) possess beneficial efficacious, metabolic, pharmacokinetic, and/or pharmacodynamic properties. Compounds of Formulae (I), (I-a), (I-b), (I-c), (I-d) and/or (I-e) are useful for their ability to inhibit Bcl-2 and Bcl-$X_L$ activities and are accordingly also useful in the treatment of diseases or medical conditions mediated alone or in part by the BCL2 family. It has been found that for certain enantiomers of the present invention, there may be differences in one or more biological and or physiological property which may be advantageous.

In particular, compounds of Formulae (I), (I-a), (I-b), (I-c), (I-d) and/or (I-e) may be used for the treatment of cancer, including solid tumors, such as: bladder cancer; breast cancer; colon cancer; ovarian cancer; AML; diffuse large B-cell lymphoma (DLBCL); CLL; small cell lung cancer (SCLC), non-small cell lung cancer (NSCLC), including the non-squamous and squamous subtypes; small cell lung cancer; pancreatic cancer; Follicular lymphoma (FL), and prostate cancer.

The invention also relates to processes for the manufacture of said compounds, to pharmaceutical compositions containing them, and to their use in the manufacture of medicaments for use in the production of an anti-proliferation and/or pro-apoptotic effect in warm-blooded animals such as man. Also in accordance with the present invention there are provided methods of using said compounds or pharmaceutically acceptable salts thereof in the treatment of cancer.

DETAILED DESCRIPTION OF THE INVENTION

I. Definitions

"ALKYL": As used herein the term "alkyl" refers to both straight and branched chain saturated hydrocarbon radicals having the specified number of carbon atoms. References to individual alkyl groups such as "propyl" are specific for the straight chain version only and references to individual branched chain alkyl groups such as 'isopropyl' are specific for the branched chain version only. In one aspect, "alkyl" may be "$C_{1-4}$alkyl." In another aspect, "alkyl" and "$C_{1-4}$alkyl" may be "$C_{1-3}$alkyl." In another aspect, "alkyl," "$C_{1-4}$alkyl," and "$C_{1-3}$alkyl," may be methyl. In some embodiments, the term "$C_1$ALKYL" refers to a saturated hydrocarbon radical having one carbon atom. In some embodiments, the term "$C_2$ALKYL" refers to saturated hydrocarbon radicals having two carbon atoms. In some embodiments, the term "$C_3$ALKYL" refers to both straight and branched chain saturated hydrocarbon radicals having one, two, or three carbon atoms. In some embodiments, the term "$C_4$ALKYL" refers to both straight and branched chain saturated hydrocarbon radicals having one, two, three or four carbon atoms.

"$C_{1-4}$ALKYL": As used herein the term "$C_{1-4}$alkyl" refers to both straight and branched chain saturated hydrocarbon radicals having one, two, three, or four carbon atoms. In some embodiments, "$C_{1-4}$alkyl" is "$C_1$alkyl". In some embodiments, "$C_{1-4}$alkyl" is "$C_2$alkyl". In some embodiments, "$C_{1-4}$alkyl" is "$C_3$alkyl". In some embodiments, "$C_{1-4}$alkyl" is "$C_4$alkyl".

"$C_{1-3}$ALKYL": As used herein the term "$C_{1-3}$alkyl" refers to both straight and branched chain saturated hydrocarbon radicals having one, two, or three carbon atoms. In some embodiments, "$C_{1-3}$alkyl" is "$C_1$alkyl". In some embodiments, "$C_{1-3}$alkyl" is "$C_2$alkyl". In some embodiments, "$C_{1-3}$alkyl" is "$C_3$alkyl".

"$C_{1-2}$ALKYL": As used herein the term "$C_{1-2}$alkyl" refers to both straight and branched chain saturated hydrocarbon radicals having one, or two carbon atoms. In some embodiments, "$C_{1-2}$alkyl" is "$C_1$alkyl". In some embodiments, "$C_{1-2}$alkyl" is "$C_2$alkyl".

"EFFECTIVE AMOUNT": As used herein, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

In particular, an effective amount of a compound of Formulae (I), (I-a), (I-b), (I-c), (I-d) and/or (I-e) for use in the treatment of cancer is an amount sufficient to symptomatically relieve in a warm-blooded animal such as man, the symptoms of cancer, to slow the progression of cancer, or to reduce in patients with symptoms of cancer the risk of getting worse.

"HALO": The terms "halogen" or "halo," as used herein, refers to fluoro, chloro, bromo and iodo. In certain embodiments, the term "halo" may refer to fluoro, chloro, and bromo. In certain embodiments, the term "halo" may refer to fluoro and chloro. In certain embodiments, the term "halo" may refer to fluoro. In certain embodiments, the term "halo" may refer to chloro. In certain embodiments, the term "halo" may refer to bromo.

"5- or 6-MEMBERED HETEROCYCLIC RING" The term "5- or 6-membered heterocyclic ring" refers to a saturated or partially saturated monocyclic ring containing 5 or 6 ring atoms, of which one ring atom is the nitrogen indicated by the arrow below in Formulae (I), (I-a), (I-b), (I-c), (I-d) and/or (I-e):

Formula (I)

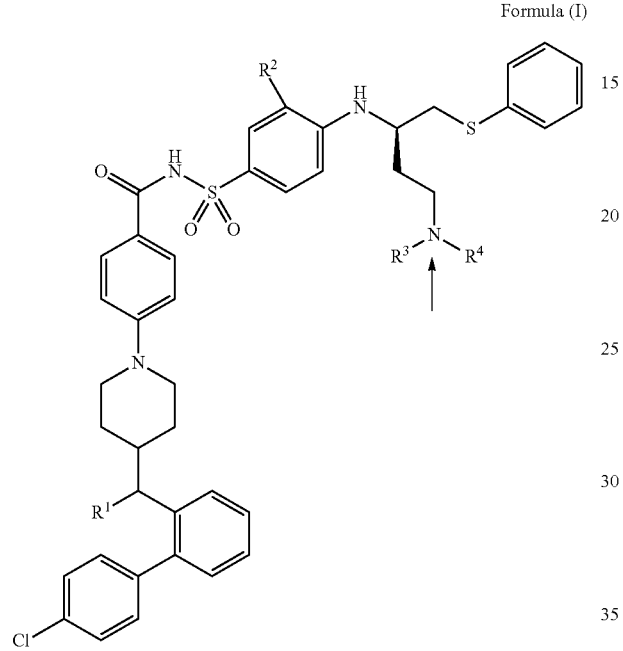

Formula (I-a)

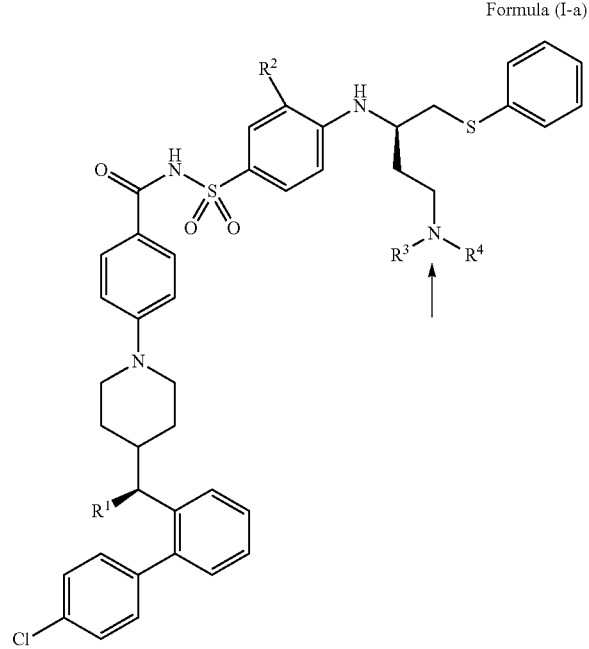

Formula (I-b)

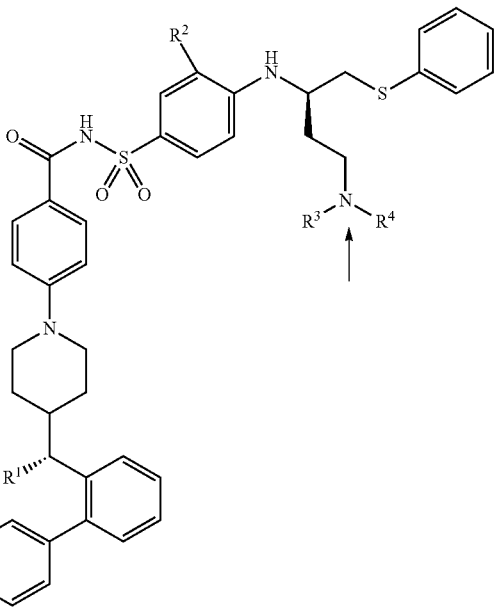

The ring may include, in addition to the indicated nitrogen, one or more heteroatoms selected from nitrogen, sulfur, and oxygen. One or more —CH$_2$— groups may be optionally replaced by a corresponding number of —C(O)— groups. Ring sulfur atoms may be optionally oxidized to form S-oxides. Illustrative examples of "5- or 6-membered heterocyclic ring" include azetidinyl, imidazolin-1-yl, imidazo lidin-1-yl, pyrazolidin-1-yl, piperazin-1-yl, piperidin-1-yl, pyrro lidin-1-yl, morpholino, and thiomorpholino.

Unless specifically stated, the bonding atom of a group may be any suitable atom of that group; for example, propyl includes prop-1-yl and prop-2-yl.

"LEAVING GROUP": As used herein, the phrase "leaving group" is intended to refer to groups readily displaceable by a nucleophile such as an amine nucleophile, and alcohol nucleophile, or a thiol nucleophile. Examples of suitable leaving groups include halo, such as chloro, fluoro, iodo, and bromo, and sulfonyloxy group, such as methanesulfonyloxy and toluene-4-sulfonyloxy.

"OPTIONALLY SUBSTITUTED": As used herein, the phrase "optionally substituted," indicates that substitution is optional and therefore it is possible for the designated group to be either substituted or unsubstituted. In the event a substitution is desired, any number of hydrogens on the designated group may be replaced with a selection from the indicated substituents, provided that the normal valency of the atoms on a particular substituent is not exceeded, and that the substitution results in a stable compound.

In one aspect, when a particular group is designated as being optionally substituted with "one or more" substituents, the particular may be unsubstituted. In another aspect, the particular group may bear one substituent. In another aspect, the particular substituent may bear two substituents. In still another aspect, the particular group may bear three substituents. In yet another aspect, the particular group may bear four substituents. In a further aspect, the particular group may bear one or two substituents. In still a further aspect, the particular group may be unsubstituted, or may bear one or two substituents.

"PHARMACEUTICALLY ACCEPTABLE": As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, formate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate.

Examples of pharmaceutically acceptable base salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically-acceptable salts are preferred, although other salts may be useful, such as in isolating or purifying the product.

"PROTECTING GROUP": As used herein, the term "protecting group" is intended to refer to those groups used to prevent selected reactive groups (such as carboxy, amino, hydroxy, and mercapto groups) from undergoing undesired reactions.

Illustrative examples of suitable protecting groups for a hydroxy group include, but are not limited to, an acyl group; alkanoyl groups such as acetyl; aroyl groups, such as benzoyl; silyl groups, such as trimethylsilyl; and arylmethyl groups, such as benzyl. The deprotection conditions for the above hydroxy protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

Illustrative examples of suitable protecting groups for an amino group include, but are not limited to, acyl groups; alkanoyl groups such as acetyl; alkoxycarbonyl groups, such as methoxycarbonyl, ethoxycarbonyl, and t-butoxycarbonyl; arylmethoxycarbonyl groups, such as benzyloxycarbonyl; and aroyl groups, such benzoyl. The deprotection conditions for the above amino protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric, phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid, for example boron trichloride). A suitable alternative protecting group for a primary amino group is, for example, a phthaloyl group, which may be removed by treatment with an alkylamine, for example dimethylaminopropylamine or 2-hydroxyethylamine, or with hydrazine. Another suitable protecting group for an amine is, for example, a cyclic ether such as tetrahydrofuran, which may be removed by treatment with a suitable acid such as trifluoroacetic acid.

The protecting groups may be removed at any convenient stage in the synthesis using conventional techniques well known in the chemical art, or they may be removed during a later reaction step or work-up.

With reference to substituent "R": for illustrative purposes, the following substituent definitions refer to the indicated structure:

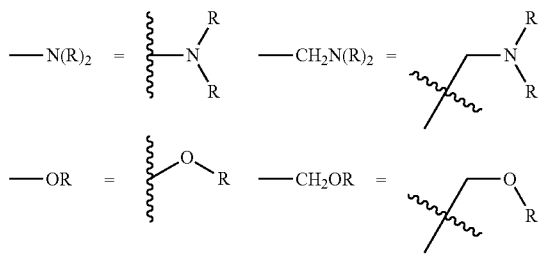

"SUBSTANTIALLY ISOLATED": As used herein, the term "substantially isolated" means a specific stereoisomer is provided (whether provided by separation, by chiral synthesis, or by other methods) it is favorably provided substantially isolated from other stereoisomers of the same compound. In one aspect, a mixture containing a particular stereoisomer of a compound of Formulae (I), (I-a), (I-b), (I-c), (I-d) and/or (I-e) may contain less than 30%, particularly less than 20%, and more particularly less than 10% by weight of other stereoisomer(s) of the same compound. In another aspect, a mixture containing a particular stereoisomer of a compound of Formulae (I), (I-a), (I-b), (I-c), (I-d) and/or (I-e) may contain less than 6%, particularly less than 3%, and more particularly less than 2% by weight of other stereoisomer(s) of the compound. In another aspect, a mixture containing a particular stereoisomer of a compound of Formulae (I), (I-a), (I-b), (I-c), (I-d) and/or (I-e) may contain less than 1%, particularly less than 0.5%, and more particularly less than 0.3%, and still more particularly less 0.1% by weight of other stereoisomer(s) of the compound.

"TREAT", "TREATING" OR "TREATMENT": The terms "treat", "treating" or "treatment" include administering a therapeutically effective amount of a compound sufficient to reduce or eliminate at least one symptom of the state, disease or disorder, e.g., Bcl-2 related conditions and diseases, e.g., cancer.

II. General Methods of Preparation

The present invention provides synthetic methodologies for preparing compounds of Formulae (I), (I-a), and/or (I-b) comprising coupling a carboxylic acid compound of formula (1-f) with a sulfonamide compound of formula (1-g) in the presence of a suitable coupling reagent and base. In certain embodiments, compounds of Formulae (I), (I-a), and/or (I-b) are further purified.

In certain embodiments, compounds of Formula (I), (I-a), and/or (I-b) are generally prepared according to the steps depicted in SCHEME 1 set forth below.

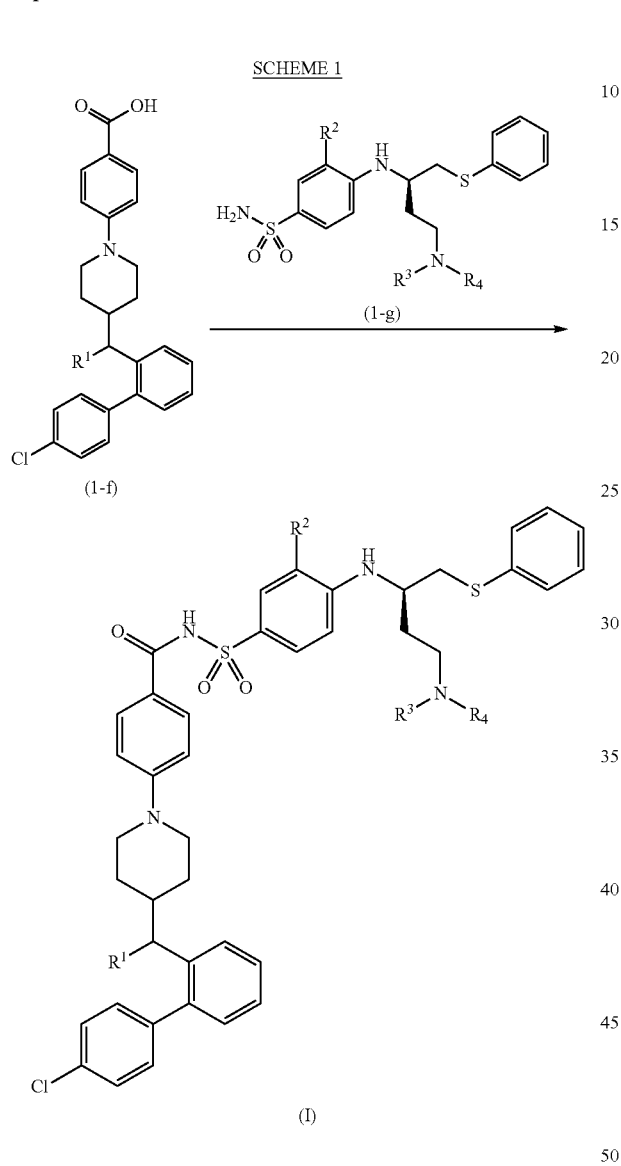

In SCHEME 1 above, $R^1$, $R^2$, $R^3$, and $R^4$ are defined in classes and subclasses as described herein.

A carboxylic acid compound (1-f) and a sulfonamide compound (1-g) may be reacted together in the presence of a suitable solvent, examples of which include but are not limited to dichloromethane, 1,2-dichloroethane, N,N-dimethyl formamide. The reaction is carried out in the presence of a suitable coupling agent such as EDC. The reaction may advantageously occur in the presence of a suitable base, examples of which include DMAP, DIPEA and TEA or combinations thereof. The reaction may be performed either at room temperature or heating. In some embodiments, the reaction is performed at room temperature. In some embodiments, the reaction is performed at 40° C.

A carboxylic acid compound of formula (1-f-i) and formula (1-f-ii) can be prepared according to SCHEME 2, depicted below:

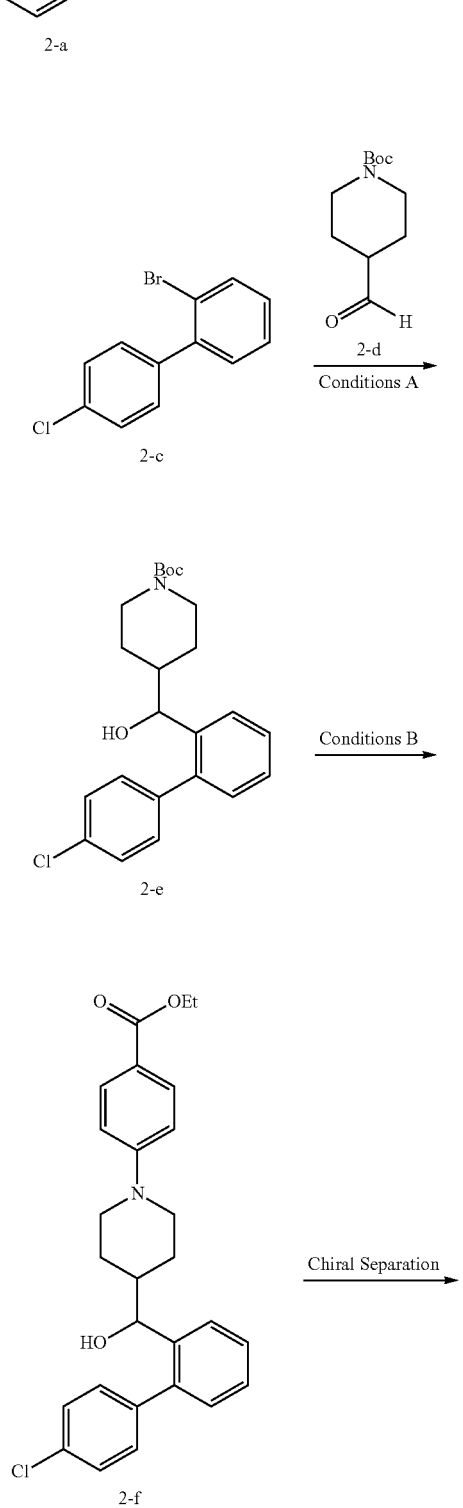

-continued

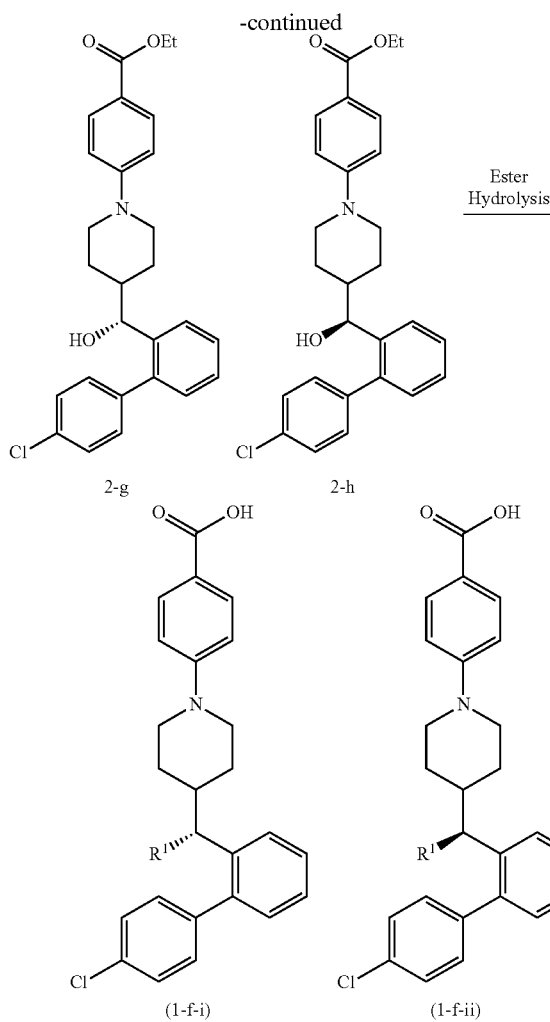

Conditions A: Alkyl lithium reagents such as
n-BuLi or Grignard reagent
Conditions B: (i) Acids such as TFA or HCl
(ii) p-F-C6H4COOEt, base or p-Br-C6H4COOEt,
Pd-catalyzed amination pr p-I-C6H4COOEt
Pd-catalyzed amination In SCHEME 2 above, $R^1$ is as defined in classes and subclasses as described herein.

As depicted in SCHEME 2 above, a boronic acid compound of formula (2-a) is reacted with di-halogenated benzene compound of formula (2-b) under Suzuki reaction conditions known to one skilled in the art to form a biphenyl compound of formula (2-c).

A biphenyl compound of formula (2-c) is converted to a corresponding aryl lithium compound using a suitable alkyllithium reagent. In some embodiments, the alkyllithium reagent is n-BuLi. In some embodiments, the alkyllithium reagent is t-BuLi. Alternatively, a biphenyl compound of formula (2-c) may be converted to a corresponding organomagnesium Grignard reagent (see Grignard reagent, Angew. Chem. Int. Ed., 2004, 43, 3333), using a suitable alkyl magnesium bromide lithium chloride complex. In some embodiments, a suitable alkyl magnesium bromide lithium chloride complex is i-Pr-MgBr LiCl complex.

A compound of formula (2-e) as a mixture of enantiomers is prepared by in situ reaction of either an aryl lithium compound or a corresponding organomagnesium Grignard reagent with an N-protected carboxylate compound of formula (2-d). Further deprotection of a compound of formula (2-d) may be performed using a suitable acid. In some embodiments, the acid is TFA. In some embodiments, the acid is HCl.

A compound of formula (2-f) as a mixture of enantiomers is prepared by performing a substitution reaction using a compound of formula (2-e) and para substituted benzoate compound in the presence of a suitable solvent and a suitable base. In some embodiments, a suitable based is triethylamine. In some embodiments, a suitable based is DIPEA. In some embodiments, a suitable base is $K_2CO_3$. In some embodiments, a suitable base is $Cs_2CO_3$. In some embodiments, a suitable para substituted benzoate compound is a halogenated benzoate compound. In some embodiments, a suitable halogenated benzoate compound is p-F—$C_6H_4$COOEt.

Alternatively, a compound of formula (2-f) is prepared using Pd-catalyzed amination (see Chem. Sci. 2011, 2, 27 and reference cited therein) using a suitable para substituted benzoate and further separating the two enantiomers (antipodes) using similar conditions to those described in the EXAMPLES, infra, to form compounds of formulae (2-g) and (2-h).

A carboxylic acid compound of formula (1-f-i) and/or (1-f-ii) is prepared by performing ester hydrolysis on compounds of formulae (2-g) and/or (2-h) ester using standard conditions known to one of ordinary skill in the art, as a mixture of enantiomers, or as a single enantiomer.

As an alternate embodiment, a carboxylic acid compound of formula (1-f-i) and/or (1-f-ii) can be prepared according to SCHEME 3, depicted below:

SCHEME 3

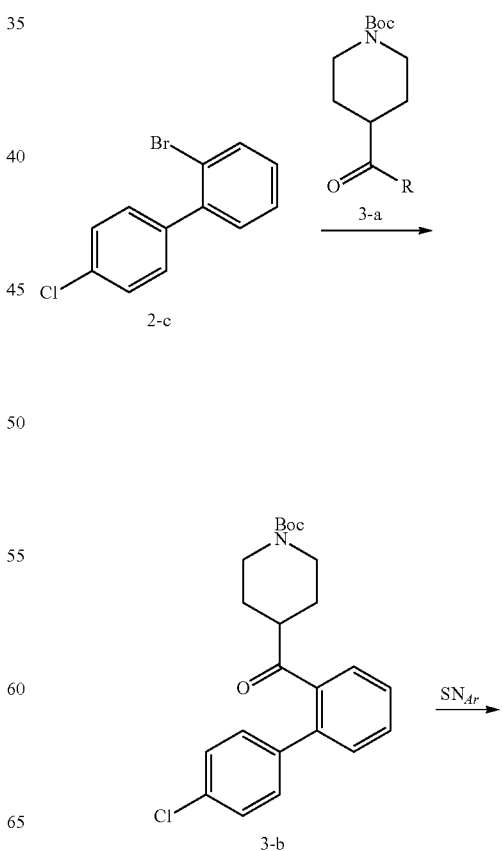

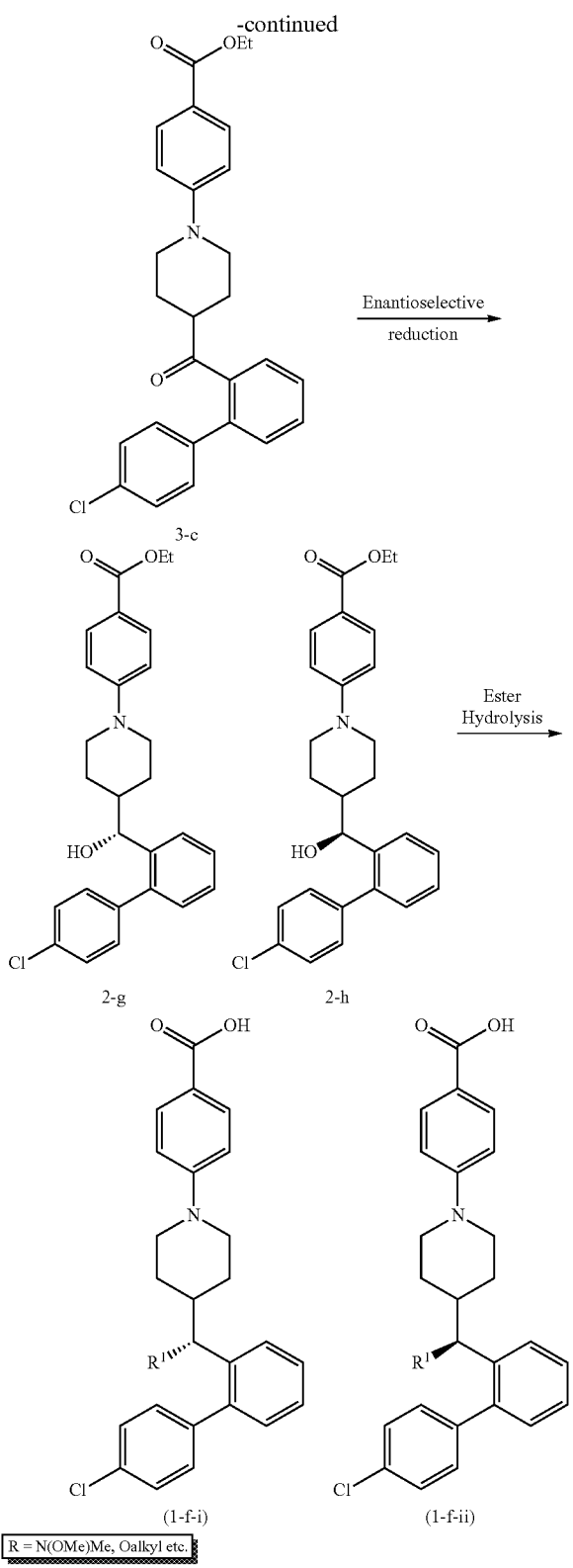

In SCHEME 3 above, $R^1$ is as defined in classes and subclasses as described herein.

Alternatively, the aryl lithium compound or a corresponding organomagnesium Grignard reagent described in SCHEME 2 above may be reacted with an N-protected compound of formula (3-a) to provide a compound of formula (3-b). A further substitution reaction using a compound of formula (3-b) and para substituted benzoate compound in the presence of a suitable solvent and a suitable base is performed using similar conditions to those described above for the formation of a compound of formula (3-c).

Performing enantioselective reduction to a compound of formula (3-c): (a) under CBS-conditions (*Angew. Chem. Int. Ed.* 1998, 37, 1986); or (b) Noyori asymmetric hydrogenation conditions (*Asymmetric Catalysis in Organic Synthesis*; John Wiley & Sons: New York, 1993, 56-82.) will provide enantio-enriched mixtures of either a compound of formula (2-g) or a compound of formula (2-h). The enantiopurity may be improved after recrystallization from a/an appropriate solvent(s).

For enantioselective reduction, conversion from a compound of formula (3-c) to a compound of formula (2-g) or (2-g) may performed by using a suitable catalyst in the presence of a suitable borane and a suitable solvent at temperatures of from about −30° C. to about 60° C. In some embodiments, a suitable catalyst is (R)-(+)-2-methyl-CBS-oxazaborolidine. In some embodiments, a suitable catalyst is (S)-(−)-2-methyl-CBS-oxazaborolidine. In some embodiments, a suitable borane is borane-tetrahydrofuran complex. In some embodiments, a suitable borane is a borane-dimethyl sulfide complex. In some embodiments, a suitable solvent is THF.

Alternatively, conversion from a compound of formula (3-c) to a compound of formaul (2-g) or (2-g) may be performed using Noyori asymmetric hydrogenation. The asymmetric hydrogenation can be performed using a suitable catalyst and base in the presence of a suitable solvent mixture in a hydrogen atmosphere. In some embodiments, a suitable base is t-BuOK. In some embodiments, a suitable solvent mixture is i-PrOH and DMF.

In some embodiments, a suitable catalyst is Ru(chiral diphosphine)(chiral amine)$Cl_2$ wherein the chiral disphosphine portion of the catalyst may be selected from, but is not limited to, S-ClMeOBIPHEP, R-ClMeOBIPHEP, S-Segphos, R-Segphos, R-CTH-Pphos, S-CTH-Pphos, S-BINAP, and R-BINAP; and wherein the chiral amine portion of the catalyst may be selected from, but is not limited to S-Daipen, R-Daipen, S,S-DACH, and R,R-DACH. In some embodiments, the chiral disphosphine portion of the catalyst is S-ClMeOBIPHEP. In some embodiments, the chiral disphosphine portion of the catalyst is R-ClMeOBIPHEP. In some embodiments, the chiral disphosphine portion of the catalyst is S-Segphos. In some embodiments, the chiral disphosphine portion of the catalyst is R-Segphos. In some embodiments, the chiral disphosphine portion of the catalyst is S-CTH-Pphos. In some embodiments, the chiral disphosphine portion of the catalyst is R-CTH-Pphos. In some embodiments, the chiral disphosphine portion of the catalyst is S-BINAP. In some embodiments, the chiral disphosphine portion of the catalyst is R-BINAP. In some embodiments the chrial amine portion of the catalyst is S-Daipen. In some embodiments the chrial amine portion of the catalyst is R-Daipen. In some embodiments the chrial amine portion of the catalyst is S,S-DACH. In some embodiments the chrial amine portion of the catalyst is R,R-DACH.

A carboxylic acid compound of formula (1-f-i) and/or (1-f-ii) is prepared by performing ester hydrolysis on compounds of formulae (2-g) and/or (2-h) ester using standard conditions known to one of ordinary skill in the art, as a mixture of enantiomers, or as a single enantiomer.

A sulfonamide compound (1-i) can be prepared by a method disclosed herein, for example, according to SCHEME 4 below.

SCHEME 4

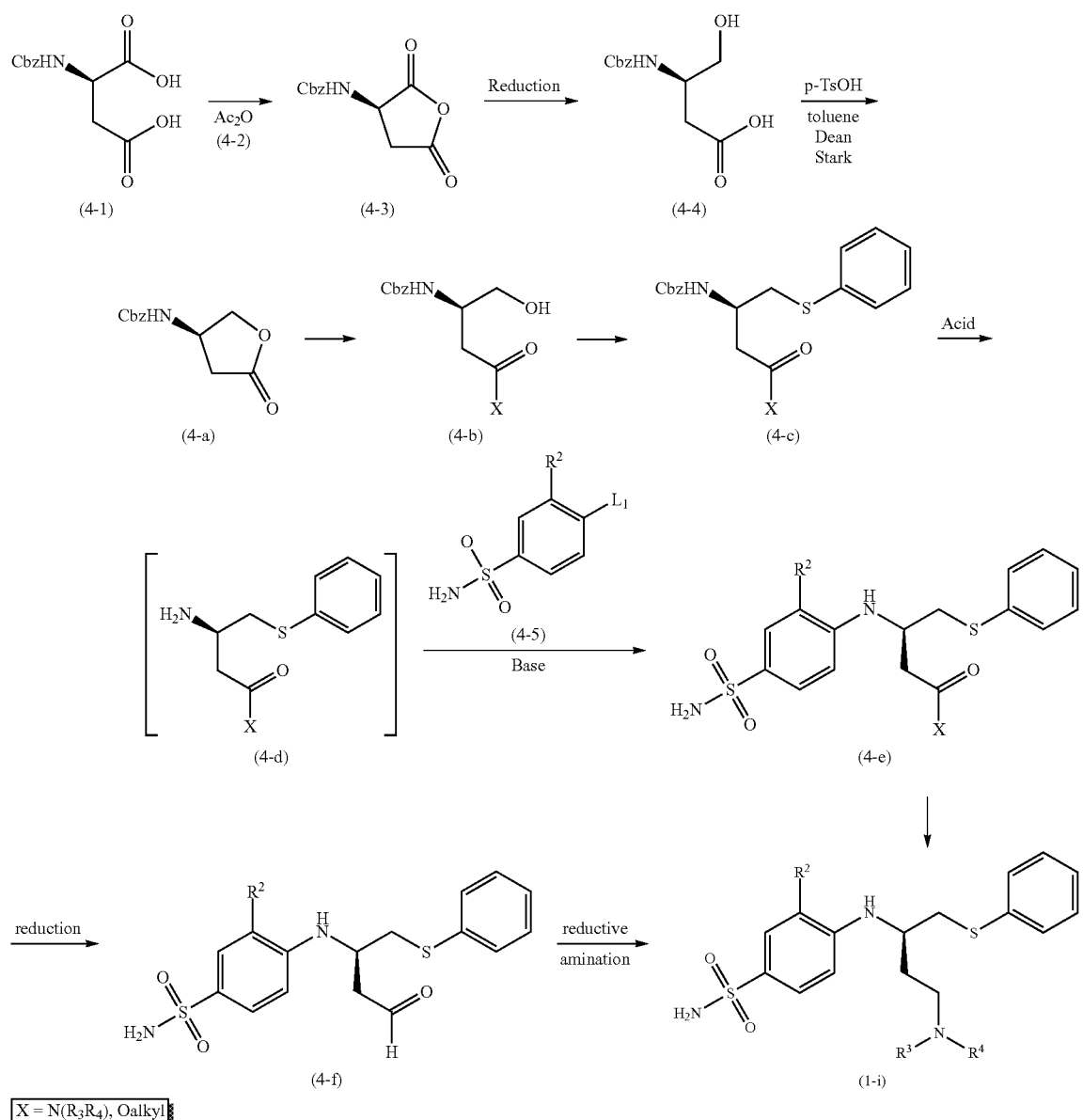

As depicted in SCHEME 4 above, X, $L_1$, $R^2$, $R^3$, and $R^4$ are defined in classes and subclasses as described herein.

A compound of formula (4-3) may be prepared by cyclizing a commercially available N-protected succinic acid, for example a compound of formula (4-1), and a suitable acid anhydride, for example, a compound of formula (4-2), using conditions known to one of ordinary skill in the art. Chemoselective reduction of a compound of formula (4-3) using methods known to one of ordinary skill in the art will provide a corresponding N-protected acid compound of formula (4-4). A lactone compound of formula (4-a) is prepared by treating the corresponding N-protected acid compound of formula (4-4) with a suitable organic acid in a suitable solvent under appropriate conditions. In some embodiments, the organic acid is p-TsOH. In some embodiments, the organic acid is camphorsulfonic acid. In some embodiments, a suitable solvent is toluene. In some embodiments, a distillation is performed using Dean-Stark conditions.

Ring-opening is performed by reacting a lactone compound of formula (4-a) in the presence of a suitable alcohol to provide a corresponding ester compound (for example, when X=OMe) using conditions known to one of ordinary skill in the art. In some embodiments, a suitable alcohol is methanol. Alternatively, ring opening can be performed in the presence of a suitable amine compound (for example, $HN(R_3R_4)$) to form a corresponding amide, depicted as a compound formula (4-b) in SCHEME 4.

A compound of formula (4-c) may be prepared by reacting a compound of formula (4-b) under Mitsunobu reaction conditions in the presence of a thiophenol compound, a suitable phosphine compound, azodicarbonyl reagent, a suitable solvent, at a temperature of about 0 to about 23° C. In some embodiments, a suitable phosphine compound is a trialkyl phosphine or a triaryl phosphine. Exemplary trialkyl phosphine compounds include, but are not limited to tributyl phosphine. Exemplary triaryl phosphine compounds include, but are not limited to triphenyl phosphine. In some embodiments a suitable azodicarbonyl reagent includes, but is not limited to diisopropylazodicarboxylate. In some embodiments, a suitable solvent is N,N-dimethylformamide. In some embodiments, a suitable solvent is dichloromethane.

A compound of formula (4-c) is deprotected using a suitable acid to form a compound of formula (4-d). In some embodiments, a suitable acid is TFA. In some embodiments, a suitable acid is HBr in acetic acid.

A compound of formula (4-d) is further coupled with an amine compound of formula (4-5) in the presence of a suitable base and a suitable solvent to form a sulfonamide compound of formula (4-e), for example, wherein X=-OAlk, at a temperature of about 50° C. to about 70° C. In some embodiments, the reaction is performed at a temperature of about 50° C. A suitable base includes, but is not limited to DIPEA, triethylamine, N-methyl morpholine, or potassium carbonate. In some embodiments, a suitable base is triethylamine. In some embodiments, a suitable base is potassium carbonate. A suitable solvent includes, but is not limited to N,N-dimethylformamide.

When X=N(R$_3$R$_4$) in a compound of formula (4-e), an amide reduction is performed using a suitable reducing agent under conditions known to one of ordinary skill in the art to form a compound of formula (1-i). In some embodiments, a suitable reducing agent is borane-tetrahydrofuran complex.

When X=-Oalk in a compound of formula (4-e), a reduction reaction is performed to form a corresponding aldehyde compound of formula (4-f), under conditions known to one of ordinary skill in the art. Reductive amination of a compound of formula (4-f) in the presence of an amine HNR$_3$R$_4$ using a suitable reducing agent, is performed under conditions known to one of ordinary skill in the art to form an amine compound of formula (1-i). Suitable reducing agents include, but are not limited to sodium acetoxyborohydride.

SCHEME 4A

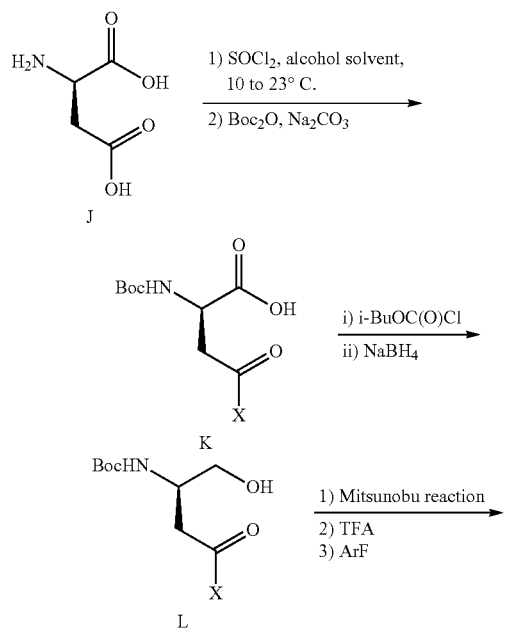

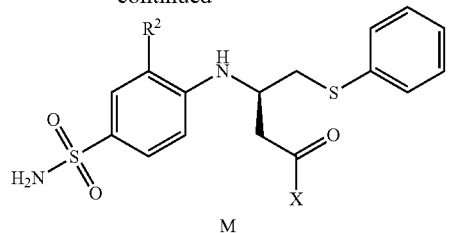

M

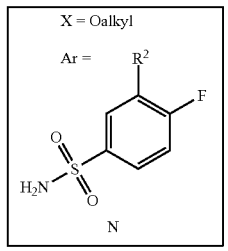

An alternative method of preparing a compound of formula (4-e) as depicted in SCHEME 4 above, is to prepare a compound of formula M by a method disclosed herein, for example, according to SCHEME 4A below.

As depicted in SCHEME 4A, D-aspartic acid (J) is converted into an N-Boc protected methyl ester compound of formula (K) via acid catalyzed esterification in the presence of a suitable alcohol solvent followed by t-butylcarboxy protection of the free NH$_2$. In some embodiments, a suitable alcohol solvent is methanol. Step 1) is carried out in the presence of a suitable acidic reagent at a temperature of about −10° C. to about 23° C. In some embodiments, a suitable acidic reagent is thionyl chloride. In some embodiments, a suitable acid catalyst is anhydrous HCl. In some embodiments, a suitable acid catalyst is anhydrous sulfuric acid. N-Boc protection is carried out in the presence of di-tert-butyl dicarbonate (Boc$_2$O) in the presence of a suitable base such potassium carbonate and in the presence of a suitable solvent mixture. Exemplary solvent mixtures include, but are not limited to ethyl acetate/water, dioxane/water, or tetrahydrofuran/water. In some embodiments, the temperature of the N-Boc protection reaction is −about 0° C. to about 23° C. In some embodiments, a suitable base is sodium bicarbonate. In some embodiments, a suitable base is sodium carbonate.

N-Boc protected alkyl ester (K) is converted to primary alcohol (L) by conversion of the acid moiety of (K) into a mixed anhydride and subsequent reduction to the corresponding alcohol. Conversion of (K) into a mixed anhydride is carried out in the presence of a suitable base. In some embodiments, a suitable base is N-methyl morpholine. In some embodiments, a suitable alkyl chloroformate is isobutyl chloroformate. In some embodiments, a suitable temperature is from about −20° C. to about 0° C. In some embodiments, a suitable solvent is tetrahydrofuran. In some embodiments, a suitable solvent is 1,2-dimethoxyethane or diethyl ether. In some embodiments, a suitable base such as triethylamine or N,N-diisopropylethylamine is used. In some embodiments, a suitable alkyl chloformate is ethyl chloroformate. In some embodiments, a suitable acyl chloride is pivaloyl chloride. Reduction of the mixed anhydride is carried out by adding a suitable reducing agent such as sodium borohydride using a suitable cosolvent such as methanol from about −10 to about 0° C. In some embodiments a suitable cosolvent is water. In some embodiments a suitable cosolvent is ethanol. In some embodiments, the acid is converted directly into an alcohol using a suitable reagent such as borane-tetrahydrofuran complex in tetrahydrofuran at a temperature such as 0 to 23° C.

Alcohol (L) is converted into sulfonamide (M) using Mitsunobu reaction conditions followed by removal of the Boc protecting group under acidic conditions and subsequent addition to aryl fluoride (N). The Mitsunobu reaction is carried out in the presence of thiophenol, a suitable trialkyl or triaryl phosphine such as tributyl phosphine, and a suitable azodicarbonyl reagent such as azodicarbonyldipiperidine at about 0 to about 23° C. using a suitable solvent such as tetrahydrofuran. In some embodiments, a suitable triarylphosphine is triphenylphospine. In some embodiments, a suitable azodicarbonyl reagent is diisopropylazodicarboxylate. In some embodiments, a suitable solvent is ether, N,N-dimethylformamide, or dichloromethane. Removal of the Boc protecting group is carried out using a suitable acid such as trifluoroacetic acid, sulfuric acid, or hydrochloric acid in a suitable solvent such as dichloromethane, dioxane, or water at 23° C. In some embodiments, the deprotection reaction is carried out from 0 to 23° C. The crude deprotected material is then added directly to aryl fluoride (N) in the presence of a suitable base such as N,N-diisopropylamine in the presence of a suitable solvent such as N,N-dimethylformamide at a temperature such as 50° C. In some embodiments, a suitable base is triethylamine or potassium carbonate. In some embodiments, a suitable temperature is 50 to 70° C.

A carboxylic acid of formulae (5-i-i) and/or (5-i-ii) can be prepared by a method disclosed herein, for example, according to SCHEME 5 below.

SCHEME 5

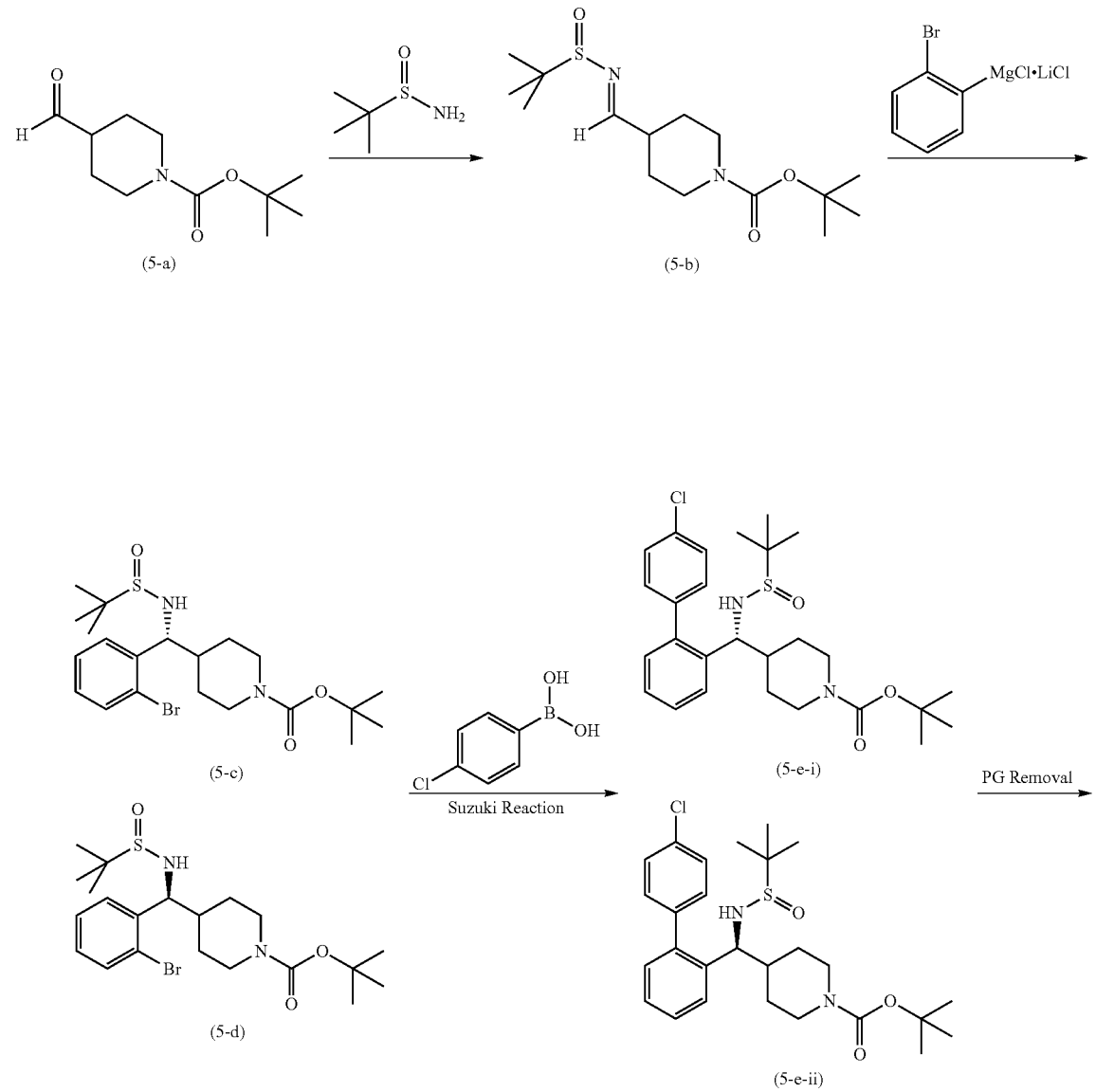

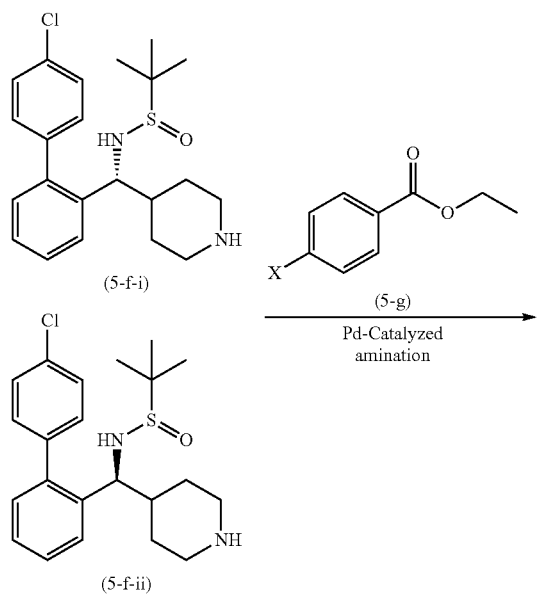
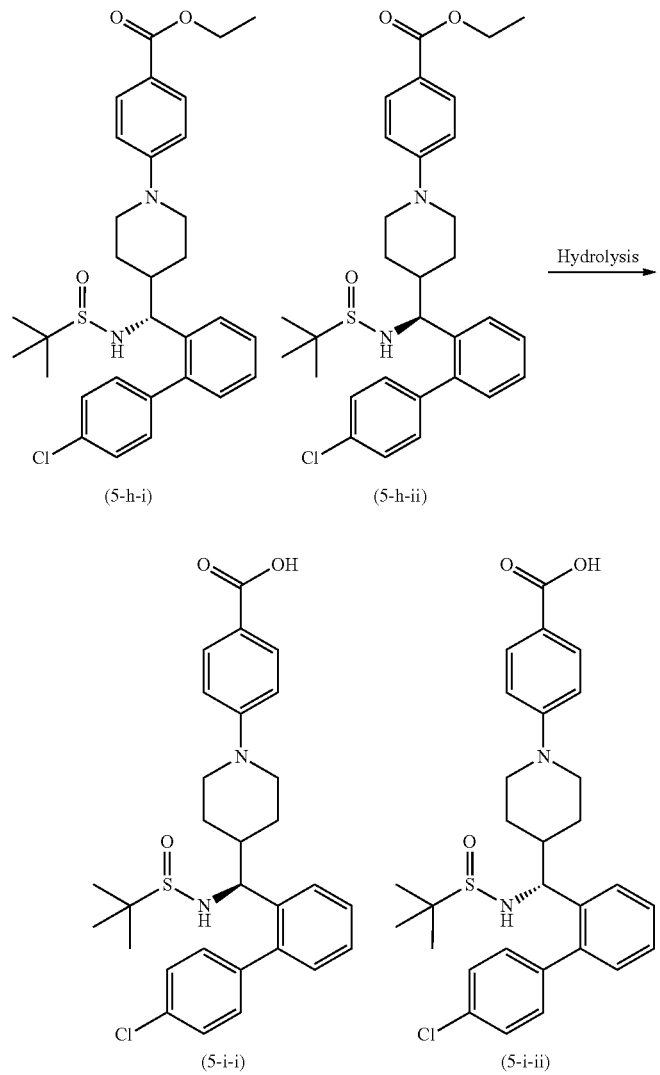

Aldehyde (5-a) is converted to sulfinylimine (5-b) using a racemic 2-methylpropane-2-sulfinamide auxilliary group and suitable acid catalyst in a suitable solvent (*Acc. Chem. Res.* 2002, 35, 984). In some embodiments, the auxilliary group is (S)-2-methylpropane-2-sulfinamide. In some embodiments, the auxilliary group is (R)-2-methylpropane-2-sulfinamide. In some embodiments a suitable acid catalyst is anhydrous copper(II) sulphate. In some embodiments, a suitable acid catalyst is titanium(IV) ethoxide. The transformation is perfomed at about 0 to about 60° C. using a suitable solvent. In some embodiments, the suitable solvent is dichloromethane. In some embodiments, the suitable solvent is tetrahydrofuran.

Sulfinylimine (5-b) is reacted with a Grignard reagent, generated according to the procedure reported in *Angew. Chem. Int. Ed.*, 2004, 43, 3333, at a temperature of from about −20° C. to about 0° C., in a suitable solvent (e.g., tetrahydrofuran) to provide a sulfinamide compound of formula (5-c) and/or (5-d).

A compound of formula (e) (5-e-i) and/or (5-e-ii) is prepared by performing a Suzuki reaction on compounds of formula (e) (5-c) and/or (5-d) under conditions known to one of ordinary skill in the art (see *J. Am. Chem. Soc.* 2005, 127, 4685; and *Nature Protocols* 2007, 2, 3115. *Aldrichimica Acta* 2006, 39, 17). In some embodiments, a suitable ligand for the reaction is dicyclohexylphosphino-2',6'-dimethoxybiphenyl. In some embodiments, a suitable palladium source is tris(dibenzylideneacetone)dipalladium(0). In some embodiments a suitable base is tripotassium phosphate.

A compound of formula (e) (5-f-i) and/or (5-f-ii) is prepared by chemoselective removal of the Boc group of formula (e) (5-e-i) and/or (5-e-ii) in the presence of an acid labile t-Bu sulfinamide group. In some embodiments, the transformation is carried out in the presence of suitable acid such as TFA, in a suitable solvent such as dichloromethane, at a temperature ranging from about 0 to about 23° C.

A compound of formula (e) (5-h-i) and/or (5-h-ii) is prepared by performing a Pd-catalyzed amination reaction on a compound of formula (e) (5-f-i) and/or (5-f-ii) in the presence of a compound of formula (5-g) under conditions known to one of ordinary skill in the art (see *Chem. Sci.* 2011, 2, 27, and reference cited therein). In some embodiments, a suitable pre-formed catalyst:ligand adduct is used such as chloro(2-dicyclophosphino-2',6'-di-isopropoxy-1,1'-biphenyl)[2-(2-aminoethylphenyl)]Pd(II) methylbutyl adduct. In some embodiments, additional dicyclohexyl(2'6'-diisopropoxybiphenyl-2-yl)phosphine is added. In some embodiments a suitable base is used, including but not limited to cesium carbonate. The transformation is performed at temperatures ranging of from about 80 to about 120° C.

A compound of formula (e) (5-i-i) and/or (5-i-ii) is prepared is prepared by performing ester hydrolysis on a compound of formula (e) (5-h-i) and/or (5-h-ii) using standard conditions known to one of ordinary skill in the art, as a mixture of diastereomers, or as a single diastereomer.

In certain embodiments, carboxylic acid (6-f), (6-i) and (6-j) are prepared according to SCHEME 6.

SCHEME 6

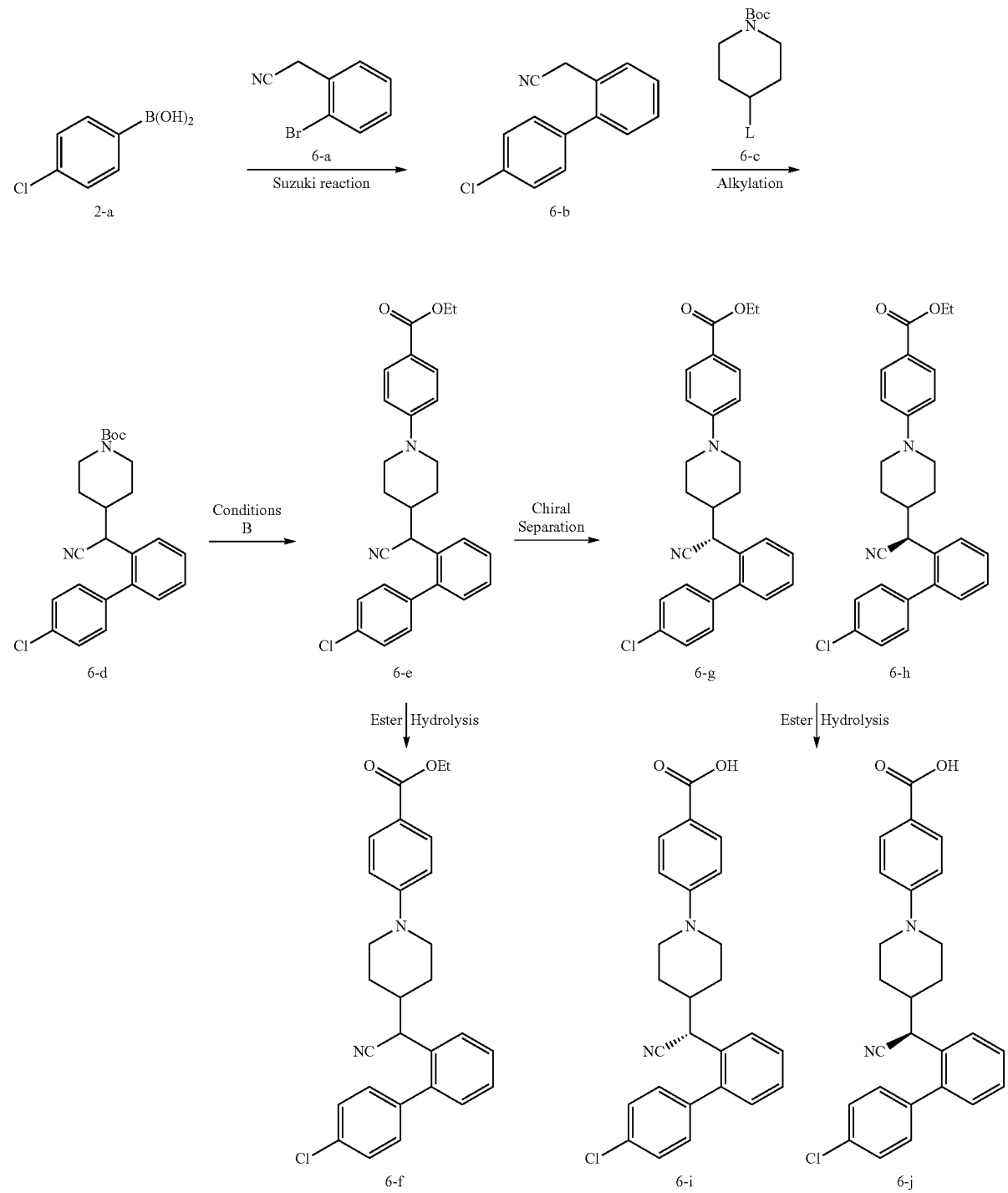

III. Compounds of the Present Invention

Compounds provided by the present invention include those described generally above, and are further illustrated by all classes, subclasses and species of each of these compounds disclosed herein.

The present invention relates to compounds of Formula (I):

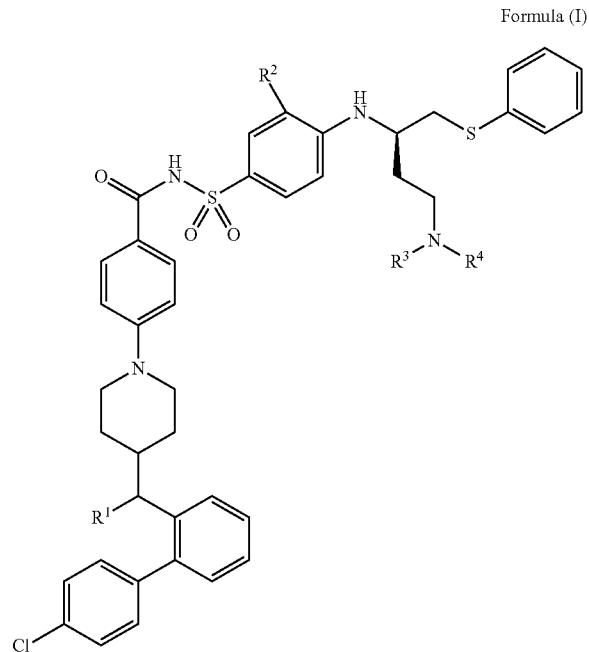

Formula (I)

and/or a pharmaceutically acceptable salt thereof, wherein:
$R^1$ is selected from —CN, —$OR^{1a}$, and —$N(R^{1a})_2$;
$R^{1a}$ in each occurrence is independently selected from H, $C_{1-4}$alkyl, —$C(O)CH_2NH_2$, —$C(O)CH_2NHCH_3$, and when $R^1$ is —$OR^{1a}$, then $R^{1a}$ is additionally selected from —P(=O)(OH)(OCH_3), —P(=O)(OCH_2CH_3)_2, —CH_2OP(=O)(OH)[OC(CH_3)_3] and —CH_2OP(=O)[OC(CH_3)_3]_2;
$R^2$ is selected from —$N(O)_2$ and —$S(O)_2CF_3$;
$R^3$ is selected from H and $C_{1-4}$alkyl, wherein said $C_{1-4}$alkyl is optionally substituted with one or more $R^{40}$;
$R^4$ is selected from H and $C_{1-4}$alkyl, wherein said $C_{1-4}$alkyl is optionally substituted with one or more $R^{40}$;
or $R^3$ and $R^4$ together with the nitrogen to which they are attached form a 5- or 6-membered heterocyclic ring, wherein
  i) said 5- or 6-membered heterocyclic ring is optionally substituted on carbon with one or more $R^{40}$; and
  ii) if said 5- or 6-membered heterocyclic ring contains a nitrogen, that nitrogen is optionally substituted with $R^{40*}$ to form a tertiary amine;
$R^{40*}$ is $C_{1-4}$alkyl and —$(CH_2)_2OP(=O)(OH)_2$, wherein said $C_{1-4}$alkyl is optionally substituted with one or more $R^a$;
$R^{40}$ in each occurrence is selected from —$OR^{40a}$, —$N(R^{40a})_2$, —$CH_2OR^{5a}$, —$CH_2N(R^{5a})_2$, —OP(=O)(OH)_2, and —OP(=O)[OC(CH_3)_3]_2;
$R^{5a}$ in each occurrence is selected from H and $C_{1-3}$alkyl;
$R^{40a}$ in each occurrence is independently selected from H and $C_{1-4}$alkyl; and
$R^a$ is selected from halo, —$OR^m$, and —$N(R^m)_2$; and
$R^m$ in each occurrence is independently selected from H and $C_{1-4}$alkyl.

Additional embodiments of the invention are as follows. These additional embodiments relate to compounds of Formulae (I), (I-a), (I-b), (I-c), (I-d) and/or (I-e) and pharmaceutically acceptable salts thereof. Such specific substituents may be used, where appropriate, with any of the definitions, claims or embodiments defined hereinbefore or hereinafter.

In some embodiments, the present invention relates to compounds of Formula (I), and/or a pharmaceutically acceptable salt thereof, wherein:
$R^1$ is selected from —CN, —$OR^{1a}$, and —$N(R^{1a})_2$;
$R^{1a}$ in each occurrence is independently selected from H, $C_{1-4}$alkyl, —$C(O)CH_2NH_2$, and —$C(O)CH_2NHCH_3$;
$R^2$ is selected from —$N(O)_2$ and —$S(O)_2CF_3$;
$R^3$ is selected from H and $C_{1-4}$alkyl, wherein said $C_{1-4}$alkyl is optionally substituted with one or more $R^{40}$;
$R^4$ is selected from H and $C_{1-4}$alkyl, wherein said $C_{1-4}$alkyl is optionally substituted with one or more $R^{40}$;
or $R^3$ and $R^4$ together with the nitrogen to which they are attached form a 5- or 6-membered heterocyclic ring, wherein
  i) said 5- or 6-membered heterocyclic ring is optionally substituted on carbon with one or more $R^{40}$; and
  ii) if said 5- or 6-membered heterocyclic ring contains a nitrogen, that nitrogen is optionally substituted with $R^{40*}$ to form a tertiary amine;
$R^{40*}$ is $C_{1-4}$alkyl, wherein said $C_{1-4}$alkyl is optionally substituted with one or more $R^a$;
$R^{40}$ in each occurrence is selected from —$OR^{40a}$, —$N(R^{40a})_2$, —$CH_2OR^{5a}$, —$CH_2N(R^{5a})_2$;
$R^{5a}$ in each occurrence is selected from H and $C_{1-3}$alkyl;
$R^{40a}$ in each occurrence is independently selected from H and $C_{1-4}$alkyl; and
$R^a$ is selected from halo, —$OR^m$, and —$N(R^m)_2$; and
$R^m$ in each occurrence is independently selected from H and $C_{1-4}$alkyl.

In some embodiments, the present invention relates to compounds of Formula (I), and/or a pharmaceutically acceptable salt thereof, wherein:
$R^1$ is selected from —CN, —$OR^{1a}$, and —$N(R^{1a})_2$;
$R^{1a}$ in each occurrence is independently selected from H, $C_{1-4}$alkyl, —$C(O)CH_2NH_2$, —$C(O)CH_2NHCH_3$, and when $R^1$ is —$OR^{1a}$, then $R^{1a}$ is additionally selected from —P(=O)(OH)(OCH_3), —P(=O)(OCH_2CH_3)_2, —CH_2OP(=O)(OH)[OC(CH_3)_3] and —CH_2OP(=O)[OC(CH_3)_3]_2;
$R^2$ is selected from —$N(O)_2$ and —$S(O)_2CF_3$;
$R^3$ is selected from H and $C_{1-4}$alkyl, wherein said $C_{1-4}$alkyl is optionally substituted with one or more $R^{40}$;
$R^4$ is selected from H and $C_{1-4}$alkyl, wherein said $C_{1-4}$alkyl is optionally substituted with one or more $R^{40}$;
or $R^3$ and $R^4$ together with the nitrogen to which they are attached form a 5- or 6-membered heterocyclic ring, wherein
  i) said 5- or 6-membered heterocyclic ring is optionally substituted on carbon with one or more $R^{40}$; and
  ii) if said 5- or 6-membered heterocyclic ring contains a nitrogen, that nitrogen is optionally substituted with $R^{40*}$ to form a tertiary amine;
$R^{40*}$ is selected from $C_{1-4}$alkyl and —$(CH_2)_2OP(=O)(OH)_2$, wherein said $C_{1-4}$alkyl is optionally substituted with one or more $R^a$;
$R^{40}$ in each occurrence is selected from —$OR^{40a}$, —$N(R^{40a})_2$, —$CH_2OR^{5a}$, —$CH_2N(R^{5a})_2$, —OP(=O)(OH)_2, and —OP(=O)[OC(CH_3)_3]_2;
$R^{5a}$ in each occurrence is selected from H and $C_{1-3}$alkyl;
$R^{40a}$ in each occurrence is independently selected from H and $C_{1-4}$alkyl; and

29

$R^a$ is selected from halo, —$OR^m$, and —$N(R^m)_2$; and
$R^m$ in each occurrence is independently selected from H and $C_{1-4}$alkyl;
and wherein at least one of $R^1$, $R^3$, or $R^4$, contains a —P(=O)— group.

In some embodiments, the present invention relates to compounds of Formula (I), and/or a pharmaceutically acceptable salt thereof, wherein:
$R^1$ is selected from —CN, —$OR^{1a}$, and —$N(R^{1a})_2$;
$R^{1a}$ in each occurrence is independently selected from H, $C_1$alkyl, —$C(O)CH_2NH_2$, and —$C(O)CH_2NHCH_3$;
$R^2$ is selected from —$N(O)_2$ and —$S(O)_2CF_3$;
$R^3$ is selected from $C_{1-2}$alkyl, wherein said $C_{1-2}$alkyl is optionally substituted with one or more $R^{40}$;
$R^4$ is selected from $C_{1-2}$alkyl, wherein said $C_{1-2}$alkyl is optionally substituted with one or more $R^{40}$;
or $R^3$ and $R^4$ together with the nitrogen to which they are attached form a 5- or 6-membered heterocyclic ring, wherein
  i) said 5- or 6-membered heterocyclic ring is optionally substituted on carbon with one or more $R^{40}$; and
  ii) if said 5- or 6-membered heterocyclic ring contains a nitrogen, that nitrogen is optionally substituted with $R^{40*}$ to form a tertiary amine;
$R^{40*}$ is selected from $C_{2-3}$alkyl wherein said $C_{2-3}$alkyl is optionally substituted with one or more $R^a$;
$R^{40}$ in each occurrence is selected from —$OR^{40a}$, —$CH_2OR^{5a}$, and —$CH_2N(R^{5a})_2$;
$R^{5a}$ in each occurrence is selected from H and $C_2$alkyl;
$R^{40a}$ in each occurrence is independently H; and
$R^a$ is selected from halo and —$OR^m$; and
$R^m$ in each occurrence is independently H.

In some embodiments, the present invention relates to compounds of Formula (I), and/or a pharmaceutically acceptable salt thereof, wherein:
$R^{1a}$ is —$OR^{1a}$;
$R^{1a}$ in each occurrence is independently selected from H, and —P(=O)(OH)($OCH_3$), —P(=O)($OCH_2CH_3$)$_2$, —$CH_2OP$(=O)(OH)[$OC(CH_3)_3$] and —$CH_2OP$(=O)[$OC(CH_3)_3$]$_2$;
$R^2$ is —$S(O)_2CF_3$;
$R^3$ is $C_{1-2}$alkyl, wherein said $C_{1-2}$alkyl is optionally substituted with one or more $R^{40}$;
$R^4$ is $C_{1-2}$alkyl, wherein said $C_{1-2}$alkyl is optionally substituted with one or more $R^{40}$;
or $R^3$ and $R^4$ together with the nitrogen to which they are attached form a 5- or 6-membered heterocyclic ring, wherein
  i) said 5- or 6-membered heterocyclic ring is optionally substituted on carbon with one or more $R^{40}$; and
  ii) if said 5- or 6-membered heterocyclic ring contains a nitrogen, that nitrogen is optionally substituted with $R^{40*}$ to form a tertiary amine;
$R^{40*}$ is —($CH_2)_2OP$(=O)(OH)$_2$;
$R^{40}$ in each occurrence is selected from –OP(=O)(OH)$_2$ and —$CH_2N(R^{5a})_2$;
$R^{5a}$ in each occurrence is selected from H and $C_2$alkyl;
$R^a$ is selected from halo, —$OR^m$, and —$N(R^m)_2$; and
$R^m$ in each occurrence is independently selected from H and $C_{1-4}$alkyl.

In some embodiments, the present invention relates to compounds of Formula (I), and/or a pharmaceutically acceptable salt thereof, wherein:
$R^1$ is —OH;
$R^2$ is —$S(O)_2CF_3$;
$R^3$ is $C_{1-2}$alkyl, wherein said $C_{1-2}$alkyl is optionally substituted with one or more $R^{40}$;

30

$R^4$ is $C_{1-2}$alkyl, wherein said $C_{1-2}$alkyl is optionally substituted with one or more $R^{40}$;
$R^{40}$ in each occurrence is selected from —$OR^{40a}$ and —OP(=O)(OH)$_2$; and
$R^{40a}$ is H.

In certain embodiments, the present invention provides compound of Formula (I):

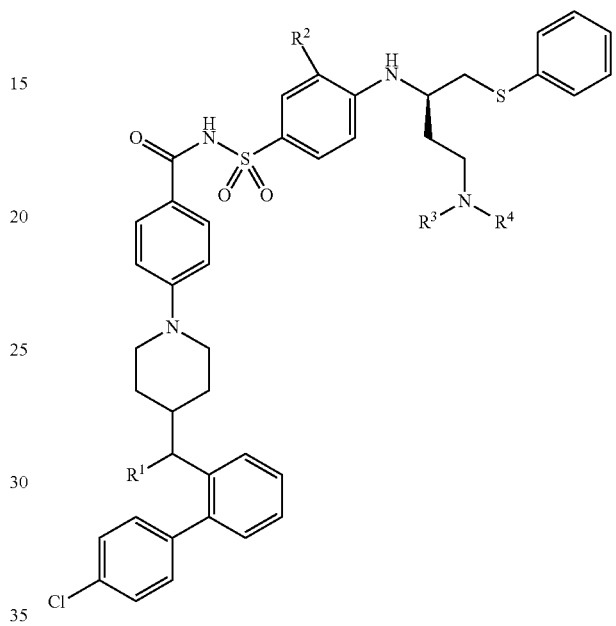

Formula (I)

and/or to pharmaceutically acceptable salts thereof, wherein:
$R^1$ is selected from —CN, —$OR^{1a}$, and —$N(R^{1a})_2$;
$R^{1a}$ in each occurrence is independently selected from H and $C_{1-4}$alkyl;
$R^2$ is selected from —$N(O)_2$ and —$S(O)_2CF_3$;
$R^3$ is selected from H and $C_{1-4}$alkyl, wherein said $C_{1-4}$alkyl is optionally substituted with one or more $R^{40}$;
$R^4$ is selected from H and $C_{1-4}$alkyl, wherein said $C_{1-4}$alkyl is optionally substituted with one or more $R^{40}$;
or $R^3$ and $R^4$ together with the nitrogen to which they are attached form a 5- or 6-membered heterocyclic ring, wherein:
  i) said 5- or 6-membered ring is not morpholino;
  ii) said 5- or 6-membered heterocyclic ring is optionally substituted on carbon with one or more $R^{40}$; and
  iii) if said 5- or 6-membered heterocyclic ring contains an —NH— moiety, that nitrogen is optionally substituted with $R^{40*}$;
$R^{40*}$ is $C_{1-4}$alkyl, wherein said $C_{1-4}$alkyl is optionally substituted with one or more $R^a$;
$R^{40}$ is selected from —$OR^{40a}$ and —$N(R^{40a})_2$;
$R^{40a}$ in each occurrence is independently selected from H and $C_{1-4}$alkyl; and
$R^a$ is selected from halo, —$OR^m$, and —$N(R^m)_2$; and
$R^m$ in each occurrence is independently selected from H and $C_{1-4}$alkyl.

In certain embodiments, the present invention provides compound of Formula (I-c):

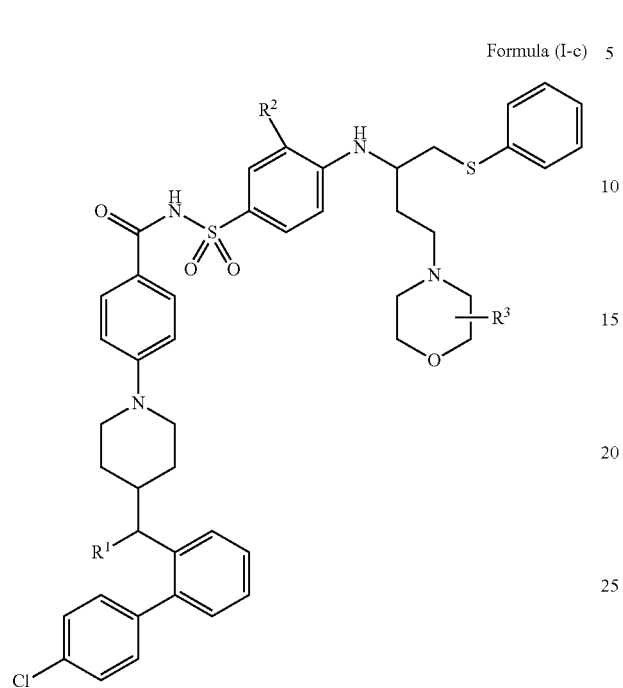

Formula (I-c)

and/or to pharmaceutically acceptable salts thereof, wherein:
$R^1$ is selected from —CN, —OR$^{1a}$, and —N(R$^{1a}$)$_2$;
$R^{1a}$ in each occurrence is independently selected from H and C$_{1-3}$alkyl;
$R^2$ is selected from —N(O)$_2$ and —S(O)$_2$CF$_3$;
$R^3$ is selected from —CH$_2$OR$^{3a}$ and —CH$_2$N(R$^{3a}$)$_2$; and
$R^{3a}$ is selected from H and C$_{1-3}$alkyl.

In certain embodiments, compounds provided by the present invention have the structure set forth in Formulae (I-d) and/or (I-e):

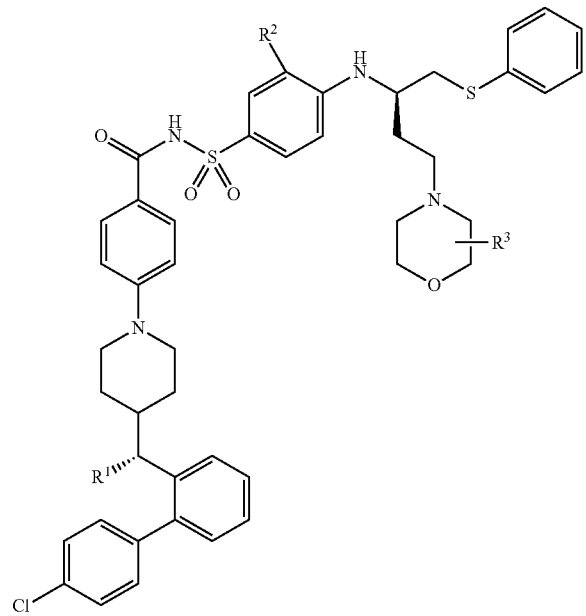

Formula (I-d)

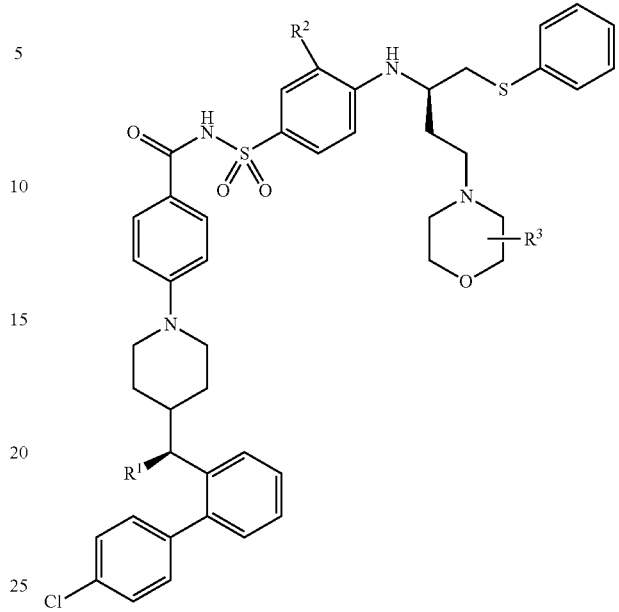

Formula (I-e)

and/or a pharmaceutically acceptable salt thereof, wherein each of $R^1$, $R^2$, and $R^3$ are as defined and described in classes and subclasses herein.

$R^1$ Embodiments

As generally defined herein, $R^1$ is selected from —CN, —OR$^{1a}$, and —N(R$^{1a}$)$_2$.

In one aspect, $R^1$ is selected from —OH and —CN.

In some embodiments, $R^1$ is —OH. In some embodiments, $R^1$ is —CN. In some embodiments $R^1$ is —NH$_2$. In some embodiments $R^1$ is —CH$_2$OP(=O)[OC(CH$_3$)$_3$]$_2$. In some embodiments $R^1$ is —CH$_2$OP(=O)(OH)[OC(CH$_3$)$_3$]. In some embodiments $R^1$ is —P(=O)(OCH$_2$CH$_3$)$_2$. In some embodiments $R^1$ is —P(=O)(OH)(OCH$_3$). In some embodiments $R^1$ is —NHC(O)CH$_2$NHCH$_3$. In some embodiments $R^1$ is —NHC(O)CH$_2$NH$_2$. In some embodiments $R^1$ is —N(CH$_3$)$_2$.

$R^2$ Embodiments

As generally defined above, $R^2$ is selected from —NO$_2$ and —SO$_2$CF$_3$.

In some embodiments, $R^2$ is —N(O)$_2$. In some embodiments, $R^2$ is —S(O)$_2$CF$_3$.

$R^3$ Embodiments

As generally defined above, $R^3$ is selected from H and C$_{1-4}$alkyl, wherein said C$_{1-4}$alkyl is optionally substituted with one or more R$^{40}$.

In one aspect, $R^3$ is selected from —CH$_2$OR$^{3a}$ and —CH$_2$N(R$^{3a}$)$_2$.

In some embodiments, $R^3$ is selected from —CH$_2$OH and —CH$_2$N(R$^{3a}$)$_2$. In some embodiments $R^3$ is methyl. In some embodiments $R^3$ is methyl optionally substituted with one or more R$^{40}$. In some embodiments $R^3$ is ethyl optionally substituted with one or more R$^{40}$. In some embodiments $R^3$ is ethyl. In some embodiments $R^3$ is —CH$_2$CH$_2$OH. In some embodiments $R^3$ is —CH$_2$CH$_2$OP(=O)(OH)$_2$.

$R^{3a}$ Embodiments

In one aspect, $R^{3a}$ in each occurrence is independently selected from H and C$_{1-3}$alkyl. In some embodiments, $R^{3a}$ is ethyl.

$R^4$ Embodiments

As generally defined above, $R^4$ is selected from H and $C_{1-4}$alkyl, wherein said $C_{1-4}$alkyl is optionally substituted with one or more $R^{40}$.

In some embodiments, $R^4$ is H. In some embodiments $R^4$ is methyl. In some embodiments $R^4$ is methyl optionally substituted with one or more $R^{40}$. In some embodiments $R^4$ is ethyl optionally substituted with one or more $R^{40}$. In some embodiments $R^4$ is ethyl. In some embodiments $R^4$ is —CH$_2$CH$_2$OH. In some embodiments $R^4$ is —CH$_2$CH$_2$OP(=O)(OH)$_2$.

$R^3$ and $R^4$ Embodiments

In one aspect, $R^3$ is $C_{1-4}$alkyl, wherein said $C_{1-4}$alkyl is optionally substituted with one or more $R^{40}$; $R^4$ is $C_{1-4}$alkyl, wherein said $C_{1-4}$alkyl is optionally substituted with one or more $R^{40}$; and $R^{40}$ is —OH.

In another aspect, $R^3$ is selected from methyl and ethyl, wherein said methyl and ethyl are optionally substituted with one or more $R^{40}$; $R^4$ is ethyl, wherein said ethyl is optionally substituted with one or more $R^{40}$; and $R^{40}$ is —OH.

In another aspect, $R^3$ is selected from methyl, ethyl, and 2-hydroxyethyl; and $R^4$ is selected from methyl and 2-hydroxyethyl.

In another aspect, $R^3$ and $R^4$ together with the nitrogen to which they are attached form a 5- or 6-membered heterocyclic ring, wherein:

i) said 5- or 6-membered ring is not morpholino;
ii) if said 5- or 6-membered heterocyclic ring contains an —NH— moiety, that nitrogen is optionally substituted with $R^{40*}$; $R^{40*}$ is $C_{1-4}$alkyl, wherein said $C_{1-4}$alkyl is optionally substituted with one or more $R^a$; and $R^a$ in each occurrence is independently selected from halo and —OH.

In another aspect, $R^3$ and $R^4$ together with the nitrogen to which they are attached form a piperazin-1-yl ring, wherein said piperazin-1-yl ring is optionally substituted on nitrogen with $R^{40*}$; $R^{40*}$ is $C_{1-4}$alkyl, wherein said $C_{1-4}$alkyl is optionally substituted with one or more $R^a$; and $R^a$ in each occurrence is independently selected from halo and —OH.

In another aspect, $R^3$ and $R^4$ together with the nitrogen to which they are attached form a piperazin-1-yl ring, wherein said piperazin-1-yl ring is optionally substituted on nitrogen with $R^{40*}$; $R^{40*}$ is selected from ethyl and propyl, wherein said ethyl and propyl are optionally substituted with one or more $R^a$; and $R^a$ in each occurrence is independently selected from fluoro and —OH.

In another aspect, $R^3$ and $R^4$ together with the nitrogen to which they are attached form a member selected from 4-(3-fluoro-2-hydroxypropyl)piperazin-1-yl and 4-(2-hydroxyethyl)piperazin-1-yl.

In some embodiments $R^3$ and $R^4$ together with the nitrogen to which they are attached form 4-(3-fluoro-2-hydroxypropyl)piperazin-1-yl. In some embodiments $R^3$ and $R^4$ together with the nitrogen to which they are attached form

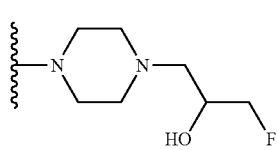 [SMILES: *N1CCN(CC(O)CF)CC1]

In some embodiments $R^3$ and $R^4$ together with the nitrogen to which they are attached form

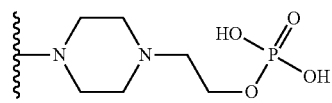

In some embodiments $R^3$ and $R^4$ together with the nitrogen to which they are attached form

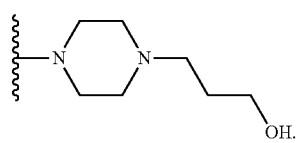

In some embodiments $R^3$ and $R^4$ together with the nitrogen to which they are attached form

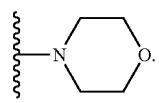

In some embodiments $R^3$ and $R^4$ together with the nitrogen to which they are attached form

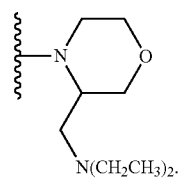

In some embodiments $R^3$ and $R^4$ together with the nitrogen to which they are attached form

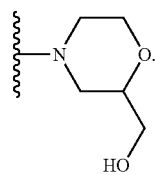

In some embodiments $R^3$ and $R^4$ together with the nitrogen to which they are attached form

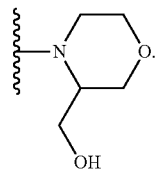 [SMILES: *N1CCOCC1CO]

In some embodiments R³ and R⁴ together with the nitrogen to which they are attached form

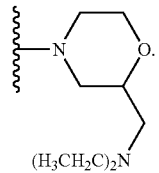

R¹, R², and R³ Embodiments

In one aspect, R¹ is selected from —OH and —CN; R² is selected from —NO₂ and —SO₂CF₃; R³ is selected from —CH₂OR$^{3a}$ and —CH₂N(R$^{3a}$)₂; and R$^{3a}$ in each occurrence is independently selected from H and $C_{1-3}$alkyl.

In another aspect, R¹ is selected from —OH and —CN; R² is selected from —NO₂ and —SO₂CF₃; R³ is selected from —CH₂OH and —CH₂N(R$^{3a}$)₂; and R$^{3a}$ is ethyl.

R¹, R², R³, and R⁴ Embodiments

In one aspect, R¹ is —OH; R² is selected from —N(O)₂ and —S(O)₂CF₃; R³ is $C_{1-4}$alkyl, wherein said $C_{1-4}$alkyl is optionally substituted with one or more R⁴⁰; R⁴ is $C_{1-4}$alkyl, wherein said $C_{1-4}$alkyl is optionally substituted with one or more R⁴⁰; or R³ and R⁴ together with the nitrogen to which they are attached form a 5- or 6-membered heterocyclic ring, wherein:
i) said 5- or 6-membered ring is not morpholino;
ii) if said 5- or 6-membered heterocyclic ring contains an —NH— moiety, that nitrogen is optionally substituted with R⁴⁰*;

R⁴⁰* is $C_{1-4}$alkyl, wherein said $C_{1-4}$alkyl is optionally substituted with one or more R$^a$; R⁴⁰ is —OH; and R$^a$ in each occurrence is independently selected from halo and —OH.

In another aspect, R¹ is —OH; R² is selected from —N(O)₂ and —S(O)₂CF₃; R³ is selected from methyl, ethyl, and 2-hydroxyethyl; R⁴ is selcted from methyl and 2-hydroxyethyl; or R³ and R⁴ together with the nitrogen to which they are attached form a piperazin-1-yl ring, wherein said piperazin-1-yl ring is optionally substituted on nitrogen with R⁴⁰*; R⁴⁰* is selected from ethyl and propyl, wherein said ethyl and propyl are optionally substituted with one or more R$^a$; and R$^a$ in each occurrence is independently selected from fluoro and —OH.

In some embodiments, R¹ is —OH; R² is —S(O)₂CF₃; R³ is methyl; and R⁴ is —CH₂CH₂OH.

In some embodiments, R¹ is —OH; R² is —S(O)₂CF₃; R³ is ethyl; and R⁴ is —CH₂CH₂OH.

In some embodiments, R¹ is —OH; R² is —S(O)₂CF₃; R³ is —CH₂CH₂OP(=O)(OH)₂; and R⁴ is ethyl.

In some embodiments, R¹ is —OH; R² is —S(O)₂CF₃; R³ is —CH₂CH₂OP(=O)(OH)₂; and R⁴ is methyl.

In one aspect there is provided a compound selected from:
4-(4-(4'-chlorobiphenyl-2-yl)(hydroxy)methyl)piperidin-1-yl)-N-(4-((R)-4-(4-(2-hydroxyethyl)piperazin-1-yl)-1-(phenylthio)butan-2-ylamino)-3-(trifluoromethylsulfonyl)phenylsulfonyl)benzamide;
4-(4-((4'-chlorobiphenyl-2-yl)(hydroxy)methyl)piperidin-1-yl)-N-(4-((R)-4-(dimethylamino)-1-(phenylthio)butan-2-ylamino)-3-nitrophenylsulfonyl)benzamide;
4-(4-(4'-chlorobiphenyl-2-yl)(hydroxy)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide;
4-(4-(4'-chlorobiphenyl-2-yl)(hydroxy)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide;
N-(4-4-(bis(2-hydroxyethyl)amino)-1-(phenylthio)butan-2-ylamino)-3-(trifluoromethylsulfonyl)phenylsulfonyl)-4-(4-((R)-(4'-chlorobiphenyl-2-yl)(hydroxy)methyl)piperidin-1-yl)benzamide; and
4-(4-(4'-chlorobiphenyl-2-yl)(hydroxy)methyl)piperidin-1-yl)-N-(4-((2R)-4-(4-(3-fluoro-2-hydroxypropyl)piperazin-1-yl)-1-(phenylthio)butan-2-ylamino)-3-(trifluoromethylsulfonyl)phenylsulfonyl)benzamide;
and/or a pharmaceutically acceptable salt thereof.

In another aspect, there is provided a compound selected from:
4-{4-[(S)-(4'-chlorobiphenyl-2-yl)(hydroxy)methyl]piperidin-1-yl}-N-[(4-{[(2R)-4-(morpholin-4-yl)-1-(phenylsulfanyl)butan-2-yl]amino}-3-[(trifluoromethyl)sulfonyl]phenyl)sulfonyl]benzamide;
4-{4-[(R)-(4'-chlorobiphenyl-2-yl)(hydroxy)methyl]piperidin-1-yl}-N-[(4-{[(2R)-4-(morpholin-4-yl)-1-(phenylsulfanyl)butan-2-yl]amino}-3-[(trifluoromethyl)sulfonyl]phenyl)sulfonyl]benzamide;
4-{4-[(S)-(4'-chlorobiphenyl-2-yl)(hydroxy)methyl]piperidin-1-yl}-N-[(4-{[(2R)-4-(morpholin-4-yl)-1-(phenylsulfanyl)butan-2-yl]amino}-3-nitrophenyl)sulfonyl]benzamide;
4-{4-[(R)-(4'-chlorobiphenyl-2-yl)(hydroxy)methyl]piperidin-1-yl}-N-[(4-{[(2R)-4-(morpholin-4-yl)-1-(phenylsulfanyl)butan-2-yl]amino}-3-nitrophenyl)sulfonyl]benzamide;
4-{4-[(4'-chlorobiphenyl-2-yl)(cyano)methyl]piperidin-1-yl}-N-[(4-{[(2R)-4-(morpholin-4-yl)-1-(phenylsulfanyl)butan-2-yl]amino}-3-[(trifluoromethyl)sulfonyl]phenyl)sulfonyl]benzamide;
4-{4-[(S)-(4'-chlorobiphenyl-2-yl)(cyano)methyl]piperidin-1-yl}-N-[(4-{[(2R)-4-(morpholin-4-yl)-1-(phenylsulfanyl)butan-2-yl]amino}-3-[(trifluoromethyl)sulfonyl]phenyl)sulfonyl]benzamide;
4-{4-[(R)-(4'-chlorobiphenyl-2-yl)(cyano)methyl]piperidin-1-yl}-N-[(4-{[(2R)-4-(morpholin-4-yl)-1-(phenylsulfanyl)butan-2-yl]amino}-3-[(trifluoromethyl)sulfonyl]phenyl)sulfonyl]benzamide;
4-{4-[(S)-(4'-chlorobiphenyl-2-yl)(hydroxy)methyl]piperidin-1-yl}-N-[(4-{[(2R)-4-[(3S)-3-{[diethylamino]methyl}morpholin-4-yl]-1-(phenylsulfanyl)butan-2-yl]amino}-3-[(trifluoromethyl)sulfonyl]phenyl)sulfonyl]benzamide;
4-{4-[(R)-(4'-chlorobiphenyl-2-yl)(hydroxy)methyl]piperidin-1-yl}-N-[(4-{[(2R)-4-[(3S)-3-{[diethylamino]methyl}morpholin-4-yl]-1-(phenylsulfanyl)butan-2-yl]amino}-3-[(trifluoromethyl)sulfonyl]phenyl)sulfonyl]benzamide;
4-{4-[(S)-(4'-chlorobiphenyl-2-yl)(hydroxy)methyl]piperidin-1-yl}-N-[(4-{[(2R)-4-[(3R)-3-{[diethylamino]methyl}morpholin-4-yl]-1-(phenylsulfanyl)butan-2-yl]amino}-3-[(trifluoromethyl)sulfonyl]phenyl)sulfonyl]benzamide;
4-{4-[(R)-(4'-chlorobiphenyl-2-yl)(hydroxy)methyl]piperidin-1-yl}-N-[(4-{[(2R)-4-[(3R)-3-{[diethylamino]methyl}morpholin-4-yl]-1-(phenylsulfanyl)butan-2-yl]amino}-3-[(trifluoromethyl)sulfonyl]phenyl)sulfonyl]benzamide;
4-{4-[(S)-(4'-chlorobiphenyl-2-yl)(hydroxy)methyl]piperidin-1-yl}-N-[(4-{[(2R)-4-(2R)-2-(hydroxymethyl)morpholin-4-yl]-1-(phenylsulfanyl)butan-2-yl]amino}-3-[(trifluoromethyl)sulfonyl]phenyl)sulfonyl]benzamide;

4-{4-[(R)-(4'-chlorobiphenyl-2-yl)(hydroxy)methyl]piperidin-1-yl}-N-[(4-{[(2R)-4[(2R)-2-(hydroxymethyl)morpholin-4-yl]-1-(phenylsulfanyl)butan-2-yl]amino}-3-[(trifluoromethyl)sulfonyl]phenyl)sulfonyl]benzamide;

4-{4-[(S)-(4'-chlorobiphenyl-2-yl)(hydroxy)methyl]piperidin-1-yl}-N-[(4-{[(2R)-4-[(2S)-2-(hydroxymethyl)morpholin-4-yl]-1-(phenylsulfanyl)butan-2-yl]amino}-3-[(trifluoromethyl)sulfonyl]phenyl)sulfonyl]benzamide;

4-{4-[(R)-(4'-chlorobiphenyl-2-yl)(hydroxy)methyl]piperidin-1-yl}-N-[(4-{[(2R)-4-[(2S)-2-(hydroxymethyl)morpholin-4-yl]-1-(phenylsulfanyl)butan-2-yl]amino}-3-[(trifluoromethyl)sulfonyl]phenyl)sulfonyl]benzamide;

4-{4-[(S)-(4'-chlorobiphenyl-2-yl)(hydroxy)methyl]piperidin-1-yl}-N-[(4-{[(2R)-4-[(3R)-3-(hydroxymethyl)morpholin-4-yl]-1-(phenylsulfanyl)butan-2-yl]amino}-3-[(trifluoromethyl)sulfonyl]phenyl)sulfonyl]benzamide;

4-{4-[(R)-(4'-chlorobiphenyl-2-yl)(hydroxy)methyl]piperidin-1-yl}-N-[(4-{[(2R)-4-[(3R)-3-(hydroxymethyl)morpholin-4-yl]-1-(phenylsulfanyl)butan-2-yl]amino}-3-[(trifluoromethyl)sulfonyl]phenyl)sulfonyl]benzamide;

4-{4-[(S)-(4'-chlorobiphenyl-2-yl)(hydroxy)methyl]piperidin-1-yl}-N-[(4-{[(2R)-4-[(3S)-3-(hydroxymethyl)morpholin-4-yl]-1-(phenylsulfanyl)butan-2-yl]amino}-3-[(trifluoromethyl)sulfonyl]phenyl)sulfonyl]benzamide;

4-{4-[(R)-(4'-chlorobiphenyl-2-yl)(hydroxy)methyl]piperidin-1-yl}-N-[(4-{[(2R)-4-[(3S)-3-(hydroxymethyl)morpholin-4-yl]-1-(phenylsulfanyl)butan-2-yl]amino}-3-[(trifluoromethyl)sulfonyl]phenyl)sulfonyl]benzamide;

4-{4-[(S)-(4'-chlorobiphenyl-2-yl)(hydroxy)methyl]piperidin-1-yl}-N-[(4-{[(2R)-4-{(2S)-2-[(diethylamino)methyl]morpholin-4-yl}-1-(phenylsulfanyl)butan-2-yl]amino}-3-[(trifluoromethyl)sulfonyl]phenyl)sulfonyl]benzamide;

4-{4-[(R)-(4'-chlorobiphenyl-2-yl)(hydroxy)methyl]piperidin-1-yl}-N-[(4-{[(2R)-4-{(2S)-2-[(diethylamino)methyl]morpholin-4-yl}-1-(phenylsulfanyl)butan-2-yl]amino}-3-[(trifluoromethyl)sulfonyl]phenyl)sulfonyl]benzamide;

4-{4-[(S)-(4'-chlorobiphenyl-2-yl)(hydroxy)methyl]piperidin-1-yl}-N-[(4-{[(2R)-4-{(2R)-2-[(diethylamino)methyl]morpholin-4-yl}-1-(phenylsulfanyl)butan-2-yl]amino}-3-[(trifluoromethyl)sulfonyl]phenyl)sulfonyl]benzamide; and 4-{4-[(R)-(4'-chlorobiphenyl-2-yl)(hydroxy)methyl]piperidin-1-yl}-N-[(4-{[(2R)-4-{(2R)-2-[(diethylamino)methyl]morpholin-4-yl}-1-(phenylsulfanyl)butan-2-yl]amino}-3-[(trifluoromethyl)sulfonyl]phenyl)sulfonyl]benzamide, and/or a pharmaceutically acceptable salt thereof.

In another aspect, there is provided a compound selected from:

4-(4-((R)-(4'-chlorobiphenyl-2-yl)(hydroxy)methyl]piperidin-1-yl)-N-(4-((R)-4-(4-(2-hydroxyethyl)piperazin-1-yl)-1-(phenylthio)butan-2-ylamino)-3-(trifluoromethylsulfonyl)phenylsulfonyl)benzamide;

4-(4-((S)-(4'-chlorobiphenyl-2-yl)(hydroxy)methyl)piperidin-1-yl)-N-(4-((S)-4-((2-hydroxyethyl)(methyl)amino)-1-(phenylthio)butan-2-ylamino)-3-(trifluoromethylsulfonyl)phenylsulfonyl)benzamide;

4-(4-((S)-(4'-chlorobiphenyl-2-yl)(hydroxy)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((S)-4-((2-hydroxyethyl)(methyl)amino)-1-(phenylthio)butan-2-ylamino)-3-(trifluoromethylsulfonyl)phenylsulfonyl)benzamide;

4-(4-((S)-(4'-chlorobiphenyl-2-yl)(hydroxy)methyl)piperidin-1-yl)-N-(4-((S)-4-(ethyl(2-hydroxyethyl)amino)-1-(phenylthio)butan-2-ylamino)-3-(trifluoromethylsulfonyl)phenylsulfonyl)benzamide;

4-(4-((S)-(4'-chlorobiphenyl-2-yl)(hydroxy)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((S)-4-(ethyl(2-hydroxyethyl)amino)-1-(phenylthio)butan-2-ylamino)-3-(trifluoromethylsulfonyl)phenylsulfonyl)benzamide;

N-(4-((R)-4-(bis(2-hydroxyethyl)amino)-1-(phenylthio)butan-2-ylamino)-3-(trifluoromethylsulfonyl)phenylsulfonyl)-4-(4-((R)-(4'-chlorobiphenyl-2-yl)(hydroxy)methyl)piperidin-1-yl)benzamide;

4-(4-((R)-(4'-chlorobiphenyl-2-yl)(hydroxy)methyl)piperidin-1-yl)-N-(4-((R)-4-(4-((R)-3-fluoro-2-hydroxypropyl)piperazin-1-yl)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-(4-((S)-3-fluoro-2-hydroxypropyl)piperazin-1-yl)-1-(phenylthio)butan-2-ylamino)-3-(trifluoromethylsulfonyl)phenylsulfonyl)benzamide;

2,2'-((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butylazanediyl)bis(ethane-2,1-diyl)bis(dihydrogen phosphate);

2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate;

2-(((S)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate;

2-(((R)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate;

2-(((S)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate;

2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate;

2-(((S)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate;

2-(((R)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate;

2-(((S)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate;

4-(4-((R)-amino(4'-chlorobiphenyl-2-yl)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide;

4-(4-((R)-amino(4'-chlorobiphenyl-2-yl)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide;

4-(4-((R)-amino(4'-chlorobiphenyl-2-yl)methyl)piperidin-1-yl)-N-(4-((R)-4-(4-(2-hydroxyethyl)piperazin-1-yl)-1-(phenylthio)butan-2-ylamino)-3-(trifluoromethylsulfonyl)phenylsulfonyl)benzamide;

4-(4-((R)-(4'-chlorobiphenyl-2-yl)(cyano)methyl)piperidin-1-yl)-N-(4-((R)-4-morpholino-1-(phenylthio)butan-2-ylamino)-3-(trifluoromethylsulfonyl)phenylsulfonyl)benzamide;

4-(4-((S)-(4'-chlorobiphenyl-2-yl)(cyano)methyl)piperidin-1-yl)-N-(4-((R)-4-morpholino-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-((R)-2-(hydroxymethyl)morpholino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-((S)-2-(hydroxymethyl)morpholino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-((R)-3-(hydroxymethyl)morpholino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-((S)-3-(hydroxymethyl)morpholino)-1-(phenylthio)butan-2-ylamino)-3-(trifluoromethylsulfonyl)phenylsulfonyl)benzamide;

(R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methyl diethyl phosphate;

(R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methyl methyl hydrogen phosphate;

4-(4-((R)-amino(4'-chlorobiphenyl-2-yl)methyl)piperidin-1-yl)-N-(4-((R)-4-morpholino-1-(phenylthio)butan-2-ylamino)-3-(trifluoromethylsulfonyl)phenylsulfonyl)benzamide;

4-(4-((R)-(4'-chlorobiphenyl-2-yl)(2-(methylamino)acetamido)methyl)piperidin-1-yl)-N-(4-((R)-4-morpholino-1-(phenylthio)butan-2-ylamino)-3-(trifluoromethylsulfonyl)phenylsulfonyl)benzamide;

4-(4-((R)-(2-aminoacetamido)(4'-chlorobiphenyl-2-yl)methyl)piperidin-1-yl)-N-(4-((R)-4-morpholino-1-(phenylthio)butan-2-ylamino)-3-(trifluoromethylsulfonyl)phenylsulfonyl)benzamide;

4-(4-((R)-(4'-chlorobiphenyl-2-yl)(dimethylamino)methyl)piperidin-1-yl)-N-(4-((R)-4-morpholino-1-(phenylthio)butan-2-ylamino)-3-(trifluoromethylsulfonyl)phenylsulfonyl)benzamide; and/or a pharmaceutically acceptable salt thereof.

Exemplary compounds of the present invention include:

4-(4-((R)-(4'-chlorobiphenyl-2-yl)(hydroxy)methyl)piperidin-1-yl)-N-(4-((R)-4-(4-(2-hydroxyethyl)piperazin-1-yl)-1-(phenylthio)butan-2-ylamino)-3-(trifluoromethylsulfonyl)phenylsulfonyl)benzamide, formic acid salt;

4-(4-((R)-(4'-chlorobiphenyl-2-yl)(hydroxy)methyl)piperidin-1-yl)-N-(4-((R)-4-(dimethylamino)-1-(phenylthio)butan-2-ylamino)-3-nitrophenylsulfonyl)benzamide;

4-(4-((R)-(4'-chlorobiphenyl-2-yl)(hydroxy)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide;

4-(4-((S)-(4'-chlorobiphenyl-2-yl)(hydroxy)methyl)piperidin-1-yl)-N-(4-((S)-4-((2-hydroxyethyl)(methyl)amino)-1-(phenylthio)butan-2-ylamino)-3-(trifluoromethylsulfonyl)phenylsulfonyl)benzamide;

4-(4-((S)-(4'-chlorobiphenyl-2-yl)(hydroxy)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((S)-4-((2-hydroxyethyl)(methyl)amino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-(2-hydroxyethyl)(methyl)amino)-1-(phenylthio)butan-2-ylamino)-3-(trifluoromethylsulfonyl)phenylsulfonyl)benzamide, formic acid salt;

4-(4-((S)-(4'-chlorobiphenyl-2-yl)(hydroxy)methyl)piperidin-1-yl)-N-(4-((S)-4-((2-hydroxyethyl)(methyl)amino)-1-(phenylthio)butan-2-ylamino)-3-(trifluoromethylsulfonyl)phenylsulfonyl)benzamide, formic acid salt;

4-(4-((S)-(4'-chlorobiphenyl-2-yl)(hydroxy)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide, formic acid salt;

4-(4-((R)-(4'-chlorobiphenyl-2-yl)(hydroxy)methyl)piperidin-1-yl)-N-(4-((S)-4-(2-hydroxyethyl)(methyl)amino)-1-(phenylthio)butan-2-ylamino)-3-(trifluoromethylsulfonyl)phenylsulfonyl)benzamide, formic acid salt;

4-(4-((R)-(4'-chlorobiphenyl-2-yl)(hydroxy)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide;

4-(4-((S)-(4'-chlorobiphenyl-2-yl)(hydroxy)methyl)piperidin-1-yl)-N-(4-((S)-4-(ethyl(2-hydroxyethyl)amino)-1-(phenylthio)butan-2-ylamino)-3-(trifluoromethylsulfonyl)phenylsulfonyl)benzamide;

4-(4-((S)-(4'-chlorobiphenyl-2-yl)(hydroxy)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((S)-4-(ethyl(2-hydroxyethyl)amino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide, formic acid salt;

4-(4-((S)-(4'-chlorobiphenyl-2-yl)(hydroxy)methyl)piperidin-1-yl)-N-(4-((S)-4-(ethyl(2-hydroxyethyl)amino)-1-(phenylthio)butan-2-ylamino)-3-(trifluoromethylsulfonyl)phenylsulfonyl)benzamide, formic acid salt;

4-(4-((S)-(4'-chlorobiphenyl-2-yl)(hydroxy)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide, formic acid salt;

4-(4-((R)-(4'-chlorobiphenyl-2-yl)(hydroxy)methyl)piperidin-1-yl)-N-(4-((S)-4-(ethyl(2-hydroxyethyl)amino)-1-(phenylthio)butan-2-ylamino)-3-(trifluoromethylsulfonyl)phenylsulfonyl)benzamide, formic acid salt;

N-(4-((R)-4-(bis(2-hydroxyethyl)amino)-1-(phenylthio)butan-2-ylamino)-3-(trifluoromethylsulfonyl)phenylsulfonyl)-4-(4-((R)-(4'-chlorobiphenyl-2-yl)(hydroxy)methyl)piperidin-1-yl)benzamide, formic acid salt;

4-(4-((R)-(4'-chlorobiphenyl-2-yl)(hydroxy)methyl)piperidin-1-yl)-N-(4-((R)-4-(4-((R)-3-fluoro-2-hydroxypropyl)piperazin-1-yl)-1-(phenylthio)butan-2-ylamino)-3-(trifluoromethylsulfonyl)phenylsulfonyl)benzamide formic acid salt;

4-(4-((R)-(4'-chlorobiphenyl-2-yl)(hydroxy)methyl)piperidin-1-yl)-N-(4-((R)-4-(4-((R)-3-fluoro-2-hydroxypropyl)piperazin-1-yl)-1-(phenylthio)butan-2-ylamino)-3-(trifluoromethylsulfonyl)phenylsulfonyl)benzamide formic;

4-(4-((R)-(4'-chlorobiphenyl-2-yl)(hydroxy)methyl)piperidin-1-yl)-N-(4-((R)-4-(4-((S)-3-fluoro-2-hydroxypropyl)piperazin-1-yl)-1-(phenylthio)butan-2-ylamino)-3-(trifluoromethylsulfonyl)phenylsulfonyl)benzamide formic acid salt, mixture of diastereomers;

4-(4-((R)-(4'-chlorobiphenyl-2-yl)(hydroxy)methyl)piperidin-1-yl)-N-(4-((R)-4-(4-((S)-3-fluoro-2-hydroxypropyl)piperazin-1-yl)-1-(phenylthio)butan-2-ylamino)-3-(trifluoromethylsulfonyl)phenylsulfonyl)benzamide;

4-(4-((R)-amino(4'-chlorobiphenyl-2-yl)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide, formic acid salt;

4-(4-((R)-amino(4'-chlorobiphenyl-2-yl)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide, formic acid salt;

4-(4-((R)-amino(4'-chlorobiphenyl-2-yl)methyl)piperidin-1-yl)-N-(4-((R)-4-(4-(2-hydroxyethyl)piperazin-1-yl)-1-(phenylthio)butan-2-ylamino)-3-(trifluoromethylsulfonyl)phenylsulfonyl)benzamide, formic acid salt;

4-(4-((S)-(4'-chlorobiphenyl-2-yl)(hydroxy)methyl)piperidin-1-yl)-N-(4-((R)-4-morpholino-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-morpholino-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-morpholino-1-(phenylthio)butan-2-ylamino)-3-nitrophenylsulfonyl)benzamide;

4-(4-((R)-(4'-chlorobiphenyl-2-yl)(cyano)methyl)piperidin-1-yl)-N-(4-((R)-4-morpholino-1-(phenylthio)butan-2-ylamino)-3-(trifluoromethylsulfonyl)phenylsulfonyl)benzamide 4-(4-((S)-(4'-chlorobiphenyl-2-yl)(cyano)methyl)piperidin-1-yl)-N-(4-((R)-4-morpholino-1-(phenylthio)butan-2-ylamino)-3-(trifluoromethylsulfonyl)phenylsulfonyl)benzamide;

4-(4-((R)-(4'-chlorobiphenyl-2-yl)(cyano)methyl)piperidin-1-yl)-N-(4-((R)-4-morpholino-1-(phenylthio)butan-2-ylamino)-3-(trifluoromethylsulfonyl)phenylsulfonyl)benzamide;

4-(4-((S)-(4'-chlorobiphenyl-2-yl)(cyano)methyl)piperidin-1-yl)-N-(4-((R)-4-morpholino-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-((S)-3-((diethylamino)methyl)morpholino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-((R)-3-((diethylamino)methyl)morpholino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-((R)-2-(hydroxymethyl)morpholino)-1-(phenylthio)butan-2-ylamino)-3-(trifluoromethylsulfonyl)phenylsulfonyl)benzamide, formic acid salt;

4-(4-((R)-(4'-chlorobiphenyl-2-yl)(hydroxy)methyl)piperidin-1-yl)-N-(4-((R)-4-((S)-2-(hydroxymethyl)morpholino)-1-(phenylthio)butan-2-ylamino)-3-(trifluoromethylsulfonyl)phenylsulfonyl)benzamide, formic acid salt;

4-(4-((R)-(4'-chlorobiphenyl-2-yl)(hydroxy)methyl)piperidin-1-yl)-N-(4-((R)-4-((R)-3-(hydroxymethyl)morpholino)-1-(phenylthio)butan-2-ylamino)-3-(trifluoromethylsulfonyl)phenylsulfonyl)benzamide, formic acid salt;

4-(4-((R)-(4'-chlorobiphenyl-2-yl)(hydroxy)methyl)piperidin-1-yl)-N-(4-((R)-4-((S)-3-(hydroxymethyl)morpholino)-1-(phenylthio)butan-2-ylamino)-3-(trifluoromethylsulfonyl)phenylsulfonyl)benzamide, hydrochloride salt;

4-(4-((R)-(4'-chlorobiphenyl-2-yl)(hydroxy)methyl)piperidin-1-yl)-N-(4-((2R)-4-(2S)-((diethylamino)methyl)morpholino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((2R)-4-(2R)-((diethylamino)methyl)morpholino)-1-(phenylthio)butan-2-ylamino)-3-(trifluoromethylsulfonyl)phenylsulfonyl)benzamide;

4-(4-((R)-amino(4'-chlorobiphenyl-2-yl)methyl)piperidin-1-yl)-N-(4-((R)-4-morpholino-1-(phenylthio)butan-2-ylamino)-3-(trifluoromethylsulfonyl)phenylsulfonyl)benzamide, formic acid salt;

4-(4-((R)-(4'-chlorobiphenyl-2-yl)(2-(methylamino)acetamido)methyl)piperidin-1-yl)-N-(4-((R)-4-morpholino-1-(phenylthio)butan-2-ylamino)-3-(trifluoromethylsulfonyl)phenylsulfonyl)benzamide, hydrochloride salt;

4-(4-((R)-(2-aminoacetamido)(4'-chlorobiphenyl-2-yl)methyl)piperidin-1-yl)-N-(4-((R)-4-morpholino-1-(phenylthio)butan-2-ylamino)-3-(trifluoromethylsulfonyl)phenylsulfonyl)benzamide hydrochloride salt; and 4-(4-((R)-(4'-chlorobiphenyl-2-yl)(dimethylamino)methyl)piperidin-1-yl)-N-(4-((R)-4-morpholino-1-(phenylthio)butan-2-ylamino)-3-(trifluoromethylsulfonyl)phenylsulfonyl)benzamide, hydrochloride salt.

Exemplary compounds of the present invention include:

2,2'-((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butylazanediyl)bis(ethane-2,1-diyl)bis(dihydrogen phosphate), hydrochloride salt;

2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate, hydrochloride salt;

2-(((S)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate, hydrochloride salt;

2-(((R)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate, hydrochloride salt;

2-(((S)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate, hydrochloride salt;

2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate;

2-(((S)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate;

2-(((R)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate;

2-(((S)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate;

2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate, hydrochloride salt;

2-(((S)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate, hydrochloride salt;

2-(((R)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate, hydrochloride salt;

2-(((S)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate, hydrochloride salt;

2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate;

2-(((S)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate;

2-(((R)-3-(4-(N-(4-(4-((S)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate;

2-(((S)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate;

2-(4-((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyppiperazin-1-yl)ethyl dihydrogen phosphate Di-tert-butyl((R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methoxy)methyl phosphate;

tert-Butyl((R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methoxy)methyl hydrogen phosphate;

(R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methyl diethyl phosphate, hydrochloride salt;

(R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methyl methyl hydrogen phosphate, hydrochloride salt;

Di-tert-butyl((R)-(4'-chlorobiphenyl-2-yl)(1-(4-(4-((R)-4-((S)-3-((diethylamino)methyl)morpholino)-1-(phenylthio)butan-2-ylamino)-3-(trifluoromethylsulfonyl)phenylsulfonylcarbamoyl)phenyl)piperidin-4-yl)methoxy)methyl phosphate; and tert-Butyl((R)-(4'-chlorobiphenyl-2-yl)(1-(4-(4-((R)-4-((S)-3-((diethylamino)methyl)morpholino)-1-(phenylthio)butan-2-ylamino)-3-(trifluoromethylsulfonyl)phenylsulfonylcarbamoyl)phenyl)piperidin-4-yl)methoxy)methyl hydrogen phosphate.

In another aspect, there is provided a compound selected from:

4-(4-((R)-(4'-chlorobiphenyl-2-yl)(hydroxy)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide;

4-(4-((R)-(4'-chlorobiphenyl-2-yl)(hydroxy)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide;

2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate; and 2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate.

and/or a pharmaceutically acceptable salt thereof.

Specific exemplary compounds described herein are set forth in the EXAMPLES below. Those skilled in the art will recognize that the compounds described herein, including those set forth in EXAMPLES, can occur in the free, non-salt, form or can occur as salts.

It is understood that any embodiment described herein can be combined with any other suitable embodiment described herein to provide additional embodiments. For example, various $R^1$ substituent embodiments can be combined with various $R^2$ and $R^3$ substituent embodiments; various $R^2$ substitutent embodiments can be combined with various $R^1$ and $R^3$ substituent embodiments; and various $R^3$ substitutent embodiments can be combined with various $R^1$ and $R^2$ substituent embodiments. As would be appreciated by one skilled in the art, any combination of substituents, or group of substituents, is considered to be within the scope of the present invention.

Compounds of Formulae (I), (I-a), (I-b), (I-c), (I-d) and/or (I-e) may form stable pharmaceutically acceptable acid or base salts or zwitterions, and in such cases administration of a compound as a salt or zwitterion may be appropriate. Salts or bases of compounds of Formulae (I), (I-a), (I-b), (I-c), (I-d) and/or (I-e) can be prepared during isolation or following purification of compounds. Compounds of Formulae (I), (I-a), (I-b), (I-c), (I-d) and/or (I-e) have at least one protonatable nitrogen atom and are consequently capable of forming acid or base salts, for example about 1 to about 3, about 1.1 to about 3, about 1.2 to about 3, about 1.3 to about 3, about 1.4 to about 3, about 1.5 to about 3, about 1.6 to about 3, about 1.7 to about 3, about 1.8 to about 3, about 1.9 to about 3, about 2.0 to about 3, about 2.1 to about 3, about 2.2 to about 3, about 2.3 to about 3, about 2.4 to about 3, about 2.5 to about 3, about 2.6 to about 3, about 2.7 to about 3, about 2.8 to about 3, or about 2.9 to about 3, equivalents of acid or base per equivalent of compound.

Salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Compound(s) of Formulae (I), (I-a), (I-b), (I-c), (I-d) and/or (I-e) are useful for their ability to inhibit Bcl-2 and Bcl-$X_L$ activity. Compounds are also useful for the treatment of all cancer types such as neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin's lymphoma, non-Hodgkin's lymphoma, Diffuse Large B Cell Lymphoma (DLBCL), Follicular Lymphoma (FL), Mantle Cell Lymphoma (MCL), Mantle Zone Lymphoma (MZL), Hairy Cell Leukemia (HCL), Peripheral T-cell Lymphoma (PTCL), Burkitt lymphoma, acute lymphatic leukemia (ALL), chronic lymphocytic leukemia (CLL/SLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

In some embodiments, compound(s) of Formulae (I), (I-a), (I-b), (I-c), (I-d) and/or (I-e) are useful for the treatment of non-Hodgkin's lymphoma. In some embodiments, compound(s) of Formulae (I), (I-a), (I-b), (I-c), (I-d) and/or (I-e) are useful for the treatment of CLL. In some embodiments, compound(s) of Formulae (I), (I-a), (I-b), (I-c), (I-d) and/or (I-e) are useful for the treatment of non-small cell lung cancer (NSCLC). In some embodiments, compound(s) of Formulae (I), (I-a), (I-b), (I-c), (I-d) and/or (I-e) are useful for the treatment of diffuse large B-cell lymphoma (DLBCL). In some embodiments, compound(s) of Formulae (I), (I-a), (I-b), (I-c), (I-d) and/or (I-e) are useful for the treatment of prostate cancer.

Compound(s) of Formulae (I), (I-a), (I-b), (I-c), (I-d) and/or (I-e) should also be useful as standards and reagents in determining the ability of a potential pharmaceutical to inhibit BH-3 containing proteins, particularly the BCL2 family. These would be provided in commercial kits comprising a compound of this invention.

Compound(s) of Formulae (I), (I-a), (I-b), (I-c), (I-d) and/or (I-e) have been shown to inhibit Bcl-2 and Bcl-$X_L$ activities as demonstrated by an assay based on the assay description below. Although pharmacological properties of compound(s) of Formulae (I), (I-a), (I-b), (I-c), (I-d) and/or (I-e) may vary with structural change, typical compounds of Formulae (I), (I-a), (I-b), (I-c), (I-d) and/or (I-e) possess Bcl-2 and Bcl-$X_L$ inhibitory activities at $IC_{50}$ concentrations (concentrations to achieve 50% inhibition) or doses at a level below 10 µM.

The following in vitro binding and cellular assays may be used to determine the activity and specificity of compounds of the present invention to bind to Bcl-2 and inhibit Bcl-2 function in a cell.

A. Bcl-2 Binding Assay(s)

Bcl-xL and Bcl-2 FP binding affinity of compound(s) of Formulae (I), (I-a), (I-b), (I-c), (I-d) and/or (I-e) may be determined using a variety of known methods. One such assay is a sensitive and quantitative in vitro binding assay using fluorescence polarization ("FP") described by Wang, J.-L.; Zhang, Z-J.; Choksi, S.; Sjam. S.; Lu, Z.; Croce, C. M.; Alnemri, E. S.; Komgold, R.; Huang, Z. Cell permeable Bcl-2 binding peptides: a chemical approach to apoptosis induction in tumor cells. Cancer Res. 2000, 60, 1498-1502).

Additionally, the binding affinity of compound(s) of Formulae (I), (I-a), (I-b), (I-c), (I-d) and/or (I-e) to Bcl-2 protein in vitro was determined by a competitive binding assay based on fluorescence polarization. For example, fluorescence polarization ("FP") assays may be developed using a c-terminal 6×HIS tagged Bcl-2 (aa 1-204) and a C-terminal 6×HIS tagged Bcl-$X_L$ (aa 1-209). The tracer may be a synthetic peptide BH-3 peptide Bim conjugated to Fluorescein isothiocyanate (FITC—DLRPEIRIAQELRRIGDEFNETYTRR). Dilutions of either Bcl-2 (1.3 nM) or Bcl-$X_L$ (0.8 nM) may be added to serial dilutions of antagonist and incubated for one hour prior to the addition of 2 nM of fluorescent peptide tracer (Anaspec, Fremont, Calif.) in the assay buffer. Final assay buffer conditions may be 20 mM HEPES, pH 7.5, 1 mM DTT, 0.005% Tween-20 and 50 mM NaCl. Samples may be read after 20-minute incubation. Fluorescence polarization values may be plotted as a function of the antagonist concentration.

When tested in an FP assay based on the FP assay described above, the inhibitory activity of the following examples were measured at the $IC_{50}$s (µM) shown in Table 1.

TABLE 1

| Example | Bcl-$X_L$ FP assay $IC_{50}$ (µM) | Bcl-2 FP assay $IC_{50}$ (µM) |
| --- | --- | --- |
| 1 | 0.001 | <0.001 |
| 2 | 0.001 | 0.0003 |
| 3 | 0.001 | <0.0003 |
| 4 | 0.0008 | 0.0005 |
| 5 | 0.001 | 0.0008 |
| 6 | 0.002 | 0.001 |
| 7 | 0.001 | 0.002 |
| 8 | 0.001 | 0.0009 |
| 9 | 0.001 | 0.0009 |
| 10 | 0.001 | 0.0007 |
| 11 | 0.003 | 0.004 |
| 12 | 0.003 | 0.003 |
| 13 | 0.015 | 0.016 |
| 14 | 0.078 | 0.253 |
| 15 | 0.001 | 0.003 |
| 16 | 0.001 | 0.0008 |
| 17 | 0.001 | 0.002 |
| 18 | 0.002 | 0.007 |
| 19 | 0.008 | 1.195 |
| 20 | 0.001 | 0.0003 |
| 21 | 0.0005 | 0.0003 |
| 22 | 0.003 | 0.0006 |
| 23 | 0.001 | 0.001 |
| 24 | 0.002 | 0.0004 |
| 25 | 0.002 | 0.0004 |
| 26 | 0.0005 | 0.0004 |
| 27 | NT | NT |
| 28 | 0.002 | 0.004 |
| 29 | 0.012 | 0.03 |

TABLE 1-continued

| Example | Bcl-X$_L$ FP assay IC$_{50}$ (µM) | Bcl-2 FP assay IC$_{50}$ (µM) |
|---|---|---|
| 30 | 0.001 | 0.001 |
| 31 | NT | NT |
| 32 | NT | NT |
| 33 | 0.033 | 0.03 |
| 34 | 0.019 | 0.027 |
| 35 | 0.022 | 0.038 |
| 36 | 0.018 | 0.024 |

B. Cell Based Assay(s)

Certain compounds of Formulae (I), (I-a), (I-b), (I-c), (I-d) and/or (I-e) may be tested in cell-based assays using Bcl-2 and Bcl-X$_L$ dependent cell lines to determine whether apoptosis is induced when the cell lines are treated with such compounds. Exemplary cell lines include FDCP-1 cell line transfected with and overexpressing Bcl-2, and FDCP-1 cell line transfected with and overexpressing Bcl-X$_L$.

In this specification the prefix C$_{x-y}$ as used in terms such as C$_{x-y}$alkyl and the like (where x and y are integers) indicates the numerical range of carbon atoms that are present in the group; for example, C$_{1-4}$alkyl includes C$_1$alkyl (methyl), C$_2$alkyl (ethyl), C$_3$alkyl (propyl and isopropyl) and C$_4$alkyl (butyl, 1-methylpropyl, 2-methylpropyl, and t-butyl).

Compounds of formulae (I), (I-a), (I-b), (I-c), (I-d) and/or (I-e) have chiral centers, and thus exist as stereoisomers. It is to be understood that the invention encompasses all such stereoisomers, including enantiomers and diastereoisomers, as well as to mixtures of these enantiomers, and/or mixtures of these diastereoisomers. Insofar as compounds of formulae (I), (I-a), (I-b), (I-c), (I-d) and/or (I-e), may exist in optically active or racemic forms, the invention includes in its definition any such optically active or racemic form which possesses the above-mentioned activity. The present invention encompasses all such stereoisomers having activity as herein defined. Throughout this application, the name of the product of this invention, where the absolute configuration of an asymmetric center is not indicated, is intended to embrace the individual stereoisomers as well as mixtures of stereoisomers.

The synthesis of optically active forms may be carried out by standard techniques of organic chemistry well known in the art, for example by synthesis from optically active starting materials or by resolution of a racemic form. Racemates may be separated into individual enantiomers using known procedures (see, for example, Advanced Organic Chemistry: 3rd Edition: author J March, p 104-107). A suitable procedure involves formation of diastereomeric derivatives by reaction of the racemic material with a chiral auxiliary, followed by separation, for example by chromatography, of the diastereomers and then cleavage of the auxiliary species. Similarly, the above-mentioned activity may be evaluated using the standard laboratory techniques referred to hereinafter.

Thus, throughout the specification, where reference is made to compounds of Formulae (I), (I-a), (I-b), (I-c), (I-d) and/or (I-e), it is to be understood that the term compound includes stereoisomers, mixtures of stereoisomers, and polymorphs that inhibit bcl-2 activity in a human or animal.

Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent.

When a specific stereoisomer is provided (whether provided by separation, by chiral synthesis, or by other methods) it is favorably provided substantially isolated from other stereoisomers of the same compound. In one aspect, a mixture containing a particular stereoisomer of a compound of Formulae (I), (I-a), (I-b), (I-c), (I-d) and/or (I-e) may contain less than 30%, particularly less than 20%, and more particularly less than 10% by weight of other stereoisomer(s) of the same compound. In another aspect, a mixture containing a particular stereoisomer of a compound of Formulae (I), (I-a), (I-b), (I-c), (I-d) and/or (I-e) may contain less than 6%, particularly less than 3%, and more particularly less than 2% by weight of other stereoisomer(s) of the compound. In another aspect, a mixture containing a particular stereoisomer of a compound of Formulae (I), (I-a), (I-b), (I-c), (I-d) and/or (I-e) may contain less than 1%, particularly less than 0.5%, and more particularly less than 0.3%, and still more particularly less 0.1% by weight of other stereoisomer(s) of the compound.

It is to be understood that, insofar as certain compounds of Formulae (I), (I-a), (I-b), (I-c), (I-d) and/or (I-e) defined above may exist in tautomeric forms, the invention includes in its definition any such tautomeric form which possesses the above-mentioned activity/activities. Thus, the invention relates to all tautomeric forms of compounds of Formulae (I), (I-a), (I-b), (I-c), (I-d) and/or (I-e) which inhibit Bcl-2 and/or Bcl-X$_L$ activities in a human or animal.

It is also to be understood that certain compounds of Formulae (I), (I-a), (I-b), (I-c), (I-d) and/or (I-e) can exist in solvated as well as unsolvated forms such as, for example, hydrated forms. It is to be understood that the invention encompasses all such solvated forms.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In some embodiments. By way of example, the R$^1$ group of formulae (I), (I-a), (I-b), (I-c), (I-d) and/or (I-e) may comprise one or more deuterium atoms. Mixtures of isomeric forms may be separated and/or purified by techniques as would be known to one skilled in this art, including but not limited to column chromatography.

Certain phosphate-bearing compounds of the present invention may be transformed by metabolic means (such as by hydrolysis, for example, with alkaline phosphatases) to a corresponding parent compound. Such phosphate-bearing compounds are designed to enhance pharmaceutically and/or pharmacokinetically based properties associated with the parent drug molecule. Exemplary advantages of a phosphate-bearing compound lie in its physical properties, such as enhanced water solubility for various types of administration (e.g., intravenous, parenteral, subcutaneous, intramuscular, etc.) at physiological pH compared to the parent drug, or it enhances absorption from the digestive tract, or it may enhance drug stability for long-term storage.

V. Methods

In one aspect, there is provided compound(s) of Formulae (I), (I-a), (I-b), (I-c), (I-d) and/or (I-e), or a pharmaceutically acceptable salt thereof, for use as a medicament.

In another aspect, there is provided use of compound(s) of Formulae (I), (I-a), (I-b), (I-c), (I-d) and/or (I-e), or a pharmaceutically acceptable salt thereof, in the manufacture of a medicament for the treatment or prophylaxis of at least one of: carcinoma, hematopoietic tumours of lymphoid lineage, hematopoietic tumors of myeloid lineage, tumors of mesenchymal origin, melanoma, seminoma, tetratocarcinoma, neuroblastoma, and glioma.

In another aspect, there is provided use of compound(s) of Formulae (I), (I-a), (I-b), (I-c), (I-d) and/or (I-e), or a pharmaceutically acceptable salt thereof, in the manufacture of a medicament for the treatment of at least one of: bladder cancer, breast cancer, colon cancer, ovarian cancer, AML, diffuse large B-cell lymphoma (DLBCL), CLL; small cell lung cancer (SCLC), non-small cell lung cancer (NSCLC), including the non-squamous and squamous subtypes, pancreatic cancer, prostate cancer, non-Hodgkin's lymphoma, Follicular Lymphoma (FL), Mantle Cell Lymphoma (MCL), Mantle Zone Lymphoma (MZL), Hairy Cell Leukemia (HCL), and Peripheral T-cell Lymphoma (PTCL).

In some embodiments, compound(s) of Formulae (I), (I-a), (I-b), (I-c), (I-d) and/or (I-e) are useful in the manufacture of a medicament for the treatment of at least one of: non-Hodgkin's lymphoma, CLL, non-small cell lung cancer (NSCLC), diffuse large B-cell lymphoma (DLBCL), and prostate cancer.

In another aspect, there is provided use of compound(s) of Formulae (I), (I-a), (I-b), (I-c), (I-d) and/or (I-e), or a pharmaceutically acceptable salt thereof, in the manufacture of a medicament for the treatment of cancer.

In another aspect, there is provided use of compound(s) of Formulae (I), (I-a), (I-b), (I-c), (I-d) and/or (I-e), or a pharmaceutically acceptable salt thereof, in the manufacture of a medicament for the production of an anti-proliferative and/or pro-apoptotic effect in a warm-blooded animal such as man.

In another aspect, there is provided use of compound(s) of Formulae (I), (I-a), (I-b), (I-c), (I-d) and/or (I-e), or a pharmaceutically acceptable salt thereof, in the manufacture of a medicament for the production of a Bcl-2 and/or Bcl-$X_L$ inhibitory effect in a warm blooded animal such as man.

In another aspect, there is provided a method for the treatment or prophylaxis of at least one of: carcinoma, hematopoietic tumours of lymphoid lineage, hematopoietic tumors of myeloid lineage, tumors of mesenchymal origin, melanoma, seminoma, tetratocarcinoma, neuroblastoma and glioma in a warm-blooded animal such as man, said method comprising administering to said animal an effective amount of compound(s) of Formulae (I), (I-a), (I-b), (I-c), (I-d) and/or (I-e), or a pharmaceutically acceptable salt thereof.

In another aspect, there is provided a method for treating at least one of: bladder cancer, breast cancer, colon cancer, ovarian cancer, AML, diffuse large B-cell lymphoma (DLBCL), CLL; small cell lung cancer (SCLC), non-small cell lung cancer (NSCLC), including the non-squamous and squamous subtypes, pancreatic cancer, prostate cancer, non-Hodgkin's lymphoma, Follicular Lymphoma (FL), Mantle Cell Lymphoma (MCL), Mantle Zone Lymphoma (MZL), Hairy Cell Leukemia (HCL), and Peripheral T-cell Lymphoma (PTCL) in a warm-blooded animal such as man, said method comprising administering to said animal an effective amount of compound(s) of Formulae (I), (I-a), (I-b), (I-c), (I-d) and/or (I-e), or a pharmaceutically acceptable salt thereof In some embodiments, compound(s) of Formulae (I), (I-a), (I-b), (I-c), (I-d) and/or (I-e) are useful for treating at least one of: non-Hodgkin's lymphoma, CLL, non-small cell lung cancer (NSCLC), diffuse large B-cell lymphoma (DLBCL), and prostate cancer.

In another aspect, there is provided a method for producing an anti-proliferative and/or pro-apoptotic effect in a warm-blooded animal such as man, said method comprising administering to said animal an effective amount of compound(s) of Formulae (I), (I-a), (I-b), (I-c), (I-d) and/or (I-e), or a pharmaceutically acceptable salt thereof.

In some embodiments, an anti-proliferative and/or pro-apoptotic effect is for treating bladder cancer, breast cancer, colon cancer, ovarian cancer, AML, diffuse large B-cell lymphoma (DLBCL), CLL; small cell lung cancer (SCLC), non-small cell lung cancer (NSCLC), including the non-squamous and squamous subtypes, pancreatic cancer, prostate cancer, non-Hodgkin's lymphoma, Follicular Lymphoma (FL), Mantle Cell Lymphoma (MCL), Mantle Zone Lymphoma (MZL), Hairy Cell Leukemia (HCL), and Peripheral T-cell Lymphoma (PTCL).

In some embodiments, compound(s) of Formulae (I), (I-a), (I-b), (I-c), (I-d) and/or (I-e) have an anti-proliferative and/or pro-apoptotic effect that is useful for treating at least one of: non-Hodgkin's lymphoma, CLL, non-small cell lung cancer (NSCLC), diffuse large B-cell lymphoma (DLBCL), and prostate cancer.

In another aspect, there is provided a method for producing a Bcl-2 and/or Bcl-$X_L$ inhibitory effect in a warm-blooded animal such as man, said method comprising administering to said animal an effective amount of compound(s) of Formulae (I), (I-a), (I-b), (I-c), (I-d) and/or (I-e), or a pharmaceutically acceptable salt thereof In another aspect, there is provided a method for treating cancer in a warm-blooded animal such as man, said method comprising administering to said animal an effective amount of compound(s) of Formulae (I), (I-a), (I-b), (I-c), (I-d) and/or (I-e), or a pharmaceutically acceptable salt thereof.

In another aspect, there is provided compound(s) of Formulae (I), (I-a), (I-b), (I-c), (I-d) and/or (I-e), or a pharmaceutically acceptable salt thereof, for use in the treatment of at least one of: carcinoma, hematopoietic tumours of lymphoid lineage, hematopoietic tumors of myeloid lineage, tumors of mesenchymal origin, melanoma, seminoma, tetratocarcinoma, neuroblastoma, and glioma.

In another aspect, there is provided compound(s) of Formulae (I), (I-a), (I-b), (I-c), (I-d) and/or (I-e), or a pharmaceutically acceptable salt thereof, for use in the treatment of at least one of: bladder cancer, breast cancer, colon cancer, ovarian cancer, AML, diffuse large B-cell lymphoma (DLBCL), CLL; small cell lung cancer (SCLC), non-small cell lung cancer (NSCLC), including the non-squamous and squamous subtypes, pancreatic cancer, prostate cancer, non-Hodgkin's lymphoma, Follicular Lymphoma (FL), Mantle Cell Lymphoma (MCL), Mantle Zone Lymphoma (MZL), Hairy Cell Leukemia (HCL), and Peripheral T-cell Lymphoma (PTCL).

In some embodiments, compound(s) of Formulae (I), (I-a), (I-b), (I-c), (I-d) and/or (I-e) are useful for treating at least one of: non-Hodgkin's lymphoma, CLL, non-small cell lung cancer (NSCLC), diffuse large B-cell lymphoma (DLBCL), and prostate cancer.

In still another aspect, there is provided compound(s) of Formulae (I), (I-a), (I-b), (I-c), (I-d) and/or (I-e), or a pharmaceutically acceptable salt thereof, for use in the production of an anti-proliferative and/or pro-apoptotic effect, in a warm-blooded animal such as man.

In some embodiments, an anti-proliferative and/or pro-apoptotic effect is for treating bladder cancer, breast cancer, colon cancer, ovarian cancer, AML, diffuse large B-cell lymphoma (DLBCL), CLL; small cell lung cancer (SCLC), non-small cell lung cancer (NSCLC), including the non-squamous and squamous subtypes, pancreatic cancer, prostate cancer, non-Hodgkin's lymphoma, Follicular Lymphoma (FL), Mantle Cell Lymphoma (MCL), Mantle Zone Lymphoma (MZL), Hairy Cell Leukemia (HCL), and Peripheral T-cell Lymphoma (PTCL).

In some embodiments, compound(s) of Formulae (I), (I-a), (I-b), (I-c), (I-d) and/or (I-e) are for use in the production of an anti-proliferative and/or pro-apoptotic effect to treat at least one of: non-Hodgkin's lymphoma, CLL, non-small cell lung cancer (NSCLC), diffuse large B-cell lymphoma (DLBCL), and prostate cancer.

In another aspect, there is provided compound(s) of Formulae (I), (I-a), (I-b), (I-c), (I-d) and/or (I-e), or a pharmaceutically acceptable salt thereof, for use in the production of a Bcl-2 and/or Bcl-$X_L$ inhibitory effect in a warm-blooded animal such as man.

In another aspect, there is provided compound(s) of Formulae (I), (I-a), (I-b), (I-c), (I-d) and/or (I-e), or a pharmaceutically acceptable salt thereof, for use in the treatment of cancer in a warm-blooded animal such as man.

VI. Compositions and Pharmaceutical Compositions

In another aspect, there is provided a pharmaceutical composition comprising a compound of Formulae (I), (I-a), (I-b), (I-c), (I-d) and/or (I-e), or a pharmaceutically acceptable salt thereof, and at least one pharmaceutically acceptable carrier, diluent, or excipient.

Compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). In some embodiments, compounds and/or compositions of the present invention are administered by intravenous (I.V.) administration.

Compositions of the present invention may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinylpyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

Pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

As stated above the size of the dose required for the therapeutic or prophylactic treatment of a particular disease state will necessarily be varied depending on the host treated, the route of administration and the severity of the illness being treated. A daily dose in the range of 0.1-50 mg/kg may be employed. Accordingly, the optimum dosage may be determined by the practitioner who is treating any particular patient.

VII. Combinations

The anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cis platin, oxaliplatin, carboplatin, cyclophosphamide, nitrogen mustard, melphalan, chlorambucil, bendamustine, busulphan, temozolamide and nitrosoureas); antimetabolites (for example gemcitabine, cpecitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine; and taxoids like taxol and taxotere; and polo kinase or kinesin motor protein inhibitors); and topoisomerase inhibitors (for example epipodophyllotoxins like etoposide and teniposide, amsacrine, topotecan, camptothecin, Pixantrone, and irinotecan); inhibitors of DNA repair mechanisms such as, but not limited to, CHK kinase, DNA-dependent protein kinase inhibitors and inhibitors of poly (ADP-ribose) polymerase (PARP inhibitors), ATM or ATR; and Hsp90 inhibitors such as tanespamycin and retaspimycin. Compounds that inhibit progression through the cell cycle such as antimitotic agents (for example, and not limited to, vinca alkaloids like vincristine, vinblastine, vindesine and vinorelbine; epothilones such as ixabepilone; and taxoids like taxol and taxotere; polo-like kinase inhibitors; and inhibitors of kinesin motor proteins such as Eg5 protein inhibitors); aurora kinase inhibitors (for example, but not limited to, AZD1152, PH739358, VX-680, MLN8054, R763, MP235, MP529, VX-528 and AX39459) and cyclin dependent kinase inhibitors such as CDK2 and/or CDK4 inhibitors (for example, flavopiridol/Alvocidib, roscovitine, seliciclib); inhibitors of centromeric protein function such as CENP-E inhibitors.

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane); inhibitors of 5*-reductase such as finasteride; and inhibitors of CYP17A1 such as abiraterone acetate;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase, inhibitors of FAK or focal-adhesion kinase, inhibitors of or antibodies to MET receptor kinase or the MET ligand hepatocyte growth factor;

(iv) inhibitors of growth factor function: for example such inhibitors include growth factor antibodies and growth factor receptor antibodies (for example the anti erbB2 antibody trastuzumab [Herceptin™], the anti-EGFR antibody panitumumab, the anti erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI-1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of spleen tyrosine kinase (SYK) such as fostamatinib disodium (R788/R406), PRT062607; inhibitors of serine/threonine kinases (for example Ras/Raf signaling inhibitors such as farnesyl transferase inhibitors, for example sorafenib (BAY 43-9006), tipifarnib (R75777) and lonafarnib (SCH66336)), inhibitors of cell signaling through MEK and/or AKT kinases, c-kit inhibitors, abl kinase inhibitors, PI3 kinase inhibitors, Flt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors; and inhibitors of JAK/STAT signaling such as Pim kinase inhibitors and Jak 1 and 2 kinase inhibitors (for example, but not limited to, AZD1480, Ruxolitinib);

(v) antiangiogenic agents such as those which inhibit the effects of vascular endothelial growth factor, [for example the anti vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin alphavbeta3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213; and inhibitors of angiopoietins or their receptors (Tie-a and Tie-2);

(vii) an endothelin receptor antagonist, for example zibotentan (ZD4054) or atrasentan;

(viii) antisense therapies, for example those which are directed to the targets listed above, such as ISIS 2503, an anti-ras antisense; or oblimerson sodium, an anti-Bcl-2 antisense;

(ix) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy;

(x) immunotherapy approaches, including for example ex vivo and in vivo approaches to increase the immunogenicity of patient tumor cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumor cell lines, approaches using anti idiotypic antibodies, approaches for T-cell enhancement including CTLA4 antibodies, and antibodies directed toward CD137, PD-1 or B7-H1, toll-receptor agonists; agonistic antibodies to CD40 such as SGN-40 (Dacetuzumab) or to the Tweak receptor such as PDL-192; agonistic antibodies to FAS; approaches using antibodies to tumor associated antigens, and antibodies that deplete target cell types (e.g. unconjugated anti-CD20 antibodies such as Rituximab, ofatumumab, Obinutuzumab, anti-CD19 antibodies such as MEDI-551, anti-CD52 antibodies such as Alemtuzumab, anti-CD37 antibodies such as TRU-016, anti-CD22 antibodies such as Inotuzumab, radiolabeled anti-CD20 antibodies Bexxar and Zevalin, and anti-CD54 antibody Campath; immunotoxins such as moxetumumab pasudotox), approaches using anti-idiotypic antibodies, approaches that enhance Natural Killer cell function, and approaches that utilize antibody-toxin conjugates (e.g. anti-CD33 antibody Mylotarg). Immune modifiers such as Revlimid (Lenalidomide);

(xi) pro-apoptotic approaches, including antibodies to death receptor 4 or death receptor 5 or antibodies binding to both death receptor 4 and death receptor 5; SMAC mimetics or compounds that inhibit the protein-protein interactions of the inhibitor of apoptosis proteins such as cIAP-1, cIAP-2 and XIAP; antisense or small interfering RNA molecules to cIAP-1, cIAP-2, XIAP or surviving;

(xii) cytokine treatment, including tumor necrosis factor alpha, and recombinant Trail protein or small molecule or protein mimetics of the Trail protein; FAS or Tweak ligands or mimetics of these ligands;

(xiii) efficacy enhancers, such as leucovorin;

(xiv) radiation; Such radiotherapy may include one or more of the following categories or radiation:

(a) external radiation therapy using electromagnetic radiation, and intraoperative radiation therapy using electromagnetic radiation;

(b) internal radiation therapy or brachytherapy; including interstitial radiation therapy or intraluminal radiation therapy; and/or (c) systemic radiation therapy, including but not limited to iodine 131 and strontium 89

(xv) inhibitors of antigen receptor signaling, including spleen tyrosine kinase (Syk) inhibitors such as fostamatinib (R788/R406), PRT062607, bruton's tyrosine kinase (Btk) inhibitors such as PCI-32765, AVL-292, Protein kinase C inhibitors such as sortrastaurin, IKK/NFkB inhibitors, PI3-kinase inhibitors such as CAL-101 (GS 1101), Enzastaurin, AZD8186, PI3-kinase inhibitors such as CAL-101 (GS 1101), Enzastaurin, AZD8186, BCL6 inhibitors; and (xvi) regulators of hematopoietic cell trafficking/homing including agents that target CXCR4 such as Plerixafor (rINN and USAN, also known as MOZOBIL, JM 3100 and AMD3100), BKT140, Syk inhibitors such as fostamatinib, agents that target VLA-4 and agents that target CD44; and (xvii) inhibitors of proteasome mediated protein degradation including but not limited to proteasome inhibitors such as Velcade™ (bortezomib), carfilzomib, inhibitors of ubiquitin ligases, and inhibitors of ubiquitin proteases, inhibitors of protein Neddylation, inhibitors of protein sumoylation.

Such conjoint treatment may be achieved by way of the simultaneous, sequential or separate dosing of the individual components of the treatment. Such combination products employ compounds of this invention, or pharmaceutically acceptable salts thereof, within the dosage range described hereinbefore and the other pharmaceutically-active agent within its approved dosage range.

In addition to its use in therapeutic medicine, compounds of Formulae (I), (I-a), (I-b), (I-c), (I-d) and/or (I-e) and pharmaceutically acceptable salts thereof are also useful as pharmacological tools in the development and standardization of in vitro and in vivo test systems for the evaluation of the effects of inhibitors of Bcl-2 and/or Bcl-$X_L$ in laboratory animals such as cats, dogs, rabbits, monkeys, rats and mice, as part of the search for new therapeutic agents.

In any of the above-mentioned pharmaceutical composition, process, method, use, medicament, and manufacturing features of the instant invention, any of the alternate embodiments of compounds of the present invention described herein also apply.

EXAMPLES

The invention will now be further described with reference to the following illustrative examples in which, unless stated otherwise:

(i) temperatures are given in degrees Celsius (° C.); operations are carried out at room temperature or ambient temperature, that is, in a range of 18-25° C.;
(ii) organic solutions were dried over anhydrous magnesium sulfate unless otherwise stated; evaporation of organic solvent was carried out using a rotary evaporator under reduced pressure (4.5-30 mmHg) with a bath temperature of up to 60° C.;
(iii) column chromatography means flash chromatography on silica gel; thin layer chromatography (TLC) was carried out on silica gel plates;
(iv) in general, the course of reactions was followed by TLC or liquid chromatography/mass spectroscopy (LC/MS) and reaction times are given for illustration only;
(v) final products have satisfactory proton nuclear magnetic resonance (NMR) spectra and/or mass spectra data;
(vi) yields are given for illustration only and are not necessarily those which can be obtained by diligent process development; preparations were repeated if more material was required;
(vii) when given, NMR data is in the form of delta values for major diagnostic protons, given in part per million (ppm) relative to tetramethylsilane (TMS) as an internal standard;
(viii) chemical symbols have their usual meanings;
(ix) in the event that the nomenclature assigned to a given compound does not correspond to the compound structure depicted herein, the structure will control;
(x) solvent ratio was given in volume:volume (v/v) terms;
(xi) "ISCO" refers to normal phase flash column chromatography using pre-packed silica gel cartridges (12 g, 40 g etc.), used according to the manufacturer's instructions, and obtained from ISCO, Inc, 4700 Superior Street Lincoln, Nebr., USA;
(xii) A "Gilson column" refers to a YMC-AQC18 reverse phase HPLC Column with dimension 20 mm/100 and 50 mm/250 in $H_2O$/MeCN with 0.1% TFA as mobile phase unless otherwise stated and used according to the manufacturer's instructions, obtained from Gilson, Inc. 3000 Parmenter Street, Middleton, Wis. 53562-0027, U.S.A.; or an Atlantis T3 reverse phase HPLC Column (Waters Corp., 34 Maple St., Milford, Mass. 01757, U.S.A) with dimension 20 mm/100 and 50 mm/250 in $H_2O$/MeCN with 0.1% TFA as mobile phase unless otherwise stated. Both columns were used with a preparative HPLC (High Performance Liquid Chromatography) instrument obtained from Gilson, Inc. 3000 Parmenter Street, Middleton, Wis. 53562-0027, U.S.A., according to the manufacturer's instructions;
(xiii) "SFC (Super Critical Fluid Chromatography)" refers to Analytical SFC (ASC-1000 Analytical SFC System with Diode Array Detector, or AMS-1000 Analytical SFC/MS system with Diode Array and Mass Spectrometer detection) and/or Preparative SFC (APS-1000 AutoPrep Preparative SFC, or MultiGram III SFC), used with carbon dioxide according to the manufacturer's instruction, obtained from Waters Corp., 34 Maple Street, Milford, Mass. 01757, U.S.A;
(xiv) Chiralpak® columns (e.g., type "IA", "IB" and/or "IC") are used according to the manufacturer's instruction obtained from Chiral Technologies, Inc. 800 North Five Points Road West Chester, Pa. 19380, USA;
(xv) Enantiomeric excess for each individual enantiomer (e.e.): >% calculated using area percent at 220 nm or 254 nm unless otherwise stated;
(xvi) Diastereomeric excess for each individual diastereomer (d.e.): >% calculated using area percent at 220 nm or 254 nm unless otherwise stated;
(xvii) Specific rotation(s) [α] were calculated based upon the equation: $[\alpha]=(100\cdot\alpha)/(l\cdot c)$, α is the observed rotation, l is the path length and c is the compound concentration;
(xviii) Observed optical rotations were measured using a PerkinElmer Model 341 Polarimeter, obtained from PerkinElmer, 940 Winter Street, Waltham, Mass. 02451, USA;
(xix) FT-IR (Fourier transform infrared spectroscopy) spectra were measured using a Nicolet Magna 560 FTIR (Thermo Fisher Scientific 81 Wyman Street, Waltham, Mass. 02454 USA) equipped with a Harrick SplitPea™ ATR assembly32 scans, 4000-600 $cm^{-1}$, sample applied directly on ATR surface, background collected prior to sample being run, then sample as background subtracted;
(xx) mass spectra were acquired when samples were separated using reverse-phase liquid chromatography (LC) and detected by electrospray ionization (ESI) mass spectrometry (MS) in positive and negative ion; values for m/z are given; generally, only ions which indicate the parent mass are reported; and unless otherwise stated, the mass ion quoted is $(M+H)^+$ or $(M-H)^+$; and
(xxi) The following abbreviations have been used:

| | |
|---|---|
| Cbz | benzyloxycarbonyl; |
| DCM | dichloromethane; |
| DCE | 1,2-dichloroethane; |
| HPLC | high-performance liquid chromatography; |
| DIPEA | N,N-diisopropylethylamine; |
| DMF | N,N-dimethylformamide; |
| EDC | 1-(3-dimethylaminopropyl)-3-ethylcarbodiimide hydrochloride; |
| HOBt | 1-hydroxybenzotriazole hydrate; |
| THF | tetrahydrofuran; |
| DMAP | 4-dimethylaminopyridine; |
| DMSO | dimethylsulfoxide; |
| EtOAc | ethyl acetate; |
| $Et_2O$ | diethyl ether; |
| r.t./R.T. | room temperature; |
| o/n | overnight; |
| hr(s) | hour(s); |
| min(s) | minute(s); |
| DMA | N,N-dimethylacetamide; |
| TEA | triethylamine; |
| TASF | tris(dimethylamino)sulfonium difluorotrimethylsilicate; and |
| HATU | 2-(7-Aza-1H-benzotriazole-1-y1)-1,1,3,3-tetramethyluronium hexafluorophosphate |

Intermediate 1

(R)-benzyl 2,5-dioxotetrahydrofuran-3-ylcarbamate

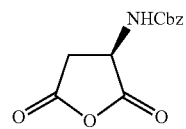 [SMILES: O=C1C[C@@H](NC(=O)OCc2ccccc2)C(=O)O1]

A mixture of (R)-2-(benzyloxycarbonylamino)succinic acid (Aldrich, 30 g, 112.26 mmol) and acetic anhydride (65.7 ml, 696.02 mmol) was stirred overnight at room temperature during which time the reaction mixture became clear. The volatiles were removed under reduced pressure (water bath temperature 65° C.) and the concentrate was azeotroped with toluene (3×50 ml) and obtained the title product after drying for ~48 hours at 60° C. under high vacuum pump (28.0 g, yield: almost quantitative).

¹H NMR (400 MHz, DMSO-$d_6$) δ ppm 2.94 (dd, 1 H) 3.28 (dd, 1 H) 4.61-4.82 (m, 1H) 5.08 (s, 2 H) 7.21-7.51 (m, 5 H) 8.16 (d, 1 H)

Optical Rotation:
Concentration: 0.14 g/dL
Lamp: Sodium
Wavelength: 589 nm
Temperature: 20° C.
Path length: 10 cm
Cell volume: 1 ml
Solvent: $CH_2Cl_2$
[α]=+13

Intermediate 2

(R)-3-(benzyloxycarbonylamino)-4-hydroxybutanoic acid

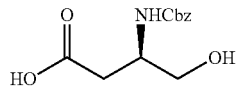

A solution of (R)-benzyl 2,5-dioxotetrahydrofuran-3-yl-carbamate (INTERMEDIATE 1, 53.28 g, 213.79 mmol) in THF (330 ml) was added over a 4 hour period using an additional funnel to a mixture of sodium borohydride (8.09 g, 213.79 mmol) in THF (330 ml) at 0° C. After the addition was complete, the mixture was warmed to room temperature and stirred for 2 hours. The solution was then concentrated under reduced pressure to ¼ of the original volume, cooled to 0° C., and carefully quenched by the slow addition of water (400 ml). The mixture was acidified to pH 4 with 1N aqueous hydrochloric acid and extracted with $Et_2O$ (5×300 ml). The combined organic layers were dried ($Na_2SO_4$) and concentrated in vacuo to provide the title product (45.9 g, yield: 85%).

¹H NMR (300 MHz, METHANOL-$d_4$) δ ppm 2.41-2.54 (m, 1 H) 2.56-2.70 (m, 1 H) 3.33 (dt, 2 H) 3.42-3.65 (m, 2 H) 3.95-4.12 (m, 1 H) 5.01-5.22 (m, 2 H) 7.14-7.46 (m, 5 H).

LCMS: (ESI) m/z 254.1 [M+H]⁺.

Optical Rotation:
Concentration: 0.14 g/dL
Lamp: Sodium
Wavelength: 589 nm
Temperature: 20° C.
Path length: 10 cm
Cell volume: 1 ml
Solvent: $CH_2Cl_2$
[α]=+13

Intermediate 3

(R)-benzyl 5-oxotetrahydrofuran-3-ylcarbamate

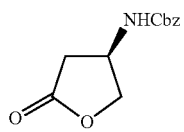 [SMILES: O=C1C[C@@H](NC(=O)OCc2ccccc2)CO1]

(R)-3-(Benzyloxycarbonylamino)-4-hydroxybutanoic acid (INTERMEDIATE 2, 27.7 g, 109.38 mmol) was dissolved in toluene (648 ml). p-Toluenesulfonic acid (367 mg, 2.13 mmol) was added to the solution and the resulting mixture was heated at reflux under Dean-Stark conditions for 3 hours. The reaction mixture was cooled to room temperature and concentrated in vacuo. Diethyl ether (200 ml) was added, and formation of crystals was observed upon standing. The crystals were filtered in vacuo. The mother liquors were concentrated in vacuo and additional diethyl ether (40 ml) was added. More crystals appeared which were filtered in vacuo. Both sets of crystals combined to give the title product (22.8 g, yield: 83%).

¹H NMR (300 MHz, CHLOROFORM-d) δ ppm 2.49 (dd, 1 H) 2.76-2.94 (m, 1 H) 4.24 (d, 1 H) 4.42-4.61 (m, 2 H) 5.03-5.24 (m, 3 H) 7.27-7.46 (m, 5 H).

LCMS: (ESI) m/z 234 [M−H]⁺.

Optical Rotation:
Concentration: 0.155 g/dL
Lamp: Sodium
Wavelength: 589 nm
Temperature: 20° C.
Path length: 10 cm
Cell volume: 1 ml
Solvent: $CH_2Cl_2$
[α]=+46

Intermediate 4

(R)-methyl 3-(benzyloxycarbonylamino)-4-hydroxybutanoate

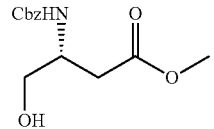

(R)-Benzyl 5-oxotetrahydrofuran-3-ylcarbamate (INTERMEDIATE 3, 27.0 g, 114.78 mmol) was dissolved in methanol (75 ml) and triethylamine (75 ml) was added at room temperature. The resulting mixture was allowed to stir overnight at this temperature. The mixture was concentrated in vacuo to provide the title product. This material was used to prepare INTERMEDIATE 5 without further purification.

¹H NMR (300 MHz, CHLOROFORM-d) δ ppm 2.67 (d, 2 H) 3.60-3.72 (m, 3 H) 3.70-3.78 (m, 1 H) 4.00-4.15 (m, 2 H) 5.03-5.18 (m, 2 H) 5.52 (br. s., 1 H) 7.28-7.42 (m, 5 H).

Intermediate 5

(R)-methyl 3-(benzyloxycarbonylamino)-4-(phenylthio)butanoate

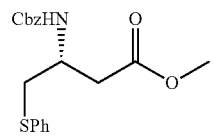

To a solution of benzenethiol (11.16 ml, 108.65 mmol), (R)-methyl 3-(benzyloxycarbonylamino)-4-hydroxybutanoate (INTERMEDIATE 4, 26.4 g, 98.77 mmol) and tributylphosphine (34.5 ml, 138.28 mmol) in anhydrous THF (350 ml) under nitrogen atmosphere was added. A solution of (E)-diazene-1,2-diylbis(piperidin-1-ylmethanone) (34.9 g, 138.22 mmol) in anhydrous THF (350 ml) was added dropwise over a 30 minute period. During the addition a white precipitate was formed and stirring was continued for 2 hours after the addition was complete. The white precipitate was filtered off and evaporation of the volatiles under reduced pressure gave a residue, which was purified by column chromatography (ISCO, eluting with 0→100% EtOAc/hexanes) to give the title product (25.0 g, yield: 70%).

$^1$H NMR (300 MHz, CHLOROFORM-d) δ ppm 2.59-2.73 (m, 1 H) 2.75-2.88 (m, 1 H) 3.04-3.19 (m, 1 H) 3.21-3.37 (m, 1 H) 3.57-3.69 (m, 3 H) 4.08-4.24 (m, 1 H) 5.00-5.14 (m, 2 H) 5.46 (br. s., 1 H) 7.14-7.48 (m, 10 H).

Intermediate 6

4-fluoro-3-(trifluoromethylsulfonyl)benzenesulfonamide

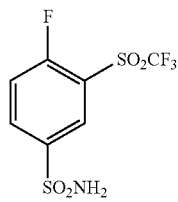

A mixture of chlorosulfonic acid (49.3 ml, 736.31 mmol) and 1-fluoro-2-(trifluoromethylsulfonyl)benzene (60.0 g, 262.9 mg) was heated at 125° C. for 18 hours. The reaction mixture was allowed to cool to room temperature and then poured carefully onto 500 ml of crushed ice. The mixture was extracted with ethyl acetate (3×300 ml) and the combined organic layer was washed with water (300 ml), brine (300 ml), dried over sodium sulfate, and concentrated under reduced pressure. The concentrate was dissolved in isopropyl alcohol (1200 ml) and cooled to −65° C. A solution of ammonium hydroxide (280 ml) was added at such rate so that the internal temperature did not rise above −60° C. After the addition was completed, the reaction mixture was allowed to warm to 0° C. over ~1.5 hours. The solution was then cooled back to approximately −50° C. and acidified by the dropwise addition of concentrated HCl (240 ml) resulting in the formation of a white precipitate. The solid was filtered off and the filtrate was concentrated under reduced pressure to remove the volatiles. The resulting mixture was filtered and the combined collected solid was washed with water (~200 ml). The filtrate was further extracted with EtOAc (2×250 ml) and the combined organic extracts were washed with water and brine, and dried over sodium sulfate and filtered. Concentration of the volatiles under reduced pressure gave an oil, which was crystallized from ethyl acetate/hexane to provide the title product (45.0 g, yield: 56%).

$^1$H NMR (400 MHz, DMSO-$d_6$) δ ppm 7.70-7.90 (m, 2 H) 7.98 (dd, 1 H) 8.32-8.60 (m, 2 H).

LCMS: (ESI) m/z 306 [M−H]$^+$.

Intermediate 7

(R)-methyl 4-(phenylthio)-3-(4-sulfamoyl-2-(trifluoromethylsulfonyl)phenylamino)-butanoate

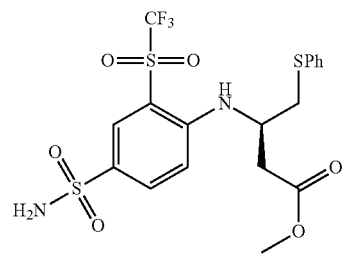

Step 1: A solution of (R)-methyl 3-(benzyloxycarbonylamino)-4-(phenylthio)butanoate (INTERMEDIATE 5, 25.6 g, 71.22 mmol), and TFA (200 ml) was heated at reflux for 1 hour. The excess reagent was removed under reduced pressure and the concentrate was azeotroped with 50 ml of DCM to give (R)-methyl 3-amino-4-(phenylthio)butanoate, trifluoroacetic acid salt, which was used in the preparation of INTERMEDIATE 7, STEP 2 without further purification.

Step 2: 4-Fluoro-3-(trifluoromethylsulfonyl)benzenesulfonamide (INTERMEDIATE 6, 21.67 g, 71.22 mmol) and DIPEA (129 ml, 738 mmol) were added to a solution of (R)-methyl 3-amino-4-(phenylthio)butanoate, trifluoroacetic acid salt (INTERMEDIATE 7, STEP 2) in DMF (20 ml). The resulting reaction mixture was heated at 50° C. for 1.5 hours, allowed to cool to room temperature, diluted with ethyl acetate (500 ml), and washed with water (250 ml) and brine (250 ml). The organic layer was dried over sodium sulfate, filtered, and concentrated under reduced pressure. The concentrate was purified by column chromatography (ISCO, eluting with 0→30% EtOAc/DCM over 54 minutes) to give the title product (20.5 g, yield: 56%).

$^1$H NMR (300 MHz, CHLOROFORM-d) δ ppm 2.75-2.88 (m, 2 H) 3.06-3.20 (m, 2 H) 3.63-3.76 (m, 3 H) 4.04-4.21 (m, 1 H) 4.84 (s, 1 H) 6.55 (d, 1 H) 7.19-7.49 (m, 5 H) 7.85 (dd, 1 H) 8.28 (d, 1 H).

LCMS: (ESI) m/z 511 [M−H]$^+$.

Intermediate 8

(R)-4-(phenylthio)-3-(4-sulfamoyl-2-(trifluoromethylsulfonyl)phenylamino)butanoic acid

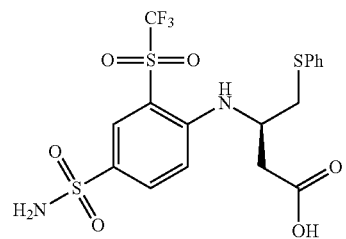

A 100 ml flask was charged with (R)-methyl 4-(phenylthio)-3-(4-sulfamoyl-2-(trifluoromethylsulfonyl)phenylamino)butanoate (INTERMEDIATE 7, 7.5 g, 14.63 mmol)

and THF (117 ml), MeOH (39 ml) and water (39 ml) were added sequentially. LiOH (1.05 g, 43.9 mmol) was added to the solution and the reaction mixture was stirred at room temperature for 3 hours. The reaction mixture was concentrated under reduced pressure to remove the volatiles, and cooled to 0° C. An aqueous solution of HCl (1N) was added dropwise to the solution and the resulting mixture was filtered. The filter cake was dried under high vacuum at 60° C. to provide the title product (6.8 g, yield: 93%).

$^1$H NMR (300 MHz, CHLOROFORM-d) δ ppm 2.70-3.02 (m, 2 H) 3.04-3.26 (m, 2 H) 4.01-4.20 (m, 1 H) 4.95 (s, 2 H) 6.54 (d, 1 H) 7.29-7.49 (m, 5 H) 7.85 (dd, 1 H) 8.26 (d, 1 H).

LCMS: (ESI) m/z 497 [M−H]$^+$.

Intermediate 9

2-bromo-4'-chlorobiphenyl

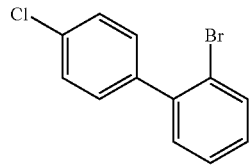 [SMILES: Clc1ccc(-c2ccccc2Br)cc1]

Sodium carbonate (19.8 g, 186.81 mmol) and tetrakis (triphenylphosphine)palladium(0) (1.05 g, 0.90 mmol) were added to a solution of 1,2-dibromobenzene (12.8 ml, 105.98 mmol) and 4-chlorophenylboronic acid (14.1 g, 90.08 mmol) in toluene (170 ml) and water (80 ml). The mixture was purged with nitrogen and heated at reflux overnight. The reaction mixture was allowed to cool to room temperature, and partitioned between saturated aq. NH$_4$Cl and ethyl acetate (500 ml). The organic layer was dried over MgSO$_4$, filtered and the volatiles were evaporated under reduced pressure to give a residue. The residue was purified by column chromatography (ISCO, 330 g silica gel column, eluting with 100% hexanes) to give the title product (17.0 g, yield: 71%).

$^1$H NMR (400 MHz, DMSO-d$_6$) δ ppm 7.34 (td, 1 H) 7.37-7.45 (m, 3 H) 7.45-7.50 (m, 1 H) 7.50-7.56 (m, 2 H) 7.75 (d, 1 H).

GC-MS: 268 [M]

Intermediate 10

(R)-(4'-chlorobiphenyl-2-yl)(piperidin-4-yl)methanol and (S)-(4'-chlorobiphenyl-2-yl)(piperidin-4-yl) methanol, mixture of enantiomers

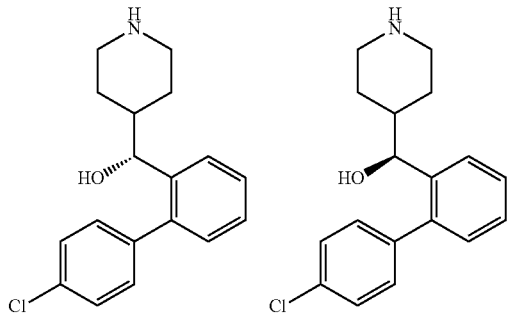 [SMILES: O[C@@H](c1ccccc1-c1ccc(Cl)cc1)C1CCNCC1 ; O[C@H](c1ccccc1-c1ccc(Cl)cc1)C1CCNCC1]

n-Butyl lithium (29.4 mL, 47.09 mmol) was added dropwise to a solution of 2-bromo-4'-chlorobiphenyl (INTERMEDIATE 9, 12 g, 44.85 mmol) in THF (220 ml) under nitrogen, at −78° C. The resulting colored mixture was stirred at −78° C. for 30 minutes and a solution of tert-butyl 4-formylpiperidine-1-carboxylate (10.04 g, 47.09 mmol) in THF (15 ml) was added. The reaction mixture was allowed to warm to 0° C. during 3 hours and then was quenched with a solution of saturated aq. NH$_4$Cl. The aqueous layer was extracted with ethyl acetate (3×) and the combined organic extracts and dried over MgSO$_4$. The mixture was filtered and evaporation of the volatiles under reduced pressure gave a residue, which was purified by column chromatography (ISCO, 330 g silica gel column, eluting with 0→40% EtOAc/hexanes) to give tert-butyl 4-[(4'-chlorobiphenyl-2-yl)(hydroxy)methyl]piperidine-1-carboxylate as a mixture of enantiomers.

Intermediate 10A (R)-(4'-chlorobiphenyl-2-yl)(piperidin-4-yl)methanol and (S)-(4'-chlorobiphenyl-2-yl)(piperidin-4-yl) methanol, mixture of enantiomers

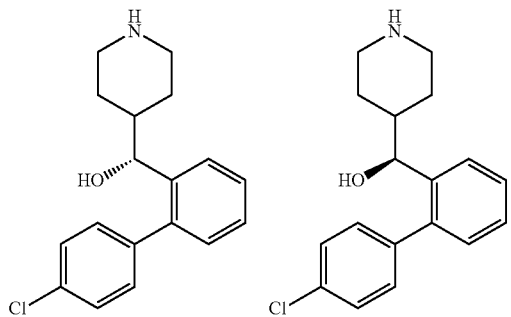 [SMILES: O[C@@H](c1ccccc1-c1ccc(Cl)cc1)C1CCNCC1 ; O[C@H](c1ccccc1-c1ccc(Cl)cc1)C1CCNCC1]

As an alternate procedure to the preparations of INTERMEDIATE 10, (R)-(4'-chlorobiphenyl-2-yl)(piperidin-4-yl) methanol and (S)-(4'-chlorobiphenyl-2-yl)(piperidin-4-yl) methanol, mixture of enantiomers, was prepared according to Steps 1 and 2 as follows.

Step 1: A heat-dried 50 ml round-bottom flask was charged, under nitrogen, with i-PrMgCl/LiCl complex (1.3 M in THF, 12.0 ml, 15.6 mmol). The flask was cooled to approximately −15° C.) and 2-bromo-4'-chlorobiphenyl (INTERMEDIATE 9, 4.01 g, 14.99 mmol) was added. The resulting mixture was stirred at −15° C. for 1 hour, then at 0° C. for 2.5 hours and was then allowed to warm up to room temperature overnight. The reaction mixture cooled to 0° C. and tert-butyl 4-formylpiperidine-1-carboxylate (3.53 g, 16.35 mmol) in THF (5.0 ml) was added dropwise over approximately 5 minutes and the resulting mixture was allowed to stir for 90 minutes at this temperature. The reaction mixture was quenched by the addition of saturated aq. NH$_4$Cl (30 ml) and extracted with EtOAc (4×60 ml). The organic layer was dried (MgSO$_4$), filtered, and evaporated under reduced pressure. The concentrate was purified by column chromatography (ISCO, 120 g silica gel column, eluting with 100% hexanes→50% EtOAc/hexanes and subsequently with 0→3% MeOH/DCM) to give (R)-tert-butyl 4-((4'-chlorobiphenyl-2-yl)(hydroxy)methyl)piperidine-1-carboxylate and (S)-tert-butyl 4-((4'-chlorobiphenyl-2-yl)(hydroxy)methyl)piperidine-1-carboxylate, mixture of enantiomers (2.04 g, yield: 43%).

¹H NMR (400 MHz, DMSO-d₆) δ ppm 0.61 (qd, 1 H) 0.81-0.96 (m, 2 H) 1.33 (s, 9 H) 1.50-1.63 (m, 1 H) 1.74-1.85 (m, 1 H) 3.63-3.78 (m, 1 H) 3.81-3.93 (m, 1 H) 4.28 (dd, 1 H) 5.21 (d, 1 H) 7.12 (d, 1 H) 7.26-7.38 (m, 3 H) 7.41 (t, 1 H) 7.50 (d, 2 H) 7.56 (d, 1 H).

LCMS: (ESI) m/z 424 [M+Na]⁺

Step 2: (R)-tert-butyl 4-((4'-chlorobiphenyl-2-yl)(hydroxy)methyl)piperidine-1-carboxylate and (S)-tert-butyl 4-((4'-chlorobiphenyl-2-yl)(hydroxy)methyl)piperidine-1-carboxylate, mixture of enantiomers (INTERMEDIATE 10, STEP 1, 1.0 g, 2.49 mmol) were dissolved in DCM (10.0 ml) and MeOH (0.4 ml) and treated with TFA (10.0 ml) at room temperature. The resulting mixture was stirred at this temperature for 40 minutes and the volatiles were evaporated under reduced pressure. The residue was dissolved in EtOAc (50 ml), washed with saturated aq. sodium bicarbonate (100 ml) and water (50 ml), dried (MgSO₄), filtered, and evaporated under vacuum to give the title product (701 mg, yield: 92%) as clear gum, which crystallized upon standing.

¹H NMR (400 MHz, DMSO-d₆) δ ppm 0.59 (qd, 1 H) 0.75-0.94 (m, 2 H) 1.40-1.53 (m, 1 H) 1.71-1.83 (m, 1 H) 2.15 (td, 1 H) 2.22-2.35 (m, 1 H) 2.61-2.71 (m, 1 H) 2.77-2.87 (m, 1 H) 4.25 (dd, 1 H) 5.08 (d, 1 H) 7.11 (d, 1 H) 7.25-7.31 (m, 1 H) 7.31-7.37 (m, 2 H) 7.40 (t, 1 H) 7.47-7.52 (m, 2 H) 7.54 (d, 1 H).

LCMS: (ESI) m/z 302 [M+H]⁺.

Intermediate 11

(R)-Ethyl 4-(4-((4'-chlorobiphenyl-2-yl)(hydroxy)methyl)piperidin-1-yl)benzoate and (S)-ethyl 4-(4-((4'-chlorobiphenyl-2-yl)(hydroxy)methyl)piperidin-1-yl)benzoate

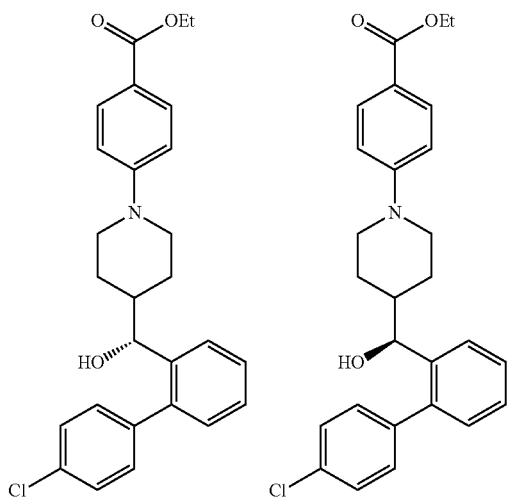 [SMILES: CCOC(=O)c1ccc(N2CCC([C@@H](O)c3ccccc3-c3ccc(Cl)cc3)CC2)cc1 ; CCOC(=O)c1ccc(N2CCC([C@H](O)c3ccccc3-c3ccc(Cl)cc3)CC2)cc1]

DIPEA (11 ml, 63 mmol) was added into a solution of (4'-chlorobiphenyl-2-yl)(piperidin-4-yl)methanol (INTERMEDIATE 10, 6.41 g, 21.24 mmol) and ethyl 4-fluorobenzoate (6.25 ml, 42.59 mmol) in dry DMSO (25 ml). The resulting solution was heated at 120° C. for 20 hours, and more triethylamine (12.2 ml, 87.67 mmol) was added. The solution was heated at 120° C. for additional 24 hours and then partitioned between ethyl acetate (500 ml) and saturated aq. NH₄Cl solution (250 ml). The organic layer was washed with water, dried over Na₂SO₄, filtered and concentrated under reduced pressure to afford a residue. This residue was purified by column chromatography (ISCO, 120 g silica column, eluting with 0→65% EtOAc/hexanes) to give the title product (5.12 g, yield: 54%) as a mixture of enantiomers.

The R and S enantiomers of the title product were separated using Chiral SFC, (Chiralpak IA column).
Column dimensions: 21×250 mm, 5μ
Modifier: 35% Isopropanol
Flow rate (ml/min): 60
Outlet Pressure (bar): 100
Detection (nm): 220

Intermediate 11A

First Eluting Compound (R)-ethyl 4-(4-((4'-chlorobiphenyl-2-yl)(hydroxy)methyl)piperidin-1-yl)benzoate The first eluting compound had a retention time of 4.97 minutes.

¹H NMR (400 MHz, DMSO-d₆) δ ppm 0.84 (qd, 1 H) 0.98-1.17 (m, 2 H) 1.27 (t, 3 H) 1.60-1.73 (m, 1 H) 1.85-1.95 (m, 1 H) 2.52-2.61 (m, 1 H) 2.63-2.74 (m, 1 H) 3.64-3.73 (m, 1 H) 3.80-3.90 (m, 1 H) 4.21 (q, 2 H) 4.31 (dd, 1 H) 5.23 (d, 1 H) 6.85 (d, 2 H) 7.14 (dd, 1 H) 7.28-7.38 (m, 3 H) 7.43 (td, 1 H) 7.46-7.52 (m, 2 H) 7.56-7.62 (m, 1 H) 7.71 (d, 2 H).

LCMS: (ESI) m/z 450 [M+H]⁺.

Optical Rotation:
Concentration: 0.1 g/dL
Lamp: Sodium
Wavelength: 589 nm
Temperature: 20° C.
Path length: 10 cm
Cell volume: 1 ml
Solvent: DCM
[α]=+107

Intermediate 11B

Second Eluting Compound (S)-ethyl 4-(4-((4'-chlorobiphenyl-2-yl)(hydroxy)methyl)piperidin-1-yl)benzoate The second eluting compound had a retention time of 6.72 minutes.

¹H NMR (400 MHz, DMSO-d₆) δ ppm 0.84 (qd, 1 H) 0.98-1.17 (m, 2 H) 1.27 (t, 3 H) 1.61-1.73 (m, 1 H) 1.85-1.94 (m, 1 H) 2.52-2.61 (m, 1 H) 2.63-2.74 (m, 1 H) 3.65-3.73 (m, 1 H) 3.80-3.89 (m, 1 H) 4.21 (q, 2 H) 4.31 (dd, 1 H) 5.23 (d, 1 H) 6.85 (d, 2 H) 7.14 (dd, 1 H) 7.28-7.38 (m, 3 H) 7.43 (td, 1 H) 7.46-7.52 (m, 2 H) 7.56-7.62 (m, 1 H) 7.71 (d, 2 H).

LCMS: (ESI) m/z 450 [M+H]⁺.

Optical Rotation:
Concentration: 0.1 g/dL
Lamp: Sodium
Wavelength: 589 nm
Temperature: 20° C.
Path length: 10 cm
Cell volume: 1 ml
Solvent: DCM
[α]=−116

Intermediate 12

(R)-Ethyl 4-(4-((tert-butyldimethylsilyloxy)(4'-chlorobiphenyl-2-yl)methyl)piperidin-1-yl)benzoate

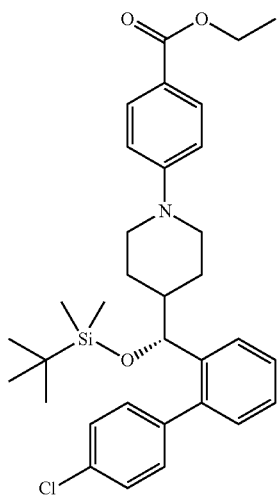 [SMILES: CCOC(=O)c1ccc(N2CCC([C@@H](O[Si](C)(C)C(C)(C)C)c3ccccc3-c3ccc(Cl)cc3)CC2)cc1]

2,6-Lutidine (1.128 ml, 9.68 mmol) was added to a solution of (R)-ethyl 4-(4-((4'-chlorobiphenyl-2-yl)(hydroxy)methyl)piperidin-1-yl)benzoate (INTERMEDIATE 11A (First Eluting Compound), 1.74 g, 3.87 mmol) in DCM (10 ml) at 0° C. tert-Butyldimethylsilyl trifluoromethanesulfonate (1.3 ml, 5.81 mmol) was added dropwise via syringe at 0° C. and the resulting mixture was allowed to warm up to room temperature for 10 minutes. Evaporation of the volatiles under reduced pressure gave a residue, which was purified by column chromatography (ISCO, 80 g silicon column, eluting with 0→10% EtOAc/hexanes) to give the title product (2.1 g, yield: almost quantitative).

$^1$H NMR (400 MHz, CHLOROFORM-d) δ ppm −0.23 (s, 3 H) −0.06 (s, 3 H) 0.86 (s, 9 H) 1.22-1.48 (m, 6 H) 1.73-1.83 (m, 1 H) 2.53-2.70 (m, 2 H) 3.70-3.78 (m, 1 H) 3.80-3.89 (m, 1 H) 4.32 (q, 2 H) 4.56-4.65 (m, 1 H) 6.82 (d, 2 H) 7.10-7.15 (m, 1 H) 7.22 (d, 2 H) 7.28-7.33 (m, 1 H) 7.36-7.43 (m, 3 H) 7.59 (d, 1 H) 7.89 (d, 2 H).

LCMS: (ESI) m/z 564 [M+H]$^+$.

Intermediate 13

(R)-4-(4-((tert-Butyldimethylsilyloxy)(4'-chlorobiphenyl-2-yl)methyl)piperidin-1-yl)benzoic acid

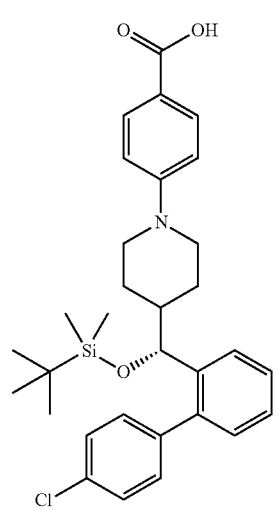 [SMILES: CC(C)(C)[Si](C)(C)O[C@@H](c1ccccc1-c1ccc(Cl)cc1)C1CCN(c2ccc(C(=O)O)cc2)CC1]

Lithium hydroxide (1.42 g, 59.29 mmol) was added to a mixture of (R)-ethyl 4-(4-((tert-butyldimethylsilyloxy)(4'-chlorobiphenyl-2-yl)methyl)piperidin-1-yl)benzoate (INTERMEDIATE 12, 3.83 g, 6.78 mmol) in THF (27 ml), MeOH (9 ml) and water (1 ml). The resulting mixture was stirred at room temperature overnight and then the volatiles were removed under reduced pressure. The concentrate was purified by column chromatography (ISCO, 80 g silica column, eluting with 0→80% EtOAc/hexanes) to give the title product (3.24 g, yield: 89%).

$^1$H NMR (400 MHz, DICHLOROMETHANE-d$_2$) δ ppm −0.23 (s, 3 H) −0.06 (s, 3 H) 0.85 (s, 9 H) 1.19-1.49 (m, 3 H) 1.52-1.64 (m, 1 H) 1.70-1.80 (m, 1 H) 2.57-2.73 (m, 2 H) 3.75-3.84 (m, 1 H) 3.85-3.94 (m, 1 H) 4.61 (d, J=4.80 Hz, 1 H) 6.82 (d, J=9.09 Hz, 2 H) 7.13 (dd, J=7.58, 1.26 Hz, 1 H) 7.24 (d, J=8.34 Hz, 2 H) 7.30 (td, J=7.45, 1.52 Hz, 1 H) 7.35-7.45 (m, 3 H) 7.60 (d, J=7.83 Hz, 1 H) 7.85-7.92 (m, 2 H).

LCMS: m/z 536 [M+H]$^+$.

Intermediate 14

(R)-Benzyl 4-(dimethylamino)-1-hydroxy-4-oxobutan-2-ylcarbamate

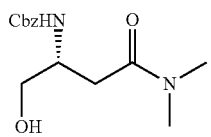 [SMILES: CN(C)C(=O)C[C@H](CO)NC(=O)OCc1ccccc1]

A solution of (R)-benzyl-5-oxotetrahydrofuran-3-ylcarbamate (INTERMEDIATE 3, 18.4 g, 7.8 mmol) in THF (100 ml) was purged, at room temperature, with gaseous dimethylamine for 5 minutes. After stirring at room temp for 14 hours, the reaction mixture was concentrated to dryness, and purified by column chromatography (silica gel, eluting first with 50% ethyl acetate/hexanes followed by 100% acetone) to give the title product (20 g, yield: 91.5%).

Intermediate 15

(R)-Benzyl 4-(dimethylamino)-4-oxo-1-(phenylthio)butan-2-ylcarbamate

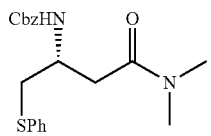

Diphenyl disulfide (55.8 g, 0.3 mol) and Bu$_3$P (75 ml, 0.3 mol) were added sequentially to a solution of (R)-benzyl 4-(dimethylamino)-1-hydroxy-4-oxobutan-2-ylcarbamate (INTERMEDIATE 14, 48 g, 0.17 mol) in toluene (100 ml). The resulting mixture was heated at 80° C. for 8 hours. The reaction mixture was allowed to cool to room temperature and the volatiles were removed in vacuo. The residue was purified by column chromatography (silica gel, 7 cm height×14 cm width, eluting with hexanes followed by 10:1, 2:1 then 1:1 hexanes/ethyl acetate) to yield the title product (40 g, yield: 63%).

$^1$H-NMR (300 MHz, DMSO-d$_6$) δ 2.59 (m, 2 H), 2.79 (s, 3 H), 2.89 (s, 3 H), 3.12 (m, 2 H), 4.71 (m, 1 H), 4.02 (m, 1 H), 5.01 (s, 2 H), 7.18 (t, 1 H), 7.26-7.41 (m, 10 H).

LCMS (ESI) m/z 373 (M+H)$^+$.

Intermediate 16

(R)-3-amino-N,N-dimethyl-4-(phenylthio)butanamide

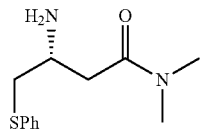

A suspension of (R)-benzyl 4-(dimethylamino)-4-oxo-1-(phenylthio)butan-2-ylcarbamate (INTERMEDIATE 15, 40 g, 0.10 mol) in 40% HBr in acetic acid (100 ml) was stirred at room temperature for 16 hours and the reaction mixture became homogeneous during this time. The mixture was concentrated to dryness, diluted with water (200 ml) and AcOH (200 ml) and washed with diethyl ether (3×50 ml). The aqueous phase was brought to approximately pH 8-9 with solid Na$_2$CO$_3$ and was extracted with CH$_2$Cl$_2$ (5×) The combined organic phases were dried (MgSO$_4$) and concentrated under reduced pressure to give the title product (15 g, 59%) that was used in the preparation of INTERMEDIATE 17 without further purification.

$^1$H-NMR (300 MHz, DMSO-d$_6$) δ 2.37 (dd, 1 H), 2.51 (dd, 1 H), 2.79 (s, 3 H), 2.89 (dd, 1 H), 2.91 (s, 3 H), 3.05-3.20 (m, 2 H), 3.32 (m, 2 H), 7.16 (t, 1 H), 7.30 (dd, 2 H), 7.35 (d, 2 H).

LCMS (ESI) m/z 239 (M+H)$^+$.

Intermediate 17

(3R)-4-N$^1$,N$^1$-dimethyl amine-1-(phenylthio)butan-2-amine

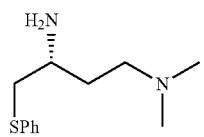

A solution of (R)-3-amino-N,N-dimethyl-4-(phenylthio) butanamide (INTERMEDIATE 16, 1.0 g, 4.2 mmol) in THF (30 ml) was treated, dropwise via an addition funnel, with a solution of BH$_3$.THF complex (16 ml, 1 M solution in THF, 16 mmol). The resulting dark solution was stirred at room temperature overnight. The mixture was cooled to 0° C. and treated dropwise with 5 ml MeOH, resulting in vigorous gas evolution. After gas evolution had ceased, the reaction mixture was concentrated to dryness, reconstituted in MeOH (35 ml) and concentrated HCl (5 ml) and brought to reflux for 4 hours. The reaction mixture was allowed to cool to room temperature, was concentrated to dryness and partitioned between saturated aqueous NaHCO$_3$ and CH$_2$Cl$_2$. The aqueous phase was extracted with CH$_2$Cl$_2$ (3×) and the combined organic phases were washed with saturated aqueous NaHCO$_3$, brine, dried (MgSO$_4$) and concentrated under reduced pressure. Concentration of the volatiles under reduced pressure gave a residue that was purified by column chromatography (silica gel, eluting with a step gradient of CH$_2$Cl$_2$ saturated with NH$_3$(g), 5% MeOH in CH$_2$Cl$_2$ saturated with NH$_3$(g), 10% MeOH/CH$_2$Cl$_2$ saturated with NH$_3$ (g) by 13% MeOH/CH$_2$Cl$_2$ saturated with NH$_3$(g)) to yield the title product (0.3 g, yield: 32%).

$^1$H-NMR (300 MHz, DMSO-d$_6$) δ 1.31 (m, 1 H), 1.64 (m, 1 H), 2.08 (m, 6 H), 2.25 (m, 2 H), 2.78 (m, 1 H), 2.98 (m, 1 H), 7.17 (m, 1 H), 7.35 (m, 4 H).

LCMS (ESI) m/z 225 (M+H)$^+$.

Intermediate 18

4-fluoro-3-nitrobenzenesulfonamide

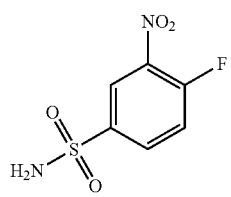 [SMILES: NS(=O)(=O)c1ccc(F)c([N+](=O)[O-])c1]

A solution of 2-fluoronitrobenzene (14.1 g, 0.10 mol) in chlorosulfonic acid (30 ml) was heated at 80° C. for 10 hours. After the reaction mixture was cooled to room temperature, it was carefully poured onto ice (about 100 g) in a 500 ml of Erlenmeyer flask cooled efficiently by ice. The resulting mixture was extracted with diethyl ether (2×200 ml), and the combined organic extracts concentrated under reduced pressure. The residue was dissolved in 70 ml 1:1 (v/v) THF/CH$_2$Cl$_2$, cooled to −78° C. and treated carefully with concentrated ammonium hydroxide (7.5 ml). The cold mixture was poured into 5 M aq. HCl (50 ml), the layers separated, the aqueous phase was extracted with ethyl acetate (2×200 ml) and the combined organic phases were washed with the 4 M aq. HCl, brine, and dried (MgSO$_4$). Removal of the volatiles under reduced pressure gave a solid. The resulting solid was re-crystallized from ethyl acetate and hexanes to give the title compound (15 g, 70%).

$^1$HNMR (300 MHz, DMSO-d$_6$) 8.53 (dd, 1 H), 8.20 (ddd, 1 H), 7.87 (dd, 1 H), 7.72 (s, 2 H).

LCMS (ESI) m/z 219 (M−H)$^-$.

Intermediate 19

(R)-4-(4-(dimethylamino)-1-(phenylthio)butan-2-ylamino)-3-nitrobenzenesulfonamide A solution of (R)—N$^1$,N$^1$-dimethylamine-4-(phenylthio) butane-1,3-diamine (INTERMEDIATE 17, 25 mg, 0.11 mmol) in DMF (5 ml) and DIPEA (0.01 ml) was treated with 4-fluoro-3-nitrobenzenesulfonamide (INTERMEDIATE 18, 24.9 mg, 0.11 mmol) in one portion and the resulting mixture was stirred at room temperature overnight. The reaction mixture was poured into water and extracted with EtOAc (2×50 ml). The combined organic layers were washed with brine, dried over Na$_2$SO$_4$ and concentrated in vacuo. The residue was purified by column chromatography (silica gel, eluting with a step gradient of CH$_2$Cl$_2$ saturated with NH$_3$(g), 5% MeOH in CH$_2$Cl$_2$ saturated with NH$_3$(g), 10% MeOH/CH$_2$Cl$_2$ saturated with NH$_3$(g) by 13% MeOH/CH$_2$Cl$_2$ saturated with NH$_3$(g)) to yield the title product (31 mg, yield: 66%) after re-crystallization from EtOAc.

$^1$H-NMR (300 MHz, DMSO-d$_6$) δ 1.83 (m, 1 H), 1.95 (m, 1 H), 2.11 (s, 6 H), 2.21 (m, 1 H), 2.43 (m, 1 H), 3.30 (br m, 2 H), 3.39 (m, 2 H), 4.10 (m, 1 H), 7.06 (d, 1 H), 7.17 (t, 2 H), 7.25 (dd, 2 H), 7.30 (d, 2 H), 7.70 (dd, 1 H), 8.38 (d, 1 H), 8.62 (d, 1 H).

LCMS (ESI) m/z 425 (M+H)$^+$.

Intermediate 20

1-(2-(tert-Butyldiphenylsilyloxy)ethyl)piperazine

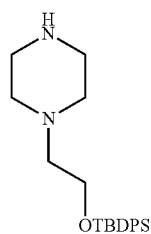

2-(piperazin-1-yl)ethanol (1.000 g, 7.68 mmol) was dissolved in DCM (35.1 ml) and pyridine (0.932 ml, 11.52 mmol) followed by DMAP (0.094 g, 0.77 mmol) were added. tert-butylchlorodiphenylsilane (2.368 ml, 9.22 mmol) was added to the solution and the reaction mixture was stirred at room temperature overnight. The reaction mixture was concentrated under reduced pressure and the concentrate was purified by column chromatography (ISCO, eluting with 10% MeOH/DCM) to give the title product (2.73 g, yield: 96%).

LCMS: (ESI) m/z 369 [M+H]$^+$.

Intermediate 21

(R)-4-(4-(4-(2-(tert-butyldiphenylsilyloxy)ethyl)piperazin-1-yl)-4-oxo-1-(phenylthio)butan-2-ylamino)-3-(trifluoromethylsulfonyl)benzenesulfonamide

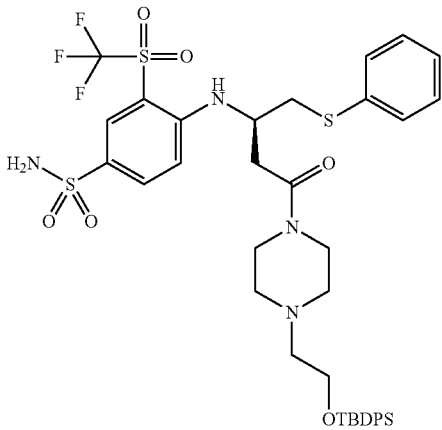

HATU (0.915 g, 2.41 mmol) and DIPEA (0.701 ml, 4.01 mmol) were added sequentially to a solution of (R)-4-(phenylthio)-3-(4-sulfamoyl-2-(trifluoromethylsulfonyl)phenylamino) butanoic acid (INTERMEDIATE 8, 1.0 g, 2.01 mmol) and 1-(2-(tert-butyldiphenylsilyloxy)ethyl)piperazine (INTERMEDIATE 20, 0.894 g, 2.21 mmol) in DMA (2.0 ml). Additional DMA (1.7 ml) was added and the resulting mixture was stirred at room temperature for 2 hrs. The mixture was diluted with EtOAc and the organic layer was washed with H$_2$O (2×), 1N NaHSO$_4$ (aq.) and saturated aq. NaHCO$_3$. The organic layer was dried (Na$_2$SO$_4$), and concentrated under reduced pressure to provide the title product (2.0 g, yield: quantitative), which was used in the preparation of INTERMEDIATE 22 without further purification.

LCMS: (ESI) m/z 849 [M+H]$^+$.

Intermediate 22

(R)-4-(4-(4-(2-(tert-Butyldiphenylsilyloxy)ethyl)piperazin-1-yl)-1-(phenylthio)butan-2-ylamino)-3-(trifluoromethylsulfonyl)benzenesulfonamide

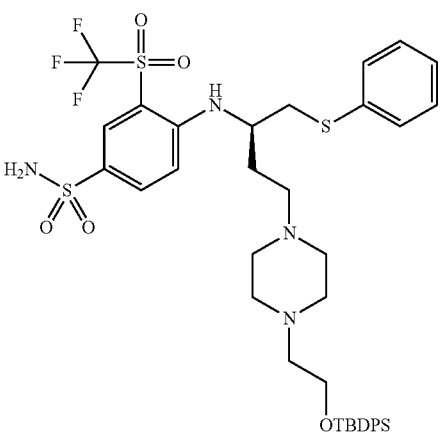

(R)-4-(4-(4-(2-(tert-Butyldiphenylsilyloxy)ethyl)piperazin-1-yl)-4-oxo-1-(phenylthio)butan-2-ylamino)-3-(trifluoromethyl sulfonyl)benzenesulfonamide (INTERMEDIATE 21, 0.98 g, 1.15 mmol) was dissolved in THF (4.6 ml), under a nitrogen atmosphere, and a solution of borane-THF complex (1M in THF; 6.93 ml, 6.93 mmol) was added. The mixture was diluted with NH$_3$ in MeOH (7N, 20 ml) and stirred at room temperature overnight. The reaction mixture was concentrated under reduced pressure, diluted with EtOAc (75 ml), washed with water (40 ml), and dried (Na$_2$SO$_4$). Evaporation of the volatiles under reduced pressure afforded a concentrate, which was purified by column chromatography (ISCO, 40 g silica gel column, eluting with 0→100% EtOAc/hexanes) to provide the title compound (245 mg, yield: 25%).

LCMS: (ESI) m/z 835 [M+H]$^+$.

Intermediate 23

2-(tert-butyldiphenylsilyloxy)-N-ethylethanamine

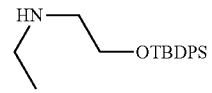

Imidazole (1.53 g, 22.44 mmol) and a solution of tert-butylchlorodiphenylsilane (4.63 g, 16.83 mmol) in DCM (10 ml) were added sequentially to a solution of 2-(ethylamino)ethanol (1.099 ml, 11.22 mmol) in DCM (30 ml) and the resulting reaction mixture was stirred at room temperature overnight. The mixture was diluted with DCM and washed with 1N aq. NaHSO$_4$ and saturated aq. NaHCO$_3$. The organic layer was dried (Na$_2$SO$_4$), concentrated under reduced pressure to give a residue which was purified by column chromatography (ISCO, 40 g silica gel column, eluting with 0→100% EtOAc/hexanes) to provide the title compound (2.95 g, yield: 80) %).

LCMS: (ESI) m/z 328 [M+H]$^+$.

Intermediate 24

(R)—N-(2-(tert-butyldiphenylsilyloxy)ethyl)-N-ethyl-4-(phenylthio)-3-(4-sulfamoyl-2-(trifluoromethylsulfonyl)phenylamino)butanamide

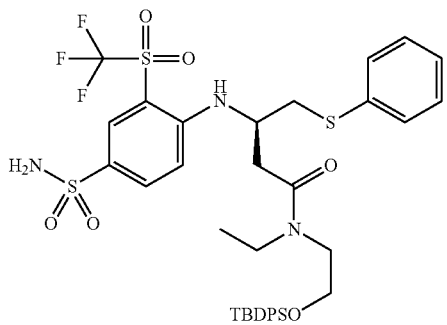

2-(tert-Butyldiphenylsilyloxy)-N-ethylethanamine (INTERMEDIATE 23, 0.263 g, 0.80 mmol) in THF (2.5 ml), diethyl 4-oxobenzo[d][1,2,3]triazin-3(4H)-yl phosphate (0.480 g, 1.60 mmol) and DIPEA (0.280 ml, 1.60 mmol) were added sequentially to a solution of (R)-4-(phenylthio)-3-(4-sulfamoyl-2-(trifluoromethylsulfonyl)phenylamino)butanoic acid (INTERMEDIATE 8, 0.4 g, 0.80 mmol) in THF (5.0 ml) and the mixture was stirred at room temperature for 3 hrs. The reaction mixture was then concentrated under reduced pressure, diluted with EtOAc and the organic layer was washed with 1N aq. NaHSO$_4$ and saturated aq. NaHCO$_3$. The organic layer was dried (Na$_2$SO$_4$), concentrated under reduced pressure to give a residue, which was purified by column chromatography (ISCO, 40 g silica gel column, eluting with 0→100% EtOAc/hexanes) to provide the title product (590 mg, yield: 91%).

LCMS: (ESI) m/z 808 [M+H]$^+$.

Intermediate 25

(R)-4-(4-(2-(tert-butyldiphenylsilyloxy)ethyl)(ethyl)amino)-1-(phenylthio)butan-2-ylamino)-3-(trifluoromethylsulfonyl)benzenesulfonamide

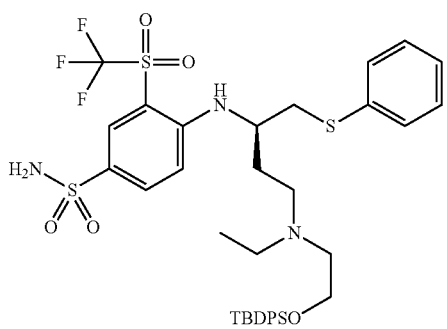

(R)—N-(2-(tert-Butyldiphenylsilyloxy)ethyl)-N-ethyl-4-(phenylthio)-3-(4-sulfamoyl-2-(trifluoromethylsulfonyl)phenylamino)butanamide (INTERMEDIATE 24, 0.59 g, 0.73 mmol) was dissolved in THF (4.6 ml), under a nitrogen atmosphere, and a solution of borane-THF complex (1M in THF; 2.2 ml, 2.2 mmol) was added and the resulting solution was stirred at ambient temperature overnight. An additional solution of borane-THF complex (1M in THF; 2.2 ml, 2.2 mmol) was added. The resulting mixture was stirred at ambient for further 6 hrs. The mixture was diluted with NH$_3$ in MeOH (7N, 20 ml) and stirred at room temperature overnight. The reaction mixture was concentrated under reduced pressure, diluted with EtOAc (75 ml), washed with water (40 ml), and dried (Na$_2$SO$_4$). Evaporation of the volatiles under reduced pressure afforded a concentrate, which was purified by column chromatography (ISCO, 40 g silica gel column, eluting with 0→100% EtOAc/hexanes) to provide the title compound (280 mg, yield: 48%).

LCMS: (ESI) m/z 796 [M+H]$^+$.

Intermediate 26

2-(tert-Butyldiphenylsilyloxy)-N-methylethanamine

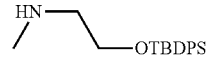

The title compound (4.1 g, yield: 49%) was prepared using a procedure similar to the one described for the synthesis of INTERMEDIATE 23 utilizing 2-(methylamino)ethanol (2.0 g, 26.6 mmol) as starting material. The title product was purified by column chromatography (ISCO, 40 g silica gel column, eluting with 0→100% DCM/10% MeOH in DCM with 1% NH$_4$OH).

LCMS: (ESI) m/z 314 [M+H]$^+$.

Intermediate 27

(R)—N-(2-(tert-butyldiphenylsilyloxy)ethyl)-N-methyl-4-(phenylthio)-3-(4-sulfamoyl-2-(trifluoromethylsulfonyl)phenylamino)butanamide

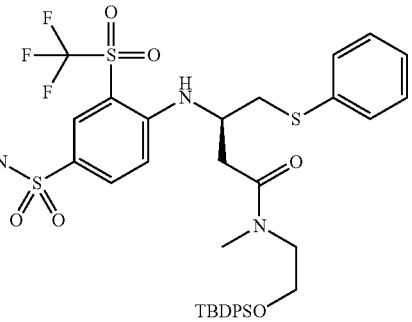

The title product (590 mg, yield: 93%) was prepared using a procedure similar to the one described for the synthesis of INTERMEDIATE 24 utilizing (R)-4-(phenylthio)-3-(4-sulfamoyl-2-(trifluoromethylsulfonyl)phenylamino)butanoic acid (INTERMEDIATE 8, 400 mg, 0.8 mmol) and 2-(tert-butyldiphenylsilyloxy)-N-methylethanamine (INTERMEDIATE 26, 251 mg, 0.8 mmol) as starting materials. The title product was purified by column chromatography (ISCO, 12 g silica gel column, eluting with 0→100% EtOAc/hexanes).

LCMS: (ESI) m/z 794 [M+H]$^+$.

Intermediate 28

(R)-4-(4-((2-(tert-butyldiphenylsilyloxy)ethyl)(methyl)amino)-1-(phenylthio)butan-2-ylamino)-3-(trifluoromethylsulfonyl)benzenesulfonamide

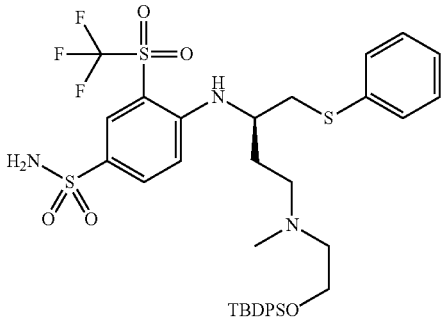

The title compound (230 mg, yield: 40%) was prepared using a procedure similar to the one described for the synthesis of INTERMEDIATE 25 utilizing (R)—N-(2-(tert-butyldiphenylsilyloxy)ethyl)-N-methyl-4-(phenylthio)-3-(4-sulfamoyl-2-(trifluoromethylsulfonyl)phenylamino)butanamide (INTERMEDIATE 27, 590 mg, 0.74 mmol) as starting material. The title compound was purified by column chromatography (ISCO, 12 g silica gel column, eluting with 0→100% EtOAc/hexanes).
LCMS: (ESI) m/z 780 [M+H]$^+$.

Intermediate 29

Bis(2-(tert-butyldiphenylsilyloxy)ethyl)amine

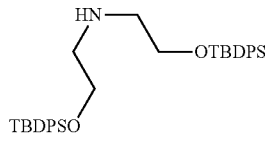

The title compound (4.8 g, yield: 87%) was prepared using a procedure similar to the one described for the synthesis of INTERMEDIATE 23 utilizing 2,2'-azanediyldiethanol (1.0 g, 9.51 mmol) as starting material. The title product was purified by column chromatography (ISCO, 40 g silica gel column, eluting with 0→50% EtOAc/hexanes).
LCMS: (ESI) m/z 582 [M+H]$^+$.

Intermediate 30

(R)—N,N-Bis(2-(tert-butyldiphenylsilyloxy)ethyl)-4-(phenylthio)-3-(4-sulfamoyl-2-(trifluoromethylsulfonyl)phenylamino)butanamide

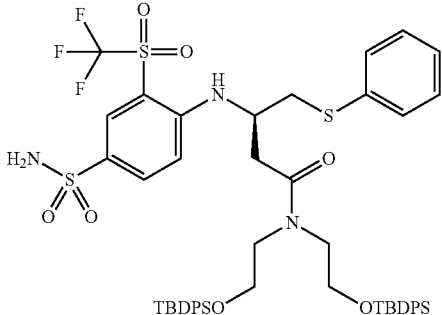

The title product (1.06 g, yield: 83%) was prepared using a procedure similar to the one described for the synthesis of INTERMEDIATE 24 utilizing (R)-4-(phenylthio)-3-(4-sulfamoyl-2-(trifluoromethylsulfonyl)phenylamino)butanoic acid (INTERMEDIATE 8, 600 mg, 1.2 mmol) and bis(2-(tert-butyldiphenylsilyloxy)ethyl)amine (INTERMEDIATE 29, 0.700 g, 1.20 mmol) as starting materials. The title product was purified by column chromatography (ISCO, 40 g silica gel column, eluting with 0→100% EtOAc/hexanes).
LCMS: (ESI) m/z 1062 [M+H]$^+$.

Intermediate 31

(R)-4-(4-(Bis(2-(tert-butyldiphenylsilyloxy)ethyl)amino)-1-(phenylthio)butan-2-ylamino)-3-(trifluoromethylsulfonyl)benzenesulfonamide

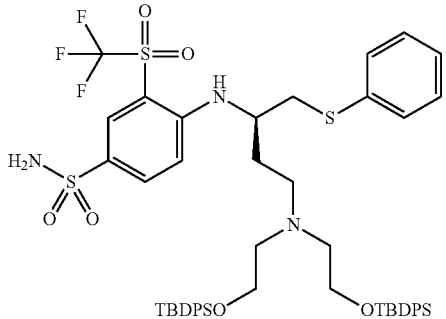

The title product (800 mg, yield: 77%) was prepared using a procedure similar to the one described for the synthesis of INTERMEDIATE 25 utilizing (R)—N,N-bis(2-(tert-butyldiphenylsilyloxy)ethyl)-4-(phenylthio)-3-(4-sulfamoyl-2-(trifluoromethylsulfonyl)phenylamino)butanamide (INTERMEDIATE 30, 1.05 g, 0.99 mmol) as starting material. The title product was purified by column chromatography (ISCO, 40 g silica gel column, eluting with 0→50% EtOAc/hexanes).
LCMS: (ESI) m/z 1048 [M+H]$^+$.

Intermediate 32

4-(4-((R)-(tert-butyldimethylsilyloxy)(4'-chlorobiphenyl-2-yl)methyl)piperidin-1-yl)-N-(4-((R)-4-(4-(2-(tert-butyldiphenylsilyloxy)ethyl)piperazin-1-yl)-1-(phenylthio)butan-2-ylamino)-3-(trifluoromethylsulfonyl)phenylsulfonyl)benzamide

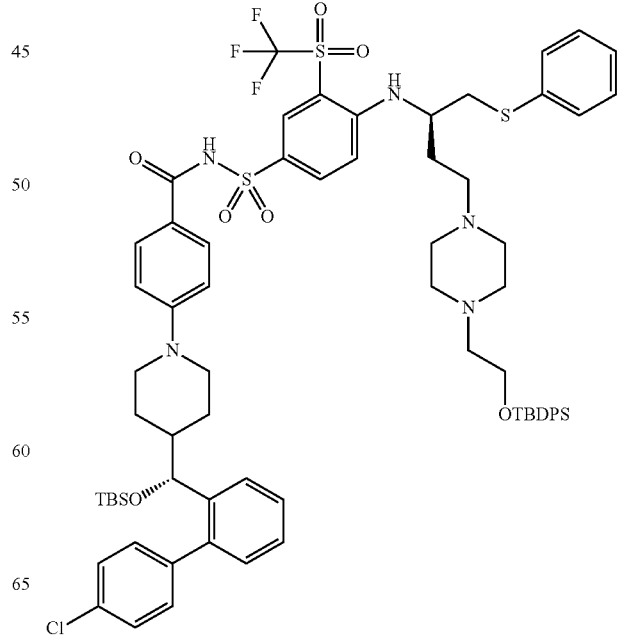

(R)-4-(4-((tert-butyldimethylsilyloxy)(4'-chlorobiphenyl-2-yl)methyl)piperidin-1-yl)benzoic acid (INTERMEDIATE 13, 56.5 mg, 0.11 mmol), (R)-4-(4-(4-(2-(tert-butyldiphenylsilyloxy)ethyl)piperazin-1-yl)-1-(phenylthio)butan-2-ylamino)-3-(trifluoromethylsulfonyl)benzenesulfonamide (INTERMEDIATE 22, 80 mg, 0.1 mmol), DMAP (35.1 mg, 0.29 mmol), and EDC (36.7 mg, 0.19 mmol) were placed in a 50 ml flask and flushed with nitrogen. DCM (0.96 ml) was added, and the solution was stirred at room temperature overnight. The reaction mixture was diluted with DCM (40 ml) and washed with 1N sodium bisulfate (35 ml) followed by a saturated aq. sodium bicarbonate (40 ml). The organic layer was dried ($Na_2SO_4$), filtered, and evaporated under reduced pressure to give the title product (147 mg, yield: quantitative), that was used in the preparation of EXAMPLE 1 without further purification.

LCMS: (ESI) m/z 1354 [M+H]+.

Intermediate 33

4-(4-((R)-(tert-butyldimethylsilyloxy)(4'-chlorobiphenyl-2-yl)methyl)piperidin-1-yl)-N-(4-((R)-4-(dimethylamino)-1-(phenylthio)butan-2-ylamino)-3-nitrophenylsulfonyl)benzamide

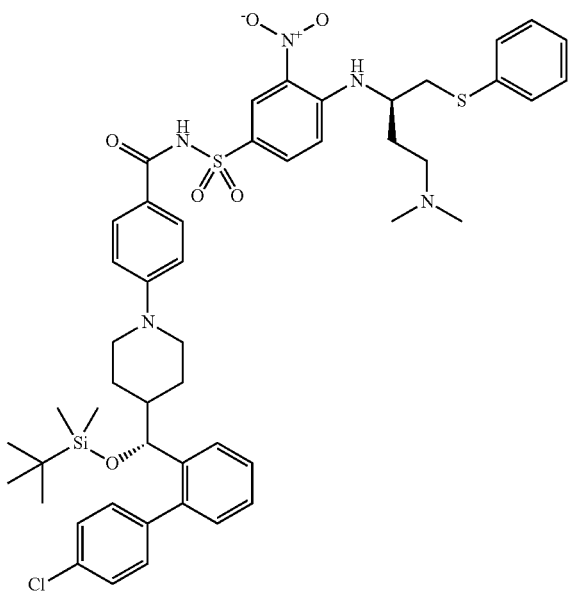

The title product (162.8 mg, yield: 32%) was prepared using a procedure similar to the one described for the synthesis of INTERMEDIATE 32 utilizing (R)-4-(4-((tert-butyldimethylsilyloxy)(4'-chlorobiphenyl-2-yl)methyl)piperidin-1-yl)benzoic acid (INTERMEDIATE 13, 249.6 mg, 0.47 mmol) and (R)-4-(4-(dimethylamino)-1-(phenylthio)butan-2-ylamino)-3-nitrobenzenesulfonamide (INTERMEDIATE 19, 208.8 mg, 0.49 mmol). The title product was purified by column chromatography (ISCO, 12 g silica gel column, eluting with 0→10% MeOH/DCM).

$^1$H NMR (300 MHz, DICHLOROMETHANE-$d_2$) δ ppm −0.24 (s, 3 H) −0.07 (s, 3 H) 0.86 (s, 9 H) 1.47-1.62 (m, 1 H) 1.68-1.81 (m, 1 H) 2.04-2.18 (m, 1 H) 2.43 (s, 6 H) 2.50-2.77 (m, 4 H) 3.15 (d, J=5.84 Hz, 2 H) 3.65-3.87 (m, 2 H) 4.07 (s, 1 H) 4.60 (d, 1 H) 6.68-6.82 (m, 3 H) 7.08-7.45 (m, 12 H) 7.54-7.63 (m, 1 H) 7.70 (d, 2 H) 7.75-7.84 (m, 1 H) 8.64 (s, 2 H).

LCMS: m/z 942 [M+H]+.
Optical Rotation:
Concentration: 0.1 g/dL
Lamp: Sodium
Wavelength: 589 nm
Temperature: 20° C.
Path length: 10 cm
Cell volume: 1 ml
Solvent: $CH_2Cl_2$
[α]=−13°

Intermediate 34

N-(4-((R)-4-((2-(tert-butyldimethylsilyloxy)ethyl)(methyl)amino)-1-(phenylthio)butan-2-ylamino)-3-(trifluoromethylsulfonyl)phenylsulfonyl)-4-(4-((R)-(4'-chlorobiphenyl-2-yl)(hydroxy)methyl)piperidin-1-yl)benzamide

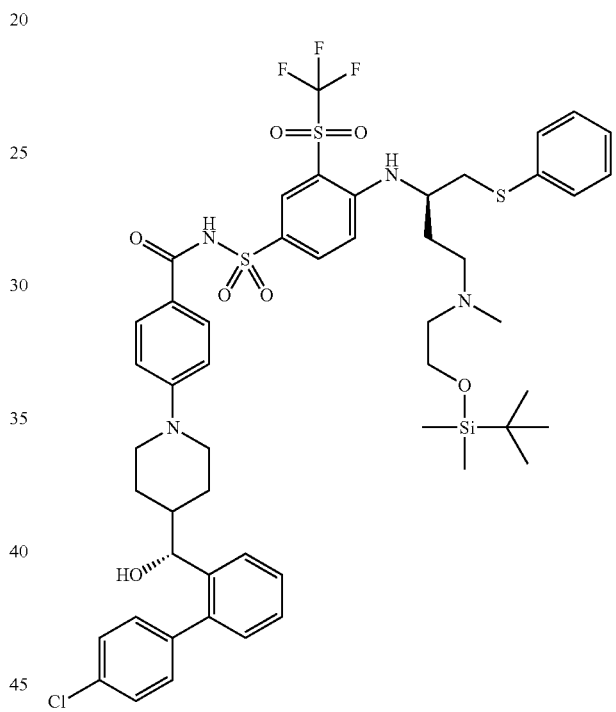

To a yellow solution of (R)-4-(4-((4'-chlorobiphenyl-2-yl)(hydroxy)methyl)piperidin-1-yl)benzoic acid (INTERMEDIATE 40, 1.64 g, 3.89 mmol), (R)-4-(4-((2-(tert-butyldimethylsilyloxy)ethyl)(methyl)amino)-1-(phenylthio)butan-2-ylamino)-3-(trifluoromethylsulfonyl)benzenesulfonamide (INTERMEDIATE 67, 2.68 g, 4.09 mmol), DMAP (0.95 g, 7.78 mmol) and dichloromethane (41 ml) was added EDC (1.492 g, 7.78 mmol). After stirring for 16 hours, the mixture was diluted with saturated aqueous sodium bicarbonate. The layers were separated and the aqueous layer was extracted with dichloromethane (×2). The combined organic layers were washed with saturated aqueous sodium chloride, dried over sodium sulfate, filtered, and concentrated under reduced pressure. The concentrate was purified by column chromatography (ISCO, 330 g $SiO_2$, isocratic 50% ethyl acetate in hexanes for 50 minutes, then 50→65% ethyl acetate in hexanes over 30 minutes followed by 65→100% ethyl acetate in hexanes over 20 min and then 0→10% methanol in ethyl acetate over 20 minutes) to afford the title product (3.25 g, yield: 79%).

¹H NMR (300 MHz, DMSO-d₆, at 27° C.) δ 10.09 (br. s, 0.4H), 8.11 (d, 1H), 7.90-8.00 (m, 1H), 7.68 (d, 2H), 7.59 (d, 1H), 7.10-7.54 (m, 12H), 6.89 (d, 2H), 6.75 (d, 2H), 5.21 (d, 1H), 4.24-4.39 (m, 1H), 4.04 (d, 1H), 3.73 (br. s., 3H), 3.52-3.66 (m, 1H), 3.19-3.38 (m, 2H), 2.67-3.01 (m, 4H), 2.39-2.66 (m, 5H), 2.00 (s, 3H), 1.53-1.71 (m, 1H), 0.96-1.15 (m, 2H), 0.83-0.93 (m, 1H), 0.81 (s, 9H), 0.00 (s, 6H).

¹⁹F NMR (282 MHz, DMSO-d₆) δ −78.91 (3F).

LCMS: (ESI) m/z 1059.4, 1061.4 [M+H]⁺.

Optical Rotation:
Concentration: 0.14 g/dL
Lamp: Sodium
Wavelength: 589 nm
Temperature: 20° C.
Path length: 10 cm
Cell volume: 1 ml
Solvent: CH₂Cl₂
[α]=−2

Intermediate 34A 4-(4-((R)-(tert-butyldimethylsilyloxy)(4'-chlorobiphenyl-2-yl)methyl)piperidin-1-yl)-N-(4-((R)-4-((2-(tert-butyldiphenylsilyloxy)ethyl)(methyl)amino)-1-(phenylthio)butan-2-ylamino)-3-(trifluoromethylsulfonyl)phenylsulfonyl)benzamide

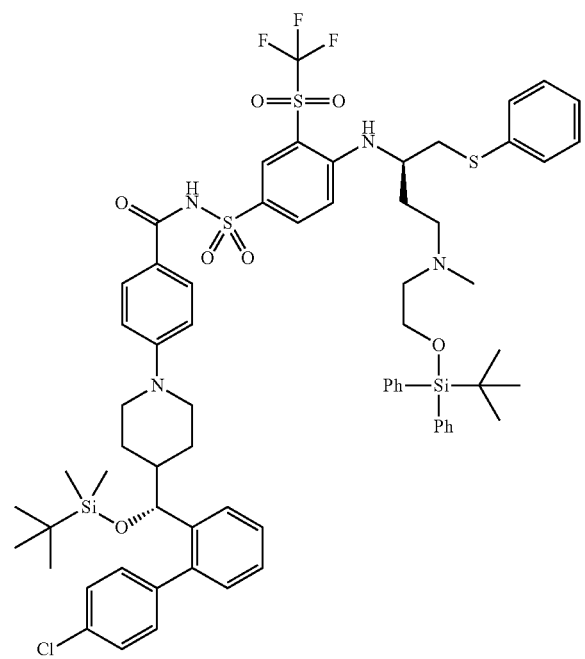 [SMILES: CN(CCO[Si](c1ccccc1)(c1ccccc1)C(C)(C)C)CC[C@H](CSc1ccccc1)Nc1ccc(S(=O)(=O)NC(=O)c2ccc(N3CCC([C@@H](O[Si](C)(C)C(C)(C)C)c4ccccc4-c4ccc(Cl)cc4)CC3)cc2)cc1S(=O)(=O)C(F)(F)F]

The title product (110 mg, yield: 88%) was prepared using a procedure similar to the one described for the synthesis of INTERMEDIATE 32 utilizing 4-(4-((tert-butyldimethylsilyloxy)(4'-chlorobiphenyl-2-yl)methyl)piperidin-1-yl)benzoic acid (INTERMEDIATE 13, 56.7 mg, 0.11 mmol) and (R)-4-(4-((2-(tert-butyldiphenylsilyloxy)ethyl)(methyl)amino)-1-(phenylthio)butan-2-ylamino)-3-(trifluoromethylsulfonyl)benzenesulfonamide (INTERMEDIATE 28, 75 mg, 0.10 mmol) as starting materials. The title product was purified by column chromatography (ISCO, 12 g silica gel column, eluting with 0→30% EtOAc/hexanes).

Intermediate 35

(S)-tert-butyl 4-(3-fluoro-2-hydroxypropyl)piperazine-1-carboxylate and (R)-tert-butyl 4-(3-fluoro-2-hydroxypropyl)piperazine-1-carboxylate, mixture of enantiomers

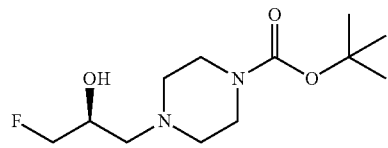

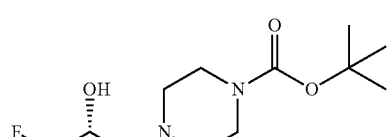

Tert-butyl piperazine-1-carboxylate (2.448 g, 13.15 mmol) was dissolved in ethanol (44.0 ml) and epifluorohydrin (1.00 g, 13.15 mmol) was added to the solution and the resulting reaction mixture was stirred at 50° C. overnight. The reaction mixture was cooled to room temperature, concentrated under reduced pressure and dried under high vacuum overnight to give the title products (0.345 g, yield: quantitative) as a mixture of enantiomers.

¹H NMR (400 MHz, CHLOROFORM-d) δ ppm 4.59-4.46 (m, 1 H), 4.45-4.32 (m, 1 H), 3.98 (m, 1 H), 3.52-3.46 (m, 4 H), 2.66-2.55 (m, 3 H), 2.47-2.38 (m, 3 H), 1.47 (s, 9 H).

LCMS: (ESI) m/z 263 [M+H]⁺.

Intermediate 36

(S)-tert-butyl 4-(2-(tert-butyldiphenylsilyloxy)-3-fluoropropyl)piperazine-1-carboxylate and (R)-tert-butyl 4-(2-(tert-butyldiphenylsilyloxy)-3-fluoropropyl)piperazine-1-carboxylate mixture of enantiomers

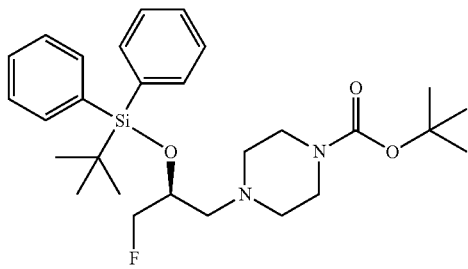

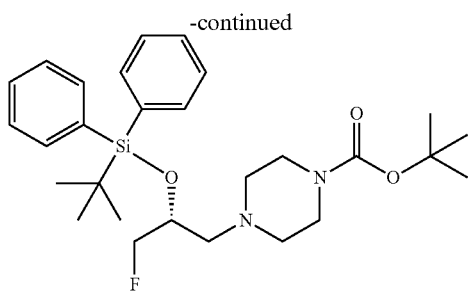

(S)-tert-butyl 4-(3-fluoro-2-hydroxypropyl)piperazine-1-carboxylate and (R)-tert-butyl 4-(3-fluoro-2-hydroxypropyl)piperazine-1-carboxylate, mixture of enantiomers (INTERMEDIATE 35, 3.45 g, 13.15 mmol) were dissolved in DMF (39.0 ml) and imidazole (1.790 g, 26.30 mmol) was added. tert-Butyldiphenylchlorosilane (5.06 ml, 19.73 mmol) was added to the solution and the reaction mixture was stirred at room temperature overnight. The reaction mixture was diluted with EtOAc and washed with H₂O (2×). The organic layer was dried (Na₂SO₄) and purified by SFC chromatography eluting with 90% CO₂/10% MeOH to provide the title products, as a mixture of enantiomers (3.77 g, yield: 57%).

$^1$H NMR (400 MHz, CHLOROFORM-d) δ ppm 7.73-7.70 (m, 4H), 7.46-7.40 (m, 6H), 4.49-4.37 (m, 2H), 3.92 (m, 1H), 3.50 (m, 1H), 3.30-3.20 (m, 4H), 2.45-2.32 (m, 2H), 2.22-2.14 (m, 3H), 1.44 (s, 9H), 1.07 (s, 9H).

LCMS: (ESI) m/z 501 [M+H]$^+$.

Intermediate 37

(S)-1-(2-(tert-butyldiphenylsilyloxy)-3-fluoropropyl)piperazine compound and (R)-1-(2-(tert-butyldiphenylsilyloxy)-3-fluoropropyl)piperazine, mixture of enantiomers

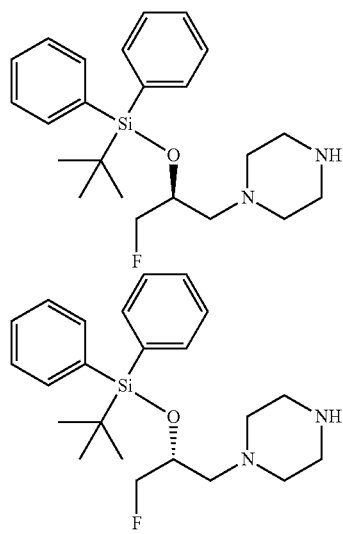

(S)-tert-butyl 4-(2-(tert-butyldiphenylsilyloxy)-3-fluoropropyl)piperazine-1-carboxylate and (R)-tert-butyl 4-(2-(tert-butyldiphenylsilyloxy)-3-fluoropropyl)piperazine-1-carboxylate mixture of enantiomers (INTERMEDIATE 36, 3.7 g, 7.39 mmol) were dissolved in DCM (31.0 ml) and TFA (5.69 ml, 73.89 mmol) was added. The reaction mixture was stirred at room temperature for 2 hours. The reaction mixture was concentrated under reduced pressure, diluted with DCM and was washed with saturated aq. NaHCO₃. The organic layer was dried (Na₂SO₄), concentrated under reduced pressure and dried under high vacuum overnight to provide the title products (3.12 g, yield: 82%).

$^1$H NMR (400 MHz, DMSO-d₆) δ ppm 7.68-7.63 (m, 4 H), 7.50-7.41 (m, 6H), 4.48 (m, 1H), 4.36 (m, 1H), 3.97 (m, 1H), 2.72 (m, 4H), 2.40-2.27 (m, 2H), 2.24-2.20 (m, 4H), 1.00 (s, 9H).

LCMS: (ESI) m/z 401 [M+H]$^+$.

Intermediate 38

4-((R)-4-(4-((R)-2-(tert-butyldiphenylsilyloxy)-3-fluoropropyl)piperazin-1-yl)-4-oxo-1-(phenylthio)butan-2-ylamino)-3-(trifluoromethylsulfonyl)benzenesulfonamide and 4-((R)-4-(4-((S)-2-(tert-butyldiphenylsilyloxy)-3-fluoropropyl)piperazin-1-yl)-4-oxo-1-(phenylthio)butan-2-ylamino)-3-(trifluoromethylsulfonyl)benzenesulfonamide, mixture of diastereomers

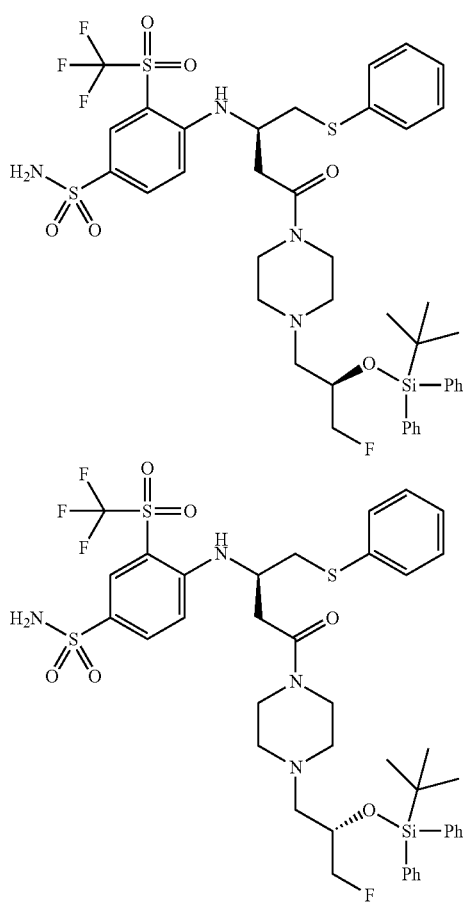

(S)-1-(2-(tert-butyldiphenylsilyloxy)-3-fluoropropyl)piperazine compound and (R)-1-(2-(tert-butyldiphenylsilyloxy)-3-fluoropropyl)piperazine, mixture of enantiomers (INTERMEDIATE 37, 0.194 g, 0.48 mmol) in THF (1.5 ml), diethyl 4-oxobenzo[d][1,2,3]triazin-3(4H)-yl phosphate (0.276 g, 0.92 mmol) and DIPEA (0.161 ml, 0.92 mmol) were added sequentially to a solution of (R)-4-(phenylthio)-3-(4- sulfamoyl-2-(trifluoromethylsulfonyl)phenylamino)bu-
tanoic acid (INTERMEDIATE 8, 0.23 g, 0.46 mmol) in THF
(3.0 ml) and the mixture was stirred at room temperature
overnight. The reaction mixture was concentrated under
reduced pressure, diluted with EtOAc and the organic layer
was washed with 1N aq. NaHSO$_4$ and saturated aq. NaHCO$_3$.
The organic layer was dried (Na$_2$SO$_4$), concentrated under
reduced pressure to give a residue which was purified by
column chromatography (ISCO, 40 g silica gel column, elut-
ing with 0→100% EtOAc/hexanes) to provide the title prod-
ucts (280 mg, yield: 69%).

$^1$H NMR (400 MHz, DICHLOROMETHANE-d$_2$) δ ppm
8.18 (d, 1H), 7.83-7.79 (m, 2 H), 7.73-7.68 (m, 4 H), 7.48-
7.23 (m, 11H), 6.62 (d, 1 H), 4.51-4.44 (m, 1H), 4.39-4.32 (m,
1H), 4.19-4.09 (m, 1H), 3.98-3.88 (m, 1H), 3.37-3.22 (m,
4H), 3.15-3.10 (m, 2H), 2.78 (dd, 1H), 2.56 (dd, 1H), 2.42-
2.32 (m, 2H), 2.20-2.08 (m, 4H), 1.05 (s, 9H).

LCMS: (ESI) m/z 881 [M+H]$^+$.

Intermediate 39

4-((R)-4-(4-((R)-2-(tert-butyldiphenylsilyloxy)-3-
fluoropropyl)piperazin-1-yl)-1-(phenylthio)butan-2-
ylamino)-3-(trifluoromethylsulfonyl)benzene-
sulfonamide and 4-((R)-4-(4-((S)-2-(tert-
butyldiphenylsilyloxy)-3-fluoropropyl)piperazin-1-
yl)-1-(phenylthio)butan-2-ylamino)-3-
(trifluoromethylsulfonyl)benzenesulfonamide
mixture of diastereomers

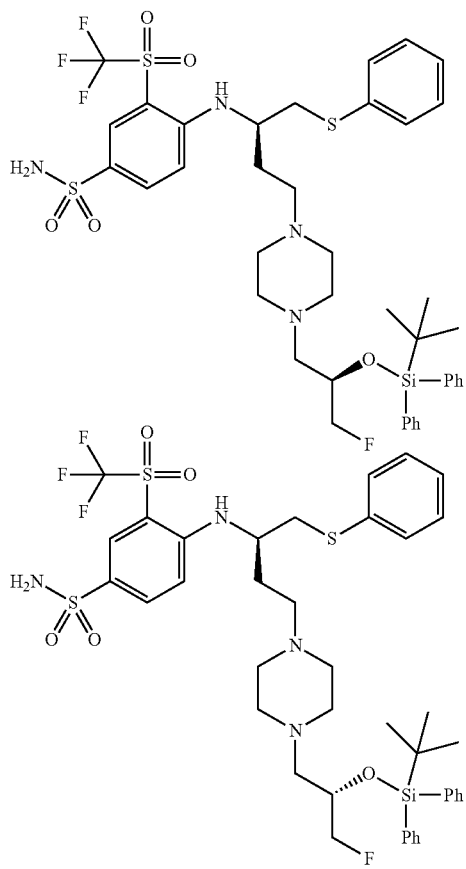

The title product (130 mg, yield: 55%) was prepared using
a procedure similar to the one described for the synthesis of
INTERMEDIATE 25 utilizing 4-((R)-4-(4-((R)-2-(tert-bu-
tyldiphenylsilyloxy)-3-fluoropropyl)piperazin-1-yl)-4-oxo-
1-(phenylthio)butan-2-ylamino)-3-(trifluoromethylsulfonyl)
benzenesulfonamide and 4-((R)-4-(4-((S)-2-(tert-
butyldiphenylsilyloxy)-3-fluoropropyl)piperazin-1-yl)-4-
oxo-1-(phenylthio)butan-2-ylamino)-3-
(trifluoromethylsulfonyl)benzenesulfonamide, mixture of
diastereomers (INTERMEDIATE 38, 0.24 g, 0.27 mmol) as
starting materials. The title products were purified by column
chromatography (ISCO, 12 g silica gel column, eluting with
0→50% DCM/MeOH/NH$_3$ (10:1:0.1).

LCMS: (ESI) m/z 867 [M+H]$^+$.

Intermediate 40

(R)-4-(4-((4'-chlorobiphenyl-2-yl)(hydroxy)methyl)
piperidin-1-yl)benzoic acid

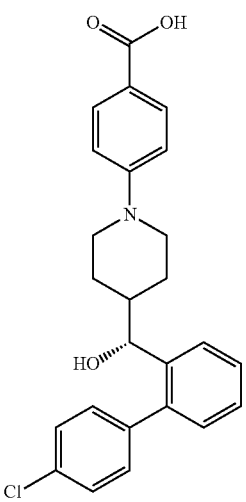 [SMILES: O=C(O)c1ccc(N2CCC([C@@H](O)c3ccccc3-c3ccc(Cl)cc3)CC2)cc1]

A solution of (R)-ethyl 4-(4-((4'-chlorobiphenyl-2-yl)(hy-
droxy)methyl)piperidin-1-yl)benzoate (INTERMEDIATE
11A (First Eluting Compound), 5.37 g, 11.93 mmol) in THF
(160 ml), water (40 ml), and methanol (40 ml) was stirred at
50° C. overnight. The volatiles were removed under reduced
pressure and the resulting residue was diluted with water (100
ml). The pH of the solution was adjusted to ~5 with 1N aq.
HCl (35 ml) promoting the formation of a precipitate. The
white solid was collected via filtration and washed with water
(~150 ml). The filter cake was dried overnight under high
vacuum at 50° C. to provide the title product (4.0 g, yield:
79%).

$^1$H NMR (400 MHz, DMSO-d$_6$) δ ppm 0.63 (qd, 3.79 Hz,
1 H) 0.72-1.00 (m, 2 H) 1.35-1.49 (m, 1 H) 1.67 (d, 1 H)
2.28-2.39 (m, 1 H) 2.46 (t, 1 H) 3.43 (d, 1 H) 3.59 (d, 1 H) 4.09
(d, 1 H) 6.63 (d, 2 H) 6.91 (dd, 1 H) 7.05-7.23 (m, 4 H)
7.23-7.29 (m, 2 H) 7.36 (d, 1 H) 7.47 (d, 2 H).

LCMS: (ESI) m/z 422 [M+H]$^+$.

Intermediate 41

Benzyl bis(2-hydroxyethyl)carbamate

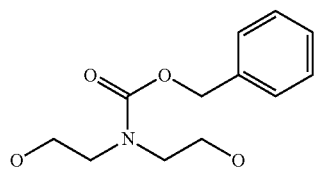 [SMILES: O=C(OCc1ccccc1)N(CCO)CCO]

A suspension of 2,2'-azanediyldiethanol (7.3 ml, 76.09 mmol), sodium carbonate (18.33 g, 172.94 mmol), acetone (125 ml), and water (125 ml) at 0° C. was treated dropwise over a 15 minute period with Cbz-Cl (10.25 ml, 69.17 mmol). The suspension was stirred an additional 3 hours at 0° C. The suspension was diluted with water (500 ml) and extracted with CHCl$_3$ (2×250 ml). The combined organic extracts were dried over sodium sulfate, filtered and concentrated under reduced pressure. The concentrate was purified by column chromatography (ISCO, eluting with MeOH/DCM, 0→10% over 40 minutes) to give the title compound (12.5 g, yield: 76%).

$^1$H NMR (400 MHz, DICHLOROMETHANE-d$_2$) δ ppm 3.04-3.22 (m, 1 H) 3.28-3.43 (m, 1 H) 3.51 (br. s., 4 H) 3.80 (d, 4 H) 5.16 (s, 2 H) 7.24-7.60 (m, 5 H).

LCMS: (ESI) m/z 262 [M+Na]$^+$.

Intermediate 42

Benzyl bis(2-(di-tert-butoxyphosphoryloxy)ethyl)carbamate

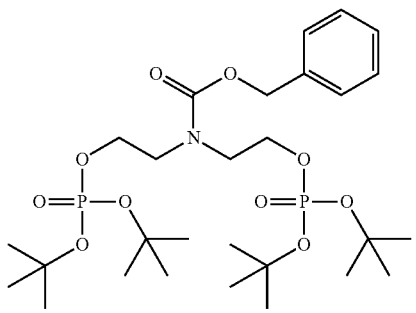 [SMILES: CC(C)(C)OP(=O)(OCCN(CCOP(=O)(OC(C)(C)C)OC(C)(C)C)C(=O)OCc1ccccc1)OC(C)(C)C]

A solution of benzyl bis(2-hydroxyethyl)carbamate (INTERMEDIATE 41, 1.8 g, 7.52 mmol), di-tert-butyl diethylphosphoramidite (5.6 ml, 18.81 mmol), and THF (80 ml), was treated with 1H-tetrazole (1.58 g, 22.57 mmol). The mixture was stirred for 30 min at ambient temperature, subsequently cooled to −78° C. and m-CPBA (7.42 g, 30.09 mmol) was added portion-wise over a 2 minute period. The mixture was stirred for 20 minutes at −78° C. and allowed to warm to room temperature. The volatiles were reduced to ⅔ of the total volume under reduced pressure while the water bath was kept at 30° C. The concentrate was diluted with ethyl acetate (300 ml), washed with 10% aq. sodium bisulfite (100 ml), saturated aq. NaHCO$_3$ (4×100 ml), dried over sodium sulfate. Evaporation of the volatiles under reduced pressure gave a residue that was purified by column chromatography (ISCO, 330 g silica gel column, eluting with 0→20% MeOH in DCM over 53 minutes) to give the title compound (2.5 g, yield: 53%).

$^1$H NMR (400 MHz, DICHLOROMETHANE-d$_2$) δ ppm 1.42-1.51 (m, 36 H) 3.58-3.66 (m, 4 H) 3.99-4.12 (m, 4 H) 5.16 (s, 2 H) 7.39 (d, 5 H).

LCMS: (ESI) m/z 624 [M+H]$^+$.

Intermediate 43

2,2'-azanediylbis(ethane-2,1-diyl) di-tert-butyl diphosphate

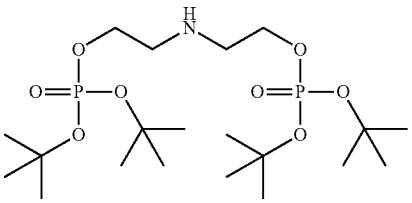 [SMILES: CC(C)(C)OP(=O)(OCCNCCOP(=O)(OC(C)(C)C)OC(C)(C)C)OC(C)(C)C]

A mixture of Pd on carbon (5%, 0.64 g, 0.30 mmol), benzyl bis(2-(di-tert-butoxyphosphoryloxy)ethyl)carbamate (INTERMEDIATE 42, 2.500 g, 4.01 mmol), and MeOH (50 ml) was stirred under an atmosphere of hydrogen for 2 hours. The catalyst was filtered through a pad of Celite® and the filtrate was concentrated under reduced pressure to give the title compound (1.65 g, 84%), which was used in the preparation of INTERMEDIATE 44 without further purification.

$^1$H NMR (400 MHz, METHANOL-d$_4$) δ ppm 1.48-1.58 (m, 36 H) 2.93 (s, 4 H) 3.99-4.22 (m, 4 H)

LCMS: m/z 490 [M+H]$^+$.

Intermediate 44

(R)-Di-tert-butyl 2,2'-(4-(phenylthio)-3-(4-sulfamoyl-2-(trifluoromethylsulfonyl)phenylamino)butylazanediyl)bis(ethane-2,1-diyl)diphosphate

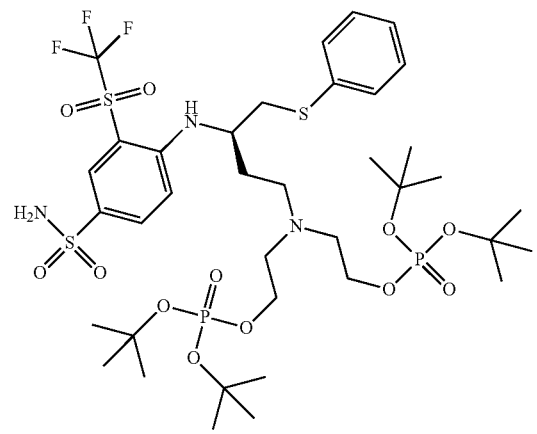 [SMILES: CC(C)(C)OP(=O)(OCCN(CCOP(=O)(OC(C)(C)C)OC(C)(C)C)CC[C@H](CSc1ccccc1)Nc1ccc(S(N)(=O)=O)cc1S(=O)(=O)C(F)(F)F)OC(C)(C)C]

2,2'-azanediylbis(ethane-2,1-diyl)di-tert-butyl diphosphate

A solution of 2,2'-azanediylbis(ethane-2,1-diyl) di-tert-butyl diphosphate (INTERMEDIATE 43, 336 mg, 0.69 mmol), (R)-4-(4-oxo-1-(phenylthio)butan-2-ylamino)-3-(trifluoromethylsulfonyl)benzenesulfonamide (INTERMEDIATE 45, 276 mg, 0.57 mmol), and DCM (10 ml) was treated with sodium triacetoxyborohydride (242 mg, 1.14 mmol). The resulting mixture was stirred at room temperature for 1 hour.

The reaction mixture was diluted with DCM (20 ml) and washed with sodium bicarbonate (saturated, 30 ml). The organic phase was dried over sodium sulfate, filtered, and concentrated under reduced pressure. The concentrate was purified by column chromatography (ISCO, eluting with 0→10% MeOH in DCM over 19 minutes) to give the title compound (311 mg, yield: 57%).

$^1$H NMR (300 MHz, DICHLOROMETHANE-$d_2$) δ ppm 1.36-1.52 (m, 36 H) 1.65 (s, 1 H) 2.04 (s, 1 H) 2.45-2.94 (m, 6 H) 3.21 (d, 2 H) 3.83 (q, 4 H) 4.05-4.31 (m, 1 H) 5.76 (s, 2 H) 6.95 (d, 2 H) 7.19-7.49 (m, 5 H) 7.96-8.09 (m, 1 H) 8.19 (d, 1 H).

LCMS: (ESI) m/z 956 [M+H]$^+$.
Optical Rotation:
Concentration: 0.1 g/dL
Lamp: Sodium
Wavelength: 589 nm
Temperature: 20° C.
Path length: 10 cm
Cell volume: 1 ml
Solvent: Dichloromethane
[α]=+12

Intermediate 45

(R)-4-(4-oxo-1-(phenylthio)butan-2-ylamino)-3-(trifluoromethylsulfonyl)benzenesulfonamide A mixture of (R)-methyl 4-(phenylthio)-3-(4-sulfamoyl-2-(trifluoromethylsulfonyl)phenylamino)butanoate (INTERMEDIATE 7, 3.1 g, 6.05 mmol) in DCM (155 ml) was cooled to −78° C. and DIBAL-H in heptane (18.1 ml, 18.1 mmol) was added dropwise. After addition was complete, the mixture was stirred for 3 hours at −78° C. Methanol (8 ml) and an aqueous solution of Rochelle's salt (15.0 ml) were added sequentially, and the reaction mixture was warmed to r.t. Water (150 ml) was added to the reaction, and the layers were separated. The organic layer was washed with water, dried (Na$_2$SO$_4$), and concentrated in vacuo to afford the title compound (2.9 g, yield: almost quantitative).

$^1$H NMR (300 MHz, CHLOROFORM-d) δ ppm 2.99 (dd2 H) 3.09-3.23 (m, 2 H) 4.22 (br. s., 1 H) 4.78 (s, 1 H) 6.59 (d, 1 H) 7.19 (d, 1 H) 7.30-7.50 (m, 3 H) 7.88 (dd, 1 H) 8.28 (d, 1 H) 9.77 (s, 1 H).

LCMS: (ESI) m/z 481 [M−H]$^+$.

On scales larger than 3.1 g, INTERMEDIATE 7 crashed out of solution in dichloromethane at −78° C. Hence, for reductions involving >3.1 g of INTERMEDIATE 7, the order of addition was reversed such that a solution of INTERMEDIATE 7 in tetrahydrofuran was added to a solution of DIBAL-H at −78° C. while maintaining an internal reaction temperature of ≤−70° C. Once addition of INTERMEDIATE 7 was completed, the reaction was stirred and worked up in a manner identical to that described above.

Intermediate 46

Di-tert-butyl 2,2'-((R)-3-(4-(N-(4-(4-((R)-(4'-chloro-biphenyl-2-yl)(hydroxy)methyl)piperidin-1-yl)ben-zoyl)sulfamoyl)-2-(trifluoromethylsulfonyl)pheny-lamino)-4-(phenylthio)butylazanediyl)bis(ethane-2, 1-diyl)diphosphate A solution of (R)-di-tert-butyl 2,2'-(4-(phenylthio)-3-(4-sulfamoyl-2-(trifluoromethylsulfonyl)phenylamino)butyla-zanediyl)bis(ethane-2,1-diyl)diphosphate (INTERMEDIATE 44, 311 mg, 0.33 mmol), (R)-4-(4-((4'-chlorobiphenyl-2-yl)(hydroxy)methyl)piperidin-1-yl)benzoic acid (INTERMEDIATE 40, 137 mg, 0.33 mmol), EDC (125 mg, 0.65 mmol), DMAP (79 mg, 0.65 mmol), triethylamine (0.1 ml, 0.65 mmol), and DCM (10 ml) was stirred at ambient temperature for 72 hours. The volatiles were removed under reduced pressure and the concentrate was purified by column chromatography (ISCO, 80 g silica gel column, eluting with 0→10% MeOH in DCM over 19 minutes) to give the title compound (258 mg, yield: 58%).

$^1$H NMR (400 MHz, DICHLOROMETHANE-$d_2$) δ ppm 0.92-1.37 (m, 3 H) 1.37-1.55 (m, 37 H) 1.56-1.89 (m, 3 H) 2.04 (s, 2 H) 2.54-2.89 (m, 8 H) 3.20 (dd, 2 H) 3.68-3.80 (m, 1 H) 3.85-4.00 (m, 5 H) 4.02-4.10 (m, 1 H) 4.40-4.60 (m, 1 H) 6.67-6.92 (m, 3 H) 7.09-7.55 (m, 13 H) 7.56-7.73 (m, 3 H) 8.07-8.21 (m, 1 H) 8.40 (d, 1 H).

LCMS: (ESI) m/z 1359 [M+H]$^+$.
Optical Rotation:
Concentration: 0.1 g/dL
Lamp: Sodium
Wavelength: 589 nm
Temperature: 20° C.
Path length: 10 cm
Cell volume: 1 ml
Solvent: Dichloromethane
[α]=+14

Intermediate 47

Benzyl ethyl(2-hydroxyethyl)carbamate

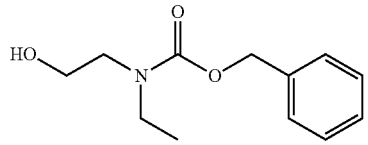 [SMILES: CCN(CCO)C(=O)OCc1ccccc1]

Benzylchloroformate (5.91 g, 34.67 mmol) and triethylamine (5.2 ml) were added sequentially to a solution of 2-(ethylamino)ethanol (3.0 g, 33.66 mmol) in DCM (180 ml) at 0° C. The ice bath was removed and the reaction mixture was allowed to stir overnight at ambient temperature. The solution was washed with 10% citric acid (100 ml) and H$_2$O (2×100 ml) and concentrated in vacuo. The organic phase was dried (MgSO$_4$), concentrated under reduced pressure, and the concentrate was purified by column chromatography (ISCO, silica gel column, eluting with 60→100% EtOAc/hexanes for 14 minutes) to give the title compound (7.29 g, yield: 97%).

$^1$H NMR (300 MHz, CHLOROFORM-d) δ ppm 1.16 (t, 3 H) 3.29-3.53 (m, 4 H) 3.79 (br. s., 2 H) 5.17 (s, 2 H) 7.27-7.45 (m, 5 H).

Intermediate 48

Benzyl 2-(di-tert-butoxyphosphoryloxy)ethyl(ethyl)carbamate

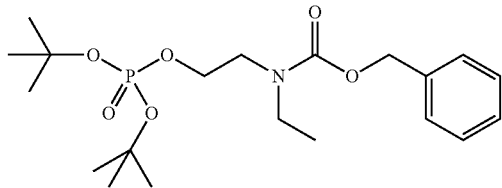 [SMILES: CCN(CCOP(=O)(OC(C)(C)C)OC(C)(C)C)C(=O)OCc1ccccc1]

A solution of benzyl ethyl(2-hydroxyethyl)carbamate (INTERMEDIATE 47, 1.0 g, 4.48 mmol) and di-tert-butyl diethylphosphoramidite (4.47 ml, 16.1 mmol) in THF (146 ml) was treated with tetrazole (1.57 g, 22.39 mmol) in one portion. The resulting mixture was stirred at r.t for 50 minutes and the clear solution became cloudy. The mixture was cooled using an acetone/dry ice bath (~−77° C.) and m-CPBA (6.96 g) was added over the course of ~1 minute. The mixture was stirred under these conditions for 20 minutes and subsequently allowed to warm to r.t. over 10 minutes. Sodium bisulfite (aq., 10% w/v, 3.41 ml) was added and the mixture was stirred for 10 minutes, concentrated in vacuo, diluted with EtOAc (200 ml), and washed with sodium bisulfite (aq., 100 ml), and NaHCO$_3$ (aq., 5% w/v, 100 ml). The organic layer was dried (Na$_2$SO$_4$), filtered, and evaporated under reduced pressure. The concentrate was purified by column chromatography (ISCO, silica gel column, eluting with 0→100% EtOAc in hexanes) to give the title compound (1.1 g, yield: 60%).

$^1$H NMR (300 MHz, CHLOROFORM-d) δ ppm 1.28 (t, 3 H) 1.40-1.53 (s, 18 H) 2.97-3.08 (m, 2 H) 3.56 (d, 2 H) 3.97-4.17 (m, 2 H) 5.15 (s, 2 H) 7.29-7.42 (m, 5 H).

Intermediate 48A

The stereochemistry for INTERMEDIATE 48 was assigned based upon the procedure described below:

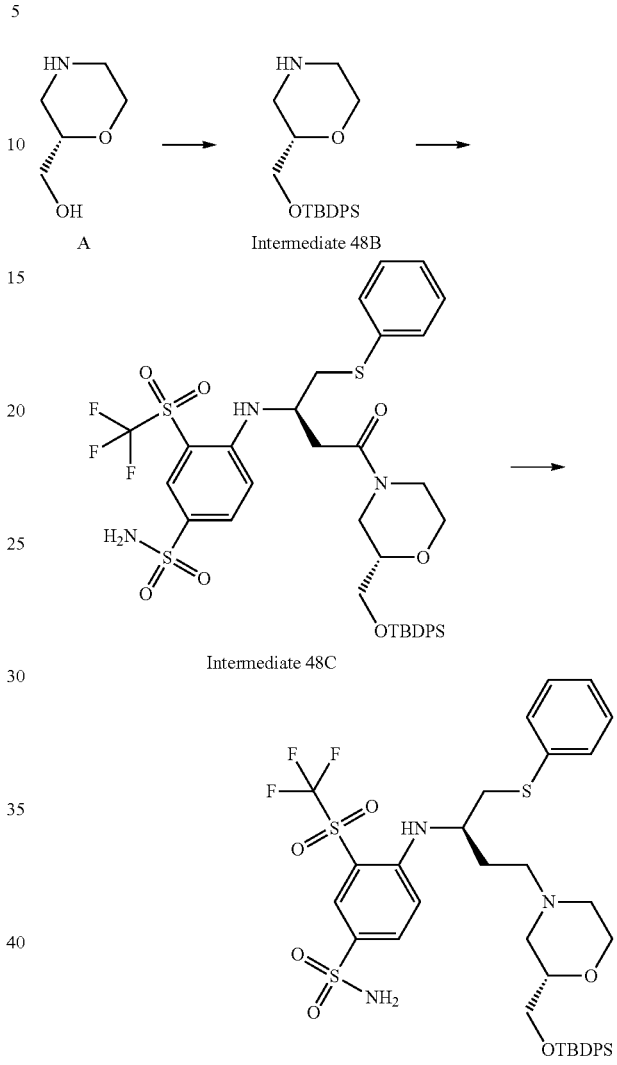

Step 1: Pyridine (0.207 ml, 2.56 mmol) and DMAP (0.021 g, 0.17 mmol) were added to a solution of (S)-morpholin-2-ylmethanol (A, Tyger Scientific Inc, 0.2 g, 1.71 mmol) in DCM (5.0 ml) followed by tert-butylchlorodiphenylsilane (0.526 ml, 2.05 mmol). The reaction mixture was stirred at room temperature for 48 hours. The reaction mixture was concentrated under reduced pressure and the concentrate was purified by column chromatography (ISCO, eluting with 10% MeOH/DCM) to provide (S)-2-((tert-butyldiphenylsilyloxy)methyl)morpholine B (INTERMEDIATE 48B, 0.26 g, yield: 43%).

LCMS: m/z 356 [M+H]$^+$.

Step 2: (R)-4-(Phenylthio)-3-(4-sulfamoyl-2-(trifluoromethylsulfonyl)phenylamino)butanoic acid (INTERMEDIATE 8, 1.51 g, 3.03 mmol) was added to a solution of (S)-2-((tert-butyldiphenylsilyloxy)methyl)morpholine (INTERMEDIATE 48B, 1.185 g, 3.33 mmol) in DMF (9.04 ml) followed by sequential addition of DIPEA (1.058 ml, 6.06 mmol), EDC (0.871 g, 4.54 mmol) and HOBT (0.696 g, 4.54 mmol). The resulting reaction mixture was stirred at room temperature overnight and was then diluted with EtOAc. The organic phase was washed with $H_2O$ (2×), 1N aq. $NaHSO_4$, saturated aq. $NaHCO_3$ and brine. The organic layer was dried ($Na_2SO_4$) and concentrated under reduced pressure to give a residue which was purified by column chromatography (ISCO, eluting with 50% EtOAc/hexanes) to provide 4-((2R)-4-(2-((tert-butyldiphenylsilyloxy)methyl)morpholino)-4-oxo-1-(phenylthio)butan-2-ylamino)-3-(trifluoromethylsulfonyl) benzenesulfonamide (INTERMEDIATE 48C, 2.380 g, yield: 94%).

LCMS: m/z 837 [M+H]$^+$.

Step 3: A solution of $BH_3$.THF complex (0.6 ml, 0.6 mmol) was added slowly to a solution of 4-((2R)-4-(2-((tert-butyldiphenylsilyloxy)methyl)morpholino)-4-oxo-1-(phenylthio)butan-2-ylamino)-3-(trifluoromethyl sulfonyl)benzenesulfonamide (INTERMEDIATE 48C, 0.083 g, 0.10 mmol) and THF (0.4 ml) and the resulting reaction mixture was stirred at room temperature overnight. The mixture was diluted with a solution of $NH_3$ in MeOH (7N, 20 mL) and was stirred at room temperature overnight. Evaporation of the volatiles under reduced pressure gave a residue, which was diluted with EtOAc. The organic phase was washed with $H_2O$ (2×), dried ($Na_2SO_4$), filtered and concentrated under reduced pressure to provide 4-((R)-4-((S)-3-((tert-butyl diphenylsilyloxy)methyl)morpholino-1-yl)-1-(phenylthio) butan-2-ylamino)-3-(trifluoromethyl sulfonyl)benzenesulfonamide (INTERMEDIATE 48D, 0.030 g, 37%), which matched INTERMEDIATE 48 upon examination on the chiral HPLC conditions previously tested.

LCMS: m/z 822 [M+H]$^+$.

Intermediate 49

Di-tert-butyl 2-(ethylamino)ethyl phosphate

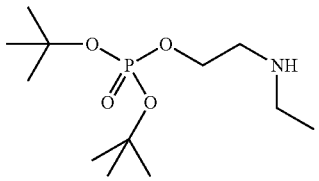 [SMILES: CCNCCOP(=O)(OC(C)(C)C)OC(C)(C)C]

Benzyl 2-(di-tert-butoxyphosphoryloxy)ethyl(ethyl)carbamate (INTERMEDIATE 48, 0.9 g, 2.17 mmol) was dissolved in methanol (5 ml), and 5% Pd on charcoal (0.10 g) was added. The reaction mixture was stirred at r.t under a hydrogen atmosphere overnight. The reaction mixture was filtered and concentrated in vacuo to give the title compound (0.57 g, yield: 94%).

$^1$H NMR (300 MHz, CHLOROFORM-d) δ ppm 1.15 (t, 3 H) 1.42-1.55 (m, 18 H) 2.72 (d, 2 H) 2.84-2.96 (m, 2 H) 4.04-4.14 (m, 2 H).

Intermediate 50

(R)-di-tert-butyl 2-(ethyl(4-(phenylthio)-3-(4-sulfamoyl-2-(trifluoromethylsulfonyl)phenylamino)butyl) amino)ethyl phosphate

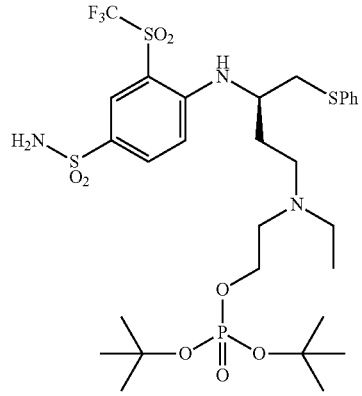

A solution of di-tert-butyl 2-(ethylamino)ethyl phosphate (INTERMEDIATE 49, 455 mg, 1.62 mmol) in 1,2-dichloroethane (0.5 ml) at r.t was added to a solution (R)-4-(4-oxo-1-(phenylthio)butan-2-ylamino)-3-(trifluoromethylsulfonyl) benzenesulfonamide (INTERMEDIATE 45, 0.78 g, 1.62 mmol) and 1,2-dichloroethane (10.0 ml). The resulting reaction mixture was stirred for 15 minutes at r.t and solid sodium triacetoxyborohydride (0.514 g, 2.42 mmol) was added. The resulting mixture was stirred at r.t for 4 hours. A solution of NaOH (aq., 0.5 N, 40 ml) and DCM (20 ml) were added to the reaction mixture. After stirring for 15 min at r.t, the layers were separated. After separation, the organic layer was washed with saturated $NaHCO_3$, brine, dried ($Na_2SO_4$), and concentrated in vacuo. The concentrate was purified by column chromatography (ISCO, silica gel, eluting with 0→100% EtOAc/hexanes) to give the title compound (610 mg, yield: 50%).

$^1$H NMR (300 MHz, CHLOROFORM-d) δ ppm 0.96 (t, 3 H) 1.32-1.53 (m, 18 H) 1.58 (s, 3 H) 2.37-2.60 (m, 4 H) 3.10 (d, 2 H) 3.71 (d, 2 H) 3.91-4.08 (m, 1 H) 5.43 (s, 2 H) 6.75 (d, 1 H) 6.98 (d, 1 H) 7.27-7.44 (m, 4 H) 7.93 (dd, 1 H) 8.26 (d, 1 H).

LCMS: (ESI) m/z 746 [M–H]$^+$.

Intermediate 51

Benzyl 2-hydroxyethyl(methyl)carbamate

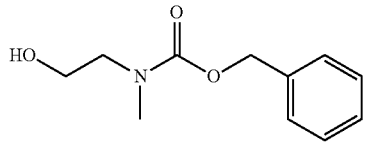

A similar procedure to that described for INTERMEDIATE 47 utilizing 2-(methylamino)ethanol (2.3 g, 30.62 mmol) as starting material was followed, with subsequent purification by column chromatography (ISCO, silica gel column, eluting with 60→100% EtOAc/hexanes for 14 minutes) to give the title product (5.96 g, yield: 93%).

$^1$H NMR (300 MHz, CHLOROFORM-d) δ ppm 2.25 (br. s., 1 H) 3.02 (s, 3 H) 3.48 (t, 2 H) 3.78 (br. s., 2 H) 5.15 (s, 2 H) 7.21-7.44 (m, 5 H).

Intermediate 52

Benzyl 2-(di-tert-butoxyphosphoryloxy)ethyl(methyl)carbamate

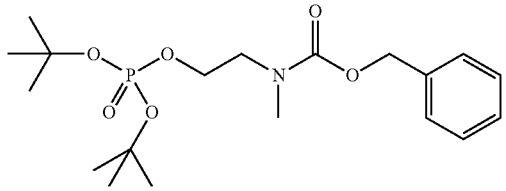 [SMILES: CN(CCOP(=O)(OC(C)(C)C)OC(C)(C)C)C(=O)OCc1ccccc1]

A similar procedure to that described for INTERMEDIATE 48 utilizing benzyl 2-hydroxyethyl(methyl)carbamate (INTERMEDIATE 51, 0.46 g, 2.20 mmol) as starting material was followed, with subsequent purification by column chromatography (ISCO, 12 g silica gel column, eluting with 0→100% EtOAc/hexanes) to give the title product (590 mg, yield: 67%).

$^1$H NMR (300 MHz, CHLOROFORM-d) δ ppm 1.39-1.53 (m, 18 H) 2.95-3.09 (m, 3 H) 3.56 (d, 2 H) 4.07 (dd, 2 H) 5.15 (s, 2 H) 7.25-7.43 (m, 5 H).

Intermediate 53

Di-tert-butyl 2-(methylamino)ethyl phosphate

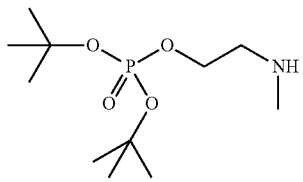 [SMILES: CNCCOP(=O)(OC(C)(C)C)OC(C)(C)C]

A similar procedure to that described for INTERMEDIATE 49 utilizing benzyl 2-(di-tert-butoxyphosphoryloxy)ethyl(methyl)carbamate (INTERMEDIATE 52, 0.59 g, 1.47 mmol) as starting material was followed, to give the title product (370 mg, yield: 95%).

$^1$H NMR (300 MHz, CHLOROFORM-d) δ ppm 1.48-1.55 (m, 18 H) 2.67 (s, 3 H) 3.11-3.22 (m, 2 H) 4.21-4.36 (m, 2 H).

Intermediate 54

(R)-di-tert-butyl 2-(methyl(4-(phenylthio)-3-(4-sulfamoyl-2-(trifluoromethylsulfonyl)phenylamino)butyl)amino)ethyl phosphate

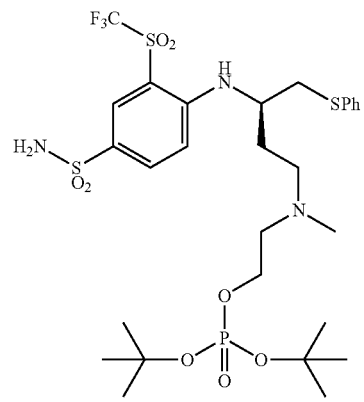

A similar procedure to that described for INTERMEDIATE 50 utilizing (R)-4-(4-oxo-1-(phenylthio)butan-2-ylamino)-3-(trifluoromethylsulfonyl)benzenesulfonamide (INTERMEDIATE 45, 0.68 g, 1.4 mmol) and di-tert-butyl 2-(methylamino)ethyl phosphate (INTERMEDIATE 53 0.37 mg, 1.4 mmol) as starting materials was followed, with subsequent purification by column chromatography (ISCO, 12 g silica gel column, eluting with 0→100% EtOAc/hexanes) to give the title product (640 mg, yield: 62%).

$^1$H NMR (300 MHz, CHLOROFORM-d) δ ppm 1.35-1.52 (m, 18 H) 2.21 (s, 3 H) 2.54 (br. s., 2 H) 3.10 (t, 2 H) 3.80 (br. s., 3 H) 3.96-4.11 (m, 2 H) 5.45 (br. s., 2 H) 6.84 (d, 1 H) 7.04 (s, 1 H) 7.27-7.44 (m, 4 H) 7.98 (dd, 1 H) 8.25 (d, 1 H).

LCMS: (ESI) m/z 732 [M–H]$^+$.

Intermediate 55

Di-tert-butyl 2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl phosphate

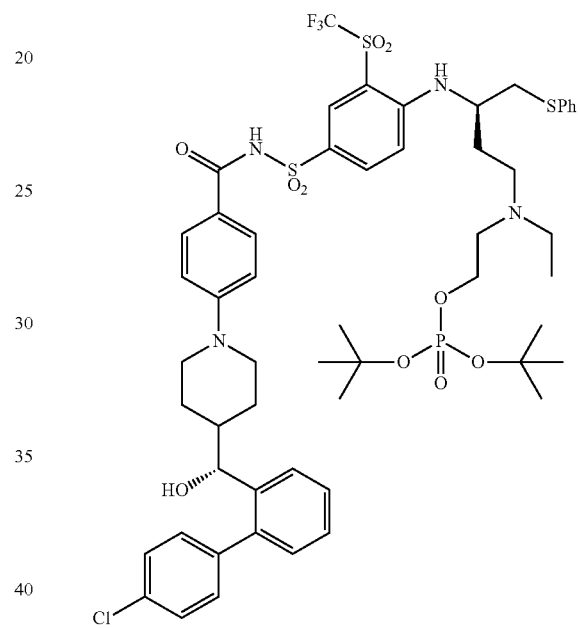

To a solution of (R)-4-(4-((4'-chlorobiphenyl-2-yl)(hydroxy)methyl)piperidin-1-yl)benzoic acid (INTERMEDIATE 40, 88 mg, 0.20 mmol), EDC (77 mg, 0.40 mmol), and DMAP (49 mg, 0.40 mmol), triethylamine (28 μl, 0.20 mmol) in 5 ml of DCM was added (R)-di-tert-butyl 2-(ethyl(4-(phenylthio)-3-(4-sulfamoyl-2-(trifluoromethylsulfonyl)phenylamino)butyl)amino)ethyl phosphate (INTERMEDIATE 50, 150 mg, 0.20 mmol). The mixture was stirred at r.t overnight. The reaction solution was diluted with DCM (20 ml) and washed with water (30 ml). The aqueous layer was extracted with DCM (30 ml) and the combined organic layers were dried over sodium sulfate, and concentrated in vacuo to an oil. This material was purified by column chromatography (ISCO, 0→100% EtOAc/hexane followed by 0→10% MeOH/EtOAc) to provide the title compound (137 mg, yield: 59%).

$^1$H NMR (300 MHz, CHLOROFORM-d) δ ppm 0.85-1.10 (m, 4 H) 1.16-1.35 (m, 1 H) 1.48 (d, 18 H) 1.81 (br. s., 3 H) 2.40-2.88 (m, 8 H) 3.11 (d, 2 H) 3.62-3.76 (m, 1 H) 3.93 (d, 4 H) 4.50 (d, 1 H) 6.58-6.70 (m, 1 H) 6.77 (d, 2 H) 7.11-7.51 (m, 12 H) 7.54-7.70 (m, 3 H) 8.12 (br. s., 1 H) 8.38 (s, 1 H).

LCMS: (ESI) m/z 1150 [M–H]$^+$.

Intermediate 56

Di-tert-butyl 2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl phosphate

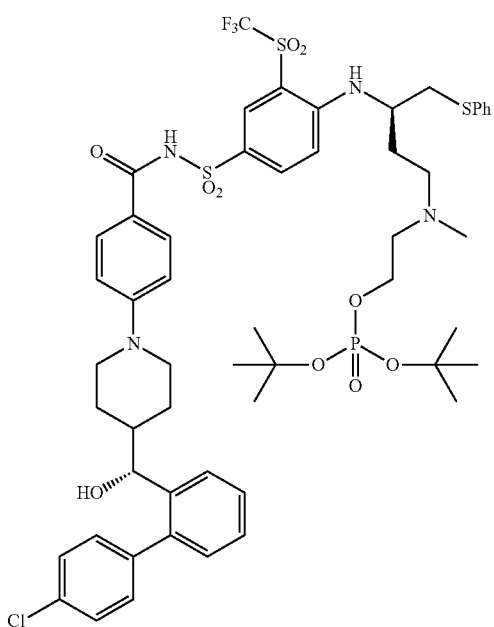

A similar procedure to that described for INTERMEDIATE 55 utilizing (R)-4-(4-((4'-chlorobiphenyl-2-yl)(hydroxy)methyl)piperidin-1-yl)benzoic acid (INTERMEDIATE 40, 63 mg, 0.14 mmol) and (R)-di-tert-butyl 2-(methyl(4-(phenylthio)-3-(4-sulfamoyl-2-(trifluoromethylsulfonyl)phenylamino)butyl)amino)ethyl phosphate (INTERMEDIATE 54, 105 mg, 0.14 mmol) as starting materials was followed, with subsequent purification by column chromatography (ISCO, 0→100% EtOAc/hexane followed by 0→10% MeOH/EtOAc) to give the title product (98 mg, yield: 60%).

$^1$H NMR (300 MHz, CHLOROFORM-d) δ ppm 0.97-1.12 (m, 2 H) 1.48 (d, 21 H) 1.79 (br. s., 4 H) 2.27 (br. s., 3 H) 2.68 (br. s., 7 H) 3.10 (br. s., 2 H) 3.69 (br. s., 1 H) 3.81-4.09 (m, 4 H) 4.50 (d, 1 H) 6.55-6.68 (m, 1 H) 6.78 (d, 2 H) 7.12-7.52 (m, 12 H) 7.53-7.67 (m, 3 H) 8.13 (d, 1 H) 8.39 (d, 1 H).

LCMS: (ESI) m/z 1138 [M+H]+.

Intermediate 57

Benzyl 4-(2-chloroethyl)piperazine-1-carboxylate

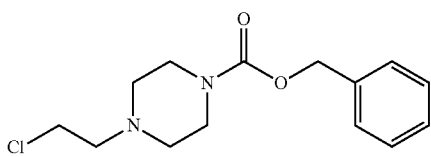 [SMILES: O=C(OCc1ccccc1)N1CCN(CCCl)CC1]

Benzyl piperazine-1-carboxylate (1.00 g, 4.54 mmol) and K2CO3 (1.255 g, 9.08 mmol) were dissolved in acetonitrile (12.87 ml) to form a suspension. 1-bromo-2-chloroethane (2.3 ml, 27.24 mmol) was added to the reaction mixture at r.t and the resulting mixture was stirred at this temperature for 96 hours. The reaction mixture was filtered, and the filtrate concentrated under reduced pressure. Purification by column chromatography (ISCO, silica gel column, eluting with 0→100% EtOAc in hexanes) gave the title compound (0.64 g, yield: 50%).

$^1$H NMR (300 MHz, CHLOROFORM-d) d ppm 7.28-7.43 (m, 5 H) 5.15 (s, 2 H) 3.48-3.65 (m, 6 H) 2.76 (t, 2 H) 2.42-2.57 (m, 4 H).

LCMS: (ESI) m/z 283 [M+H]+.

Intermediate 58

Benzyl 4-(2-(di-tert-butoxyphosphoryloxy)ethyl)piperazine-1-carboxylate

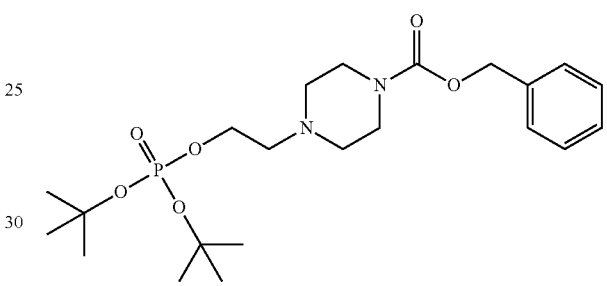

A solution of benzyl 4-(2-chloroethyl)piperazine-1-carboxylate (INTERMEDIATE 57 0.12 g, 0.42 mmol) in toluene (1.415 ml) was treated with silver di-tert-butyl phosphate (INTERMEDIATE 59, 0.148 g, 0.47 mmol). The reaction mixture was stirred at 100° C. for 100 mins. The reaction mixture was filtered and the filtrate was concentrated under reduced pressure to give the title compound (0.14 g, yield: 73%), which was used in the preparation of INTERMEDIATE 60, without further purification.

$^1$H NMR (300 MHz, CHLOROFORM-d) δ ppm 7.31-7.43 (m, 5 H) 5.15 (s, 2 H) 4.01-4.14 (m, 2 H) 3.47-3.60 (m, 4 H) 2.69 (t, 2 H) 2.44-2.57 (m, 4 H) 1.50 (s, 18 H).

LCMS: (ESI) m/z 457 [M+H]+.

Intermediate 59

Silver di-tert-butyl phosphate

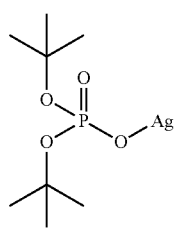

Potassium di-tert-butyl phosphate (18.94 g, 76.28 mmol) was dissolved in water (140 ml) and cooled in an ice bath. The solution was swirled by hand and treated dropwise with concentrated HCl (~28 ml), which resulted in a white precipitate.

The precipitate was collected on a Büchner funnel, washed with water (70 ml), and air-dried for several minutes. In a 2 L beaker, the resulting damp powder (15.09 g) was dissolved in a mixture of barium hydroxide octahydrate (24.12 g, 76.45 mmol) in water (400 ml). Carbon dioxide (g) was bubbled through the solution resulting in copious formation of white precipitate. The mixture was filtered through Buchner funnel, and the cloudy filtrate was evaporated to give a white solid (~21 g). Most of the material was dissolved in MeOH (~250 ml). A white, powdery suspension was removed by filtration through Celite® and the clear filtrate was evaporated to give damp white solid (~20 g). The material was dissolved in MeOH (25-30 ml), and precipitated by the addition of acetone (900 ml). The white precipitate was collected on a Buchner funnel and washed with acetone to give barium di-tert-butyl phosphate as a white solid (14.60 g, 26.27 mmol). The barium di-tert-butyl phosphate was dissolved in water (100 ml), and added to a solution of silver sulfate (8.19 g, 26.27 mmol) in water (1100 ml), which resulted in formation of a white precipitate. The mixture was filtered through Celite® and the clear filtrate was evaporated to give a white solid. Most of the material was dissolved in MeOH (~600 ml) and a white powdery suspension was removed by filtration through Celite®. The filtrate was concentrated, treated with toluene (~200 ml) and evaporated to dryness to give the title compound (15.1 g, yield: 62%).

LCMS: (ESI) m/z 209 [M-Ag].

Intermediate 60

Di-tert-butyl 2-(piperazin-1-yl)ethyl phosphate

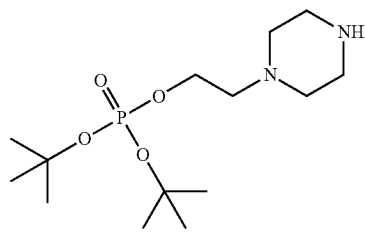 [SMILES: CC(C)(C)OP(=O)(OCCN1CCNCC1)OC(C)(C)C]

A 100 ml flask was charged with benzyl 4-(2-(di-tert-butoxyphosphoryloxy)ethyl)piperazine-1-carboxylate (INTERMEDIATE 58, 0.90 g, 1.97 mmol) in MeOH (19.7 ml) and 10% palladium on charcoal (0.042 g, 0.04 mmol). The reaction mixture was stirred under a hydrogen atmosphere overnight. The reaction mixture was filtered and the filtrate concentrated in vacuo to give the title compound (0.63 g, yield: 99%), which was used in the preparation of INTERMEDIATE 61 without further purification.

$^1$H NMR (300 MHz, CHLOROFORM-d) δ ppm 4.08 (d, 2 H) 3.50 (s, 3 H) 2.89-2.99 (m, 4 H) 2.67 (t, 2 H) 2.51-2.61 (m, 4 H) 1.50 (s, 18 H). LCMS: (ESI) m/z 323 [M+H]$^+$.

Intermediate 61

(R)-di-tert-butyl 2-(4-(4-(phenylthio)-3-(4-sulfa-moyl-2-(trifluoromethylsulfonyl)phenylamino)butyl) piperazin-1-yl)ethyl phosphate

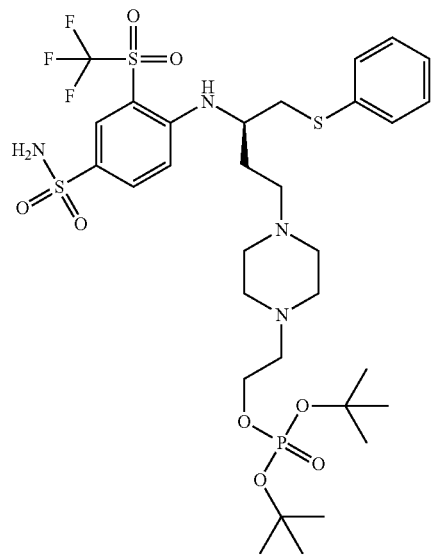 [SMILES: CC(C)(C)OP(=O)(OCCN1CCN(CC[C@H](CSc2ccccc2)Nc2ccc(S(N)(=O)=O)cc2S(=O)(=O)C(F)(F)F)CC1)OC(C)(C)C]

A solution of di-tert-butyl 2-(piperazin-1-yl)ethyl phosphate (INTERMEDIATE 60, 0.31 g, 0.95 mmol) in 1,2-dichloroethane (4 ml) was added to a solution of (R)-4-(4-oxo-1-(phenylthio)butan-2-ylamino)-3-(trifluoromethylsulfonyl)benzenesulfonamide (INTERMEDIATE 45, 0.46 g, 0.95 mmol) in dichloroethane (5.0 ml) at room temperature. The reaction mixture was allowed to stir for 15 minutes at r.t, and solid sodium triacetoxyborohydride (0.30 g, 1.43 mmol) was added. The mixture was stirred for 1 hour at ambient temperature. To the reaction mixture was added 0.5 N NaOH (10 ml) and DCM (20 ml). After stirring for 15 mins at r.t, the layers were separated and the organic layer was washed with NaHCO$_3$ (saturated aq.) and brine, and dried (Na$_2$SO$_4$). The volatiles were removed under reduced pressure. Purification by column chromatography (ISCO, silica gel, eluting with 0→100% EtOAc/hexanes) gave the title compound (0.71 g, yield: 94%).

$^1$H NMR (300 MHz, CHLOROFORM-d) δ ppm 8.26 (d, 1 H) 7.91 (dd, 1 H) 7.29-7.44 (m, 6 H) 5.24 (br. s., 2 H) 4.07 (br. s., 2 H) 3.94 (br. s., 1 H) 3.10 (d, 2 H) 2.74 (br. s., 3 H) 2.57 (br. s., 4 H) 2.41 (br. s., 5 H) 2.07 (br. s., 1 H) 1.51 (d, 18 H).

LCMS: (ESI) m/z 790 [M+H]$^+$.

Intermediate 62 di-tert-butyl 2-(4-((R)-3-(4-(N-(4-(4-((R)-(tert-butyldimethylsilyloxy)(4'-chlorobiphenyl-2-yl)methyl)piperidin-1-yl)benzoyl)sulfamoyl)-2-(trifluoromethylsulfonyl)phenylamino)-4-(phenylthio)butyl)piperazin-1-yl)ethyl phosphate

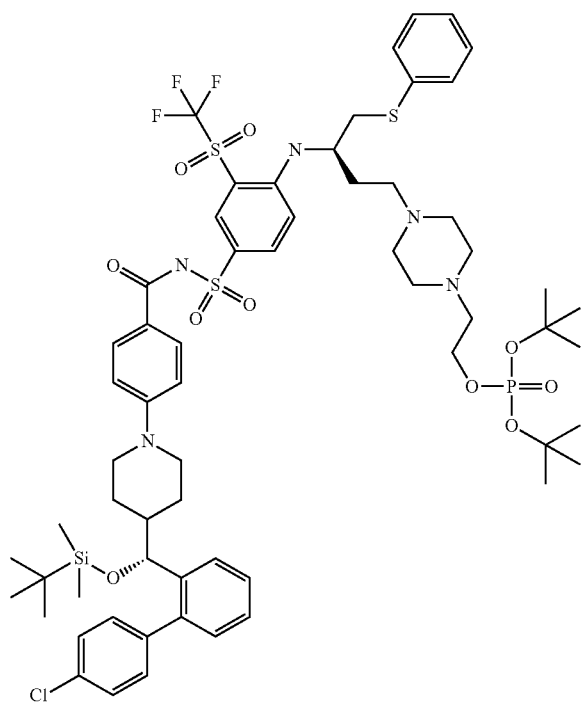 [SMILES: CC(C)(C)OP(=O)(OCCN1CCN(CC[C@H](CSc2ccccc2)Nc2ccc(S(=O)(=O)NC(=O)c3ccc(N4CCC([C@@H](O[Si](C)(C)C(C)(C)C)c5ccccc5-c5ccc(Cl)cc5)CC4)cc3)cc2S(=O)(=O)C(F)(F)F)CC1)OC(C)(C)C]

(R)-4-(4-((tert-butyldimethylsilyloxy)(4'-chlorobiphenyl-2-yl)methyl)piperidin-1-yl)benzoic acid (INTERMEDIATE 13, 170 mg, 0.32 mmol), (R)-di-tert-butyl 2-(4-(4-(phenylthio)-3-(4-sulfamoyl-2-(trifluoromethylsulfonyl)phenylamino)butyl)piperazin-1-yl)ethyl phosphate (INTERMEDIATE 61, 275 mg, 0.35 mmol), DMAP (116 mg, 0.95 mmol) and EDC (122 mg, 0.63 mmol) were dissolved in DCM (3.2 ml). The reaction mixture was stirred at r.t. for 72 hours. The mixture was diluted with DCM (10 ml) and washed with NaHCO$_3$ solution (saturated, aq., 5 ml) and brine (5 ml). The collected organic layer was dried over Na$_2$SO$_4$ and concentrated to give the title compound (446 mg, yield: almost quantitative). The title compound was used in the preparation of EXAMPLE 10 without further purification.

LCMS: (ESI) 1307 [M+H]$^+$.

Intermediate 63

2-(tert-butyldimethylsilyloxy)-N-ethylethanamine

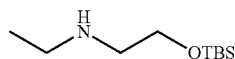

DIPEA (5.48 ml, 31.38 mmol) and tert-butylchlorodimethylsilane (6.76 g, 22.42 mmol) were added to a solution of 2-(ethylamino)ethanol (1.998 g, 22.42 mmol) in DCM (39.3 ml) at room temperature. The mixture was stirred at room temperature for 20 hours, partitioned between H$_2$O/Et$_2$O (50 ml/50 ml). The aqeuous phase was extracted with ether (3×30 ml). The combined organic layers were concentrated under reduced pressure to give a residue which was re-dissolved in DCM (50 ml), dried (Na$_2$SO$_4$), filtered and concentrated under vacuum to give the title compound (3.9 g, yield: 85%).

$^1$H NMR (300 MHz, CHLOROFORM-d) δ ppm 3.66 (t, 2 H) 2.55-2.69 (m, 4 H) 1.43 (br. s., 1 H) 1.05 (t, 3 H) 0.80-0.86 (m, 9 H) −0.03-0.05 (m, 6 H).

LCMS: m/z 204 [M+H]$^+$.

Intermediate 64

2-(tert-butyldimethylsilyloxy)-N-methylethanamine

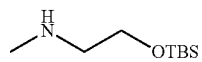

A similar procedure to that described for INTERMEDIATE 63 utilizing 2-(methylamino)ethanol (2.0 g, 26.68 mmol) as starting material was followed, to give the title product (4.17 g, yield: 83%).

LCMS: m/z 190 [M+H]$^+$.

$^1$H NMR (300 MHz, CHLOROFORM-d) δ ppm 3.61-3.69 (m, 2 H) 2.57-2.65 (m, 2 H) 2.39 (s, 3 H) 1.47 (br. s., 1 H) 0.80-0.87 (m, 9 H) −0.04-0.01 (m, 6 H).

Intermediate 65

(R)-4-(4-((2-(tert-butyldimethylsilyloxy)ethyl)(ethyl)amino)-1-(phenylthio)butan-2-ylamino)-3-(trifluoromethylsulfonyl)benzenesulfonamide

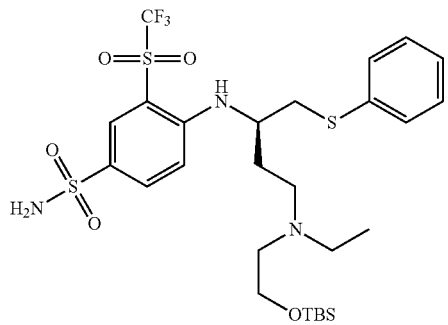 [SMILES: CCN(CCO[Si](C)(C)C(C)(C)C)CC[C@H](CSc1ccccc1)Nc1ccc(S(N)(=O)=O)cc1S(=O)(=O)C(F)(F)F]

To a solution of (R)-4-(4-oxo-1-(phenylthio)butan-2-ylamino)-3-(trifluoromethylsulfonyl)benzenesulfonamide (INTERMEDIATE 45, 3.98 g, 8.25 mmol) and 2-(tert-butyldimethylsilyloxy)-N-ethylethanamine (INTERMEDIATE 63, 1.68 g, 8.25 mmol) in 1,2-dichloroethane (27.5 ml) was added sodium triacetoxyborohydride (2.62 g, 12.37 mmol). The resulting mixture was stirred in the dark for 11.5 h and was then quenched with 0.5 M aqueous sodium hydroxide (50 ml). After vigorous stirring for 10 min, the opaque mixture became clear. The layers were diluted with ethyl acetate and then separated. The organic layer was washed with saturated aqueous sodium bicarbonate and saturated aqueous sodium chloride before being dried over sodium sulfate, filtered, and concentrated under reduced pressure. The resulting residue was purified by column chromatography (ISCO, 330 g SiO$_2$, 50→100% ethyl acetate in hexanes for 20 mins then 0→20% methanol in ethyl acetate for 20 mins followed by 0→20% methanol in ethyl acetate over 20 min) to afford the title product (3.41 g, yield: 62%).

LCMS: (ESI) m/z 670 [M+H]$^+$.

Intermediate 66

N-(4-((R)-4-((2-(tert-butyldimethylsilyloxy)ethyl)(ethyl)amino)-1-(phenylthio)butan-2-ylamino)-3-(trifluoromethylsulfonyl)phenylsulfonyl)-4-(4-((R)-(4'-chlorobiphenyl-2-yl)(hydroxy)methyl)piperidin-1-yl)benzamide

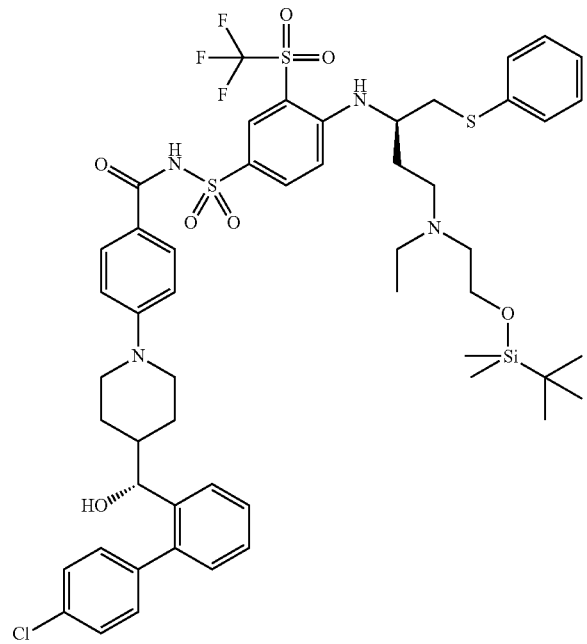 [SMILES: CCN(CCO[Si](C)(C)C(C)(C)C)CC[C@H](CSc1ccccc1)Nc1ccc(S(=O)(=O)NC(=O)c2ccc(N3CCC([C@@H](O)c4ccccc4-c4ccc(Cl)cc4)CC3)cc2)cc1S(=O)(=O)C(F)(F)F]

(R)-4-(4-((4'-chlorobiphenyl-2-yl)(hydroxy)methyl)piperidin-1-yl)benzoic acid (INTERMEDIATE 40, 2.15 g, 5.10 mmol), (R)-4-(4-((2-(tert-butyldimethylsilyloxy)ethyl)(ethyl)amino)-1-(phenylthio)butan-2-ylamino)-3-(trifluoromethylsulfonyl)benzenesulfonamide (INTERMEDIATE 65, 3.41 g, 5.10 mmol), DMAP (1.87 g, 15.29 mmol) and EDC (1.954 g, 10.19 mmol) were dissolved in DCM (17 ml). The reaction mixture was stirred at r.t. overnight, diluted with DCM (50 ml) and washed with NH$_4$Cl solution (saturated, aq., 20 ml), saturated aq. NaHCO$_3$ (20 ml) and brine (20 ml). The collected organic layer was dried over Na$_2$SO$_4$ and concentrated under reduced pressure. The concentrate was purified by column chromatography (ISCO, 12 g silica gel, eluted with 0→20% MeOH in EtOAc) to provide the title compound (3.41 g, yield: 62%).

$^1$H NMR (300 MHz, DICHLOROMETHANE-d2) δ ppm 8.27 (s, 1 H) 7.92 (d, 1 H) 7.63 (d, 2 H) 7.55-7.59 (m, 1 H) 7.30-7.45 (m, 5 H) 7.15-7.30 (m, 6 H) 7.06 (d, 1 H) 6.74 (d, 2 H) 6.63 (d, 1 H) 4.46 (d, 1 H) 3.94 (d, 1 H) 3.83 (d, 1 H) 3.62-3.72 (m, 3 H) 3.08 (d, 2 H) 2.55-2.78 (m, 9 H) 2.00 (br. s., 2 H) 1.88 (br. s., 1 H) 1.69-1.83 (m, 2 H) 1.20-1.35 (m, 1 H) 1.15 (br. s., 1 H) 0.94-1.06 (m, 4 H) 0.80-0.87 (m, 9 H) 0.00 (s, 6 H).

LCMS: (ESI) m/z 1074 [M+H]$^+$.

Intermediate 67

(R)-4-(4-((2-(tert-butyldimethylsilyloxy)ethyl)(methyl)amino)-1-(phenylthio)butan-2-ylamino)-3-(trifluoromethylsulfonyl)benzenesulfonamide

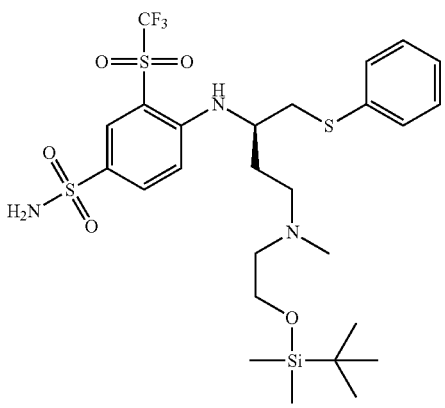 [SMILES: CN(CCO[Si](C)(C)C(C)(C)C)CC[C@H](CSc1ccccc1)Nc1ccc(S(N)(=O)=O)cc1S(=O)(=O)C(F)(F)F]

To a solution of (R)-4-(4-oxo-1-(phenylthio)butan-2-ylamino)-3-(trifluoromethylsulfonyl)benzenesulfonamide (INTERMEDIATE 45, 3.98 g, 8.25 mmol) and 2-(tert-butyldimethylsilyloxy)-N-methylethanamine (INTERMEDIATE 64, 1.56 g, 8.25 mmol) in 1,2-dichloroethane (27.5 ml) was added sodium triacetoxyborohydride (2.62 g, 12.37 mmol). The resulting mixture was stirred in the dark for 11.5 hours and then sodium hydroxide (0.5 M, aq., 50 ml) was added. The mixture was diluted with dichloromethane (70 ml) and stirred vigorously for 10 min. The layers were separated, and the organic layer was washed with saturated aqueous sodium bicarbonate. The organic layer was then diluted heavily with ethyl acetate and washed with saturated aqueous sodium chloride (×2) before being dried over sodium sulfate, filtered, and concentrated under reduced pressure. The resulting residue was purified by column chromatography (ISCO, 330 g SiO$_2$, 0→50% ethyl acetate in hexanes over 30 min, then isocratic hold for 30 min, then 50→100% ethyl acetate in hexanes over 20 min) to afford the title product (2.68 g, yield: 49.5%). Additional impure title product was also obtained (1.65 g), which was further purified by reverse phase HPLC (Column: Xbridge Phenyl OBD 19 mm×100 mm, 5 μm; eluting with 65→80% acetonitrile in water (10 mM NH$_4$OAc, pH 8) over 15 min). Product fractions were combined, diluted with saturated aqueous sodium bicarbonate, and extracted with ethyl acetate (×3). The combined organic layers were dried over sodium sulfate, filtered, and concentrated under reduced pressure to afford additional title product (1.05 g, yield: 19%).

$^1$H NMR (300 MHz, CHLOROFORM-d) δ 8.21 (d, 1H), 7.75 (dd, 1H), 7.33-7.47 (m, 3H), 7.20-7.32 (m, 3H), 6.56 (d,

1H), 4.74 (br. s., 2H), 3.80-3.97 (m, 1H), 3.52-3.71 (m, 2H), 3.04 (d, 2H), 2.31-2.65 (m, 4H), 2.21 (br. s., 3H), 2.01 (s, 1H), 1.61-1.80 (m, 1H), 0.79-0.88 (m, 9H), 0.00 (s, 6H).

LCMS: (ESI) m/z 654 [M−H]+.

Optical Rotation:
Concentration: 0.15 g/dL
Lamp: Sodium
Wavelength: 589 nm
Temperature: 20° C.
Path length: 10 cm
Cell volume: 1 ml
Solvent: $CH_2Cl_2$
[α]=−111

Intermediate 68

(R)-4-(4-morpholino-4-oxo-1-(phenylthio)butan-2-ylamino)-3-(trifluoromethylsulfonyl)benzene-sulfonamide

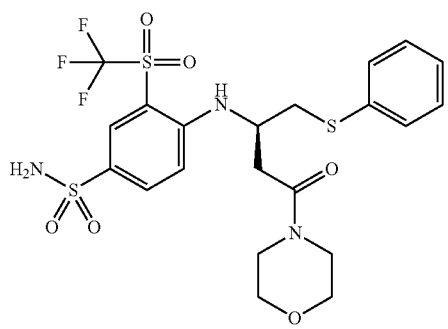 [SMILES: NS(=O)(=O)c1ccc(N[C@@H](CSc2ccccc2)CC(=O)N2CCOCC2)c(S(=O)(=O)C(F)(F)F)c1]

A solution of (R)-4-(phenylthio)-3-(4-sulfamoyl-2-(trifluoromethylsulfonyl)phenylamino) butanoic acid (INTERMEDIATE 8, 1.99 g, 4.01 mmol) and HATU (1.83 g, 4.82 mmol) in DMA (18.0 ml) was treated with morpholine (0.35 ml, 4.02 mmol) and DIPEA (1.40 ml, 8.02 mmol). The resulting reaction mixture was stirred at room temperature for 1 hour and then diluted with EtOAc (250 ml). The organic layer was washed with water (3×250 ml), 1M aq. NaHSO4 (200 ml), and saturated aq. NaHCO3 (200 ml). The organic layer was dried ($Na_2SO_4$), filtered, and evaporated under reduced pressure to provide a sticky foam. The foam was dissolved in EtOAc (40 ml) and washed with water (2×250 ml). During the second wash material precipitated. EtOAc (80 ml) was added and the resulting mixture was shaken, resulting in redissolution of the precipitate. The mixture was further dried ($Na_2SO_4$), filtered, and evaporated under reduced pressure. The residue was dissolved in a few ml of DCM resulting in the formation of a precipitate. Finally, evaporation of the volatiles under reduced pressure afforded the title product (2.02 g, yield: 89%).

LCMS: (ESI) m/z 568 [M+H]+.

Optical Rotation:
Concentration: 0.1 g/dL
Lamp: Sodium
Wavelength: 589 nm
Temperature: 20° C.
Path length: 10 cm
Cell volume: 1 ml
Solvent: $CH_2Cl_2$
[α]=−122

Intermediate 69

(R)-4-(4-morpholino-1-(phenylthio)butan-2-ylamino)-3-(trifluoromethylsulfonyl)benzene-sulfonamide

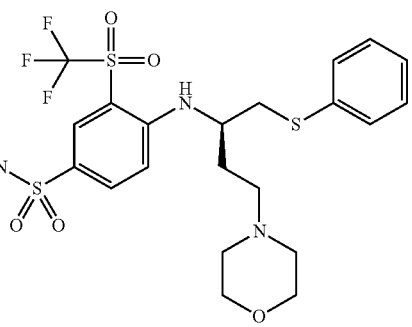

(R)-4-(4-morpholino-4-oxo-1-(phenylthio)butan-2-ylamino)-3-(trifluoromethylsulfonyl)benzenesulfonamide (INTERMEDIATE 68, 2.01 g, 3.5 mmol) was dissolved in a solution of borane-THF complex (1M in THF, 8.0 ml, 8.0 mmol) and the resulting solution was stirred at room temperature overnight. The flask was opened to atmosphere and cautiously treated with MeOH (4.0 ml) followed by concentrated HCl (1.55 ml). The resulting mixture was heated at reflux for 3 hours and was then allowed to cool to room temperature. The pH of the mixture was adjusted to approximately 10 by the addition of aqueous solution of $Na_2CO_3$ (2 M) resulting in a precipitate. The mixture was dissolved in EtOAc (250 ml) and washed with water (125 ml), brine (125 ml), and dried ($Na_2SO_4$). Evaporation of the volatiles under reduced pressure afforded a concentrate, which was purified by column chromatography (ISCO, 80 g silica gel column, eluting with 0→100% EtOAc/hexanes) to provide the title product (1.33 g, yield: 68%).

$^1$H NMR (300 MHz, DMSO-$d_6$) δ ppm 1.65-1.81 (m, 1 H) 1.87-2.02 (m, 1 H) 2.09-2.40 (m, 6 H) 3.43-3.57 (m, 4 H) 4.02-4.18 (m, 1 H) 6.91 (d, 1 H) 7.06 (d, 1 H) 7.16-7.42 (m, 7 H) 7.85 (dd, 1 H) 7.98 (d, 1 H).

LCMS: (ESI) m/z: 554 [M+H]+.

Optical Rotation:
Concentration: 0.1 g/dL
Lamp: Sodium
Wavelength: 589 nm
Temperature: 20° C.
Path length: 10 cm
Cell volume: 1 ml
Solvent: $CH_2Cl_2$
[α]=−147

Intermediate 70

(S)-4-(4-((4'-chlorobiphenyl-2-yl)(hydroxy)methyl)piperidin-1-yl)benzoic acid

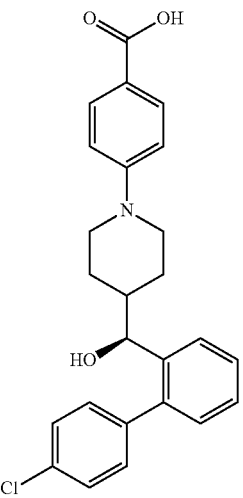 [SMILES: O=C(O)c1ccc(N2CCC([C@H](O)c3ccccc3-c3ccc(Cl)cc3)CC2)cc1]

(S)-Ethyl 4-(4-((4'-chlorobiphenyl-2-yl)(hydroxy)methyl)piperidin-1-yl)benzoate (INTERMEDIATE 11B, 150.0 mg, 0.33 mmol) was dissolved in THF (6.0 ml) and methanol (1.4 ml). A solution of LiOH (40.6 mg) in water (1.4 ml) was added. The solution was heated at 50° overnight. The reaction mixture was allowed to cool to room temperature and then concentrated under reduced pressure. The residue was diluted with water (5 ml), acidified with 1N aq. HCl (2.0 ml), and extracted with DCM (2×5 ml). The extract was dried (MgSO$_4$), filtered through cotton, and evaporated under vacuum to provide the title product as a substantially separated enantiomer (155 mg, yield: almost quantitative) $^1$H NMR (400 MHz, DICHLOROMETHANE-d$_2$) δ ppm 0.79-0.94 (m, 1 H) 0.98-1.12 (m, 1 H) 1.14-1.40 (m, 4 H) 2.04 (m, 1 H) 2.67 (td, J=12.51, 2.78 Hz, 1 H) 2.78 (td, 1 H) 3.74 (d, 1 H) 3.91 (m, 1 H) 4.48 (d, 1 H) 6.81 (d, 2 H) 7.17-7.29 (m, 3 H) 7.31-7.49 (m, 4 H) 7.61 (dd, 1 H) 7.84-7.93 (m, 2 H).

LCMS: (ESI) m/z 420 [M−H]$^+$.
Optical Rotation:
Concentration: 0.1 g/dL
Lamp: Sodium
Wavelength: 589 nm
Temperature: 20° C.
Path length: 10 cm
Cell volume: 1 ml
Solvent: CH$_2$Cl$_2$
[α]=−107

Intermediate 71

(R)-benzyl 4-morpholino-4-oxo-1-(phenylthio)butan-2-ylcarbamate

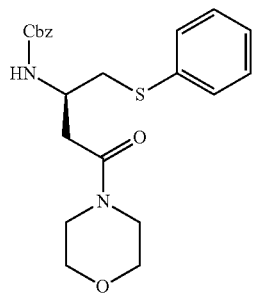 [SMILES: O=C(N[C@@H](CSc1ccccc1)CC(=O)N1CCOCC1)OCc1ccccc1]

Morpholine (130 g, 1.49 mol) was added to a solution of (R)-benzyl 5-oxotetrahydrofuran-3-ylcarbamate (INTERMEDIATE 3, 34.46 g, 0.147 mmol) in THF, and the resulting mixture was allowed to stir at room temperature overnight. The reaction mixture was concentrated to dryness under reduced pressure and the concentrate was re-dissolved in EtOAc. The organic layer was washed with dilute HCl, dried over Na$_2$SO$_4$ and concentrated under reduced pressure to give a thick, colorless oil (24.2 g). A solution of the resulting oil (27.2 g, 84 mmol) in toluene (250 ml) was treated with diphenyl disulfide (20.3 g, 109.2 mmol) followed by Bu$_3$P (27.2 ml, 109.2 mmol). The reaction mixture was heated at 80° C. overnight under a nitrogen atmosphere. Evaporation of the volatiles under reduced pressure gave a residue, which was purified by column chromatography (silica gel, 7 cm height× 14 cm width, eluting with hexanes followed by 10:1, 2:1 then 1:1 v/v hexanes/EtOAc) to give the title product (25 g, yield: 71.5%).

LCMS: (ESI) m/z 413 [M−H]$^+$.

Intermediate 72

(R)-3-amino-1-morpholino-4-(phenylthio)butan-1-one

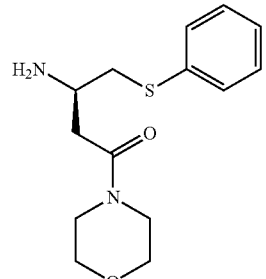

A suspension of (R)-benzyl 4-morpholino-4-oxo-1-(phenylthio)butan-2-ylcarbamate (INTERMEDIATE 71, 25 g, 60 mmol) in 40% HBr in acetic acid (500 ml) was stirred at room temperature for 50 hrs. The reaction mixture became homogeneous during this time. The reaction mixture was concentrated to dryness, diluted with water (400 ml) and 5% aq. HCl (200 ml) and washed with diethyl ether (3×100 ml). The aqueous phase was brought to pH ~8-9 with solid Na$_2$CO$_3$ and extracted vigorously with CH$_2$Cl$_2$ (5×). The combined organic layers were dried (MgSO$_4$) and concentrated under reduced pressure to give the title product (16.9 g, yield: almost quantitative), which was used in the preparation of Intermediate 73 without further purification.

$^1$H-NMR (300 MHz, DMSO-d$_6$) δ 2.42 (dd, 1 H), 2.57 (dd, 1 H), 2.77 (m 3 H), 2.97-3.02 (m, 1 H), 3.06-3.14 (m, 1 H), 3.37 (m, 2 H), 3.59 (m, 6 H), 7.18 (t, 1H), 7.27 (d, 2H), 7.37 (d, 2H).

LCMS: (ESI) m/z 281 (M+H)$^+$.

Intermediate 73

(R)-4-(4-morpholino-4-oxo-1-(phenylthio)butan-2-ylamino)-3-nitrobenzenesulfonamide

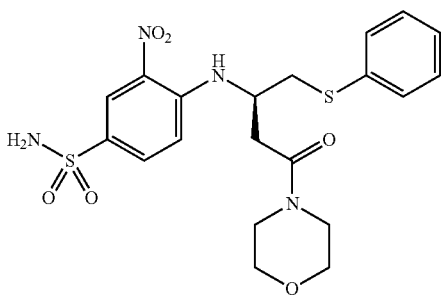 [SMILES: NS(=O)(=O)c1ccc(N[C@@H](CSc2ccccc2)CC(=O)N2CCOCC2)c([N+](=O)[O-])c1]

To a solution of (R)-3-amino-1-morpholino-4-(phenylthio)butan-1-one (INTERMEDIATE 72, 375.5 mg, 1.34 mmol) in DMF (2.5 ml) and DIPEA (1.20 Ml, 6.87 mmol) was added 4-fluoro-3-nitrobenzenesulfonamide (INTERMEDIATE 18, 325.8 mg, 1.48 mmol), and the resulting dark solution was stirred at 50° C. overnight, under a nitrogen atmosphere. The mixture was diluted with EtOAc (50 ml) and washed with water and brine (30 ml each), dried ($Na_2SO_4$), filtered, and evaporated under reduced pressure. The concentrate was purified by column chromatography (ISCO, 40 g silica gel column, eluting with 0→100% EtOAc/DCM) to give the title product (532.5 mg, yield: 83%).

$^1$H NMR (400 MHz, DICHLOROMETHANE-$d_2$) δ ppm 2.72 (dd, 1 H) 2.85-2.97 (m, 1 H) 3.25-3.44 (m, 4 H) 3.48-3.68 (m, 6 H) 4.26-4.39 (m, 1 H) 4.96 (s, 2 H) 6.76 (d, 1 H) 7.23-7.37 (m, 3 H) 7.37-7.46 (m, 2 H) 7.74 (dd, 1 H) 8.61 (d, 1 H) 9.08 (d, 1 H).

LCMS: (ESI) m/z 481 [M+H]$^+$.

Optical Rotation:
Concentration: 0.1 g/dL
Lamp: Sodium
Wavelength: 589 nm
Temperature: 20° C.
Path length: 10 cm
Cell volume: 1 ml
Solvent: $CH_2Cl_2$
[α]=−212

Intermediate 74

(R)-4-(4-morpholino-1-(phenylthio)butan-2-ylamino)-3-nitrobenzenesulfonamide

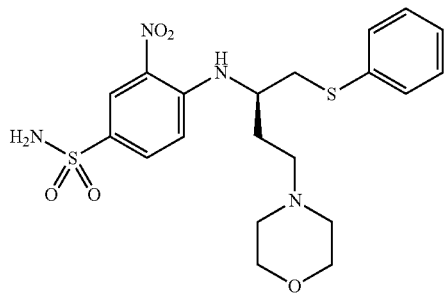 [SMILES: NS(=O)(=O)c1ccc(N[C@H](CCN2CCOCC2)CSc2ccccc2)c([N+](=O)[O-])c1]

(R)-4-(4-Morpholino-4-oxo-1-(phenylthio)butan-2-ylamino)-3-nitrobenzenesulfonamide (INTERMEDIATE 73, 523.6 mg, 1.09 mmol) was dissolved under a nitrogen atmosphere in a solution of borane-THF complex (1M in THF; 2.4 ml, 2.4 mmol) and the resulting solution was stirred at room temperature overnight. The flask was opened to atmosphere and cautiously treated with MeOH (1.20 ml) followed by concentrated HCl (0.48 ml). The resulting mixture was heated at reflux for 3 hours and was then allowed to cool to room temperature. The pH of the mixture was adjusted to approximately 10 by the addition of aqueous solution of $Na_2CO_3$ (4 M) resulting in a precipitate. The mixture was dissolved in EtOAc (75 ml) and washed with water (40 ml), brine (40 ml), and dried ($Na_2SO_4$). Evaporation of the volatiles under reduced pressure afforded a concentrate, which was purified by column chromatography (ISCO, 40 g silica gel column, eluting with 0→100% EtOAc/hexanes) to provide the title product (406.6 mg, yield: 80%).

$^1$H NMR (400 MHz, DMSO-$d_6$) δ ppm 1.75-1.87 (m, 1 H) 1.93-2.06 (m, 1 H) 2.14-2.43 (m, 6 H) 3.37 (m, 2 H) 3.45-3.59 (m, 4 H) 4.16 (m, 1 H) 7.12 (d, 1 H) 7.16-7.22 (m, 1 H) 7.23-7.29 (m, 2 H) 7.29-7.35 (m, 4 H) 7.71 (dd, 1 H) 8.36-8.45 (m, 2 H).

LCMS: (ESI) m/z 467 [M+H]$^+$.

Intermediate 75

4-(4-((R)-(tert-butyldimethylsilyloxy)(4'-chlorobiphenyl-2-yl)methyl)piperidin-1-yl)-N-(4-((R)-4-morpholino-1-(phenylthio)butan-2-ylamino)-3-nitrophenylsulfonyl)benzamide

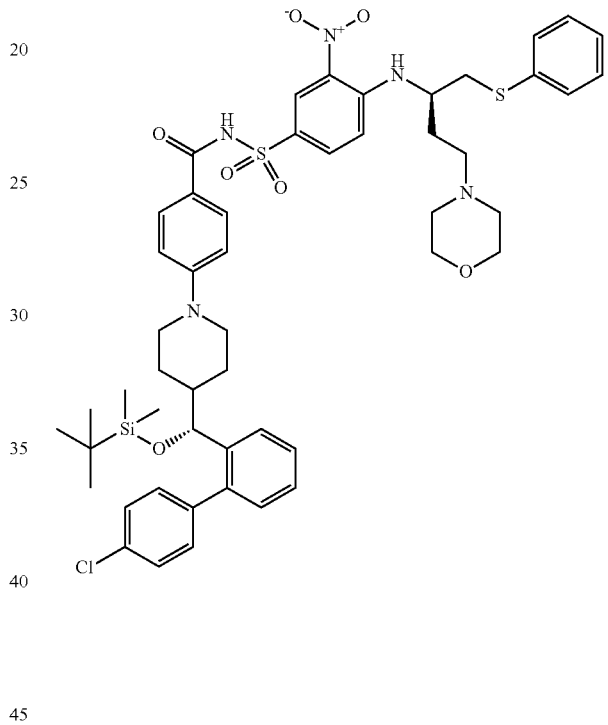

The title product (346.6 mg, yield: 75%) was prepared using a procedure similar to the one described for the synthesis of INTERMEDIATE 33. (R)-4-(4-((tert-Butyldimethylsilyloxy)(4'-chlorobiphenyl-2-yl)methyl)piperidin-1-yl)benzoic acid (INTERMEDIATE 13, 250.7 mg, 0.47 mmol) and (R)-4-(4-morpholino-1-(phenylthio)butan-2-ylamino)-3-nitrobenzenesulfonamide (INTERMEDIATE 74, 229.0 mg, 0.49 mmol) were used as starting materials. The resulting product was purified by column chromatography (ISCO, 12 g silica gel column, eluting with 0→10% MeOH/DCM), providing the title product.

$^1$H NMR (400 MHz, DICHLOROMETHANE-$d_2$) δ ppm −0.24 (s, 3 H) −0.07 (s, 3 H) 0.84 (s, 9 H) 1.50-1.62 (m, 1 H) 1.68-1.84 (m, 2 H) 2.04-2.15 (m, 1 H) 2.23-2.49 (m, 6 H) 2.56-2.72 (m, 2 H) 3.18 (d, 2 H) 3.55-3.69 (m, 4 H) 3.72-3.80 (m, 1 H) 3.81-3.90 (m, 1 H) 4.55-4.63 (m, 1 H) 6.78 (d, 2 H) 6.84 (d, 1 H) 7.12 (dd, 1 H) 7.17-7.44 (m, 11 H) 7.59 (d, 3 H) 7.93 (dd, 1 H) 8.55-8.63 (m, 1 H) 8.77 (d, 1 H).

LCMS: (ESI) m/z 984 [M+H]$^+$.

Intermediate 76

4-(4-((R)-(tert-butyldimethylsilyloxy)(4'-chlorobiphenyl-2-yl)methyl)piperidin-1-yl)-N-(4-((R)-4-morpholino-1-(phenylthio)butan-2-ylamino)-3-(trifluoromethylsulfonyl)phenylsulfonyl)benzamide

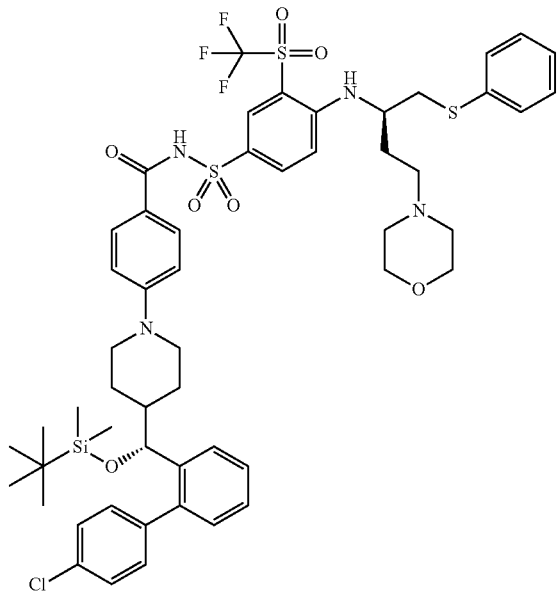

The title product (71.4 mg, yield: 33%) was prepared using a procedure similar to the one described for the synthesis of INTERMEDIATE 33. (R)-4-(4-((tert-Butyldimethylsilyloxy)(4'-chlorobiphenyl-2-yl)methyl)piperidin-1-yl)benzoic acid (INTERMEDIATE 13, 106.7 mg, 0.2 mmol) and (R)-4-(4-morpholino-1-(phenylthio)butan-2-ylamino)-3-(trifluoromethylsulfonyl)benzenesulfonamide (INTERMEDIATE 69, 117 mg, 0.21 mmol) were used as starting materials. The resulting product was purified by column chromatography (ISCO, 4 g silica gel column, eluting with 0→100% EtOAc/hexanes), providing the title product.

$^1$H NMR (400 MHz, CHLOROFORM-d) δ ppm −0.24 (s, 3 H) −0.07 (s, 3 H) 0.85 (s, 9 H) 1.38 (m, 2 H) 1.47-1.80 (m, 5 H) 2.08-2.19 (m, 1 H) 2.25-2.51 (m, 6 H) 2.57-2.73 (m, 2 H) 2.99-3.15 (m, 2 H) 3.60-3.72 (m, 4 H) 3.72-3.80 (m, 1 H) 3.81-3.89 (m, 1 H) 3.89-3.98 (m, 1 H) 4.56-4.63 (m, 1 H) 6.59-6.66 (m, 1 H) 6.78 (d, 2 H) 7.06-7.15 (m, 2 H) 7.20 (d, 2 H) 7.35-7.43 (m, 5 H) 7.53-7.65 (m, 3 H) 8.10-8.16 (m, 1 H) 8.35-8.40 (m, 1 H).

LCMS: (ESI) m/z 1071 [M+H]$^+$.

Intermediate 77

2-(4'-chlorobiphenyl-2-yl)acetonitrile

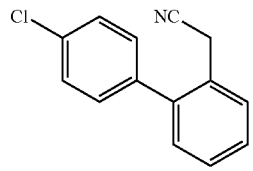 [SMILES: N#CCc1ccccc1-c1ccc(Cl)cc1]

2-(2-bromophenyl)acetonitrile (5.00 g, 25.5 mmol), 4-chlorophenylboronic acid (4.30 g, 27.5 mmol), and tetrakis(triphenylphosphine)palladium(0) (0.48 g 0.42 mmol) were mixed with toluene (57 ml) in a 250 ml 3-necked flask. A reflux condenser was attached and the flask was purged with nitrogen. Aqueous solution of Na$_2$CO$_3$ (2M, 29 ml, 58 mmol) was added by syringe, and the atmosphere was evacuated and replaced with nitrogen. The reaction mixture was heated at reflux overnight, and then allowed to cool at ambient temperature. The mixture was partitioned between saturated aq. NH$_4$Cl and EtOAc (200 ml each). The organic phase was separated, dried (MgSO$_4$), filtered through diatomaceous earth and the filtrate was evaporated under reduced pressure. The residue was purified by column chromatography (ISCO, 120 g silica gel column, 0→20% EtOAc/hexanes) to give the tile compound (5.44 g, yield: 94%).

$^1$H NMR (400 MHz, DMSO-d$_6$) δ ppm 3.91 (s, 2 H), 7.26-7.33 (m, 1 H), 7.36-7.49 (m, 4 H), 7.50-7.59 (m, 3 H).

LCMS: (ESI) m/z 228 [M+H]$^+$.

Intermediate 78

(R)-tert-butyl 4-((4'-chlorobiphenyl-2-yl)(cyano)methyl)piperidine-1-carboxylate and (S)-tert-butyl 4-((4'-chlorobiphenyl-2-yl)(cyano)methyl)piperidine-1-carboxylate, mixture of enantiomers

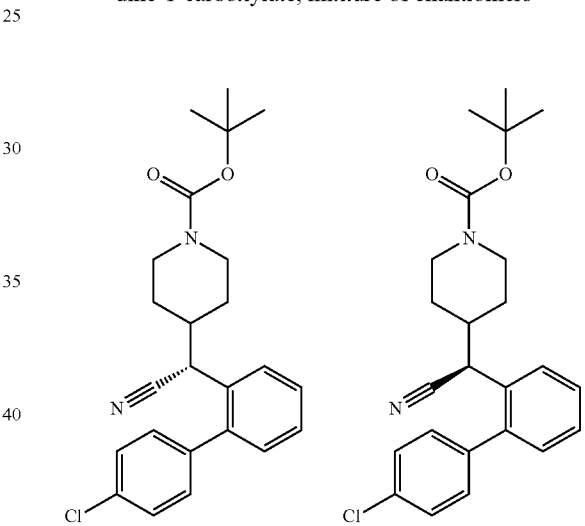

NaH (0.84 g, 60% oil dispersion, 21 mmol) was suspended in DMF (5.0 ml) and the suspension was treated with 2-(4'-chlorobiphenyl-2-yl)acetonitrile (INTERMEDIATE 77, 4.1 g, 17.9 mmol) causing the mixture to turn red. The reaction mixture was stirred at room temperature for 1 hour, during which time more precipitate was observed. The mixture was cooled to 0° C. and tert-butyl 4-iodopiperidine-1-carboxylate (5.59 g, 17.97 mmol) was added along with more DMF (5.0 ml) in order to facilitate stirring. The mixture was stirred at 0° C. for 2 hours and was then allowed to warm to room temperature for 36 hours. The mixture was diluted with saturated aq. NH$_4$Cl (50 ml) and water (50 ml) and extracted with DCM (3×50 ml). The extracts were washed with water (150 ml), dried (MgSO4), filtered, and evaporated under reduced pressure. The concentrate was purified by column chromatography (ISCO, 330 g silica gel column, 0→25% EtOAc/hexanes) to give the title products as a mixture of enantiomers.

$^1$H NMR (400 MHz, DMSO-d$_6$) δ ppm 0.73 (qd, 1 H), 1.06-1.20 (m, 2 H), 1.35 (s, 9 H), 1.65-1.73 (m, 1 H), 1.83-1.95 (m, 1 H), 2.54-2.69 (m, 1 H), 3.72-3.82 (m, 1 H), 3.85 (d, 1 H), 3.88-3.97 (m, 1 H), 7.27 (dd, 1 H), 7.30-7.37 (m, 2 H), 7.42-7.48 (m, 1 H), 7.48-7.61 (m, 4 H).

LCMS: (ESI) m/z 433 [M+Na]$^+$

Intermediate 79

(R)-2-(4'-chlorobiphenyl-2-yl)-2-(piperidin-4-yl)acetonitrile and (S)-2-(4'-chlorobiphenyl-2-yl)-2-(piperidin-4-yl)acetonitrile, mixture of enantiomers

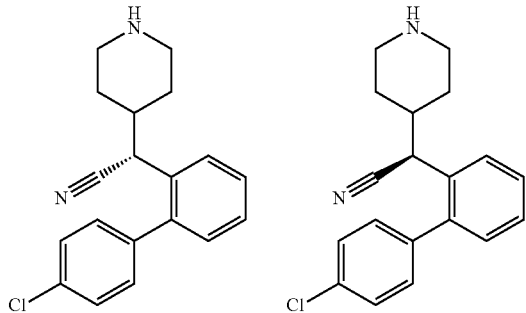 [SMILES: N#C[C@@H](c1ccccc1-c1ccc(Cl)cc1)C1CCNCC1 ; N#C[C@H](c1ccccc1-c1ccc(Cl)cc1)C1CCNCC1]

(R)-tert-butyl 4-((4'-chlorobiphenyl-2-yl)(cyano)methyl)piperidine-1-carboxylate and (S)-tert-butyl 4-((4'-chlorobiphenyl-2-yl)(cyano)methyl)piperidine-1-carboxylate, mixture of enantiomers (INTERMEDIATE 78, 501 mg, 1.22 mmol) were mixed with DCM (3.0 ml) and MeOH (0.12 ml) and treated with TFA (3.0 ml). The reaction mixture was stirred at room temperature for 15 minutes whereupon the volatiles were removed under reduced pressure. The resulting mixture was mixed with water (~15 ml) and made basic (pH ~11) by the addition of small portions of $K_2CO_3$ solid, with cautious (but ultimately vigorous) swirling. The resulting cloudy mixture was extracted with DCM (3×15 ml), and the combined extracts were washed with water (20 ml), dried ($MgSO_4$), filtered, and evaporated under reduced pressure to provide the title products (397 mg, yield: quantitative) as a mixture of enantiomers.

$^1$H NMR (400 MHz, DMSO-$d_6$) δ ppm 0.75 (qd, 1 H), 1.02-1.15 (m, 2 H), 1.57-1.66 (m, 1 H), 1.67-1.78 (m, 1 H), 2.18 (td, 1 H), 2.32 (td, 2 H), 2.69-2.78 (m, 1 H), 2.83-2.91 (m, 1 H), 3.80 (d, 1 H), 7.26 (d, 1 H), 7.33 (d, 2 H), 7.44 (t, 1 H), 7.50 (t, 1 H), 7.53-7.59 (m, 3 H).

FTIR shows nitrile stretch at 2238/cm.

Intermediate 80

(R)-tert-butyl 4-(4-((4'-chlorobiphenyl-2-yl)(cyano)methyl)piperidin-1-yl)benzoate and (S)-tert-butyl 4-(4-((4'-chlorobiphenyl-2-yl)(cyano)methyl)piperidin-1-yl)benzoate, mixture of enantiomers

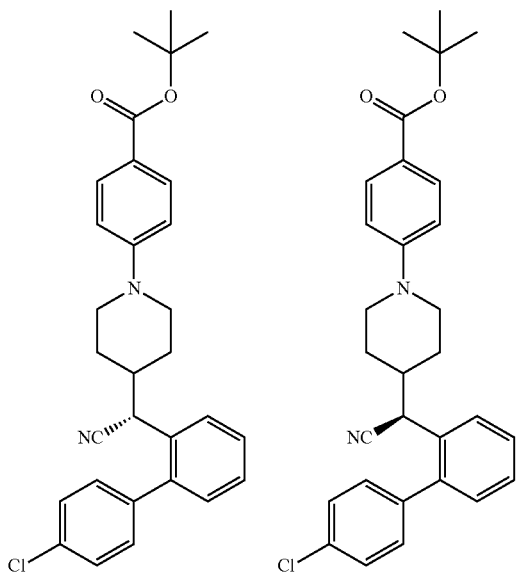 [SMILES: CC(C)(C)OC(=O)c1ccc(N2CCC([C@@H](C#N)c3ccccc3-c3ccc(Cl)cc3)CC2)cc1 ; CC(C)(C)OC(=O)c1ccc(N2CCC([C@H](C#N)c3ccccc3-c3ccc(Cl)cc3)CC2)cc1]

(R)-2-(4'-chlorobiphenyl-2-yl)-2-(piperidin-4-yl)acetonitrile and (S)-2-(4'-chlorobiphenyl-2-yl)-2-(piperidin-4-yl)acetonitrile, mixture of enantiomers (INTERMEDIATE 79, 196.4 mg, 0.63 mmol) were added to a mixture of tert-butyl 4-fluorobenzoate (152.2 mg, 1.39 mmol) in DMSO (0.6 ml), and DIPEA (0.132 ml, 1.49 mmol). The resulting mixture was heated at 120° C. for 8 hours, whereupon more tert-butyl 4-fluorobenzoate (121.0 mg) was added and heating was continued for an additional 24 hours. Additional DIPEA (0.13 ml) was added and heating was continued for another 48 hours. The mixture was diluted with EtOAc (20 ml), washed with water (3×20 ml) and brine (20 ml), dried ($MgSO_4$), filtered, and evaporated under reduced pressure. The concentrate was purified by column chromatography (ISCO, 4 g silica gel column, 0→20%, eluting with EtOAc/hexanes) to provide the title products (62.6 mg, yield: 20%) as a mixture of enantiomers.

$^1$H NMR (400 MHz, DMSO-$d_6$) δ ppm 0.90-1.02 (m, 1 H), 1.21-1.39 (m, 2 H), 1.49 (s, 9 H), 1.72-1.81 (m, 1 H), 2.53-2.63 (m, 1 H), 2.65-2.77 (m, 1 H), 3.74 (d, 1 H), 3.89 (d, 2 H), 6.86 (d, 2 H), 7.26-7.31 (m, 1 H), 7.32-7.38 (m, 2 H), 7.46 (td, 1 H), 7.50-7.57 (m, 3 H), 7.58-7.63 (m, 1 H), 7.67 (d, 2 H).

LCMS: (ESI) m/z 487 [M+H]$^+$.

The R and S enantiomers of the title product were separated using Chiral SFC, (Chiralpak IA column), providing INTERMEDIATE 81 and INTERMEDIATE 82 as substantially separated enantiomers.

Column dimensions: 21×250 mm, 5μ
Modifier: 25% Methanol/0.1% dimethylethylamine
Flow rate (ml/min): 60
Outlet Pressure (bar): 100
Detection (nm): 210

Intermediate 81

First Eluting Compound (R)-tert-butyl 4-(4-((4'-chlorobiphenyl-2-yl)(cyano)methyl)piperidin-1-yl)benzoate The first eluting compound had a retention time of 9.62 minutes.

$^1$H NMR (400 MHz, DMSO-$d_6$) δ ppm 0.89-1.02 (m, 1 H), 1.21-1.39 (m, 2 H), 1.49 (s, 9 H), 1.72-1.81 (m, 1 H), 1.91-2.03 (m, 1 H), 2.53-2.63 (m, 1 H), 2.65-2.77 (m, 1 H), 3.74 (d, 1 H), 3.84-3.94 (m, 2 H), 6.86 (d, 2 H), 7.25-7.31 (m, 1 H), 7.32-7.38 (m, 2 H), 7.43-7.49 (m, 1 H), 7.50-7.57 (m, 3 H), 7.58-7.63 (m, 1 H), 7.64-7.70 (m, 2 H).

LCMS: (ESI) m/z 487 [M+H]$^+$.

Intermediate 82

Second Eluting Compound (S)-tert-butyl 4-(4-((4'-chlorobiphenyl-2-yl)(cyano)methyl)piperidin-1-yl)benzoate The second eluting compound had a retention time of 12.95 minutes.

$^1$H NMR (400 MHz, DMSO-$d_6$) δ ppm 0.96 (qd, 1 H), 1.21-1.39 (m, 2 H), 1.49 (s, 9 H), 1.72-1.81 (m, 1 H), 1.91-2.03 (m, 1 H), 2.58 (td, 1 H), 2.65-2.77 (m, 1 H), 3.70-3.78 (m, 1 H), 3.84-3.94 (m, 2 H), 6.87 (d, 2 H), 7.28 (dd, 1 H), 7.32-7.38 (m, 2 H), 7.46 (td, 1 H), 7.50-7.57 (m, 3 H), 7.58-7.63 (m, 1 H), 7.67 (d, 2 H).

LCMS: (ESI) m/z 487 [M+H]$^+$.

Intermediate 83

(R)-4-(4-((4'-chlorobiphenyl-2-yl)(cyano)methyl)piperidin-1-yl)benzoic acid and (S)-4-(4-((4'-chlorobiphenyl-2-yl)(cyano)methyl)piperidin-1-yl)benzoic acid hydrochloride salts, mixture of enantiomers

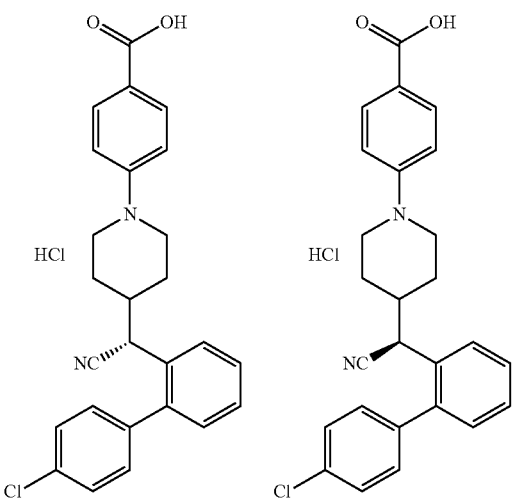 [SMILES: N#C[C@@H](c1ccccc1-c1ccc(Cl)cc1)C1CCN(c2ccc(C(=O)O)cc2)CC1 ; Cl ; N#C[C@H](c1ccccc1-c1ccc(Cl)cc1)C1CCN(c2ccc(C(=O)O)cc2)CC1 ; Cl]

(R)-tert-Butyl 4-(4-((4'-chlorobiphenyl-2-yl)(cyano)methyl)piperidin-1-yl)benzoate and (S)-tert-butyl 4-(4-((4'-chlorobiphenyl-2-yl)(cyano)methyl)piperidin-1-yl)benzoate, mixture of enantiomers (INTERMEDIATE 80, 213.5 mg, 0.44 mmol) were dissolved in DCM (2.0 ml) and MeOH (0.1 ml) and treated with TFA (2.0 ml, 25.96 mmol). The mixture was stirred at room temperature for 30 minutes and then the solvent was evaporated under reduced pressure. The residue was dissolved sequentially and evaporated to dryness with toluene and DCM to provide the corresponding trifluoroacetate salts (251.3 mg). The material was dissolved in MeOH (6 ml), and 2 M HCl in ether (2 ml) was added. After stirring the solution for 10 minutes, the volatiles were removed under reduced pressure to give the title products (182 mg, yield: 89%) as a mixture of enantiomers.

$^1$H NMR (300 MHz, DMSO-d$_6$) δ ppm 0.89-1.08 (m, 1 H), 1.19-1.45 (m, 2 H), 1.71-1.85 (m, 1 H), 1.89-2.07 (m, 1 H), 2.55-2.68 (m, 1 H) 2.69-2.82 (m, 1 H), 3.66-3.80 (m, 1 H), 3.82-3.94 (m, 2 H), 6.91 (d, 2 H), 7.28 (d, 1 H), 7.35 (d, 2 H), 7.40-7.50 (m, 1 H), 7.49-7.57 (m, 3 H), 7.57-7.64 (m, 1 H), 7.73 (d, 2 H).

LCMS: (ESI) m/z 431 [M+H]$^+$.

Intermediate 84

(R)-4-(4-((4'-chlorobiphenyl-2-yl)(cyano)methyl)piperidin-1-yl)benzoic acid, hydrochloride salt

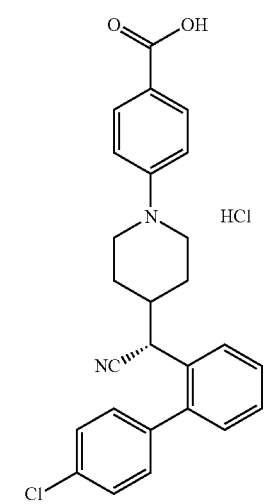 [SMILES: N#C[C@@H](c1ccccc1-c1ccc(Cl)cc1)C1CCN(c2ccc(C(=O)O)cc2)CC1 ; Cl]

The title product (215 mg, yield: quantitative) was obtained using a procedure similar to the one described for the synthesis of INTERMEDIATE 83. (R)-tert-Butyl 4-(4-((4'-chlorobiphenyl-2-yl)(cyano)methyl)piperidin-1-yl)benzoate (INTERMEDIATE 81, 103.8 mg, 0.21 mmol) was used as a starting material.

$^1$H NMR (400 MHz, DMSO-d$_6$) δ ppm 0.97 (qd, 1 H), 1.21-1.42 (m, 2 H), 1.73-1.83 (m, 1 H), 1.91-2.03 (m, 1 H), 2.56-2.65 (m, 1 H), 2.69-2.80 (m, 1 H), 3.68-3.79 (m, 1 H), 3.83-3.93 (m, 2 H), 7.27 (d, 1 H), 7.34 (d, 2 H), 7.42-7.48 (m, 1 H), 7.49-7.56 (m, 3 H), 7.57-7.62 (m, 1 H), 7.72 (d, 2 H).

LCMS: (ESI) m/z 431 [M+H]$^+$.

Intermediate 85

(S)-4-(4-((4'-chlorobiphenyl-2-yl)(cyano)methyl)piperidin-1-yl)benzoic acid, HCl salt

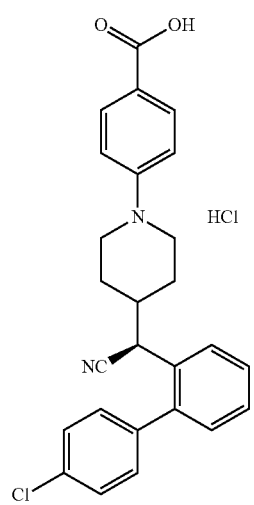 [SMILES: N#C[C@H](c1ccccc1-c1ccc(Cl)cc1)C1CCN(c2ccc(C(=O)O)cc2)CC1 ; Cl]

The title product (215 mg, yield: quantitative) was obtained using a procedure similar to the one described for the synthesis of INTERMEDIATE 83. (S)-tert-Butyl 4-(4-((4'-chlorobiphenyl-2-yl)(cyano)methyl)piperidin-1-yl)benzoate (INTERMEDIATE 82, 101.8 mg, 0.21 mmol) was used as starting material.

$^1$H NMR (400 MHz, DMSO-d$_6$) δ ppm 0.90-1.03 (m, 1 H), 1.21-1.40 (m, 3 H), 1.73-1.82 (m, 1 H), 1.91-2.03 (m, 1 H), 2.55-2.65 (m, 1 H), 2.69-2.80 (m, 1 H), 3.68-3.80 (m, 1 H), 3.84-3.95 (m, 2 H), 6.89 (d, 2 H), 7.27 (dd, 1 H), 7.31-7.39 (m, 2 H), 7.45 (td, 1 H), 7.49-7.57 (m, 3 H), 7.58-7.63 (m, 1 H), 7.69-7.79 (m, 2 H).

LCMS: (ESI) m/z 431 [M+H]$^+$.

Intermediate 86

(S)—N-ethyl-N-(morpholin-3-ylmethyl)ethanamine hydrochloride salt

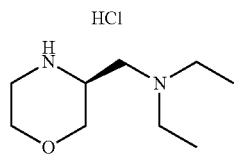

Step 1: A solution of (S)-tert-butyl 3-(aminomethyl)morpholine-4-carboxylate (1.0 g, 4.62 mmol) in MeOH (15 ml) was treated with acetaldehyde (0.204 g, 4.62 mmol). The reaction mixture was stirred at 0° C. for 15 minutes and sodium triacetoxyborohydride (2.450 g, 11.56 mmol) was added all at once. The resulting mixture was stirred for 24 h and the mixture was diluted with DCM (15 ml) and washed with saturated aq. sodium bicarbonate (15 ml). The organic phase dried over sodium sulfate, filtered, and concentrated under pressure to give a residue which was purified by column chromatography (ISCO, 12 g silica gel column, eluting with 0→20% MeOH in DCM) to give (S)-tert-butyl 3-((diethylamino)methyl)morpholine-4-carboxylate (INTERMEDIATE 86, STEP 1).

LCMS: (ESI) m/z 273 [M+H]$^+$.

Step 2: (S)-tert-butyl 3-((diethylamino)methyl)morpholine-4-carboxylate (INTERMEDIATE 86, STEP 1) was dissolved with TFA/DCM, (10 ml, 1:1 v/v) and the resulting mixture was stirred for 1 hour at room temperature. The volatiles were removed under reduced pressure and the concentrate was treated with 4N HCl in dioxane (5 ml), stirred for 10 minutes and the volatiles were removed under reduced pressure. The resulting semi solid was triturated with diethyl ether (2×30 ml), filtered and dried to give the title product (0.65 g, yield: 67%).

LCMS: (ESI) m/z 173 [M+H]$^+$.

Intermediate 86A

Intermediate 86 was also prepared according to the following procedure:

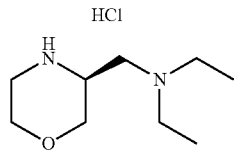

Step 1: To a solution of (S)-tert-butyl 3-(aminomethyl)morpholine-4-carboxylate (commercially available, 0.62 g, 2.87 mmol) in dichloromethane (28.0 ml) were added sequentially pyridine (0.5 ml, 5.73 mmol) and acetyl chloride (0.25 ml, 3.44 mmol). After 30 min the reaction was diluted with saturated aqueous sodium bicarbonate and saturated aqueous sodium chloride. The resulting mixture was extracted with ethyl acetate (×3), and the combined organic layers were then dried over sodium sulfate, filtered, and concentrated under reduced pressure. The resulting light yellow oil was purified by flash column chromatography (ISCO, SiO$_2$, 0-10% methanol in ethyl acetate over 10 min) to afford (S)-tert-butyl 3-(acetamidomethyl)morpholine-4-carboxylate (0.741 g, yield: almost quantitative, INTERMEDIATE 86A STEP 1).

$^1$H NMR (300 MHz, CHLOROFORM-d) δ 5.85 (br. s., 1H), 3.92-4.26 (m, 2H), 3.67-3.91 (m, 3H), 3.56-3.64 (m, 1H), 3.46 (dt, 1H), 3.09-3.32 (m, 2H), 1.96 (s, 3H), 1.49 (s, 9H).

LCMS: (ESI) m/z 259 [M+H]$^+$.

Step 2: To a degassed solution of (S)-tert-butyl 3-(acetamidomethyl)morpholine-4-carboxylate (INTERMEDIATE 86A, Step 1, 0.69 g, 2.68 mmol) and DMF (20 ml) was added sequentially iodoethane (1.297 ml, 16.05 mmol) and 60% sodium hydride in mineral oil (0.118 g, 2.94 mmol) in one portion. After 15 min, the reaction was diluted with ethyl acetate and washed with water (×2). The aqueous layer were extracted with ethyl acetate, and then the combined organic layers were washed with saturated aqueous sodium chloride. The organic layers were dried over sodium sulfate, filtered, and concentrated under reduced pressure. The resulting light yellow oil was purified by flash column chromatoghraphy (SiO$_2$, ISCO, 0-100% ethyl acetate in hexanes over 10 min, then 10% methanol in ethyl acetate for 5 min) to afford (S)-tert-butyl 3-((N-ethylacetamido)methyl)morpholine-4-carboxylate (0.586 g, yield: 76%, INTERMEDIATE 86A, Step 2).

$^1$H NMR (300 MHz, DMSO-d$_6$, 87° C.) δ 4.07 (br. s., 1H), 3.80 (d, 1H), 3.05-3.74 (m, 9H), 2.00 (s, 3H), 1.38-1.46 (m, 9H), 1.10 (t, 3H).

LCMS: (ESI) m/z 287 [M+H]$^+$.

Step 3: To a solution of (S)-tert-butyl 3-((N-ethylacetamido)methyl)morpholine-4-carboxylate (INTERMEDIATE 86A, Step 2, 0.04 g, 0.14 mmol) and diphenylsilane (0.052 ml, 0.28 mmol) in tetrahydrofuran (1.345 ml) at rt was added carbonyltris(triphenylphosphine)rhodium(I) hydride (6.42 mg, 6.98 μmol). After a brief surge of gas evolution, the now yellow reaction was stirred for 30 min and then quenched with 1N aqueous hydrogen chloride. The mixture was extracted with ether, and the aqueous layer was basified with 50% aqueous sodium hydroxide. The aqueous layer was the extracted with ethyl acetate (×4), and the combined organic layers were dried over sodium sulfate, filtered, and concentrated under reduced pressure to afford (S)-tert-butyl 3-((diethylamino)methyl)morpholine-4-carboxylate (0.038 g, yield: almost quantitative) (INTERMEDIATE 86A, Step 3).

$^1$H NMR (300 MHz, CHLOROFORM-d) δ 3.98 (d, 1H), 3.58-3.82 (m, 3H), 3.29-3.46 (m, 2H), 2.90-3.04 (m, 1H), 2.71-2.86 (m, 1H), 2.36-2.63 (m, 4H), 2.21 (d, 1H), 1.36-1.42 (m, 9H), 0.87-1.01 (m, 6H).

LCMS: (ESI) m/z 273 [M+H]$^+$.

Step 4: To (S)-tert-butyl 3-((diethylamino)methyl)morpholine-4-carboxylate (0.348 g, 1.28 mmol INTERMEDIATE 86A, Step 3) was added 32 wt % hydrochloric acid in water (1.5 ml, 15.80 mmol). After gas evolution ceased, the mixture was concentrated under reduced pressure. The resulting yellow residue was treated with 5% methanol in dichloromethane and reconcentrated (×3) to afford (S)—N-ethyl-N-(morpholin-3-ylmethyl)ethanamine hydrochloride salt (INTERMEDIATE 86, yield: almost quantitative).

$^1$H NMR (300 MHz, METHANOL-$d_4$) δ 4.20 (dd, 1H), 3.99-4.13 (m, 2H), 3.79-3.96 (m, 2H), 3.60-3.70 (m, 1H), 3.27-3.54 (m, 6H), 1.43 (t, 6H).

LCMS: (ESI) m/z 173 [M+H]$^+$.

Intermediate 87

4-((R)-4-((S)-3-((diethylamino)methyl)morpholino)-4-oxo-1-(phenylthio)butan-2-ylamino)-3-(trifluoromethylsulfonyl)benzenesulfonamide

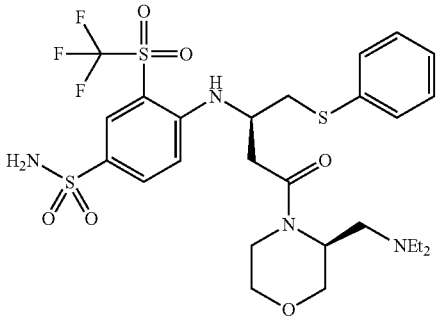

To a solution of (R)-4-(phenylthio)-3-(4-sulfamoyl-2-(trifluoromethylsulfonyl)phenylamino) butanoic acid (INTERMEDIATE 8, 500 mg, 1.00 mmol), (S)—N-ethyl-N-(morpholin-3-ylmethyl)ethanamine hydrochloride salt (INTERMEDIATE 86, 50 mg, 1.2 mmol), DIPEA (0.526 ml, 3.01 mmol), in DMA (5 ml) was added HATU (458 mg, 1.20 mmol). The mixture was stirred for 1 hour at room temperature and diluted with ethyl acetate (200 ml). The mixture was washed successively with 1 M aq. sodium bisulfate, saturated sodium bicarbonate, and brine. The organic phase was dried over sodium sulfate, filtered, and concentrated under reduced pressure. The concentrate was purified column chromatography (ISCO, eluting with 0→100% DCM/10% 2 M ammonia in MeOH in DCM over 24 minutes) to give the title product (380 mg, yield: 58%).

LCMS: (ESI) m/z 653 [M+H]$^+$.

Intermediate 88

4-((R)-4-((S)-3-((diethylamino)methyl)morpholino)-1-(phenylthio)butan-2-ylamino)-3-(trifluoromethylsulfonyl)benzenesulfonamide

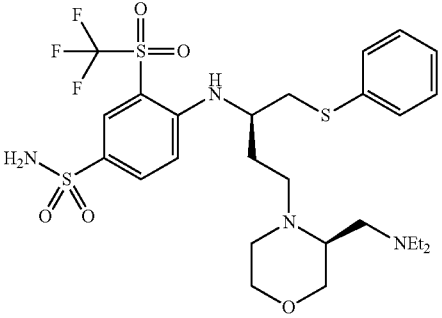

A mixture of 4-((R)-4-((S)-3-((diethylamino)methyl)morpholino)-4-oxo-1-(phenylthio)butan-2-ylamino)-3-(trifluoromethylsulfonyl)benzenesulfonamide (INTERMEDIATE 87, 360 mg, 0.55 mmol) and 1 M borane-tetrahydrofuran complex in THF (1191 µl, 1.19 mmol) was stirred at room temperature for 16 hours. The reaction mixture was treated carefully with MeOH (5 ml) and concentrated HCl (1 ml). The mixture was heated at 80° C. for 3 hours, cooled to r.t, and the pH was adjusted to pH 10 with 4 N aqueous sodium carbonate. The mixture was diluted with ethyl acetate (300 ml), washed successively with water (150 ml) and brine (150 ml), dried over sodium sulfate, filtered, and concentrated under reduced pressure. The concentrate was purified by column chromatography (ISCO, eluting with 0→20% MeOH/DCM over 15 minutes) to give the title product (130 mg, yield: 37%).

$^1$H NMR (400 MHz, METHANOL-$d_4$) δ ppm 0.79 (t, 6 H) 1.53-1.69 (m, 1 H) 1.91-2.45 (m, 11 H) 2.63-2.87 (m, 2 H) 2.98-3.24 (m, 5 H) 3.43 (ddd, 1 H) 3.60 (dt, 1 H) 3.68 (dd, 1 H) 3.87-4.05 (m, 1 H) 6.68 (d, 1 H) 7.07-7.26 (m, 3 H) 7.26-7.39 (m, 2 H) 7.75 (dd, 1 H) 8.04 (d, 1 H).

LCMS: (ESI) m/z 639 [M+H]$^+$.

Intermediate 89

4-(4-((R)-(tert-butyldimethylsilyloxy)(4'-chlorobiphenyl-2-yl)methyl)piperidin-1-yl)-N-(4-((R)-4-4S)-3-((diethylamino)methyl)morpholino)-1-(phenylthio)butan-2-ylamino)-3-(trifluoromethylsulfonyl)phenylsulfonyl)benzamide

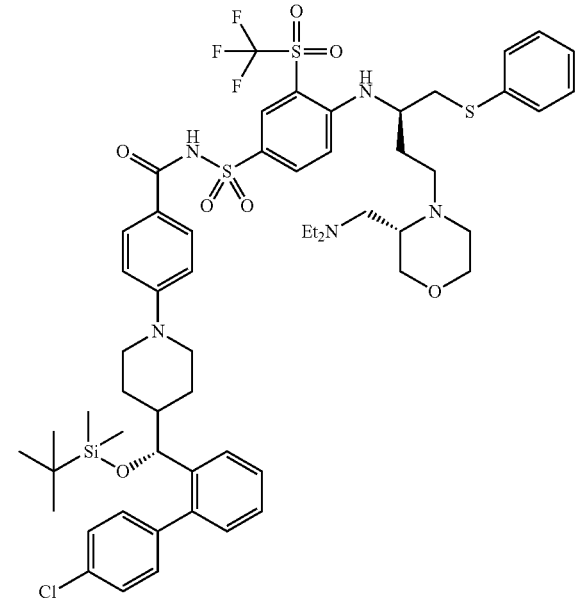

A solution of (R)-4-(4-((tert-butyldimethylsilyloxy)(4'-chlorobiphenyl-2-yl)methyl)piperidin-1-yl)benzoic acid, (INTERMEDIATE 13, 109 mg, 0.20 mmol), 4-((R)-4-((S)-3-((diethylamino)methyl)morpholino)-1-(phenylthio)butan-2-ylamino)-3-(trifluoromethylsulfonyl)benzenesulfonamide (INTERMEDIATE 88, 130 mg, 0.20 mmol), EDC (78 mg, 0.41 mmol), DMAP (49.7 mg, 0.41 mmol), TEA (0.028 ml, 0.20 mmol) and DCM (5 ml) was stirred overnight at room temperature. The reaction mixture was diluted with DCM (50 ml) and washed successively with water (2×50 ml) and brine (50 ml). The organic phase was dried over sodium sulfate, filtered, and concentrated under reduced pressure. The concentrate was purified by column chromatography (ISCO, eluting with 0→20 MeOH/DCM over 19 minutes) to give the title product (100 mg, yield: 42.5%), $^1$H NMR (400 MHz, DICHLOROMETHANE-d$_2$) δ ppm 0.00 (s, 3 H) 0.17 (s, 3 H) 1.09 (s, 9 H) 1.19 (t, 6 H) 1.51 (br. s., 5 H) 1.69-1.93 (m, 2 H) 1.92-2.05 (m, 1 H) 2.24-2.38 (m, 1 H) 2.41-2.53 (m, 1 H) 2.59-3.05 (m, 11 H) 3.30 (t, 2 H) 3.54-3.65 (m, 1 H) 3.71-3.80 (m, 1 H) 3.92 (d, 3 H) 3.99-4.09 (m, 1 H) 4.10-4.24 (m, 1 H) 4.84 (br. s., 1 H) 6.86 (d, 1 H) 7.00 (d, J=8.84 Hz, 2 H) 7.13 (d, 1 H) 7.36 (dd, 1 H) 7.40-7.72 (m, 11 H) 7.76-7.88 (m, 1 H) 7.95 (d, 2 H) 8.24 (s, 1 H) 8.53 (d, 1 H).

LCMS: (ESI) m/z 1156 [M+H]$^+$.

Intermediate 90

(R)—N-ethyl-N-(morpholin-3-ylmethyl)ethanamine hydrochloride salt

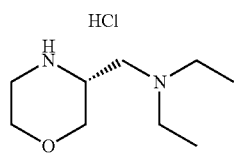

Step 1: A solution of (R)-tert-butyl 3-(aminomethyl)morpholine-4-carboxylate (commercially available, 250 mg, 1.16 mmol) and DCM (7 ml) at 0° C. was treated with acetaldehyde (0.162 ml, 2.89 mmol). The reaction mixture was stirred at 0° C. for 15 minutes and sodium triacetoxyborohydride (612 mg, 2.89 mmol) was added all at once. The resulting mixture was stirred for 24 h and the mixture was diluted with 20 ml of DCM (20 ml) and washed with saturated aq. sodium bicarbonate (20 ml). The organic phase was dried over sodium sulfate, filtered, and concentrate under pressure to give (R)-tert-butyl 3-((diethylamino)methyl)morpholine-4-carboxylate (INTERMEDIATE 90, STEP 1)

LCMS: (ESI) m/z 273 [M+H]$^+$.

Step 2: (R)-tert-butyl 3-((diethylamino)methyl)morpholine-4-carboxylate (INTERMEDIATE 90, STEP 1) was dissolved with TFA/DCM, (6 ml, 1:1 v/v) and the resulting mixture was stirred for 1 h at room temperature. The volatiles were removed under reduced pressure and the concentrate was treated with 4N HCl in dioxane (3 ml), stirred for 10 minutes and the volatiles were removed under reduced pressure. The resulting semi solid was triturated with diethyl ether (2×30 ml) and dried to give the title product (140 mg, yield: 58%).

LCMS: (ESI) m/z 173 [M+H]$^+$.

Intermediate 91

4-((R)-4-((R)-3-((diethylamino)methyl)morpholino)-4-oxo-1-(phenylthio)butan-2-ylamino)-3-(trifluoromethylsulfonyl)benzenesulfonamide

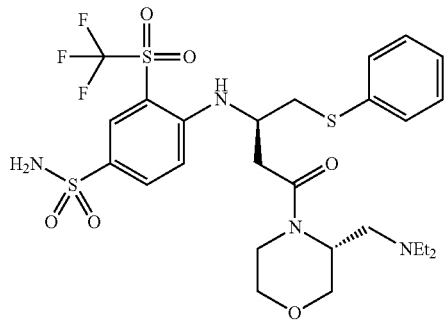

To a solution of (R)-4-(phenylthio)-3-(4-sulfamoyl-2-(trifluoromethylsulfonyl)phenylamino)butanoic acid (INTERMEDIATE 8, 500 mg, 1.00 mmol), (R)—N-ethyl-N-(morpholin-3-ylmethyl)ethanamine hydrochloride salt (INTERMEDIATE 90, 209 mg, 1.00 mmol), DIPEA (0.701 ml, 4.01 mmol) in DMA (5 ml) was added HATU (458 mg, 1.20 mmol). The mixture was stirred for 1 h at room temperature and diluted with ethyl acetate (200 ml). The mixture was washed successively with 1M aq. sodium bisulfate, saturated sodium bicarbonate, and brine. The organic phase was dried over sodium sulfate, filtered, and concentrated under reduced pressure. The concentrate was purified column chromatography (ISCO, eluting with 0→100% DCM/10% 2 M ammonia in MeOH in DCM over 24 minutes) to give the title product (200 mg, yield: 30.5%).

$^1$H NMR (400 MHz, METHANOL-d$_4$) δ ppm 0.75-1.06 (m, 6 H) 2.32-2.67 (m, 6 H) 2.69-2.89 (m, 3 H) 3.11-3.42 (m, 7 H) 3.45-3.57 (m, 1 H) 3.67-3.92 (m, 3 H) 4.26 (d, 2 H) 6.73 (d, 1 H) 7.08-7.26 (m, 3 H) 7.27-7.37 (m, 2 H) 7.65-7.83 (m, 1 H) 7.96-8.12 (m, 1 H).

LCMS: (ESI) m/z 653 [M+H]$^+$.

Intermediate 92

4-((R)-4-((R)-3-((diethylamino)methyl)morpholino)-1-(phenylthio)butan-2-ylamino)-3-(trifluoromethylsulfonyl)benzenesulfonamide

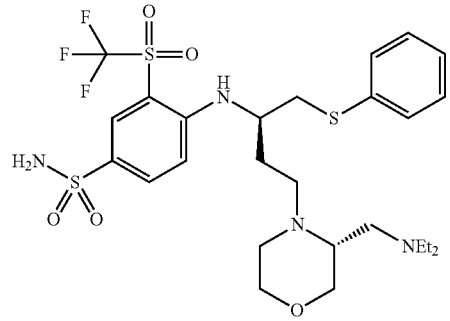

A mixture of 4-((R)-4-((R)-3-((diethylamino)methyl)morpholino)-4-oxo-1-(phenylthio)butan-2-ylamino)-3-(trifluoromethylsulfonyl)benzenesulfonamide (INTERMEDIATE 91, 200 mg, 0.31 mmol) and 1 M borane-tetrahydrofuran complex (662 μl, 0.66 mmol) was stirred at room temperature for 16 hours. The reaction mixture was treated carefully with MeOH (5 ml) and concentrated HCl (1 ml). The mixture was heated at 80° C. for 3 hours, cooled to r.t, and the pH was adjusted to pH 10 with 4 N aqueous sodium carbonate. The mixture was diluted with ethyl acetate (300 ml), washed successively with water (150 ml) and brine (150 ml), dried over sodium sulfate, filtered, and concentrated under reduced pressure. The concentrate was purified by column chromatography (ISCO, eluting with 0→20% MeOH/DCM over 15 minutes) to give the title product (109 mg, yield: 56%).

$^1$H NMR (400 MHz, METHANOL-d$_4$) δ ppm 0.79-0.91 (m, 6 H) 1.54-1.74 (m, 1 H) 1.89-2.07 (m, 1 H) 2.13-2.48 (m, 10 H) 2.58 (ddd, 1 H) 2.75 (ddd, 1 H) 3.02-3.24 (m, 3 H) 3.36 (dd, 1 H) 3.46-3.65 (m, 3 H) 3.95 (dd, 1 H) 6.74 (d, 1 H) 7.08-7.26 (m, 3 H) 7.26-7.38 (m, 2 H) 7.78 (dd, 1 H) 8.04 (d, 1 H).

LCMS: (ESI) m/z 639 [M+H]$^+$.

Intermediate 93

4-(4-((R)-(tert-butyldimethylsilyloxy)(4'-chlorobiphenyl-2-yl)methyl)piperidin-1-yl)-N-(4-((R)-4-((R)-3-((diethylamino)methyl)morpholino)-1-(phenylthio)butan-2-ylamino)-3-(trifluoromethylsulfonyl)phenylsulfonyl)benzamide

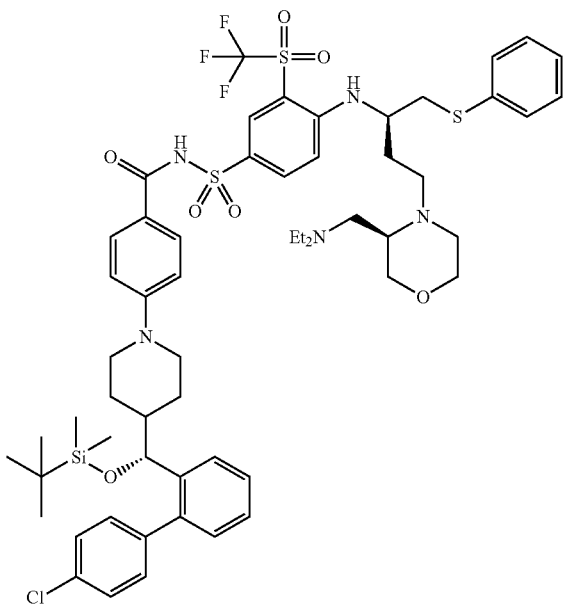

The title product (100 mg, yield: 55%) was prepared using a procedure similar to the one described for the synthesis of INTERMEDIATE 89. (R)-4-(4-((tert-Butyldimethylsilyloxy)(4'-chlorobiphenyl-2-yl)methyl)piperidin-1-yl)benzoic acid, (INTERMEDIATE 13, 84 mg, 0.16 mmol) and 4-((R)-4-((R)-3-((diethylamino)methyl)morpholino)-1-(phenylthio)butan-2-ylamino)-3-(trifluoromethylsulfonyl)benzenesulfonamide (INTERMEDIATE 92, 100 mg, 0.16 mmol) were used as starting materials. The resulting product was purified by column chromatography (ISCO, eluting with 0→20% MeOH/DCM for 19 minutes), providing the title product.

$^1$H NMR (400 MHz, DICHLOROMETHANE-d$_2$) δ ppm 0.00 (s, 3 H) 0.17 (s, 3 H) 1.09 (s, 9 H) 1.29 (t, 6 H) 1.40-1.69 (m, 4 H) 1.71-1.92 (m, 2 H) 1.92-2.06 (m, 1 H) 2.24 (s, 1 H) 2.58 (br. s., 3 H) 2.71-3.09 (m, 10 H) 3.35 (dd, 2 H) 3.71 (br. s., 3 H) 3.84 (br. s., 1 H) 3.90-3.99 (m, 1 H) 3.99-4.09 (m, 1 H) 4.16-4.30 (m, 1 H) 4.76-4.96 (m, 1 H) 6.76-7.11 (m, 5 H) 7.36 (dd, 1 H) 7.41-7.70 (m, 13 H) 7.74-7.87 (m, 1 H) 7.91 (d, 2 H) 8.19 (s, 1 H) 8.53 (d, 1 H).

LCMS: (ESI) m/z 1158 [M+H]$^+$.

Intermediate 94

(R)-tert-Butyl 2-((tert-butyldiphenylsilyloxy)methyl)morpholine-4-carboxylate and (S)-tert-butyl 2-((tert-butyldiphenylsilyloxy)methyl)morpholine-4-carboxylate, mixture of enantiomers

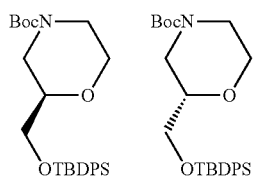

Pyridine (0.313 ml, 3.87 mmol) and DMAP (0.031 g, 0.26 mmol) were added to a solution of (R)-tert-butyl 2-(hydroxymethyl)morpholine-4-carboxylate and (S)-tert-butyl 2-(hydroxymethyl)morpholine-4-carboxylate, mixture of enantiomers (commercially available, 0.560 g, 2.58 mmol) in DCM (7.48 ml) at ambient temperature. tert-Butylchlorodiphenylsilane (0.795 ml, 3.09 mmol) was added and the reaction mixture was stirred at room temperature overnight. The mixture was concentrated under reduced pressure and the concentrate was purified by column chromatography (ISCO, eluting with 0→100% EtOAc/hexanes) to give the title products as a mixture of enantiomers (0.853 g, yield: 73%).

LCMS: (ESI) m/z 456 [M+H]$^+$.

Intermediate 95

(R)-2-((tert-butyldiphenylsilyloxy)methyl)morpholine compound and (S)-2-((tert-butyldiphenylsilyloxy)methyl)morpholine hydrochloride salts, mixture of enantiomers

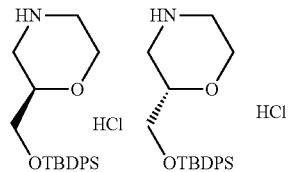

HCl (4M in Dioxane, 3.24 ml, 93.27 mmol) was added dropwise into a solution of (R)-tert-Butyl 2-((tert-butyldiphenylsilyloxy)methyl)morpholine-4-carboxylate and (S)-tert-butyl 2-((tert-butyldiphenylsilyloxy)methyl)morpholine-4-carboxylate, mixture of enantiomers (INTERMEDIATE 94, 0.85 g, 1.87 mmol) in DCM (2.98 ml), and the resulting reaction mixture was stirred at room temperature for 30 minutes. The volatiles were removed under reduced pressure to afford the title product as a mixture of enantiomers (0.73 g, yield: quantitative).

LCMS: (ESI) m/z 356 [M+H]$^+$.

Intermediate 96

4-((R)-4-((R)-2-((tert-butyldiphenylsilyloxy)methyl)morpholino)-4-oxo-1-(phenylthio)butan-2-ylamino)-3-(trifluoromethylsulfonyl)benzenesulfonamide and 4-((R)-4-((S)-2-((tert-butyldiphenylsilyloxy)methyl)morpholino)-4-oxo-1-(phenylthio)butan-2-ylamino)-3-(trifluoromethylsulfonyl)benzenesulfonamide

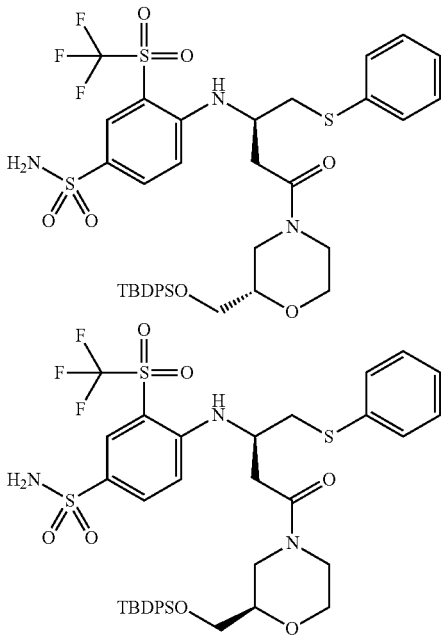

(R)-4-(phenylthio)-3-(4-sulfamoyl-2-(trifluoromethylsulfonyl)phenylamino)butanoic acid (INTERMEDIATE 8, 0.850 g, 1.71 mmol) was added to a solution of (R)-2-((tert-butyldiphenylsilyloxy)methyl)morpholine compound and (S)-2-((tert-butyldiphenylsilyloxy)methyl)morpholine hydrochloride salts, mixture of enantiomers (INTERMEDIATE 95, 0.735 g, 1.88 mmol) in DMF (5.09 ml) followed by sequential addition of DIPEA (0.596 ml, 3.41 mmol), EDC (0.490 g, 2.56 mmol) and HOBT (0.392 g, 2.56 mmol). The resulting reaction mixture was stirred at room temperature overnight. The mixture was diluted with EtOAc and washed with $H_2O$ (2×), 1N aq. $NaHSO_4$, saturated aq. $NaHCO_3$ and brine. The organic layer was dried ($Na_2SO_4$) and concentrated under reduced pressure. The concentrate was purified by column chromatography (ISCO, eluting with 50% EtOAc/hexanes) to provide the title products as a mixture of enantiomers (1.6 g, yield: quantitative).

LCMS: (ESI) m/z 836 [M+H]$^+$.

Intermediate 97

4-((R)-4-((R)-2-((tert-butyldiphenylsilyloxy)methyl)morpholino)-1-(phenylthio)butan-2-ylamino)-3-(trifluoromethylsulfonyl)benzenesulfonamide and 4-((R)-4-((S)-2-((tert-butyldiphenylsilyloxy)methyl)morpholino)-1-(phenylthio)butan-2-ylamino)-3-(trifluoromethylsulfonyl)benzenesulfonamide

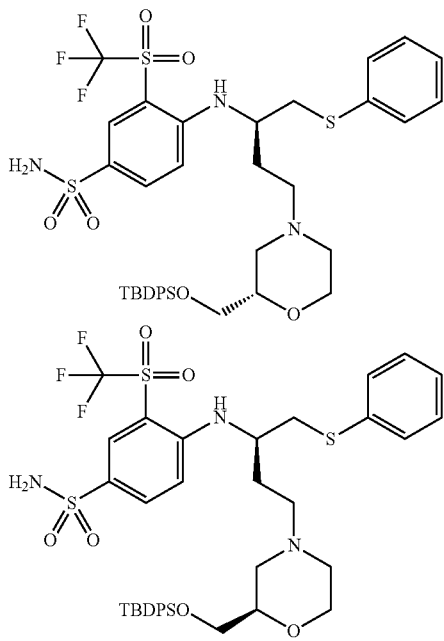

A solution of $BH_3$.THF complex in THF (10.23 ml, 10.23 mmol) was added slowly to a solution of 4-((R)-4-((R)-2-((tert-butyldiphenylsilyloxy)methyl)morpholino)-4-oxo-1-(phenylthio)butan-2-ylamino)-3-(trifluoromethylsulfonyl)benzenesulfonamide and 4-((R)-4-((S)-2-((tert-butyldiphenylsilyloxy)methyl)morpholino)-4-oxo-1-(phenylthio)butan-2-ylamino)-3-(trifluoromethylsulfonyl)benzenesulfonamide (INTERMEDIATE 96, 1.43 g, 1.71 mmol) and THF (4 ml) and the resulting reaction mixture was stirred at room temperature overnight. The mixture was diluted with a solution of $NH_3$ in MeOH (7N, 20 ml) and stirred at room temperature overnight. Evaporation of the volatiles under reduced pressure gave a residue, which was diluted with EtOAc. The organic phase was washed with $H_2O$ (2×), dried ($Na_2SO_4$), filtered and concentrated under reduced pressure to provide the title products (0.52 g, 37%) as a mixture of diastereomers.

LCMS: (ESI) m/z 822 [M+H]$^+$.

The resulting two diastereomers of the title product were separated using Chiral HPLC providing INTERMEDIATE 98 and INTERMEDIATE 99 as substantially separated diastereomers.

Column: Chiralpak IC column

Column dimensions: 4.6×100 mm, 5µ

Mobile phase: 80% hexanes, 20% isopropanol

Flow rate (ml/min): 1.0 ml/min

Detection (nm): 220 nm

Intermediate 98

4-((R)-4-((R)-2-((tert-butyldiphenylsilyloxy)methyl)morpholino)-1-(phenylthio)butan-2-ylamino)-3-(trifluoromethyl sulfonyl)benzenesulfonamide

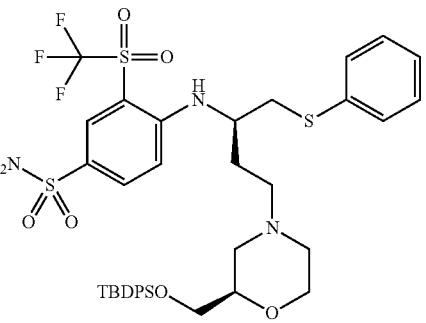

The first eluting compound had a retention time of 5.84 minutes, 86% d.e. (294 mg, yield: 21%).

$^1$H NMR (300 MHz, METHANOL-d4) δ ppm 1.07 (s, 5 H) 1.02 (s, 5 H) 1.73-1.91 (m, 2 H) 2.04-2.16 (m, 2 H) 2.36-2.45 (m, 2 H) 2.53 (d, 1 H) 2.73 (d, 1 H) 2.92 (d, 1 H) 3.12-3.29 (m, 2 H) 3.50-3.64 (m, 4 H) 3.71 (dd, 1 H) 3.81 (t, 1 H) 4.06 (d, 1 H) 6.86 (d, 1 H) 7.22-7.33 (m, 3 H) 7.35-7.48 (m, 9 H) 7.62-7.73 (m, 4 H) 7.87 (dt, 1 H) 8.15 (s, 1 H).

LCMS: (ESI) m/z 822 [M+H]$^+$.

Optical Rotation:

Concentration: 0.1 g/dL

Lamp: Sodium

Wavelength: 589 nm

Temperature: 20° C.

Path length: 10 cm

Cell volume: 1 ml

Solvent: Methanol

[α]=−88

Intermediate 99

4-((R)-4-((S)-2-((tert-butyldiphenylsilyloxy)methyl)morpholino)-1-(phenylthio)butan-2-ylamino)-3-(trifluoromethylsulfonyl)benzenesulfonamide

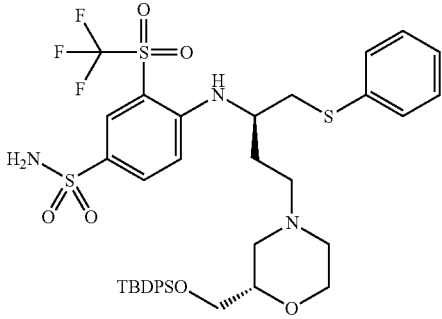

The second eluting compound had a retention time of 6.86 minutes, 92% d.e. (223 mg, yield: 16%).

¹H NMR (300 MHz, METHANOL-d4) δ ppm 1.07 (s, 5 H) 1.02 (s, 5 H) 1.73-1.91 (m, 2 H) 2.04-2.16 (m, 2 H) 2.36-2.45 (m, 2 H) 2.53 (d, 1 H) 2.73 (d, 1 H) 2.92 (d, 1 H) 3.12-3.29 (m, 2 H) 3.50-3.64 (m, 4 H) 3.71 (dd, 1 H) 3.81 (t, 1 H) 4.06 (d, 1 H) 6.86 (d, 1 H) 7.22-7.33 (m, 3 H) 7.35-7.48 (m, 9 H) 7.62-7.73 (m, 4 H) 7.87 (dt, 1 H) 8.15 (s, 1 H).

LCMS: (ESI) m/z 822 [M+H]⁺.

Optical Rotation:
Concentration: 0.1 g/dL
Lamp: Sodium
Wavelength: 589 nm
Temperature: 20° C.
Path length: 10 cm
Cell volume: 1 ml
Solvent: Methanol
[α]=−65

Intermediate 100

4-(4-((R)-(tert-butyldimethylsilyloxy)(4'-chlorobiphenyl-2-yl)methyl)piperidin-1-yl)-N-(4-((R)-4-((R)-2-((tert-butyldiphenylsilyloxy)methyl)morpholino)-1-(phenylthio)butan-2-ylamino)-3-(trifluoromethylsulfonyl)phenylsulfonyl)benzamide

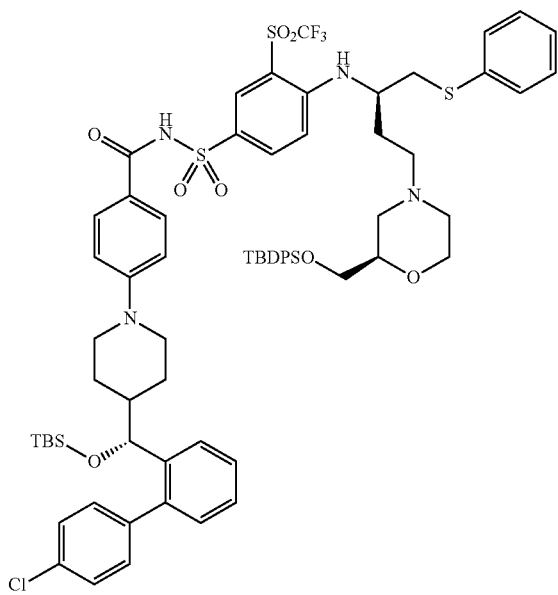

The title product (77 mg, 66%) was prepared using a procedure similar to the one described for the synthesis of INTERMEDIATE 33. (R)-4-(4-((tert-Butyldimethylsilyloxy)(4'-chlorobiphenyl-2-yl)methyl)piperidin-1-yl)benzoic acid (INTERMEDIATE 13, 51.7 mg, 0.10 mmol) and 4-((R)-4-((R)-2-((tert-butyldiphenylsilyloxy)methyl)morpholino)-1-(phenylthio)butan-2-ylamino)-3-(trifluoromethyl sulfonyl)benzenesulfonamide (INTERMEDIATE 98, 72 mg, 0.09 mmol) were used as starting materials. The title product was used in the preparation of EXAMPLE 22 without further purification.

LCMS: (ESI) m/z 1340 [M+H]⁺.

Intermediate 101

4-(4-((R)-(tert-butyldimethylsilyloxy)(4'-chlorobiphenyl-2-yl)methyl)piperidin-1-yl)-N-(4-((R)-4-4S)-2-((tert-butyldiphenylsilyloxy)methyl)morpholino)-1-(phenylthio)butan-2-ylamino)-3-(trifluoromethylsulfonyl)phenylsulfonyl)benzamide

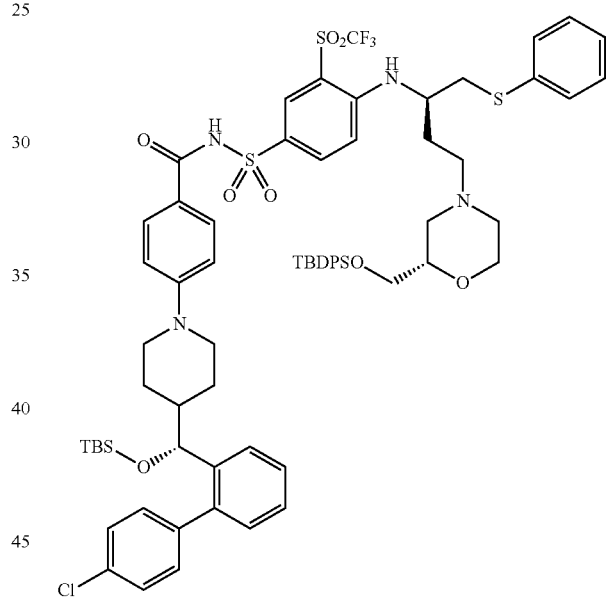

The title product (99 mg, yield: almost quantitative) was prepared using a procedure similar to the one described for the synthesis of INTERMEDIATE 33. (R)-4-(4-((tert-Butyldimethylsilyloxy)(4'-chlorobiphenyl-2-yl)methyl)piperidin-1-yl)benzoic acid (INTERMEDIATE 13, 43.6 mg, 0.08 mmol) and 4-((R)-4-((S)-2-((tert-butyldiphenylsilyloxy)methyl)morpholino)-1-(phenylthio)butan-2-ylamino)-3-(trifluoromethylsulfonyl)benzenesulfonamide (INTERMEDIATE 99, 61 mg, 0.07 mmol) were used as starting materials. The title product was used in the preparation of EXAMPLE 23 without further purification.

LCMS: (ESI) m/z 1340 [M+H]⁺.

Intermediate 102

(S)-tert-butyl 3-((tert-butyldiphenylsilyloxy)methyl)morpholine-4-carboxylate

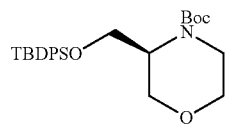

To a solution of (S)-tert-butyl 3-(hydroxymethyl)morpholine-4-carboxylate (1.00 g, 4.60 mmol) in DCM (10 ml) were added sequentially triethylamine (1.3 ml, 9.21 mmol), tert-butylchlorodiphenylsilane (1.414 ml, 5.52 mmol) and DMAP (0.56 g, 4.60 mmol) and the resulting mixture was stirred overnight at ambient temperature. The mixture was diluted with water and the aqueous phase was extracted with DCM. The organic layer was separated and concentrated under reduced pressure. The concentrate was purified by column chromatography (ISCO, eluting with 0→50% EtOAc/hexanes) to afford the title product (1.0 g, yield: 48%).
LCMS: (ESI) m/z 478 [M+Na]+.

Intermediate 103

(S)-3-((tert-butyldiphenylsilyloxy)methyl)morpholine, HCl salt

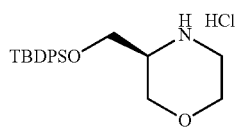

(S)-tert-Butyl 3-((tert-butyldiphenylsilyloxy)methyl)morpholine-4-carboxylate (INTERMEDIATE 102, 1.0 g, 2.19 mmol) in 1,4-dioxane (10 ml) was treated with HCl (4M in Dioxane, 0.76 ml, 21.95 mmol) and the resulting mixture was stirred at room temperature overnight. Evaporation of the volatiles under reduced pressure gave the title product (0.8 g, yield: 93%).
LCMS: (ESI) m/z 356 [M+H]+.

Intermediate 104

4-((R)-4-((S)-3-((tert-butyldiphenylsilyloxy)methyl)morpholino)-4-oxo-1-(phenylthio)butan-2-ylamino)-3-(trifluoromethylsulfonyl)benzenesulfonamide

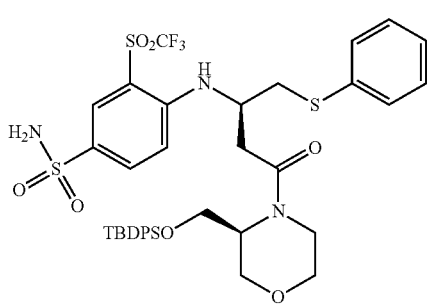

(R)-4-(Phenylthio)-3-(4-sulfamoyl-2-(trifluoromethylsulfonyl)phenylamino)butanoic acid (INTERMEDIATE 8, 0.8 g, 1.60 mmol) was added to a solution of (S)-3-((tert-butyldiphenylsilyloxy)methyl)morpholine, hydrochloride salt (INTERMEDIATE 103, 0.57 g, 1.60 mmol), DIPEA (0.84 ml, 4.81 mmol) and HATU (0.92 g, 2.41 mmol) in DCM (10 ml) and the resulting mixture was stirred at room temperature for 2 hours. The mixture was diluted with DCM and washed with H2O (2×), 1N aq. NaHSO4 and saturated aq. NaHCO3. The organic layer was dried (Na2SO4), concentrated under reduced pressure and purified by column chromatography (ISCO, eluting with 0→100% DCM/10% MeOH in DCM) to provide the title product (0.5 g, yield: 37%).
LCMS: (ESI) m/z 834 [M−H]+.

Intermediate 105

4-((R)-4-((S)-3-((tert-butyldiphenylsilyloxy)methyl)morpholino)-1-(phenylthio)butan-2-ylamino)-3-(trifluoromethylsulfonyl)benzenesulfonamide

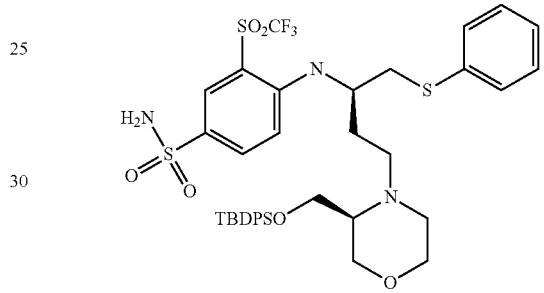

The title product (0.1 g, yield: 51%) was prepared using a procedure similar to the one described for the synthesis of INTERMEDIATE 97. 4-((R)-4-((S)-3-((tert-Butyldiphenylsilyloxy)methyl)morpholino)-4-oxo-1-(phenylthio)butan-2-ylamino)-3-(trifluoromethylsulfonyl)benzenesulfonamide (INTERMEDIATE 104, 0.2 g, 0.24 mmol) was as starting material. The title product was purified by column chromatography (ISCO, eluting with 0→50% EtOAc/hexanes).
LCMS: (ESI) m/z 822 [M+H]+.

Intermediate 106

(R)-tert-butyl 3-((tert-butyldiphenylsilyloxy)methyl)morpholine-4-carboxylate

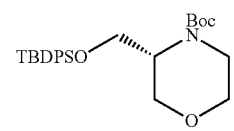

The title product (2.0 g, yield: 95%) was prepared using a procedure similar to the one described for the synthesis of INTERMEDIATE 102. (R)-tert-Butyl 3-(hydroxymethyl)morpholine-4-carboxylate (commercially available, 1.0 g, 4.60 mmol) and tert-butylchlorodiphenylsilane (1.4 ml, 5.52 mmol) were used as starting materials. The title product was purified by column chromatography (ISCO, eluting with 0→50% EtOAc/hexanes).
LCMS: (ESI)m/z 478 [M+Na]+.

Intermediate 107

(R)-3-((tert-butyldiphenylsilyloxy)methyl)morpholine, hydrochloride salt

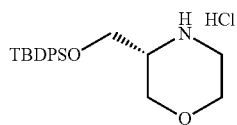

The title product (1.2 g, yield: 77%) was prepared using a procedure similar to the one described for the synthesis of INTERMEDIATE 103. (R)-tert-Butyl 3-((tert-butyldiphenylsilyloxy)methyl)morpholine-4-carboxylate (INTERMEDIATE 106, 2.0 g, 4.39 mmol) was used as starting material. The title product was obtained as a hydrochloride salt after evaporation of the volatiles under reduced pressure.
LCMS: (ESI)m/z 356 [M+H]$^+$.

Intermediate 108

4-((R)-4-((R)-3-((tert-butyldiphenylsilyloxy)methyl)morpholino)-4-oxo-1-(phenylthio)butan-2-ylamino)-3-(trifluoromethylsulfonyl)benzenesulfonamide

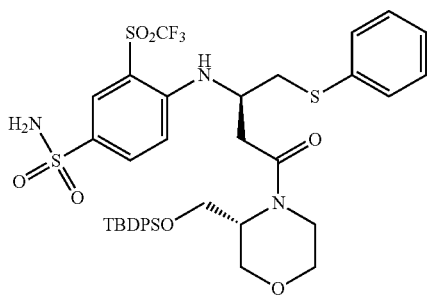

The title product (0.2 g, yield: 24%) was prepared using a procedure similar to the one described for the synthesis of INTERMEDIATE 104. (R)-3-((tert-Butyldiphenylsilyloxy)methyl)morpholine, hydrochloride salt (INTERMEDIATE 107, 0.200 g, 0.24 mmol) and (R)-4-(phenylthio)-3-(4-sulfamoyl-2-(trifluoromethylsulfonyl)phenylamino)butanoic acid (INTERMEDIATE 8, 0.500 g, 1.00 mmol) were used as starting material. The title product was purified by column chromatography (ISCO, eluting with 0→100% DCM/10% MeOH in DCM).
LCMS: (ESI) m/z 834 [M−H]$^+$.

Intermediate 109

4-((R)-4-((R)-3-((tert-butyldiphenylsilyloxy)methyl)morpholino)-1-(phenylthio)butan-2-ylamino)-3-(trifluoromethylsulfonyl)benzenesulfonamide

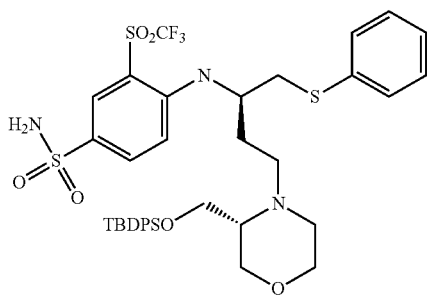

The title product (0.082 g, yield: 75%) was prepared using a procedure similar to the one described for the synthesis of INTERMEDIATE 97. 4-((R)-4-((R)-3-((tert-Butyldiphenylsilyloxy)methyl)morpholino)-4-oxo-1-(phenylthio)butan-2-ylamino)-3-(trifluoromethylsulfonyl)benzenesulfonamide (INTERMEDIATE 108, 0.120 g, 0.14 mmol) was used as starting material. The title product was purified by column chromatography (ISCO, eluting with 0→50% EtOAc/hexanes).
LCMS: (ESI) m/z 822 [M+H]$^+$.

Intermediate 110

4-(4-((R)-(tert-butyldimethylsilyloxy)(4'-chlorobiphenyl-2-yl)methyl)piperidin-1-yl)-N-(4-((R)-4-((R)-3-((tert-butyldiphenylsilyloxy)methyl)morpholino)-1-(phenylthio)butan-2-ylamino)-3-(trifluoromethylsulfonyl)phenylsulfonyl)benzamide

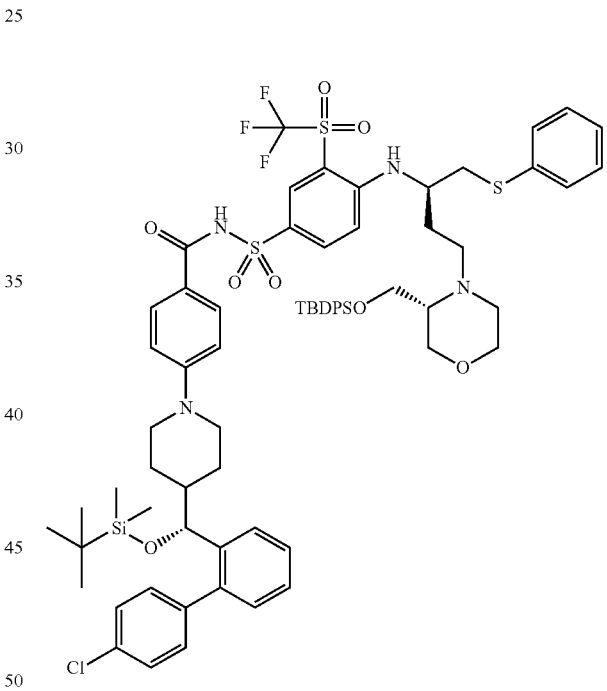

The title product (134 mg, yield: 77%) was prepared using a procedure similar to the one described for the synthesis of INTERMEDIATE 33. (R)-4-(4-((tert-Butyldimethylsilyloxy)(4'-chlorobiphenyl-2-yl)methyl)piperidin-1-yl)benzoic acid (INTERMEDIATE 13, 67.7 mg, 0.13 mmol) and 4-((R)-4-((R)-3-((tert-butyldiphenylsilyloxy)methyl)morpholino)-1-(phenylthio)butan-2-ylamino)-3-(trifluoromethylsulfonyl)benzenesulfonamide (INTERMEDIATE 109, 94.4 mg, 0.11 mmol) were used as starting materials. The resulting product was purified by column chromatography (ISCO, 12 g silica gel column, eluting with 0→30% EtOAc/hexanes), providing the title compound.

Intermediate 111

(R)-tert-butyl 2-((diethylamino)methyl)morpholine-4-carboxylate and (S)-tert-butyl 2-((diethylamino)methyl)morpholine-4-carboxylate, mixture of enantiomers

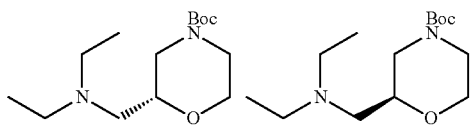

Potassium carbonate (3.20 g, 23.12 mmol) and iodoethane (1.9 ml, 23.12 mmol) were added sequentially to a solution of (R)-tert-butyl 2-(aminomethyl)morpholine-4-carboxylate and (S)-tert-butyl 2-(aminomethyl)morpholine-4-carboxylate, mixture of enantiomers (commercially available, 1.0 g, 4.62 mmol) in EtOH (21.25 ml) was added and the resulting mixture was heated at 80° C. for 3 hours. The reaction mixture was cooled to r.t, diluted with EtOAc and filtered over a pad of Celite® with copious washings (EtOAc). The filtrate was concentrated under reduced pressure and the concentrate by column chromatography (ISCO, eluting with 100% DCM→100% DCM/MeOH/NH$_3$ (10:1:0.1 v/v/v)) to give the title product as a mixture of enantiomers (1.1 g, yield: 85%).

$^1$H NMR (400 MHz, DICHLOROMETHANE-d$_2$) δ ppm 4.0-3.75 (m, 4H), 3.56 (m, 1H), 3.00-2.55 (m, 8H), 1.48 (s, 9H), 1.26 (m, 6H).

LCMS: (ESI) m/z 273 [M+H]$^+$.

Intermediate 112

(R)—N-ethyl-N-(morpholin-2-ylmethyl)ethanamine and (S)—N-ethyl-N-(morpholin-2-ylmethyl)ethanamine, mixture of enantiomers

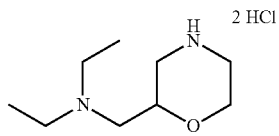

To a solution of (R)-tert-butyl 2-((diethylamino)methyl)morpholine-4-carboxylate and (S)-tert-butyl 2-((diethylamino)methyl)morpholine-4-carboxylate, mixture of enantiomers (INTERMEDIATE 111, 1.03 g, 3.78 mmol) in MeOH (15.8 ml) was added HCl (4M in dioxane, 9.45 ml, 37.81 mmol) and the reaction mixture was stirred at room temperature for 1 hour. The reaction mixture was concentrated under reduced pressure and dried under vacuum overnight to provide the title product as a mixture of enantiomers in the form of a dihydrochloride salt (0.92 g, yield: 99%).

$^1$H NMR (400 MHz, DMSO-d$_6$) δ ppm 4.34 (m, 1H), 3.99 (m, 1H), 3.88-3.82 (m, 3H), 3.27 (d, 2H), 3.20-3.10 (m, 4H), 2.94 (m, 1H), 2.82 (m, 1H), 1.21 (m, 6H).

Intermediate 113

4-((R)-4-((R)-2-((diethylamino)methyl)morpholino)-4-oxo-1-(phenylthio)butan-2-ylamino)-3-(trifluoromethylsulfonyl)benzenesulfonamide and 4-((R)-4-((S)-2-((diethylamino)methyl)morpholino)-4-oxo-1-(phenylthio)butan-2-ylamino)-3-(trifluoromethylsulfonyl)benzenesulfonamide hydrochloride salts, mixture of diastereomers

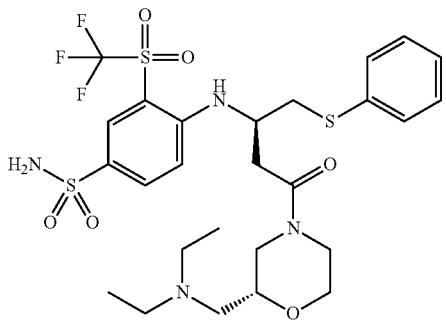 [SMILES: CCN(CC)CC1CN(CC[C@H](CSc2ccccc2)Nc2ccc(S(N)(=O)=O)cc2S(=O)(=O)C(F)(F)F)CCO1]

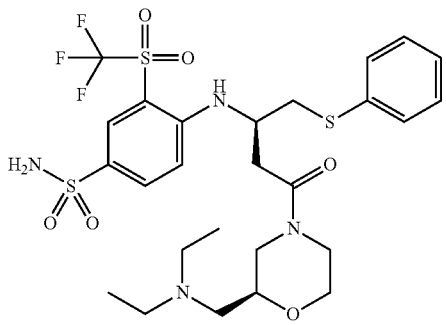

The title product (1.05 g, yield: 43%) was prepared using a procedure similar to the one described for the synthesis of INTERMEDIATE 104. (R)—N-ethyl-N-(morpholin-2-ylmethyl)ethanamine and (S)—N-ethyl-N-(morpholin-2-ylmethyl)ethanamine hydrochloride salts, mixture of enantiomers (INTERMEDIATE 112, 0.91 g, 3.71 mmol) and (R)-4-(phenylthio)-3-(4-sulfamoyl-2-(trifluoromethylsulfonyl)phenylamino)butanoic acid (INTERMEDIATE 8, 1.850 g, 3.71 mmol) were used as starting material. The title product was purified by column chromatography (ISCO, eluting with 0→100% DCM to 10% MeOH/0.1% NH$_3$ in DCM) as a mixture of diastereomers.

$^1$H NMR (400 MHz, CHLOROFORM-d) δ ppm 8.15 (s, 1 H), 7.85-7.70 (m, 2 H), 7.43 (m, 2 H), 7.35-7.27 (m, 2 H), 6.58 (m, 1 H), 4.40 (m, 1 H), 4.16 (m, 1 H), 3.91 (m, 1 H), 3.55-3.40 (m, 2 H), 3.35-3.05 (m, 3 H), 3.00-2.37 (m, 10 H), 1.04 (m, 6 H).

LCMS: (ESI) m/z 653 [M+H]$^+$.

Intermediate 114

4-((R)-4-((R)-2-((diethylamino)methyl)morpholino)-1-(phenylthio)butan-2-ylamino)-3-(trifluoromethylsulfonyl)benzenesulfonamide and 4-((R)-4-((S)-2-((diethylamino)methyl)morpholino)-1-(phenylthio)butan-2-ylamino)-3-(trifluoromethylsulfonyl)benzenesulfonamide, mixture of diastereomers

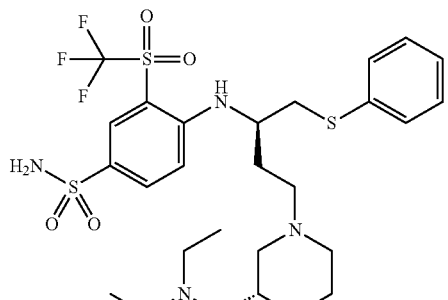

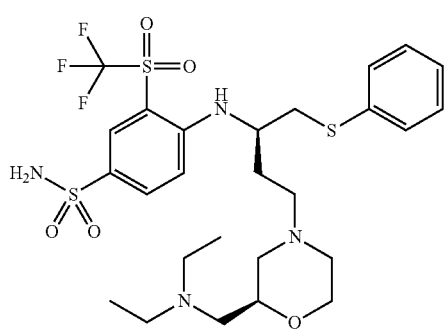 [SMILES: CCN(CC)CC1CN(CC[C@H](CSc2ccccc2)Nc2ccc(S(N)(=O)=O)cc2S(=O)(=O)C(F)(F)F)CCO1]

The title product (0.75 g, yield: 83%) w was prepared using a procedure similar to the one described for the synthesis of INTERMEDIATE 97. 4-((R)-4-((R)-2-((diethylamino)methyl)morpholino)-4-oxo-1-(phenylthio)butan-2-ylamino)-3-(trifluoromethylsulfonyl)benzenesulfonamide and 4-((R)-4-((S)-2-((diethylamino)methyl)morpholino)-4-oxo-1-(phenylthio)butan-2-ylamino)-3-(trifluoromethylsulfonyl)benzenesulfonamide, mixture of diastereomers (INTERMEDIATE 113, 0.92 g, 1.41 mmol) was used as starting material. The title product was obtained as a mixture of diastereomers after evaporation of the volatiles under reduced pressure.

LCMS: (ESI) m/z 639 [M+H]$^+$.

The resulting two diastereomers of the title product were separated using were separated using Chiral SFC, providing INTERMEDIATES 115 and 116 as substantially separated diastereomers.

Column: Chiralpak IB column
Column dimensions: 21×250 mm, 5μ
Modifier: 15% Methanol, 0.1% dimethylethylamine
Flow rate (ml/min): 60
Outlet Pressure (bar): 100
Detection (nm): 220

Intermediate 115

4-((2R)-4-(2-((diethylamino)methyl)morpholino)-1-(phenylthio)butan-2-ylamino)-3-(trifluoromethylsulfonyl)benzenesulfonamide, first eluting compound

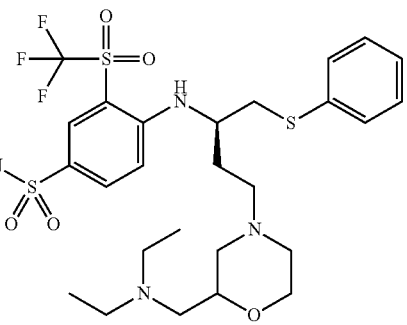

The first eluting compound had a retention time of 17.41 minutes.

LCMS: (ESI) m/z 639 [M+H]$^+$.

Intermediate 116

4-((2R)-4-(2-((diethylamino)methyl)morpholino)-1-(phenylthio)butan-2-ylamino)-3-(trifluoromethylsulfonyl)benzenesulfonamide, second eluting compound

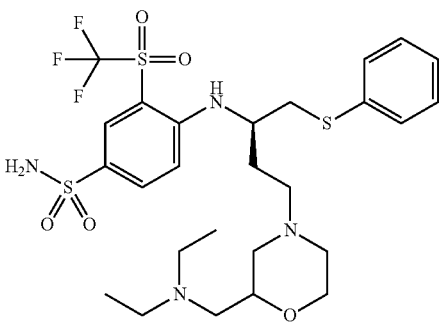

The second eluting compound had a retention time of 19.18 minutes.

Intermediate 117

4-(4-((R)-(tert-butyldimethylsilyloxy)(4'-chlorobiphenyl-2-yl)methyl)piperidin-1-yl)-N-(4-42R)-4-(2-((diethylamino)methyl)morpholino)-1-(phenylthio)butan-2-ylamino)-3-(trifluoromethylsulfonyl)phenylsulfonyl)benzamide, single diastereomer

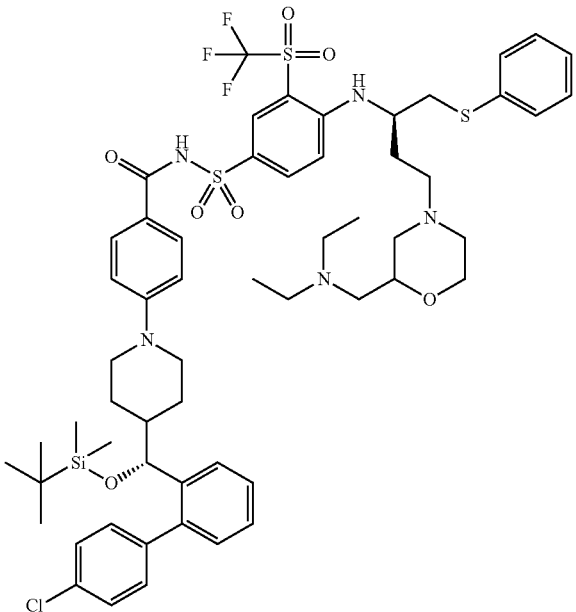 [SMILES: CCN(CC)CC1CN(CC[C@H](CSc2ccccc2)Nc2ccc(S(=O)(=O)NC(=O)c3ccc(N4CCC([C@@H](O[Si](C)(C)C(C)(C)C)c5ccccc5-c5ccc(Cl)cc5)CC4)cc3)cc2S(=O)(=O)C(F)(F)F)CCO1]

The title product (199 mg, yield: 74%) was prepared using a procedure similar to the one described for the synthesis of INTERMEDIATE 33. (R)-4-(4-((tert-Butyldimethylsilyloxy)(4'-chlorobiphenyl-2-yl)methyl)piperidin-1-yl)benzoic acid (INTERMEDIATE 13, 125 mg, 0.23 mmol) and 4-((2R)-4-(2-((diethylamino)methyl)morpholino)-1-(phenylthio)butan-2-ylamino)-3-(trifluoromethylsulfonyl)benzenesulfonamide (INTERMEDIATE 115, first eluting compound 149 mg, 0.23 mmol) were used as starting materials. The title product was obtained after evaporating the volatiles under reduced pressure, and was used in the preparation of EXAMPLE 26 without further purification.

LCMS: (ESI) m/z 1156 [M+H]$^+$.

Intermediate 118

(R)-4-(4-((4'-chlorobiphenyl-2-yl)(di-tert-butoxyphosphonooxymethoxy)methyl)piperidin-1-yl)benzoic acid

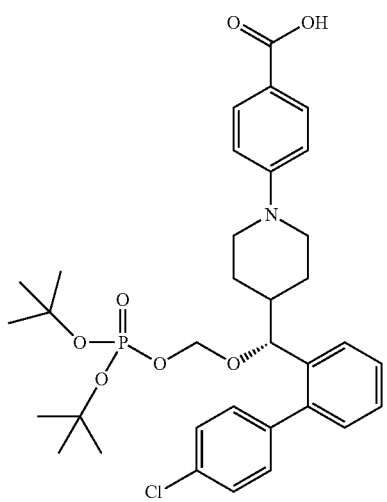 [SMILES: CC(C)(C)OP(=O)(OCO[C@@H](c1ccccc1-c1ccc(Cl)cc1)C1CCN(c2ccc(C(=O)O)cc2)CC1)OC(C)(C)C]

A solution of (R)-4-(4-((4'-chlorobiphenyl-2-yl)(hydroxy)methyl)piperidin-1-yl)benzoic acid (INTERMEDIATE 40, 360 mg, 0.85 mmol) in toluene (4.0 ml) was treated with paraformaldehyde (128 mg, 4.27 mmol) and the resulting mixture was cooled at 0° C. HCl (g) was slowly bubbled in the solution through a pipet. The mixture was allowed to stir for 1 hour whereupon it was dried over CaCl$_2$ pellets, resulting in effervescence. The solution was removed by pipet and then spun under reduced pressure (40 mbar) for a few minutes to remove excess HCl. The clear yellow solution was stirred and treated with silver di-tert-butyl phosphate (INTERMEDIATE 59, 0.90 g). At 0.25 hours the reaction was filtered through Celite® using a Büchner funnel, and the filter cake was washed with several portions of toluene. Evaporation of the filtrate under reduced pressure afforded a residue that was purified by column chromatography (ISCO, eluting with 0→50% EtOAc/CH$_2$Cl$_2$ for 14 minutes) to provide the title product (150 mg, yield: 25%).

$^1$H NMR (300 MHz, DMSO-d$_6$) δ ppm 0.93-1.43 (m, 21 H) 1.68-1.93 (m, 2 H) 2.52-2.75 (m, 2 H) 3.66-3.78 (m, 1 H) 3.78-3.90 (m, 1 H) 4.53 (d, 1 H) 4.71-4.83 (m, 1 H) 5.04-5.15 (m, 1 H) 6.86 (d, 2 H) 7.20 (d, 1 H) 7.26-7.53 (m, 7 H) 7.71 (d, 2 H) 12.17 (s, 1 H).

LCMS: m/z 644 [M+H]$^+$.

Intermediate 119

(R)-ethyl 4-(4-((4'-chlorobiphenyl-2-yl)(diethoxyphosphoryloxy)methyl)piperidin-1-yl)benzoate

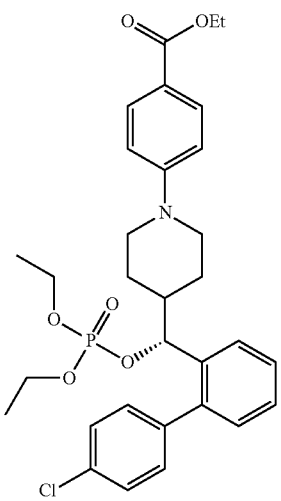 [SMILES: CCOC(=O)c1ccc(N2CCC([C@@H](OP(=O)(OCC)OCC)c3ccccc3-c3ccc(Cl)cc3)CC2)cc1]

A solution of (R)-ethyl 4-(4-((4'-chlorobiphenyl-2-yl)(hydroxy)methyl)piperidin-1-yl)benzoate (INTERMEDIATE 11A, 600 mg, 1.33 mmol), CBr$_4$ (575 mg, 1.73 mmol), and pyridine (2 ml) at 0° C. was treated dropwise over a 10 minute period with triethyl phosphite (0.56 ml, 3.33 mmol). The solution was stirred at 0° C. for about 10 minutes and then the ice bath was removed. The reaction was stirred overnight at r.t. whereupon the excess pyridine was removed under reduced pressure and the concentrate was taken up in 50 ml of DCM. The organic layer was washed successively with 50 ml each of 0.5 N aq. HCl, saturated aqueous sodium bicarbonate, and water. The organic layers were dried over sodium sulfate, filtered and adsorbed onto silica gel. Purification by column chromatography (ISCO, 80 g silica gel column, eluting with 0→100% EtOAc/hexanes over 24 minutes) gave the title compound (500 mg, yield: 64%).

¹H NMR (400 MHz, DICHLOROMETHANE-d₂) δ ppm 1.00-1.16 (m, 1 H) 1.18-1.29 (m, 7 H) 1.28-1.46 (m, 4 H) 1.74-1.92 (m, 1 H) 2.01 (dt, 1 H) 2.61 (td, 1 H) 2.73 (td, 1 H) 3.71 (d, 1 H) 3.79-3.91 (m, 1 H) 3.91-4.00 (m, 3 H) 4.07 (dt, 1 H) 4.31 (q, 2 H) 5.25 (t, 1 H) 6.82 (d, 2 H) 7.24 (dd, 1 H) 7.34-7.54 (m, 6 H) 7.63 (dd, 1 H) 7.79-7.97 (m, 2 H).
³¹P NMR (121 MHz, DICHLOROMETHANE-d₂) δ ppm −1.76 (s, 2 P).
LCMS: (ESI) m/z 586, [M+H]⁺.

Intermediate 120

(R)-4-(4-((4'-chlorobiphenyl-2-yl)(diethoxyphosphoryloxy)methyl)piperidin-1-yl)benzoic acid

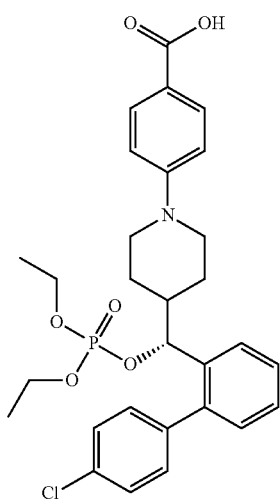 [SMILES: CCOP(=O)(OCC)O[C@@H](c1ccccc1-c1ccc(Cl)cc1)C1CCN(c2ccc(C(=O)O)cc2)CC1]

A solution of (R)-ethyl 4-(4-((4'-chlorobiphenyl-2-yl)(diethoxyphosphoryloxy)methyl)piperidin-1-yl)benzoate (INTERMEDIATE 119, 500 mg, 0.85 mmol) in THF (10 ml) and MeOH (2.5 ml), at room temperature, was treated with a solution of lithium hydroxide (102 mg, 4.27 mmol) in water (2.5 ml). The reaction was heated to 30° C. overnight and subsequently warmed to 40° C. for about 5 hours. The mixture was allowed to cool to room temperature whereupon the volatiles were removed under reduced pressure. The concentrate was diluted with 30 ml of water, acidified with a few drops of 6N HCl to provide a white precipitate. The precipitate was collected by vacuum filtration to give the title compound (410 mg, yield: 86%).
¹H NMR (400 MHz, DICHLOROMETHANE-d₂) δ ppm 1.01-1.15 (m, 1 H) 1.21 (tdd, 7 H) 1.28-1.44 (m, 1 H) 1.81-1.94 (m, 1 H) 1.94-2.07 (m, 1 H) 2.64 (d, 1 H) 2.76 (m, 1H) 3.68-3.81 (m, 1 H) 3.85-4.01 (m, 4 H) 4.01-4.15 (m, 1 H) 5.24 (t, 1 H) 6.83 (d, 2 H) 7.23 (dd, 1 H) 7.37-7.54 (m, 6 H) 7.58-7.68 (m, 1 H) 7.86-7.95 (m, 2 H).
³¹P NMR (121 MHz, DICHLOROMETHANE-d₂) δ ppm −1.45 (s, 2 P).
LCMS: (ESI) m/z 558 [M+H]⁺.
Optical Rotation:
Concentration: 0.1 g/dL
Lamp: Sodium
Wavelength: 589 nm
Temperature: 20° C.
Path length: 10 cm
Cell volume: 1 ml
Solvent: Dichloromethane
[α]=+76

Intermediate 121

(R)-ethyl 4-(4-((4'-chlorobiphenyl-2-yl)(dimethoxyphosphoryloxy)methyl)piperidin-1-yl)benzoate

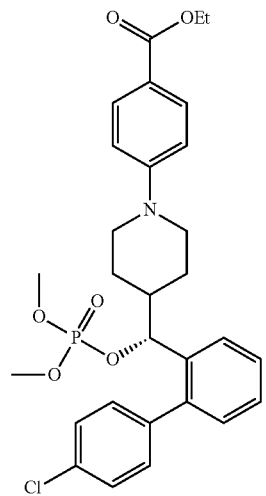

A similar procedure to that described for INTERMEDIATE 119 utilizing (R)-ethyl 4-(4-((4'-chlorobiphenyl-2-yl)(hydroxy)methyl)piperidin-1-yl)benzoate (INTERMEDIATE 11A, 600 mg, 1.33 mmol) and trimethyl phosphite (0.473 ml, 4.0 mmol) as starting material was followed, with subsequent purification by column chromatography (ISCO, 0→100% EtOAc/hexane over 24 minutes) to give the title compound (500 mg, yield: 67%). The title compound was used in the preparation of INTERMEDIATE 122 without further purification.
¹H NMR (400 MHz, DICHLOROMETHANE-d₂) δ ppm 0.88-1.02 (m, 1 H) 1.06-1.12 (m, 1 H) 1.17-1.31 (m, 5 H) 1.63-1.79 (m, 1 H) 1.80-1.89 (m, 1 H) 2.48 (td, 1 H) 2.60 (td, 1 H) 3.42-3.56 (m, 7 H) 3.58 (d, 1 H) 3.65-3.80 (m, 1 H) 4.17 (q, 2 H) 5.11 (t, 1 H) 6.58-6.75 (m, 2 H) 7.11 (dd, 1 H) 7.25-7.40 (m, 6 H) 7.51 (dd, 1 H) 7.68-7.85 (m, 2 H).
³¹P NMR (121 MHz, DICHLOROMETHANE-d₂) δ ppm 0.68 (s, 1 P).
LCMS: (ESI) m/z 558, [M+H]⁺.

Intermediate 122

(R)-4-(4-((4'-chlorobiphenyl-2-yl)(dimethoxyphosphoryloxy)methyl)piperidin-1-yl)benzoic acid

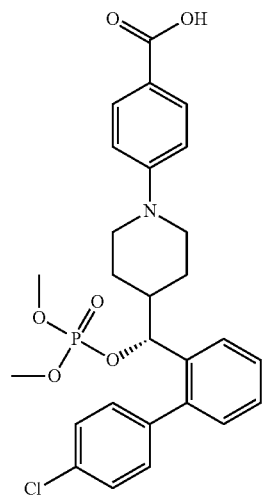 [SMILES: COP(=O)(OC)O[C@@H](c1ccccc1-c1ccc(Cl)cc1)C1CCN(c2ccc(C(=O)O)cc2)CC1]

A mixture of lithium hydroxide (107 mg, 4.48 mmol), (R)-ethyl 4-(4-((4'-chlorobiphenyl-2-yl)(dimethoxyphosphoryloxy)methyl)piperidin-1-yl)benzoate (INTERMEDIATE 121, 500 mg, 0.9 mmol), THF (10 ml), water (2.5 ml), and MeOH (2.5 ml) was heated at 35° C. overnight. The reaction mixture was concentrated under reduced pressure, diluted with water (10 ml) and acidified with an aqueous solution of 6 N HCl, resulting in a precipitate. The solid was collected by filtration to give the title compound (270 mg, yield: 57%). The title compound was used in the preparation of EXAMPLE 30 without further purification.

$^1$H NMR (400 MHz, DICHLOROMETHANE-$d_2$) δ ppm 0.91-1.40 (m, 4 H) 1.70-2.05 (m, 2 H) 2.48-2.62 (m, 1 H) 2.70 (m, 1 H) 3.19-3.63 (m, 7 H) 3.69-3.83 (m, 1 H) 5.16 (t, 1 H) 6.77 (m, 1 H) 7.12 (m, 1 H) 7.21-7.46 (m, 7 H) 7.52 (m, 1 H) 7.79 (m, 2 H).

LCMS: (ESI) m/z 530 [M+H]$^+$.

Optical Rotation:

Concentration: 0.2 g/dL

Lamp: Sodium

Wavelength: 589 nm

Temperature: 20° C.

Path length: 10 cm

Cell volume: 1 ml

Solvent: Dichloromethane

[α]=+51

Intermediate 123

(S,E)-tert-butyl 4-((tert-butylsulfinylimino)methyl)piperidine-1-carboxylate

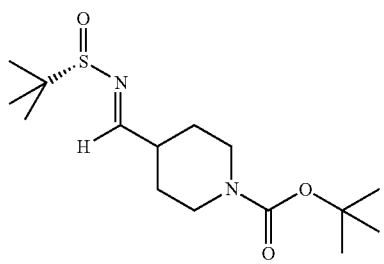 [SMILES: CC(C)(C)OC(=O)N1CCC(/C=N/[S@@](=O)C(C)(C)C)CC1]

A solution of (S)-2-methylpropane-2-sulfinamide (2.0 g, 16.50 mmol) in THF (8.0 ml) and titanium(IV) ethoxide (17.3 ml, 82.51 mmol) were added sequentially to a solution of tert-butyl 4-formylpiperidine-1-carboxylate (3.70 g, 17.33 mmol) in THF (8.0 ml). The resulting mixture was stirred at r.t for 2 hours. The reaction mixture was poured into ice/water and the suspension filtered. The filtrate was extracted with EtOAc and the organic layer was dried with MgSO$_4$, filtered and the filtrate was concentrated under reduced pressure. The residue was dried under vacuum to provide the title compound (4.45 g, yield: 85%).

LCMS: (ESI) m/z 317 [M+H]$^+$.

Intermediate 124 tert-Butyl 4-((R)-(2-bromophenyl)((S)-1,1-dimethylethylsulfinamido)methyl)piperidine-1-carboxylate and tert-butyl 4-((S)-(2-bromophenyl)((S)-1,1-dimethylethylsulfinamido)methyl)piperidine-1-carboxylate, mixture of diastereomers

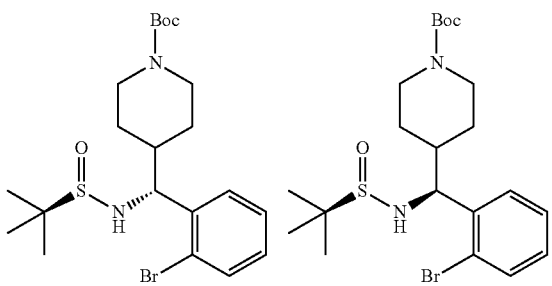

A solution of isopropylmagnesium chloride lithium chloride complex (24.9 ml, 32.39 mmol, 1.3 M THF) was cooled to −15° C. 1,2-dibromobenzene (3.80 ml, 31.60 mmol) was added and the mixture was stirred at −15° C. for 2 hours. A solution of (S,E)-tert-butyl 4-((tert-butylsulfinylimino)methyl)piperidine-1-carboxylate (INTERMEDIATE 123, 2.50 g, 3.90 mmol) in THF (10.8 ml) was added dropwise to the first mixture and the resulting reaction mixture was stirred at −15° C. overnight. The reaction mixture was allowed to warm to 0° C. and quenched with saturated. aq. NH$_4$Cl. The mixture was diluted with EtOAc and washed with H$_2$O. The organic layer was dried over Na$_2$SO$_4$, filtered and the filtrate concentrated under reduced pressure to to give a residue which was purified by column chromatography (ISCO, silica gel column, eluting with 0→100% EtOAc/hexanes) to provide the title compounds (3.0 g, yield: 80%) as a mixture of diastereomers (ratio of 2:1 in favor of tert-butyl 4-((R)-(2-bromophenyl)((S)-1,1-dimethylethylsulfinamido)methyl)piperidine-1-carboxylate).

LCMS: (ESI) m/z 474 [M+H]$^+$.

Intermediate 125 tert-Butyl 4-((R)-(4'-chlorobiphenyl-2-yl)((S)-1,1-dimethylethylsulfinamido)methyl)piperidine-1-carboxylate and tert-butyl 4-((S)-(4'-chlorobiphenyl-2-yl)((S)-1,1-dimethylethylsulfinamido)methyl)piperidine-1-carboxylate, mixture of diastereomers

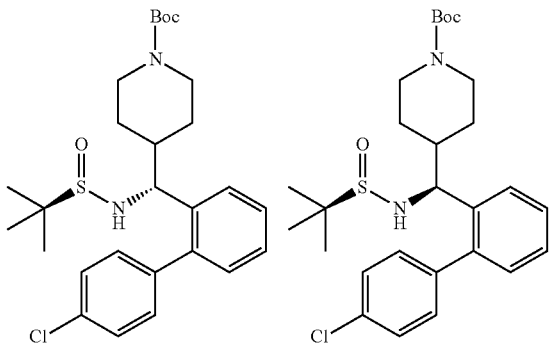

A suspension of the diastereomeric mixture of tert-butyl 4-((R)-(2-bromophenyl)((S)-1,1-dimethylethylsulfinamido)methyl)piperidine-1-carboxylate and tert-butyl 4-((S)-(2-bromophenyl)((S)-1,1-dimethylethylsulfinamido)methyl)piperidine-1-carboxylate (INTERMEDIATE 124, 2.98 g, 6.29 mmol), 4-chlorophenylboronic acid (1.48 g, 9.44 mmol), 2-dicyclohexylphosphino-2',6'-dimethoxybiphenyl (0.258 g, 0.63 mmol), tris(dibenzylideneacetone)dipalladium(0) (0.231 g, 0.25 mmol) and tripotassium phosphate (4.01 g, 18.88 mmol) in degassed toluene (15.0 ml) and H$_2$O (6.0 ml) was stirred at 100° C. for 5 hours. The reaction mixture was cooled to r.t, diluted with EtOAc and filtered through a pad of Celite®. The organic layer was separated and dried over Na$_2$SO$_4$, filtered and the filtrate concentrated to provide a residue which was purified by column chromatography (ISCO, silica gel column, eluting with 0→100% EtOAc/hexanes) to provide the title compounds (2.42, yield: 76%), as a mixture of diastereomers.

LCMS: (ESI) m/z 505 [M+H]$^+$.

Intermediate 126

(S)—N—((R)-(4'-chlorobiphenyl-2-yl)(piperidin-4-yl)methyl)-2-methylpropane-2-sulfinamide and
(S)—N—((S)-(4'-chlorobiphenyl-2-yl)(piperidin-4-yl)methyl)-2-methylpropane-2-sulfinamide trifluoroacetic salt, mixture of diastereomers

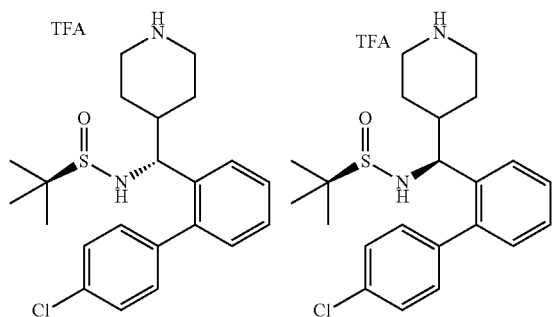

TFA (3.55 ml, 46.13 mmol) was added to a solution of tert-butyl 4-((R)-(4'-chlorobiphenyl-2-yl)((S)-1,1-dimethylethylsulfinamido)methyl)piperidine-1-carboxylate and tert-butyl 4-((S)-(4 '-chlorobiphenyl-2-yl)((S)-1,1-dimethylethylsulfinamido)methyl)piperidine-1-carboxylate, mixture of diastereomers (INTERMEDIATE 125, 2.33 g, 4.61 mmol) in DCM (43 ml) and the reaction mixture was stirred at r.t for 1 hour. The reaction mixture was concentrated under reduced pressure, diluted with EtOAc and washed with saturated aq. NaHCO$_3$ (2×). The organic layer was dried over Na$_2$SO$_4$, filtered and the filtrate was concentrated under reduced pressure. The residue obtained was dried under vacuum to provide title compounds (2.44 g, yield: almost quantitative) as a mixture of diastereomers.

LCMS: (ESI) m/z 405 [M+H]$^+$.

Intermediate 127

Ethyl 4-(4-((R)-(4'-chlorobiphenyl-2-yl)((S)-1,1-dimethylethylsulfinamido)methyl)piperidin-1-yl) benzoate and Ethyl 4-(4-((S)-(4'-chlorobiphenyl-2-yl)((S)-1,1-dimethylethylsulfinamido)methyl) piperidin-1-yl)benzoate, mixture of diastereomers

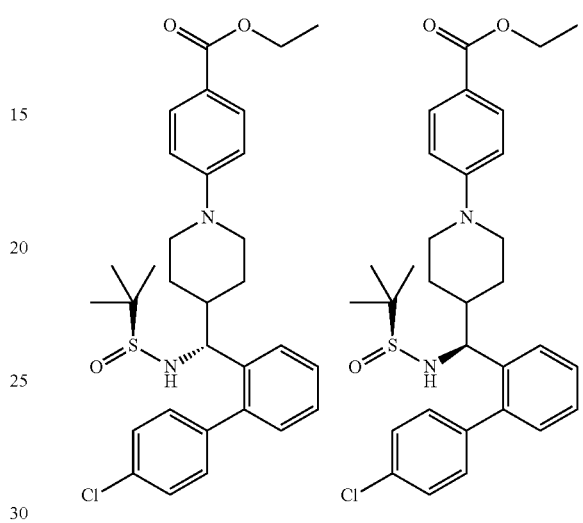

A suspension of (S)—N—((R)-(4'-chlorobiphenyl-2-yl)(piperidin-4-yl)methyl)-2-methylpropane-2-sulfinamide and (S)—N—((S)-(4'-chlorobiphenyl-2-yl)(piperidin-4-yl)methyl)-2-methylpropane-2-sulfinamide trifluoroacetic salt, mixture of diastereomers (INTERMEDIATE 126, 2.39 g, 4.61 mmol), chloro(2-dicyclohexylphosphino-2',6'-di-isopropoxy-1,1'-biphenyl)[2-(2-aminoethylphenyl)]Pd(II) methylbutyl ether adduct (0.168 g, 0.23 mmol), dicyclohexyl (2',6'-diisopropoxybiphenyl-2-yl)phosphine (0.108 g, 0.23 mmol), ethyl 4-iodobenzoate (0.77 ml, 4.61 mmol), and cesium carbonate (5.26 g, 16.14 mmol) in degassed toluene (22.3 ml) was stirred at 110° C. for 1.5 hours. The reaction mixture was cooled to r.t, diluted with EtOAc and filtered over a pad of Celite. The filtrate was concentrated under reduced pressure to provide a residue which was purified by column chromatography (ISCO, silica gel column, eluting with 0→100% EtOAc/hexanes) to provide title compound (2.10, yield: 82%), as a mixture of diastereomers.

LCMS: (ESI)m/z 553 [M+H]$^+$.

The two diastereomers were separated using Chiral SFC providing ethyl 4-(4-((R)-(4'-chlorobiphenyl-2-yl)((S)-1,1-dimethylethylsulfinamido)methyl)piperidin-1-yl)benzoate (INTERMEDIATE 128) as the major diastereomer (1.23 g) and ethyl 4-(4-((S)-(4'-chlorobiphenyl-2-yl)((S)-1,1-dimethylethylsulfinamido)methyl)piperidin-1-yl)benzoate (INTERMEDIATE 129) as the minor diastereomer (0.59 g)

Column: Chiralpak AD column
Column dimensions: 30×250 mm, 5μ
Mobile phase: CO$_2$ 75% and EtOH 25%.
Flow rate (ml/min): 120 ml/min
Detection (nm): 220 nm

Intermediate 130

4-(4-((R)-(4'-chlorobiphenyl-2-yl)((S)-1,1-dimethyl-ethylsulfinamido)methyl)piperidin-1-yl)benzoic acid

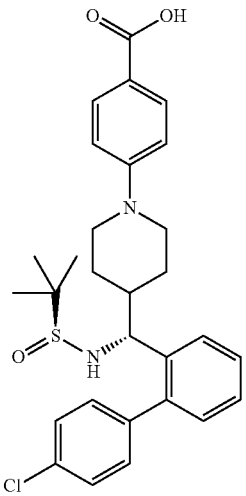 [SMILES: CC(C)(C)[S@](=O)N[C@@H](c1ccccc1-c1ccc(Cl)cc1)C1CCN(c2ccc(C(=O)O)cc2)CC1]

To a solution of ethyl 4-(4-((R)-(4'-chlorobiphenyl-2-yl)((S)-1,1-dimethylethylsulfinamido)methyl)piperidin-1-yl)benzoate (INTERMEDIATE 128, 0.40 g, 0.62 mmol) in THF (4.3 ml) was added MeOH (1.4 ml) and a solution of LiOH (0.09 g, 4.44 mmol) in water (1.4 ml). The reaction mixture was stirred at 40° C. overnight. The reaction mixture was cooled to rt, concentrated under reduced pressure, and the residue suspended in water. The suspension was cooled to 0° C., acidified to pH ~2 using 1N HCl aq., filtered, and the filtercake dried in a vacuum oven to provide the title compound (0.38 g, yield: almost quantitative).

LCMS: (ESI) m/z 525 [M+H]+.

Intermediate 131

4-(4-((R)-(4'-chlorobiphenyl-2-yl)((S)-1,1-dimethylethylsulfinamido)methyl)piperidin-1-yl)-N-(4-((R)-4-morpholino-1-(phenylthio)butan-2-ylamino)-3-(trifluoromethylsulfonyl)phenylsulfonyl)benzamide 4-(4-((R)-(4'-chlorobiphenyl-2-yl)((S)-1,1-dimethylethylsulfinamido)methyl)piperidin-1-yl)benzoic acid (INTERMEDIATE 130, 0.150 g, 0.29 mmol), DMAP (70 mg, 0.57 mmol), and EDC (0.110 g, 0.57 mmol) were placed in a 40 ml vial and flushed with nitrogen. DCM (4.0 ml) and DIPEA (0.10 ml, 0.57 mmol) were added, and the solution was stirred at r.t for 10 minutes. A solution of (R)-4-(4-morpholino-1-(phenylthio)butan-2-ylamino)-3-(trifluoromethylsulfonyl)benzenesulfonamide (INTERMEDIATE 69, 0.158 g, 0.29 mmol) in DCM (1.6 ml) was added to the solution and the reaction mixture was stirred at r.t overnight. The mixture was diluted with DCM and washed with 1N sodium bisulfate (aq.) followed by a saturated aq. sodium bicarbonate. The organic layer was dried (Na$_2$SO$_4$), filtered, and evaporated under reduced pressure to give a residue which was purified by column chromatography (ISCO, silica gel column, eluting with 0→100% DCM/MeOH/NH$_3$ (10:1:0.1 v/v/v)) to provide the title compound (0.21 g, yield: 69%).

$^1$H NMR (400 MHz, DICHLOROMETHANE-d$_2$) δ ppm 8.30 (d, 1H), 8.01 (dd, 1H), 7.70-7.67 (m, 2H), 7.45-7.18 (m, 14H), 6.96-6.93 (m, 1H), 6.70-6.65 (m, 3H), 4.29 (m, 1H), 3.96 (m, 1H), 3.76-3.73 (m, 1H), 3.62-3.55 (m, 6H), 3.11-3.06 (m, 2H), 2.65-2.48 (m, 2H), 2.38-2.25 (m, 6H), 2.06 (m, 2H), 1.81 (m, 1H), 1.69-1.62 (m, 2H), 1.17 (s, 9H), 1.11-0.95 (m, 3H).

LCMS: (ESI) m/z 1060 [M+H]+.

Intermediate 132 tert-Butyl 2-(((R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methylamino)-2-oxoethyl(methyl)carbamate

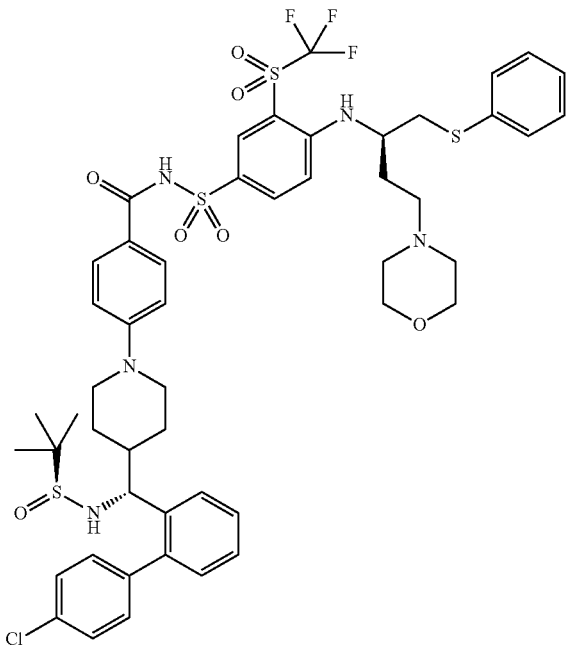 [SMILES: CC(C)(C)[S@](=O)N[C@@H](c1ccccc1-c1ccc(Cl)cc1)C1CCN(c2ccc(C(=O)NS(=O)(=O)c3ccc(N[C@H](CCN4CCOCC4)CSc4ccccc4)c(S(=O)(=O)C(F)(F)F)c3)cc2)CC1]

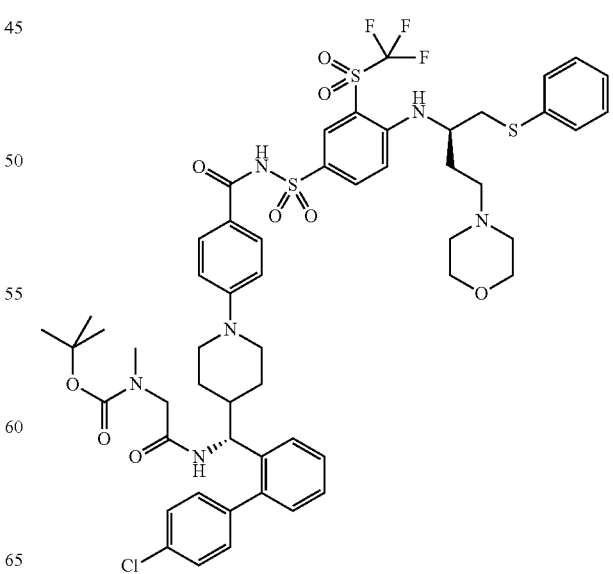

DIPEA (0.08 ml, 0.46 mmol) was added to a solution of 4-(4-((R)-amino(4'-chlorobiphenyl-2-yl)methyl)piperidin-1-yl)-N-(4-((R)-4-morpholino-1-(phenylthio)butan-2-ylamino)-3-(trifluoromethylsulfonyl)phenylsulfonyl)benzamide, formic acid salt (EXAMPLE 33, 0.11 g, 0.11 mmol), 2-(tert-butoxycarbonyl(methyl)amino)acetic acid (22 mg, 0.11 mmol) and HATU (52 mg, 0.14 mmol) in DMF (2.2 ml) and the resulting mixture was stirred at r.t for 1 hour. The reaction mixture was concentrated under reduced pressure, diluted with DCM and washed with H$_2$O, 1N NaHSO$_4$ (aq.) and saturated aq. NaHCO$_3$. The organic layer was dried with Na$_2$SO$_4$, filtered and the filtrate was concentrated under reduced pressure to provide a residue which was purified by column chromatography (ISCO, silica gel column, eluting with 0→100% DCM/MeOH/NH$_3$ (10:1:0.1)) to provide the title compound (94 mg, yield: 73%).

LCMS: (ESI) m/z 1127 [M+H]$^+$.

Intermediate 133

(R)-ethyl 4-(4-((4'-chlorobiphenyl-2-yl)(dimethylamino)methyl)piperidin-1-yl)benzoate

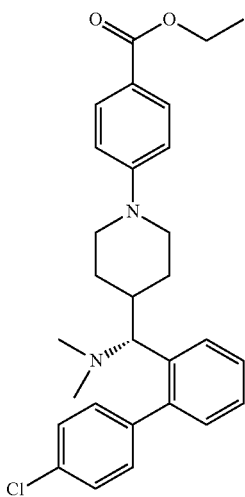 [SMILES: CCOC(=O)c1ccc(N2CCC([C@H](c3ccccc3-c3ccc(Cl)cc3)N(C)C)CC2)cc1]

Step 1: HCl (1.16 ml, 4.63 mmol, 4.0M in dioxane) was added to a solution of ethyl 4-(4-((R)-(4'-chlorobiphenyl-2-yl)((S)-1,1-dimethylethylsulfinamido)methyl)piperidin-1-yl)benzoate (INTERMEDIATE 128, 0.128 g, 0.23 mmol) in MeOH (3.5 ml) and the reaction mixture was stirred at r.t. for 3 hours. The reaction mixture was concentrated under reduced pressure and dried under vacuum to provide (R)-ethyl 4-(4-(amino(4'-chlorobiphenyl-2-yl)methyl)piperidin-1-yl)benzoate hydrochloride salt (INTERMEDIATE 133, STEP 1, 0.12 g), which was used in the preparation of INTERMEDIATE 133, STEP 2 without further purification.

LCMS: (ESI) m/z 449 [M+H]$^+$.

Step 2: Formaldehyde (0.17 ml, 2.3 mmol, 37 wt % in MeOH) and sodium triacetoxyborohydride (0.49 g, 2.30 mmol) were added sequentially to a solution of (R)-ethyl 4-(4-(amino (4'-chlorobiphenyl-2-yl)methyl)piperidin-1-yl) benzoate hydrochloride salt (INTERMEDIATE 133, STEP 1, 0.12 g, 0.23 mmol) in DCM (2.1 ml) and the reaction mixture was stirred for 2 hours. The reaction mixture was diluted with DCM and washed with saturated aq. NaHCO$_3$. The organic layer was dried (Na$_2$SO$_4$), filtered and the filtrate was concentrated under reduced pressure to give the title compound (0.11 g, yield: almost quantitative) after drying under vacuum.

LCMS: (ESI) m/z 477 [M+H]$^+$.

Example 1

4-(4-((R)-(4'-chlorobiphenyl-2-yl)(hydroxy)methyl)piperidin-1-yl)-N-(4-((R)-4-(4-(2-hydroxyethyl)piperazin-1-yl)-1-(phenylthio)butan-2-ylamino)-3-(trifluoromethylsulfonyl)phenylsulfonyl)benzamide, formic acid salt

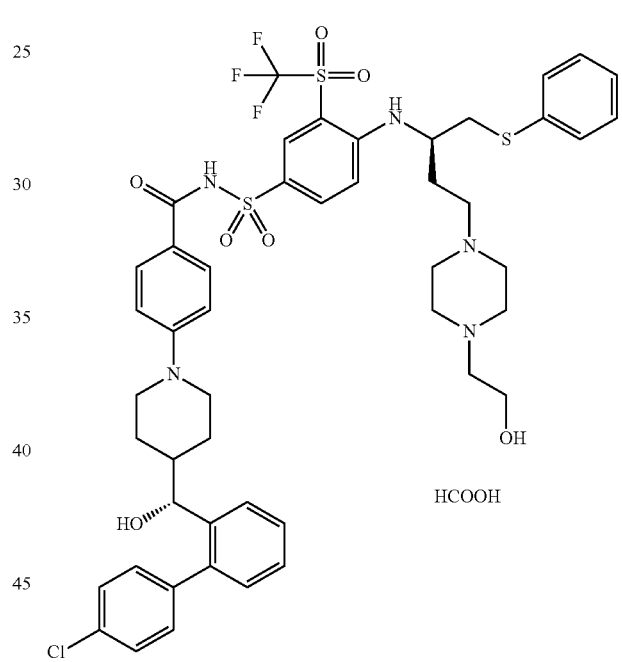

TBAF (1M solution in THF, 192 µl, 0.19 mmol) was added dropwise to a solution of 4-(4-((R)-(tert-butyldimethylsilyloxy)(4'-chlorobiphenyl-2-yl)methyl)piperidin-1-yl)-N-(4(4R)-4-(4-(2-(tert-butyldiphenylsilyloxy)ethyl)piperazin-1-yl)-1-(phenylthio)butan-2-ylamino)-3-(trifluoromethylsulfonyl)phenylsulfonyl)benzamide (INTERMEDIATE 32, 130 mg, 0.10 mmol) in THF (702 µl) and the resulting reaction mixture was stirred at room temperature overnight. HCl (1 ml, 4M in dioxane) was added to the mixture and stirred for an additional 1 hour at room temperature. The reaction mixture was diluted with EtOAc and the organic layer washed with H$_2$O (2×) and dried (Na$_2$SO$_4$). Evaporation of the volatiles under reduced pressure gave a residue, which was purified by reverse phase HPLC (Gilson column, eluting with 15→70% H$_2$O/MeCN with 0.1% formic acid for 14 minutes) to provide the title product (78 mg, yield: 78%).

$^1$H NMR (300 MHz, DMSO-d6) δ ppm 8.07 (d, 1 H) 7.95 (dd, 1 H) 7.67 (d, 2 H) 7.59 (d, 1 H) 7.49 (d, 2 H) 7.43 (t, 1 H) 7.25-7.38 (m, 7 H) 7.07-7.23 (m, 3 H) 6.90 (d, 1 H) 6.73 (d, 3 H) 5.21 (br. s., 1 H) 4.25-4.36 (m, 2 H) 4.02 (d, 1 H) 3.73 (d, 1 H) 3.61-3.68 (m, 3 H) 3.22-3.33 (m, 4 H) 2.83-3.03 (m, 6 H) 2.69-2.82 (m, 2 H) 2.61 (dd, 4 H) 2.43 (d, 3 H) 1.90 (d, 2 H) 1.74 (d, 1 H) 1.60 (d, 1 H) 1.14-1.22 (m, 2 H) 0.95-1.08 (m, 2 H) 0.86 (d, 1 H).

LCMS: (ESI) m/z 1001 [M+H]+.

Example 2

4-(4-((R)-(4'-chlorobiphenyl-2-yl)(hydroxy)methyl)piperidin-1-yl)-N-(4-((R)-4-(dimethylamino)-1-(phenylthio)butan-2-ylamino)-3-nitrophenylsulfonyl)benzamide

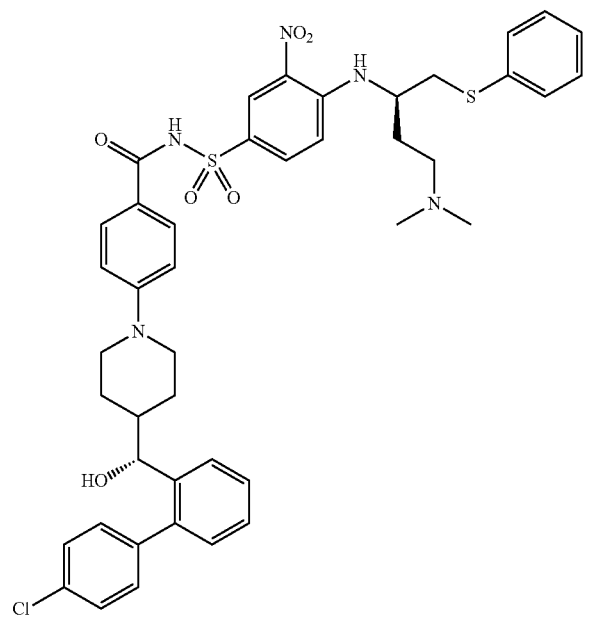 [SMILES: CN(C)CC[C@H](CSc1ccccc1)Nc1ccc(S(=O)(=O)NC(=O)c2ccc(N3CCC([C@@H](O)c4ccccc4-c4ccc(Cl)cc4)CC3)cc2)cc1[N+](=O)[O-]]

The title compound (77.2 mg, yield: 59%) was prepared using a procedure similar to the one described for EXAMPLE 1 utilizing 4-(4-((R)-(tert-butyldimethylsilyloxy)(4'-chlorobiphenyl-2-yl)methyl)piperidin-1-yl)-N-(4-((R)-4-(dimethylamino)-1-(phenylthio)butan-2-ylamino)-3-nitrophenylsulfonyl)benzamide (INTERMEDIATE 33, 147.5 mg, 0.16 mmol) as starting material. The title product was purified by column chromatography (ISCO, 4 g silica gel column, eluting with 0→4.5% MeOH/DCM) followed by [ISCO, 12 g silica gel column, eluting with 0→8% MeOH/DCM and 0→100% (10% 2M NH$_3$ in MeOH/90% DCM)].

$^1$H NMR (400 MHz, DMSO-d$_6$) δ ppm 0.85 (m, 1 H) 0.96-1.05 (m, 1 H) 1.05-1.17 (m, 1 H) 1.53-1.66 (m, 1 H) 1.84-2.13 (m, 3 H) 2.73-2.96 (m, 2 H) 3.55 (d, 1 H) 3.71 (m, 1 H) 4.06 (m, 1 H) 4.31 (dd, 1 H) 5.20 (d, 1 H) 6.71 (d, 2 H) 6.89 (d, 1 H) 7.09-7.20 (m, 2 H) 7.24 (t, 2 H) 7.28-7.39 (m, 5 H) 7.42 (t, 1 H) 7.49 (d, 2 H) 7.58 (d, 1 H) 7.67 (d, 2 H) 7.79 (dd, 1 H) 8.24 (d, 1 H) 8.44 (d, 1 H).

LCMS: (ESI) m/z 828 [M+H]+.

Optical Rotation:

Concentration: 0.1 g/dL

Lamp: Sodium

Wavelength: 589 nm

Temperature: 20° C.

Path length: 10 cm

Cell volume: 1 ml

Solvent: CH$_2$Cl$_2$

[α]=−16°

Example 3

4-(4-((R)-(4'-chlorobiphenyl-2-yl)(hydroxy)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide

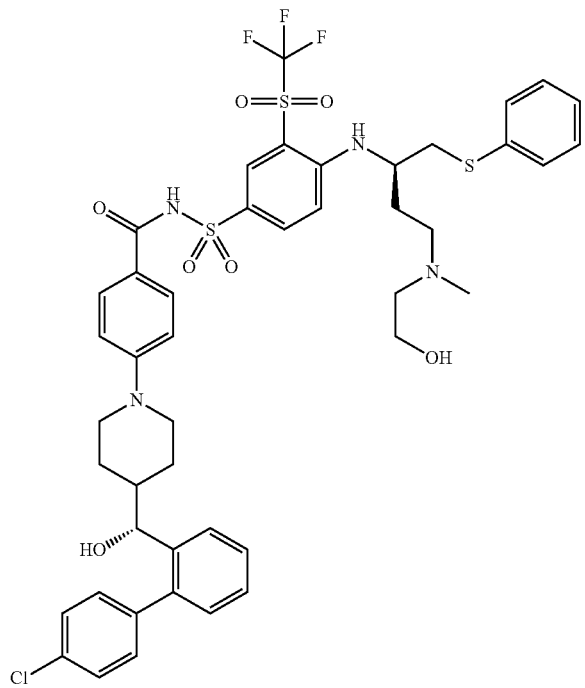 [SMILES: CN(CCO)CC[C@H](CSc1ccccc1)Nc1ccc(S(=O)(=O)NC(=O)c2ccc(N3CCC([C@@H](O)c4ccccc4-c4ccc(Cl)cc4)CC3)cc2)cc1S(=O)(=O)C(F)(F)F]

To a solution of N-(4-((R)-4-((2-(tert-butyldimethylsilyloxy)ethyl)(methyl)amino)-1-(phenylthio)butan-2-ylamino)-3-(trifluoromethylsulfonyl)phenylsulfonyl)-4-(4-((R)-(4'-chlorobiphenyl-2-yl)(hydroxy)methyl)piperidin-1-yl)benzamide (INTERMEDIATE 34, 2.96 g, 2.51 mmol) in dioxane (5.03 ml) and methanol (5.03 ml) was added slowly HCl (4M in dioxane, 15.08 ml, 60.33 mmol). Approximately half way through addition, a slight exotherm was noted, and the reaction was cooled to 0° C. Addition of hydrochloric acid in dioxane (4M) continued, and once complete, the ice bath was removed. The resulting yellow solution was allowed to warm to r.t. and stirred for 3 min before being concentrated under reduced pressure to half volume and diluted with ethyl acetate. The resulting mixture was washed with sodium bicarbonate (saturated, aqueous) and sodium chloride (saturated, aqueous) before being dried over sodium sulfate, filtered, and concentrated. Upon concentration, a thick oily residue precipitated out of solution and this material was redissolved in acetone before being reconcentrated to a beige film. This film was dissolved in 10% methanol in ethyl acetate and purified by column chromatography (ISCO, 330 g SiO$_2$, isocratic 15% methanol in ethyl acetate for 30 min) to afford the title compound (1.90 g, yield: 80%).

$^1$H NMR (300 MHz, METHANOL-d$_4$) δ 8.27 (s, 1H), 8.04 (dd, 1H), 7.82 (d, 2H), 7.62 (d, 1H), 7.09-7.50 (m, 12H), 6.66-6.86 (m, 3H), 4.44 (d, 1H), 3.99 (br. s., 1H), 3.69-3.85 (m, 3H), 3.62 (d, 1H), 3.12-3.29 (m, 2H), 2.86-3.05 (m, 4H), 2.60-2.75 (m, 4H), 2.46-2.58 (m, 1H), 2.11-2.28 (m, 1H), 1.88-2.12 (m, 2H), 1.65-1.84 (m, 1H), 1.08-1.35 (m, 2H), 0.88-1.07 (m, 1H).

$^{19}$F NMR (282 MHz, METHANOL-d$_4$) δ −80.88 (3F).

LCMS: (ESI) m/z 945.4, 947.4 [M+H]$^+$.

Optical Rotation:
Concentration: 0.305 g/dL
Lamp: Sodium
Wavelength: 589 nm
Temperature: 20° C.
Path length: 10 cm
Cell volume: 1 ml
Solvent: CH$_2$Cl$_2$
[α]=+28

Example 3A 4-(4-((R)-(4'-chlorobiphenyl-2-yl)(hydroxy)methyl) piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide, formic acid salt

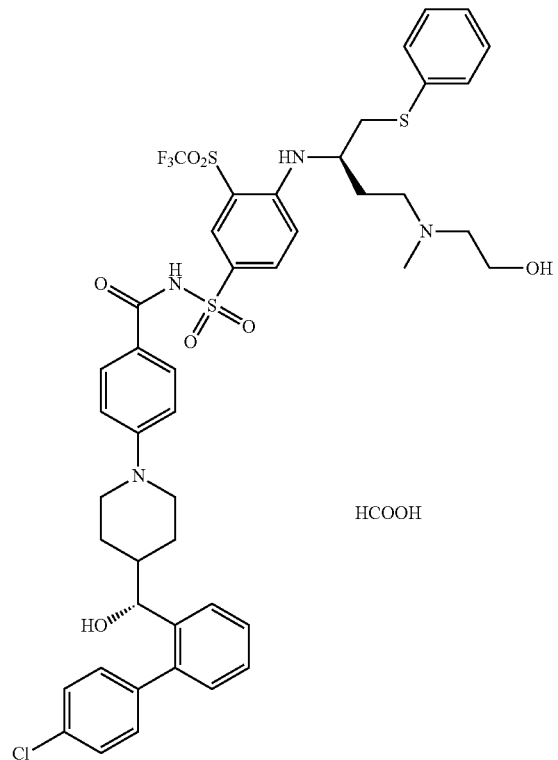

As an alternate procedure to Example 3, a solution of 4-(4-((R)-(tert-butyldimethylsilyloxy)(4'-chlorobiphenyl-2-yl)methyl)piperidin-1-yl)-N-(4-((R)-4-((2-(tert-butyldiphenylsilyloxy)ethyl)(methyl)amino)-1-(phenylthio)butan-2-ylamino)-3-(trifluoromethylsulfonyl)phenylsulfonyl) benzamide (INTERMEDIATE 34A, 110 mg, 0.08 mmol) in THF was treated with a solution of TBAF (0.169 mL, 0.17 mmol, 1M in THF) and the resulting solution was stirred at room temperature overnight. HCl (2 ml, 4N in dioxane) was added to the solution and the mixture was allowed to stir for 30 minutes at ambient temperature. Evaporation of the volatiles under reduced pressure gave a residue, which was purified by reverse phase HPLC (Gilson column, eluting with 10→70% H$_2$O/MeCN with 0.1% formic acid for 14 minutes) to provide the title product (53.3 mg, yield: 66%).

$^1$H NMR (DMSO-d6, 300Mz) δ 8.14 (s, 1H) 8.10 (s, 1H) 7.97 (d, 1H) 7.67 (d, 2 H) 7.59 (d, 1H) 7.49 (d, 2H) 7.43 (t, 1H) 7.26-7.37 (m, 7H) 7.21 (d, 1H) 7.14 (d, 1H) 6.93 (d, 1 H) 6.74 (d, 2H) 5.20 (d, 1H) 4.28-4.33 (m, 1H) 3.99-4.09 (m, 1H) 3.71-3.79 (m, 1H) 3.55-3.66 (m, 3H) 2.93-3.14 (m, 4H) 2.65 (s, 3H) 2.40-2.61 (m, 3H) 1.99-2.14 (m, 2H) 1.88-1.95 (m, 1H) 1.56-1.68 (m, 1H) 0.96-1.26 (m, 2H) 0.79-0.93 (m, 1H).

LCMS: (ESI) m/z 946 [M+H]$^+$.

Example 4

4-(4-((R)-(4'-chlorobiphenyl-2-yl)(hydroxy)methyl) piperidin-1-yl)-N-(4-((R)-4-(ethyl(2-hydroxyethyl) amino)-1-(phenylthio)butan-2-ylamino)-3-(trifluoromethylsulfonyl)phenylsulfonyl)benzamide

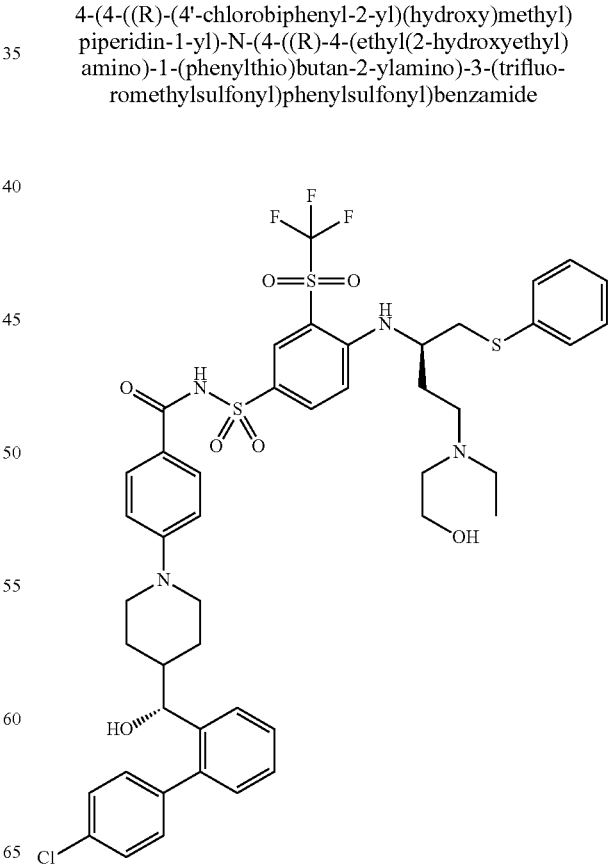

A solution of HCl in dioxane (4M, 11.18 ml, 44.70 mmol) was added slowly to a light yellow solution of N-(4-((R)-4-((2-(tert-butyldimethylsilyloxy)ethyl)(ethyl)amino)-1-(phenylthio)butan-2-ylamino)-3-(trifluoromethylsulfonyl)phenylsulfonyl)-4-(4-((R)-(4'-chlorobiphenyl-2-yl)(hydroxy)methyl)piperidin-1-yl)benzamide (INTERMEDIATE 66, 2.4 g, 2.24 mmol) in DCM (11.2 ml) at 0° C. Once the addition was complete, the ice bath was removed. The resulting solution was allowed to warm to r.t. and stirred for 1 hour before being concentrated under reduced pressure to half volume and diluted with ethyl acetate. The resulting mixture was washed with sodium bicarbonate (saturated, aqueous) and sodium chloride (saturated, aqueous) before being dried over sodium sulfate, filtered, and concentrated under reduced pressure. The concentrate was purified by column chromatography (ISCO, silica gel, 0→20% methanol in ethyl acetate for 30 min) to provide the title compound (1.64 g, yield: 76%).

$^1$H NMR (300 MHz, DICHLOROMETHANE-d2) d ppm 8.25 (s, 1 H) 8.03 (d, 1 H) 7.77 (d, 2 H) 7.61 (d, 1 H) 7.39-7.48 (m, 2 H) 7.31-7.39 (m, 4 H) 7.17-7.30 (m, 6 H) 6.90 (d, 1 H) 6.69 (d, 3 H) 4.49 (d, 1 H) 3.91 (br.s., 2 H) 3.55-3.81 (m, 5 H) 3.09 (d, 2 H) 2.76-2.96 (m, 6 H) 2.47-2.72 (m, 3 H) 2.04-2.15 (m, 1 H) 1.84-1.99 (m, 2 H) 1.76 (dd, 1 H) 1.23-1.36 (m, 2 H) 1.13-1.23 (m, 1 H) 1.01-1.13 (m, 4 H).

LCMS: (ESI) m/z 959 [M+H]$^+$.

Example 4A 4-(4-((R)-(4'-chlorobiphenyl-2-yl)(hydroxy)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide, formic acid salt

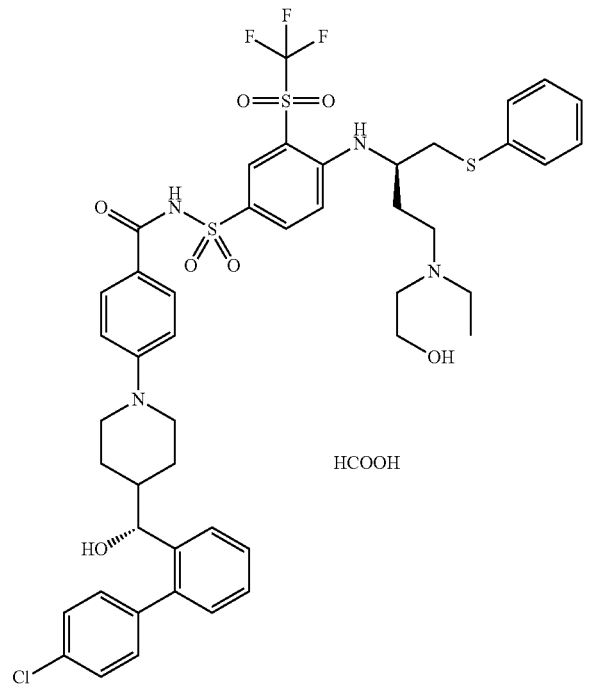 [SMILES: CCN(CCO)CC[C@H](CSc1ccccc1)Nc1ccc(S(=O)(=O)NC(=O)c2ccc(N3CCC([C@@H](O)c4ccccc4-c4ccc(Cl)cc4)CC3)cc2)cc1S(=O)(=O)C(F)(F)F ; "HCOOH"]

Step 1: (R)-4-(4-((tert-butyldimethylsilyloxy)(4'-chlorobiphenyl-2-yl)methyl)piperidin-1-yl)benzoic acid (INTERMEDIATE 13, 160 mg, 0.3 mmol), (R)-4-(4-((2-(tert-butyldiphenylsilyloxy)ethyl)(ethyl)amino)-1-(phenylthio)butan-2-ylamino)-3-(trifluoromethylsulfonyl)benzenesulfonamide (INTERMEDIATE 25, 216 mg, 0.27 mmol), DMAP (100 mg, 0.82 mmol), and EDC (104 mg, 0.54 mmol) were placed in a 50 ml flask and flushed with nitrogen. DCM (3 ml) was added, and the solution was stirred at room temperature overnight. The reaction mixture was diluted with DCM (40 ml) and washed with 1N aq. sodium bisulfate (35 ml) followed by a saturated aq. sodium bicarbonate (40 ml). The organic layer was dried (Na$_2$SO$_4$), filtered, and evaporated under reduced pressure to give a residue, which was purified by column chromatography (ISCO, 40 g silica gel column, eluting with 0→25% EtOAc/hexanes) to give 4-(4-((R)-(tert-butyldimethylsilyloxy)(4'-chlorobiphenyl-2-yl)methyl)piperidin-1-yl)-N-(4-((R)-4-((2-(tert-butyldiphenylsilyloxy)ethyl)(ethyl)amino)-1-(phenylthio)butan-2-ylamino)-3-(trifluoromethylsulfonyl)phenylsulfonyl)benzamide (EXAMPLE 4A, STEP 1, 140 mg), that was used in the preparation of EXAMPLE 4A, STEP 2, without further purification.

Step 2: TBAF (0.54 ml 0.54 mmol, 1M in THF) was added dropwise to a solution of 4-(4-((R)-(tert-butyldimethylsilyloxy)(4'-chlorobiphenyl-2-yl)methyl)piperidin-1-yl)-N-(4-((R)-4-((2-(tert-butyldiphenylsilyloxy)ethyl)(ethyl)amino)-1-(phenylthio)butan-2-ylamino)-3-(trifluoromethylsulfonyl)phenylsulfonyl)benzamide (EXAMPLE 4A, STEP 1, 140 mg), in THF (2 ml) and the resulting reaction mixture was stirred at room temperature overnight. HCl (2 ml, 4M in dioxane) was added to the mixture and stirred for an additional 30 minutes at room temperature. The reaction mixture was diluted with EtOAc and the organic layer was washed with H$_2$O (2×) and dried (Na$_2$SO$_4$). Evaporation of the volatiles under reduced pressure gave a residue, which was purified by reverse phase HPLC (Gilson column, eluting with 10→70% H$_2$O/MeCN with 0.1% formic acid for 14 minutes) to provide the title product (60.4 mg, yield: 23%).

$^1$H NMR (DMSO-d6, 300Mz) δ 8.09 (d, 1H) 7.97 (s, 1H) 7.67 (d, 2 H) 7.59 (d, 1H) 7.49 (d, 2H) 7.43 (t, 1H) 7.26-7.36 (m, 7 H) 7.20 (d, 1H) 7.14 (d, 1H) 6.90-6.96 (m, 1H) 6.73 (d, 1H) 5.28 (bs, 1 H) 5.19 (d, 1H) 4.31 (t, 1H) 4.05 (t, 1H) 3.53-3.76 (m, 4H) 2.96-3.21 (m, 4H) 2.38-2.69 (m, 5H) 2.0-2.14 (m, 2H) 1.90 (d, 1H) 1.53-1.68 (m, 1H) 0.98-1.23 (m, 6H) 0.81-0.91 (m, 1H).

LCMS: m/z 960 [M+H]$^+$.

Example 5

N-(4-((R)-4-(bis(2-hydroxyethyl)amino)-1-(phenylthio)butan-2-ylamino)-3-(trifluoromethylsulfonyl)phenylsulfonyl)-4-(4-((R)-(4'-chlorobiphenyl-2-yl)(hydroxy)methyl)piperidin-1-yl)benzamide, formic acid salt

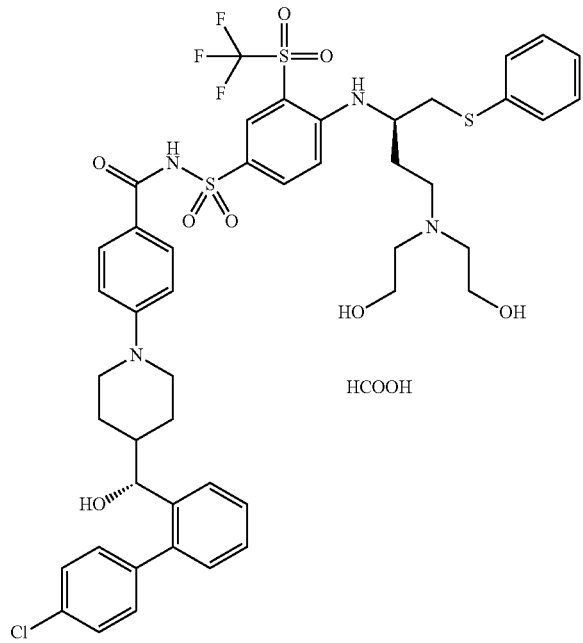 [SMILES: O=C(NS(=O)(=O)c1ccc(N[C@H](CCN(CCO)CCO)CSc2ccccc2)c(S(=O)(=O)C(F)(F)F)c1)c1ccc(N2CCC([C@@H](O)c3ccccc3-c3ccc(Cl)cc3)CC2)cc1 ; "HCOOH"]

HCOOH

Step 1: (R)-4-(4-((tert-butyldimethylsilyloxy)(4'-chlorobiphenyl-2-yl)methyl)piperidin-1-yl)benzoic acid (INTERMEDIATE 13, 225 mg, 0.22 mmol), DMAP (140 mg, 1.14 mmol), (R)-4-(4-(bis(2-(tert-butyldiphenylsilyloxy)ethyl)amino)-1-(phenylthio)butan-2-ylamino)-3-(trifluoromethylsulfonyl)benzenesulfonamide (INTERMEDIATE 31, 400 mg, 0.38 mmol), and EDC (146 mg, 0.76 mmol) were placed in a 50 ml flask and flushed with nitrogen. DCM (3 ml) was added and the solution was stirred at room temperature overnight. The reaction mixture was diluted with DCM (40 ml) and washed with sodium bisulfate (1N, 35 ml) followed by a sodium bicarbonate (saturated, aq., 40 ml). The organic layer was dried ($Na_2SO_4$), filtered, and evaporated under reduced pressure to give a residue, which was purified by column chromatography (ISCO, 40 g silica gel column, eluting with 0→25% EtOAc/hexanes) to give 4-(4-((R)-(tert-butyldimethylsilyloxy)(4'-chlorobiphenyl-2-yl)methyl)piperidin-1-yl)-N-(4-((R)-4-((2-(tert-butyldiphenylsilyl)ethyl)(2-(tert-butyldiphenylsilyloxy)ethyl)amino)-1-(phenylthio)butan-2-ylamino)-3-(trifluoromethyl sulfonyl)phenylsulfonyl)benzamide (EXAMPLE 5, STEP 1, 252 mg), that was used in the preparation of EXAMPLE 5, STEP 2 without further purification.

Step 2: A solution of TBAF (0.76 ml 0.76 mmol, 1M in THF) was added dropwise to a solution of 4-(4-((R)-(tert-butyldimethylsilyloxy)(4'-chlorobiphenyl-2-yl)methyl)piperidin-1-yl)-N-(4-((R)-4-((2-(tert-butyldiphenylsilyl)ethyl)(2-(tert-butyldiphenylsilyloxy)ethyl)amino)-1-(phenylthio)butan-2-ylamino)-3-(trifluoromethyl sulfonyl)phenylsulfonyl)benzamide (EXAMPLE 5, STEP 1, 252 mg) in THF (2 ml) and the resulting reaction mixture was stirred at room temperature overnight. HCl (2 ml, 4M in dioxane) was added to the mixture and stirred for an additional 30 minutes at room temperature. The reaction mixture was diluted with EtOAc and the organic layer was washed with $H_2O$ (2×) and dried ($Na_2SO_4$). Evaporation of the volatiles under reduced pressure gave a residue, which was purified by reverse phase HPLC (Gilson column, eluting with 10→70% $H_2O$/MeCN with 0.1% formic acid for 14 minutes) to provide the title product (150.2 mg, yield: 40%).

$^1$H NMR (DMSO-d6, 300Mz) δ 8.10 (s, 2H) 7.97 (d, 1H) 7.67 (d, 2 H) 7.59 (d, 1H) 7.49 (d, 2H) 7.43 (t, 1H) 7.24-7.37 (m, 7H) 7.19 (d, 1H) 7.15 (d, 1H) 6.93-6.99 (m, 1H) 6.75 (d, 2H) 5.20 (d, 1H) 5.05 (bs, 1H) 4.28-4.33 (m, 1H) 4.02-4.12 (m, 1H) 3.72-3.79 (m, 1H) 3.54-3.69 (m, 5H) 2.98-3.18 (m, 5H) 2.40-2.68 (m, 4H) 1.84-2.16 (m, 3H) 1.56-1.68 (m, 1H) 0.98-1.18 (m, 2H) 0.78-0.93 (m, 1H).

LCMS: (ESI) m/z 975 [M+H]$^+$.

Example 6

4-(4-((R)-(4'-chlorobiphenyl-2-yl)(hydroxy)methyl)piperidin-1-yl)-N-(4-((R)-4-(4-((R)-3-fluoro-2-hydroxypropyl)piperazin-1-yl)-1-(phenylthio)butan-2-ylamino)-3-(trifluoromethylsulfonyl)phenylsulfonyl)benzamide and 4-(4-((R)-(4'-chlorobiphenyl-2-yl)(hydroxy)methyl)piperidin-1-yl)-N-(4-((R)-4-(4-((S)-3-fluoro-2-hydroxypropyl)piperazin-1-yl)-1-(phenylthio)butan-2-ylamino)-3-(trifluoromethylsulfonyl)phenylsulfonyl)benzamide formic acid salt, mixture of diastereomers

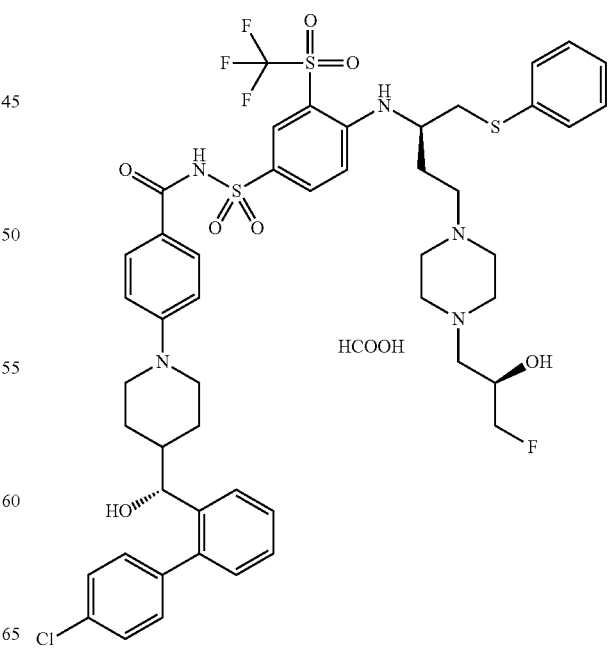

HCOOH

-continued

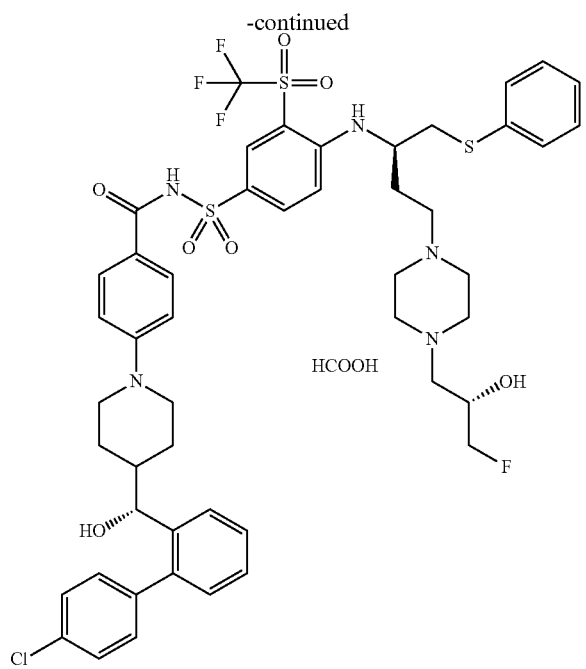

HCOOH

Step 1: (R)-4-(4-((4'-chlorobiphenyl-2-yl)(hydroxy)methyl)piperidin-1-yl)benzoic acid (INTERMEDIATE 40, 58 mg, 0.14 mmol), 4-((R)-4-(4-((R)-2-(tert-butyldiphenylsilyloxy)-3-fluoropropyl)piperazin-1-yl)-1-(phenylthio)butan-2-ylamino)-3-(trifluoromethylsulfonyl)benzenesulfonamide and 4-((R)-4-(4-((S)-2-(tert-butyldiphenylsilyloxy)-3-fluoropropyl)piperazin-1-yl)-1-(phenylthio)butan-2-ylamino)-3-(trifluoromethylsulfonyl)benzenesulfonamide mixture of diastereomers (INTERMEDIATE 39, 120 mg, 0.14 mmol), DMAP (34 mg, 0.28 mmol), and EDC (53 mg, 0.28 mmol) were placed in a 40 ml vial and flushed with nitrogen. DCM (2.8 ml) was added, and the solution was stirred at room temperature overnight. The reaction mixture was diluted with DCM and washed with 1N aq. sodium bisulfate followed by a saturated aq. sodium bicarbonate. The organic layer was dried (Na$_2$SO$_4$), filtered, and evaporated under reduced pressure to give N-(4-((2R)-4-(4-(2-(tert-butyldiphenylsilyloxy)-3-fluoropropyl)piperazin-1-yl)-1-(phenylthio)butan-2-ylamino)-3-(trifluoromethylsulfonyl)phenylsulfonyl)-4-(4-((R)-(4'-chlorobiphenyl-2-yl)(hydroxy)methyl)piperidin-1-yl)benzamide (EXAMPLE 6, STEP 1, 180 mg), which was used in the preparation of EXAMPLE 6, STEP 2, without further purification.

LCMS: m/z 1270 [M+H]$^+$.

Step 2: A solution of TASF (0.43 ml, 0.43 mmol, 1M in DMF) was added dropwise to a solution of N-(4-((2R)-4-(4-(2-(tert-butyldiphenylsilyloxy)-3-fluoropropyl)piperazin-1-yl)-1-(phenylthio)butan-2-ylamino)-3-(trifluoromethylsulfonyl)phenylsulfonyl)-4-(4-((R)-(4'-chlorobiphenyl-2-yl)(hydroxy)methyl)piperidin-1-yl)benzamide (EXAMPLE 6, STEP 1, 180 mg) in DMF (1 ml) and the resulting reaction mixture was stirred at room temperature for 1 h. The reaction mixture was diluted with DCM/MeOH (10:1 v/v), washed with H$_2$O, dried (Na$_2$SO$_4$), filtered, and evaporation of the volatiles under reduced pressure gave a residue, which was purified by reverse phase HPLC (Gilson column, eluting with 40→60% H$_2$O/MeCN with 0.1% formic acid for 5 minutes) to provide the title product (48.0 mg, yield: 33%).

$^1$H NMR (400 MHz, DMSO-d$_6$) δ ppm 8.08 (d, 1 H), 7.94-7.90 (m, 1H), 7.66 (d, J=8.80 Hz, 2 H), 7.60-7.55 (m, 1 H), 7.51-7.46 (m, 2H), 7.45-7.40 (m, 1 H), 7.37-7.26 (m, 8 H), 7.21-7.12 (m, 2 H), 6.93-6.88 (m, 1 H), 6.77-6.71 (m, 3 H), 5.21 (d, J=4.3 Hz, 1 H), 4.41-4.20 (m, 4 H), 4.05-3.85 (m, 3 H), 3.77-3.70 (m, 1 H), 3.60-3.55 (m, 2 H), 2.66-2.53 (m, 8 H), 2.45-2.42 (m, 5 H), 2.00-1.85 (m, 2 H), 1.75 (m, 1 H), 1.15-0.99 (m, 3 H), 0.90-0.81 (m, 1 H).

LCMS: (ESI) m/z 1032 [M+H]$^+$.

Example 7

2,2'-((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butylazanediyl)bis(ethane-2,1-diyl)bis(dihydrogen phosphate), hydrochloride salt

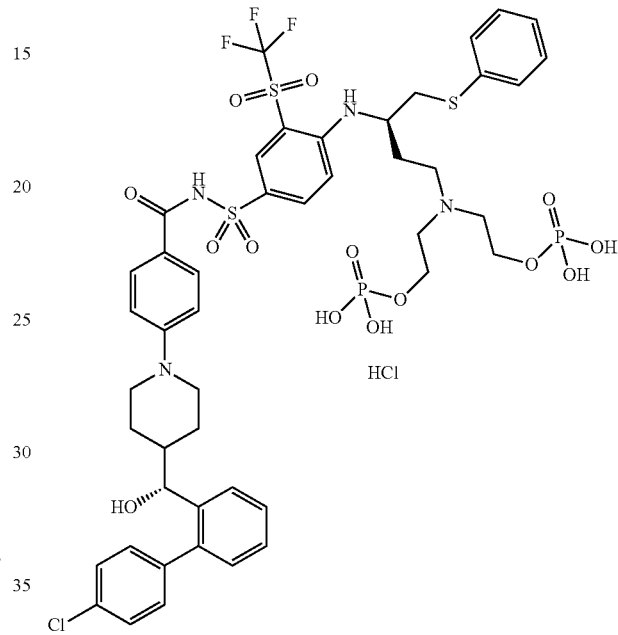

A solution of di-tert-butyl 2,2'-((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butylazanediyl)bis(ethane-2,1-diyl) diphosphate (INTERMEDIATE 46, 250 mg, 0.18 mmol) and DCM (5 ml) was treated with a solution of HCl (4M in dioxane, 0.92 ml, 3.68 mmol). A white precipitate was observed and the mixture was allowed to stir vigorously for 45 minutes. The title compound was collected by filtration (185 mg, yield: 89%).

$^1$H NMR (400 MHz, METHANOL-d$_4$) δ ppm 1.41 (br. s., 2 H) 1.54-1.71 (m, 1 H) 1.91-2.09 (m, 1 H) 2.31 (br. s., 3 H) 3.29 (br. s., 1 H) 3.36-3.51 (m, 4 H) 3.53-3.66 (m, 5 H) 3.70-3.83 (m, 1 H) 4.12-4.24 (m, 1 H) 4.35 (br. s., 4 H) 4.56 (d, 1 H) 7.05 (d, 1 H) 7.13-7.28 (m, 4 H) 7.32-7.41 (m, 5 H) 7.42-7.52 (m, 3 H) 7.58 (d, 2 H) 7.68 (d, 1 H) 7.96 (d, 2 H) 8.11 (dd, 1 H) 8.35 (d, 1 H).

$^{31}$P NMR (121 MHz, METHANOL-d$_4$) δ ppm 0.05 (t, 2 P).
$^{31}$P NMR (121 MHz, METHANOL-d$_4$) δ ppm 0.05 (s, 2 P) (decoupled)

Optical Rotation:
Concentration: 0.2 g/dL
Lamp: Sodium
Wavelength: 589 nm
Temperature: 20° C.
Path length: 10 cm
Cell volume: 1 ml
Solvent: MeOH
[α]=+3

Example 8

2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl dihydrogen phosphate, hydrochloride salt

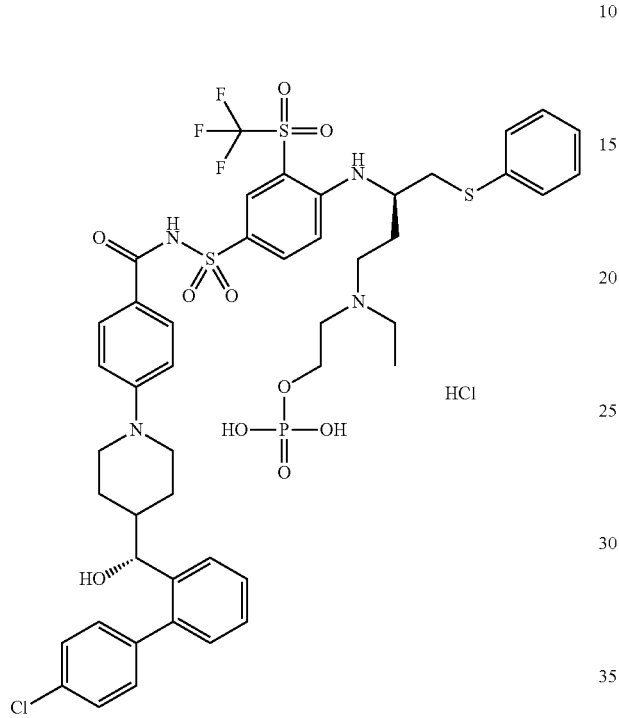

A solution of di-tert-butyl 2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(ethyl)amino)ethyl phosphate (INTERMEDIATE 55, 147 mg, 0.14 mmol) in DCM (3.17 ml) was treated with a solution of HCl (4M in dioxane, 0.60 ml). When the addition was completed, a white precipitate was observed. The mixture was diluted with MeOH after an hour and the volatiles were evaporated under reduced pressure to give a gummy residue. The material was dissolved in MeOH, and diluted with ~20 ml DCM, resulting in a white precipitate. The mixture was concentrated under reduced pressure to provide a white solid. The material was triturated in 10-15 ml $CH_2Cl_2$, and dried under high vacuum to provide the title compound (108 mg, 95%).

$^1$H NMR (300 MHz, METHANOL-$d_4$) δ ppm 1.34 (t, 5 H) 1.46-1.66 (m, 1 H) 1.87-2.05 (m, 1 H) 2.07-2.38 (m, 3 H) 3.12-3.40 (m, 8 H) 3.42-3.52 (m, 2 H) 3.52-3.65 (m, 1 H) 3.70-3.84 (m, 1 H) 4.04-4.21 (m, 1 H) 4.23-4.37 (m, 2 H) 4.46-4.59 (m, 1 H) 6.94-7.10 (m, 2 H) 7.21 (d, 4 H) 7.30-7.52 (m, 9 H) 7.58-7.73 (m, 1 H) 7.92 (d, 2 H) 8.04-8.16 (m, 1 H) 8.27-8.40 (m, 1 H).

LCMS: (ESI) m/z 1037 [M–H]$^+$.

Example 9

2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate, hydrochloride salt

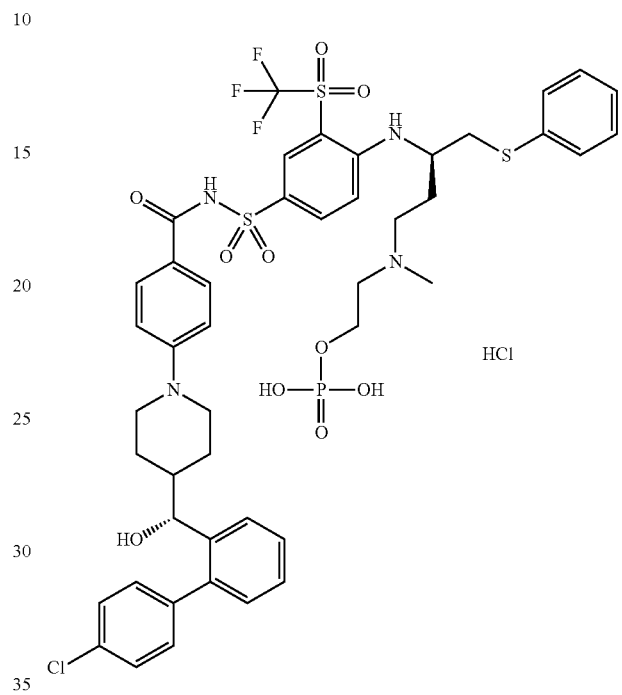

A solution of di-tert-butyl 2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl phosphate (INTERMEDIATE 56, 140 mg, 0.13 mmol) in DCM (3 ml) was treated with a solution of HCl (4M in dioxane, 0.6 ml). When the addition was completed, a white precipitate was observed. The mixture was diluted with MeOH after an hour and the volatiles were evaporated under reduced pressure to give a gummy residue. The material was dissolved in MeOH, and diluted with ~20 ml DCM, resulting in a white precipitate. The mixture was concentrated under reduced pressure to provide a white solid. The material was triturated in 10-15 ml $CH_2Cl_2$, and dried under high vacuum to provide the title compound (120 mg, yield: 95%).

$^1$H NMR (300 MHz, METHANOL-$d_4$) δ ppm 1.07-1.39 (m, 4 H) 1.83-2.00 (m, 1 H) 2.08-2.38 (m, 3 H) 2.99-3.38 (m, 8 H) 3.40-3.52 (m, 2 H) 3.57-3.69 (m, 1 H) 3.74-3.90 (m, 1 H) 4.03-4.19 (m, 1 H) 4.19-4.36 (m, 2 H) 4.45-4.58 (m, 1 H) 6.92-7.09 (m, 2 H) 7.10-7.52 (m, 13 H) 7.59-7.71 (m, 1 H) 7.77-7.94 (m, 2 H) 8.02-8.17 (m, 1 H) 8.28-8.41 (m, 1 H).

LCMS: (ESI) m/z 1023 [M–H]$^+$.

Example 10

2-(4-((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)piperazin-1-yl)ethyl dihydrogen phosphate

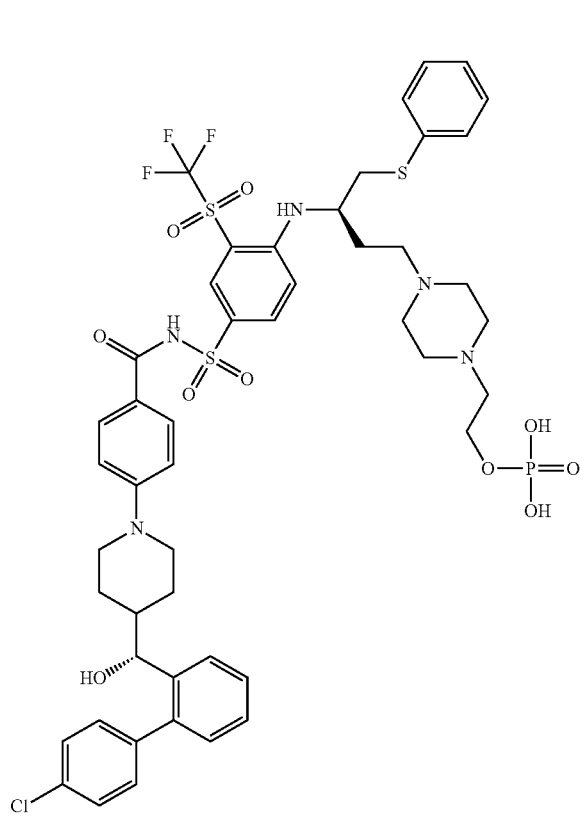 [SMILES: O=C(NS(=O)(=O)c1ccc(N[C@H](CCN2CCN(CCOP(=O)(O)O)CC2)CSc2ccccc2)c(S(=O)(=O)C(F)(F)F)c1)c1ccc(N2CCC([C@@H](O)c3ccccc3-c3ccc(Cl)cc3)CC2)cc1]

Di-tert-butyl 2-(4-((R)-3-(4-(N-(4-(4-((R)-(tert-butyldimethylsilyloxy)(4'-chlorobiphenyl-2-yl)methyl)piperidin-1-yl)benzoyl)sulfamoyl)-2-(trifluoromethylsulfonyl)phenylamino)-4-(phenylthio)butyl)piperazin-1-yl)ethyl phosphate (INTERMEDIATE 62, 414 mg, 0.32 mmol) was dissolved in DCM (0.5 ml) and treated with a solution of HCl (4M in dioxane, 4.0 ml, 15.84 mmol) at rt, to provide a cloudy solution. The reaction mixture was concentrated under reduced pressure to provide an oily residue which was purified by reverse phase HPLC (Gilson column, eluting with 20→95% MeCN in 10 mM NH$_4$OAc with 5% MeCN over 15 min). The collected fractions were concentrated and washed with water and filtered to remove NH$_4$OAc and provide the title compound (120 mg, yield: 35%).

$^1$H NMR (300 MHz, METHANOL-d4) δ ppm 8.28 (d, 1 H) 8.04 (dd, 1 H) 7.78 (d, 2 H) 7.59-7.66 (m, 1 H) 7.34-7.47 (m, 5 H) 7.24-7.34 (m, 5 H) 7.16-7.23 (m, 2 H) 6.83 (d, 3 H) 4.44 (d, 1 H) 4.01-4.15 (m, 3 H) 3.83 (d, 1 H) 3.66 (d, 1 H) 3.08-3.26 (m, 7 H) 2.63-2.79 (m, 3 H) 2.41-2.63 (m, 5 H) 1.99-2.16 (m, 2 H) 1.69-1.85 (m, 2 H) 1.10-1.35 (m, 3 H) 0.98 (dd, 1 H).

LCMS: (ESI) m/z 1080 [M+H]$^+$.

Example 11

4-(4-((R)-amino(4'-chlorobiphenyl-2-yl)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide, formic acid salt

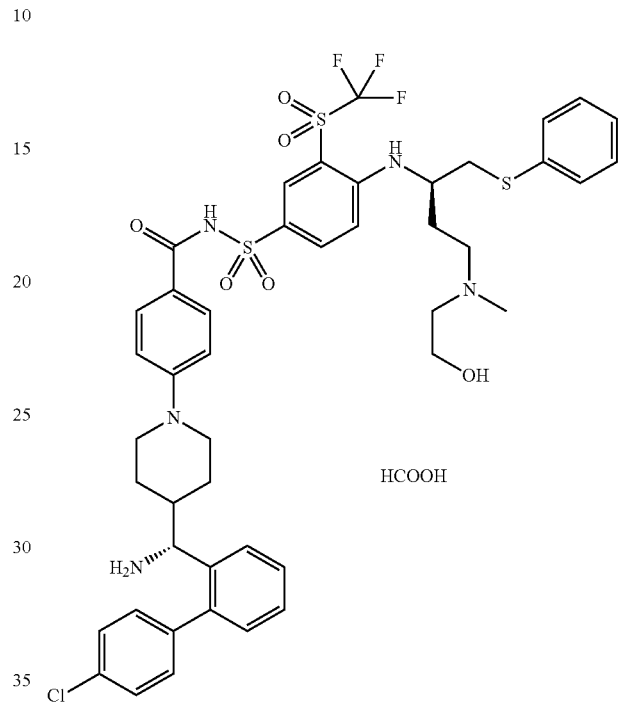

Step 1: 4-(4-((R)-(4'-chlorobiphenyl-2-yl)((S)-1,1-dimethylethylsulfinamido)methyl)piperidin-1-yl)benzoic acid (INTERMEDIATE 130, 0.12 g, 0.23 mmol), DMAP (56 mg, 0.46 mmol), and EDC (88 mg, 0.46 mmol) were placed in a 40 ml vial and flushed with nitrogen. DCM (3.0 ml) and DIPEA (0.08 ml, 0.46 mmol) were added and the solution was stirred at r.t for 15 min. A solution of (R)-4-(4-((2-(tert-butyldiphenylsilyloxy)ethyl)(methyl)amino)-1-(phenylthio)butan-2-ylamino)-3-(trifluoromethylsulfonyl)benzenesulfonamide (INTERMEDIATE 28, 0.178 g, 0.23 mmol) in DCM (1.5 ml) was added to the solution and the reaction mixture was stirred at r.t overnight. The reaction mixture was diluted with DCM and washed with sodium bisulfate (1N, aq.) followed by a sodium bicarbonate (saturated, aq.). The organic layer was dried (Na$_2$SO$_4$), filtered, and evaporated under reduced pressure to give a residue which was dried under vacuum to provide N-(4-((R)-4-((2-(tert-butyldiphenylsilyloxy)ethyl)(methyl)amino)-1-(phenylthio)butan-2-ylamino)-3-(trifluoromethyl sulfonyl)phenylsulfonyl)-4-(4-((R)-(4'-chlorobiphenyl-2-yl)((S)-1,1-dimethylethylsulfinamido)methyl)piperidin-1-yl)benzamide (EXAMPLE 11, STEP 1, 0.26 g) which was used in the preparation of EXAMPLE 11, STEP 2 without further purification.

Step 2: A solution of TASF (0.40 ml. 0.40 mmol, 1.0M in DMF) was added to a solution of N-(4-((R)-4-((2-(tert-butyldiphenylsilyloxy)ethyl)(methyl)amino)-1-(phenylthio)butan-2-ylamino)-3-(trifluoromethyl sulfonyl)phenylsulfonyl)-4-(4-((R)-(4'-chlorobiphenyl-2-yl)((S)-1,1-dimethylethylsulfinamido)methyl)piperidin-1-yl)benzamide (EXAMPLE 11, STEP 1, 0.26 g, 0.20 mmol) in DMF (1.6 ml) and the reaction mixture was stirred at r.t for 1 hour. The reaction mixture was concentrated under reduced pressure, diluted with DCM and washed with H₂O. The organic layer was dried (Na₂SO₄), concentrated under reduced pressure and dried under vacuum to give 4-(4-((R)-(4'-chlorobiphenyl-2-yl)((S)-1,1-dimethylethylsulfinamido)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide (EXAMPLE 11, STEP 2, 0.25 g) which was used in the preparation of EXAMPLE 11, STEP 3, without further purification.

Step 3: A solution of HCl (1.00 ml, 4.00 mmol, 4.0M in dioxane) was added to a solution of 4-(4-((R)-(4'-chlorobiphenyl-2-yl)((S)-1,1-dimethylethylsulfinamido)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide (EXAMPLE 11, STEP 2, 0.21 g, 0.20 mmol) in MeOH (1.0 ml) and the reaction mixture was stirred at r.t for 1 hour. The reaction mixture was concentrated under reduced pressure to provide a residue that was purified by reverse phase HPLC (Gilson column, eluting with 30→50% H₂O/MeCN with 0.1% formic acid for 10 minutes) to provide the title compound (0.1 g, yield: 51% for 3 steps).

¹H NMR (400 MHz, DMSO-d₆) δ ppm 8.05 (d, 1 H), 7.92 (dd, 1 H), 7.71-7.67 (m, 3H), 7.59-7.52 (m, 3H), 7.49-7.45 (m, 1H), 7.37-7.34 (m, 4 H), 7.30-7.26 (m, 3H), 7.20-7.17 (m, 1 H), 6.83 (d, 1 H), 6.78-6.72 (m, 3H), 4.00 (m, 1H), 3.87-3.84 (m, 1H), 3.78-3.75 (m, 1H), 3.32-3.16 (m, 5H), 2.67-2.54 (m, 5H), 2.46-2.43 (m, 1H), 2.31 (s, 3H), 1.98-1.90 (m, 2H), 1.83-1.75 (m, 2H), 1.19-1.08 (m, 2H), 0.82-0.74 (m, 1H).

LCMS: (ESI) m/z 944 [M+H]⁺.

Example 12

4-(4-((R)-amino(4'-chlorobiphenyl-2-yl)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide, formic acid salt

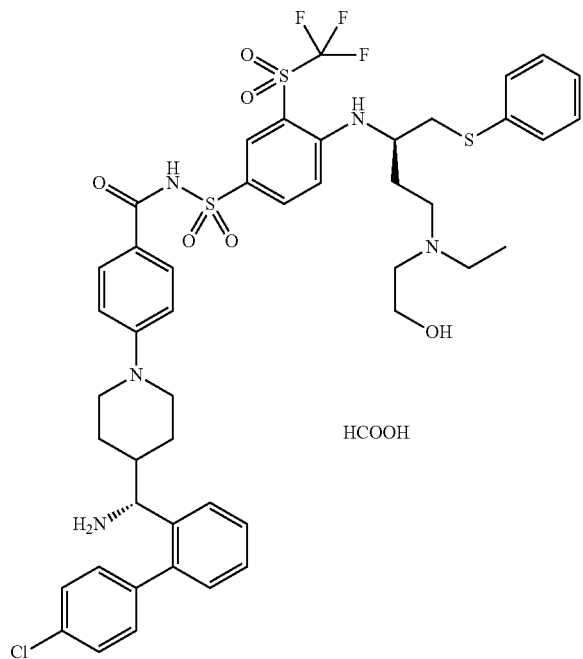 [SMILES: CCN(CCO)CC[C@H](CSc1ccccc1)Nc1ccc(S(=O)(=O)NC(=O)c2ccc(N3CCC([C@@H](N)c4ccccc4-c4ccc(Cl)cc4)CC3)cc2)cc1S(=O)(=O)C(F)(F)F ; "HCOOH"]

4-(4-((R)-(4'-chlorobiphenyl-2-yl)((S)-1,1-dimethylethylsulfinamido)methyl)piperidin-1-yl)benzoic acid (INTERMEDIATE 130, 0.12 g, 0.23 mmol), DMAP (56 mg, 0.46 mmol), and EDC (88 mg, 0.46 mmol) were placed in a 40 ml vial and flushed with nitrogen. DCM (3.0 ml) and DIPEA (0.08 ml, 0.46 mmol) were added, and the solution was stirred at r.t for 15 min. A solution of (R)-4-(4-((2-(tert-butyldiphenylsilyloxy)ethyl)(ethyl)amino)-1-(phenylthio)butan-2-ylamino)-3-(trifluoromethylsulfonyl)benzenesulfonamide (INTERMEDIATE 25, 0.18 g, 0.23 mmol) in DCM (1.5 ml) was added to the solution and the reaction mixture was stirred at r.t overnight. The reaction mixture was diluted with DCM and washed with sodium bisulfate (1N, aq.) followed by sodium bicarbonate (saturated, aq). The organic layer was dried (Na₂SO₄), filtered, and evaporated under reduced pressure to give a residue that was dried under vacuum to provide N-(4-((R)-4-((2-(tert-butyldiphenylsilyloxy)ethyl)(ethyl)amino)-1-(phenylthio)butan-2-ylamino)-3-(trifluoromethylsulfonyl)phenylsulfonyl)-4-(4-((R)-(4'-chlorobiphenyl-2-yl)((S)-1,1-dimethylethylsulfinamido)methyl)piperidin-1-yl)benzamide (EXAMPLE 12, STEP 1, 0.31 g) which was used in the preparation of EXAMPLE 12, STEP 2 without further purification.

Step 2: A solution of TASF (0.46 ml. 0.46 mmol, 1 M in DMF) was added to a solution of N-(4-((R)-4-((2-(tert-butyldiphenylsilyloxy)ethyl)(ethyl)amino)-1-(phenylthio)butan-2-ylamino)-3-(trifluoromethylsulfonyl)phenylsulfonyl)-4-(4-((R)-(4'-chlorobiphenyl-2-yl)((S)-1,1-dimethylethylsulfinamido)methyl)piperidin-1-yl)benzamide (EXAMPLE 12, STEP 1, 0.30 g, 0.23 mmol) in DMF (1.9 ml) and the reaction mixture was stirred at r.t for 1 hour. The reaction mixture was concentrated under reduced pressure, diluted with DCM and washed with H₂O. The organic layer was dried (Na₂SO₄), concentrated under reduced pressure and dried under vacuum to give 4-(4-((R)-(4'-chlorobiphenyl-2-yl)((S)-1,1-dimethylethylsulfinamido)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide (EXAMPLE 12, STEP 2, 0.28 g) which was used in the preparation of EXAMPLE 12, STEP 3, without further purification.

Step 3: A solution of HCl (1.15 ml, 4.60 mmol, 4 M in dioxane) was added to a solution of 4-(4-((R)-(4'-chlorobiphenyl-2-yl)((S)-1,1-dimethylethylsulfinamido)methyl)piperidin-1-yl)-N-(4-((R)-4-(ethyl(2-hydroxyethyl)amino)-1-(phenylthio)butan-2-ylamino)-3-(trifluoromethyl sulfonyl)phenylsulfonyl)benzamide (EXAMPLE 12, STEP 2, 0.244 g, 0.23 mmol) in MeOH (1.2 ml) and the reaction mixture was stirred at r.t for 1 hour. The reaction mixture was concentrated under reduced pressure to provide a residue which was purified by reverse phase HPLC (Gilson column, eluting with 30→50% H₂O/MeCN with 0.1% formic acid for 10 minutes) to provide the title compound (0.12 g, yield: 52% for 3 steps).

¹H NMR (400 MHz, DMSO-d₆) δ ppm 8.05 (d, 1 H), 7.91 (dd, 1 H), 7.71-7.67 (m, 3H), 7.59-7.53 (m, 3H), 7.49-7.45 (m, 1H), 7.37-7.34 (m, 4 H), 7.30-7.26 (m, 3H), 7.21-7.17 (m, 1H), 6.82 (d, 1 H), 6.74-6.68 (m, 3H), 4.00 (m, 1H), 3.87-3.84 (m, 1H), 3.78-3.75 (m, 1H) 3.58-3.55 (m, 1H), 3.32-3.19 (m, 4H), 2.65-2.55 (m, 7H), 2.46-2.43 (m, 1H), 1.99-1.90 (m, 2H), 1.84-1.73 (m, 2H), 1.18-1.08 (m, 2H), 0.93 (t, 3 H), 0.82-0.73 (m, 1H).

LCMS: (ESI) m/z 958 [M+H]⁺.

Example 13

4-(4-((R)-amino(4'-chlorobiphenyl-2-yl)methyl)piperidin-1-yl)-N-(4-((R)-4-(4-(2-hydroxyethyl)piperazin-1-yl)-1-(phenylthio)butan-2-ylamino)-3-(trifluoromethylsulfonyl)phenylsulfonyl)benzamide, formic acid salt

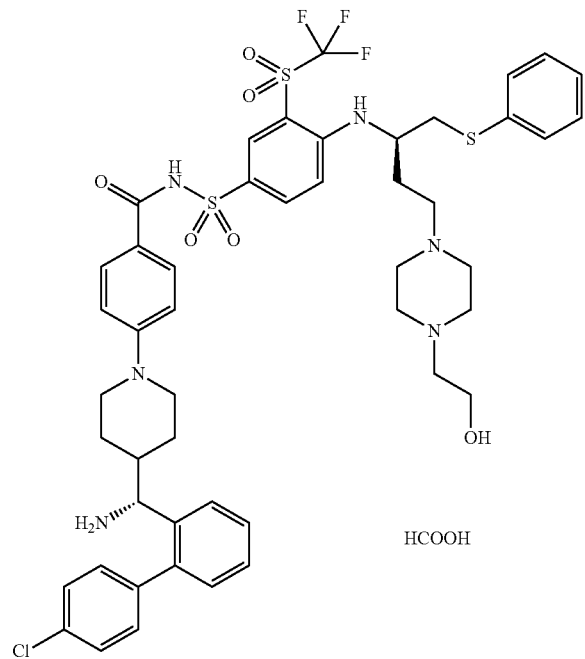 [SMILES: N[C@@H](c1ccccc1-c1ccc(Cl)cc1)C1CCN(c2ccc(C(=O)NS(=O)(=O)c3ccc(N[C@H](CCN4CCN(CCO)CC4)CSc4ccccc4)c(S(=O)(=O)C(F)(F)F)c3)cc2)CC1 ; "HCOOH"]

Step 1: 4-(4-((R)-(4'-chlorobiphenyl-2-yl)((S)-1,1-dimethylethylsulfinamido)methyl)piperidin-1-yl)benzoic acid (INTERMEDIATE 130, 0.150 g, 0.29 mmol), DMAP (70 mg, 0.57 mmol), and EDC (0.110 g, 0.57 mmol) were placed in a 40 ml vial and flushed with nitrogen. DCM (4.0 ml) and DIPEA (0.10 ml, 0.57 mmol) were added, and the solution was stirred at r.t for 15 min. A solution of (R)-4-(4-(4-(2-(tert-butyldiphenylsilyloxy)ethyl)piperazin-1-yl)-1-(phenylthio)butan-2-ylamino)-3-(trifluoromethylsulfonyl)benzenesulfonamide (INTERMEDIATE 22, 0.24 g, 0.29 mmol) in DCM (1.6 ml) was added to the solution and the reaction mixture was stirred at r.t overnight. The reaction mixture was diluted with DCM and washed with sodium bisulfate (1N, aq.) followed by sodium bicarbonate (saturated, aq.). The organic layer was dried ($Na_2SO_4$), filtered, and evaporated under reduced pressure to give a residue which was dried under vacuum to provide N-(4-((R)-4-(4-(2-(tert-butyldiphenylsilyloxy)ethyl)piperazin-1-yl)-1-(phenylthio)butan-2-ylamino)-3-(trifluoromethylsulfonyl)phenylsulfonyl)-4-(4-((R)-(4'-chlorobiphenyl-2-yl)((S)-1,1-dimethylethylsulfinamido)methyl)piperidin-1-yl)benzamide (EXAMPLE 13, STEP 1, 0.40 g) which was used in the preparation of EXAMPLE 13, STEP 2, without further purification.

Step 2: A solution of TASF (0.58 ml. 0.58 mmol, 1.0M in DMF) was added to a solution of N-(4-((R)-4-(4-(2-(tert-butyldiphenylsilyloxy)ethyl)piperazin-1-yl)-1-(phenylthio)butan-2-ylamino)-3-(trifluoromethyl sulfonyl)phenylsulfonyl)-4-(4-((R)-(4'-chlorobiphenyl-2-yl)((S)-1,1-dimethylethylsulfinamido)methyl)piperidin-1-yl)benzamide (EXAMPLE 13, STEP 2, 0.39 g, 0.29 mmol) in DMF (2.3 ml) and the reaction mixture was stirred at r.t for 1 hour. The reaction mixture was concentrated under reduced pressure, diluted with DCM and washed with $H_2O$. The organic layer was dried ($Na_2SO_4$), concentrated under reduced pressure, after filtration, and dried under vacuum to give 4-(4-((R)-(4'-chlorobiphenyl-2-yl)((S)-1,1-dimethylethylsulfinamido)methyl)piperidin-1-yl)-N-(4-((R)-4-(4-(2-hydroxyethyl)piperazin-1-yl)-1-(phenylthio)butan-2-ylamino)-3-(trifluoromethylsulfonyl)phenylsulfonyl)benzamide (EXAMPLE 13, STEP 2, 0.41 g) which was used in the preparation of EXAMPLE 13, STEP 3 without further purification.

Step 3: A solution of HCl (1.45 ml, 5.80 mmol, 4.0M in dioxane) was added to a solution of 4-(4-((R)-(4'-chlorobiphenyl-2-yl)((S)-1,1-dimethylethylsulfinamido)methyl)piperidin-1-yl)-N-(4-((R)-4-(4-(2-hydroxyethyl)piperazin-1-yl)-1-(phenylthio)butan-2-ylamino)-3-(trifluoromethylsulfonyl)phenylsulfonyl)benzamide (EXAMPLE 13, STEP 2, 0.4 g, 0.29 mmol) in MeOH (1.5 ml) and the reaction mixture was stirred at r.t for 1 hour. The reaction mixture was concentrated under reduced pressure to provide a residue which was purified by reverse phase HPLC (Gilson column, eluting with 30→45% $H_2O$/MeCN with 0.1% formic acid for 10 minutes) to provide the title compound (0.16 g, yield: 49% for 3 steps).

$^1$H NMR (400 MHz, DMSO-$d_6$) δ ppm 8.05 (d, 1 H), 7.91 (dd, 1 H), 7.72-7.68 (m, 3H), 7.60-7.53 (m, 3H), 7.50-7.46 (m, 1H), 7.38-7.34 (m, 4 H), 7.31-7.27 (m, 3H), 7.21-7.18 (m, 1 H), 6.84 (d, 1 H), 6.74 (d, 2 H), 6.67 (d, 1 H), 4.00 (m, 1H), 3.88-3.86 (m, 1H), 3.79-3.76 (m, 1H), 3.34-3.21 (m, 4H), 2.69-2.54 (m, 7H), 2.47-2.44 (m, 2H), 2.40-2.29 (m, 5H), 1.99-1.91 (m, 2H), 1.84-1.81 (m, 1H), 1.73-1.66 (m, 1H), 1.20-1.08 (m, 3H), 0.83-0.74 (m, 1H).

LCMS: (ESI) m/z 999 [M+H]$^+$.

Example 14

4-(4-((S)-(4'-chlorobiphenyl-2-yl)(hydroxy)methyl)piperidin-1-yl)-N-(4-((R)-4-morpholino-1-(phenylthio)butan-2-ylamino)-3-(trifluoromethylsulfonyl)phenylsulfonyl)benzamide

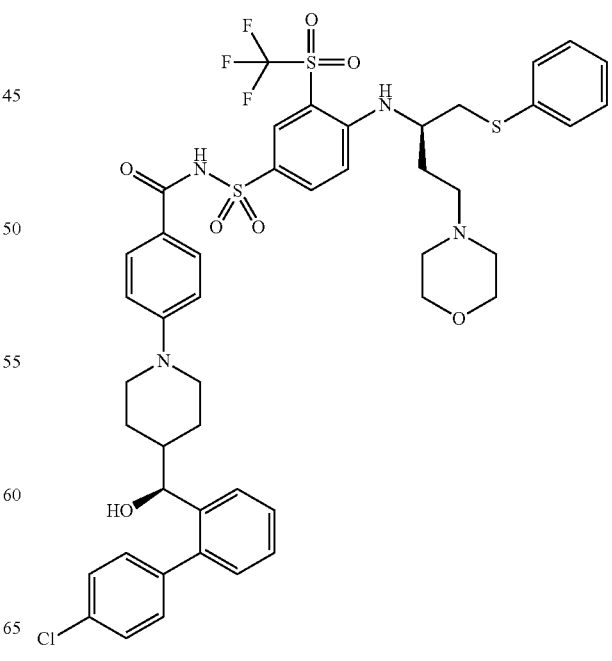

(S)-4-(4-((4'-Chlorobiphenyl-2-yl)(hydroxy)methyl)piperidin-1-yl)benzoic acid (INTERMEDIATE 70, 137.4 mg, 0.33 mmol), (R)-4-(4-morpholino-1-(phenylthio)butan-2-ylamino)-3-(trifluoromethylsulfonyl)benzenesulfonamide (INTERMEDIATE 69, 190.3 mg, 0.34 mmol), DMAP (81.0 mg, 0.66 mmol), and EDC (134.5 mg, 0.70 mmol) were placed in a 50 ml flask and flushed with nitrogen. DCM (6.5 ml) was added, and the solution was stirred at room temperature overnight. The reaction mixture was diluted with DCM (40 ml) and washed with 1N aq. sodium bisulfate (35 ml) followed by a saturated aq. sodium bicarbonate (40 ml). The organic layer was dried ($Na_2SO_4$), filtered, and evaporated under reduced pressure. The concentrate was purified by column chromatography (ISCO, 12 g silica gel column, eluting with 0→10% MeOH in DCM). Clean fractions were combined, evaporated under vacuum, and dried overnight in a 40° C. vacuum oven to provide the title product as a substantially separated isomer (129.3 mg, yield: 41.5%).

$^1$H NMR (400 MHz, DMSO-d6) d ppm 0.74-0.90 (m, 1 H) 0.95-1.15 (m, 2 H) 1.65 (m, 1 H) 1.88 (m, 2 H) 2.60-2.71 (m, 1 H) 3.45-3.61 (m, 4 H) 3.66 (m, 1 H) 3.82 (m, 1 H) 4.05-4.14 (m, 1 H) 4.30 (dd, 1 H) 5.21 (d, 1 H) 6.79 (d, 2 H) 6.91 (m, 1 H) 7.02 (d, 1 H) 7.11-7.21 (m, 2 H) 7.23-7.38 (m, 7 H) 7.42 (t, 1 H) 7.48 (d, 2H) 7.58 (d, 1 H) 7.67 (d, 2 H) 7.94 (dd, 1 H) 8.13 (d, 1 H).

LCMS: (ESI) m/z 957 [M+H]$^+$.
Optical Rotation:
Concentration: 0.1 g/dL
Lamp: Sodium
Wavelength: 589 nm
Temperature: 20° C.
Path length: 10 cm
Cell volume: 1 ml
Solvent: $CH_2Cl_2$
[α]=−128

Example 15

4-(4-((R)-(4'-chlorobiphenyl-2-yl)(hydroxy)methyl)piperidin-1-yl)-N-(4-((R)-4-morpholino-1-(phenylthio)butan-2-ylamino)-3-(trifluoromethylsulfonyl)phenylsulfonyl)benzamide

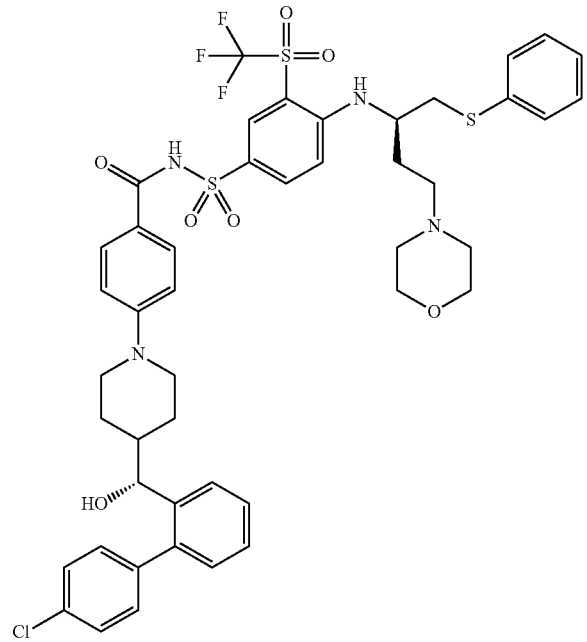 [SMILES: O=C(NS(=O)(=O)c1ccc(N[C@H](CCN2CCOCC2)CSc2ccccc2)c(S(=O)(=O)C(F)(F)F)c1)c1ccc(N2CCC([C@@H](O)c3ccccc3-c3ccc(Cl)cc3)CC2)cc1]

The title product (34.1 mg, yield: 59%) was prepared using a procedure similar to the one described for the synthesis of EXAMPLE 16. 4-(4-((R)-(tert-butyldimethylsilyloxy)(4'-chlorobiphenyl-2-yl)methyl)piperidin-1-yl)-N-(4-((R)-4-morpholino-1-(phenylthio)butan-2-ylamino)-3-(trifluoromethylsulfonyl)phenylsulfonyl)benzamide (INTERMEDIATE 76, 64.7 mg, 0.06 mmol) was used as starting material. The resulting product was purified by column chromatography (ISCO, 4 g silica gel column, eluting with 0→5% MeOH/DCM) followed by further purification by column chromatography (ISCO, 4 g silica gel column, eluting with 0→100% DCM/[10% 2M $NH_3$ in MeOH/90% DCM]), providing the title product.

$^1$H NMR (400 MHz, DMSO-d$_6$) δ ppm 0.76-1.17 (m, 4 H) 1.57-1.69 (m, 1 H) 1.69-1.81 (m, 1 H) 1.84-2.02 (m, 2 H) 2.57-2.69 (m, 2 H) 3.44-3.57 (m, 5 H) 3.58-3.67 (m, 1 H) 3.74-3.83 (m, 1 H) 3.99-4.11 (m, 1 H) 4.27-4.33 (m, 1 H) 5.19-5.23 (m, 1 H) 6.72-6.80 (m, 2 H) 6.80-6.88 (m, 1 H) 6.90-6.99 (m, 1 H) 7.11-7.22 (m, 2 H) 7.23-7.38 (m, 8 H) 7.39-7.45 (m, 1 H) 7.48 (d, 2 H) 7.56-7.61 (m, 1 H) 7.66 (d, 2 H) 7.89-7.95 (m, 1 H) 8.08-8.13 (m, 1 H).

LCMS: m/z 957 [M+H]$^+$.
Optical Rotation:
Concentration: 0.1 g/dL
Lamp: Sodium
Wavelength: 589 nm
Temperature: 20° C.
Path length: 10 cm
Cell volume: 1 ml
Solvent: $CH_2Cl_2$
[α]=−9

Example 16

4-(4-((R)-(4'-chlorobiphenyl-2-yl)(hydroxy)methyl)piperidin-1-yl)-N-(4-((R)-4-morpholino-1-(phenylthio)butan-2-ylamino)-3-nitrophenylsulfonyl)benzamide

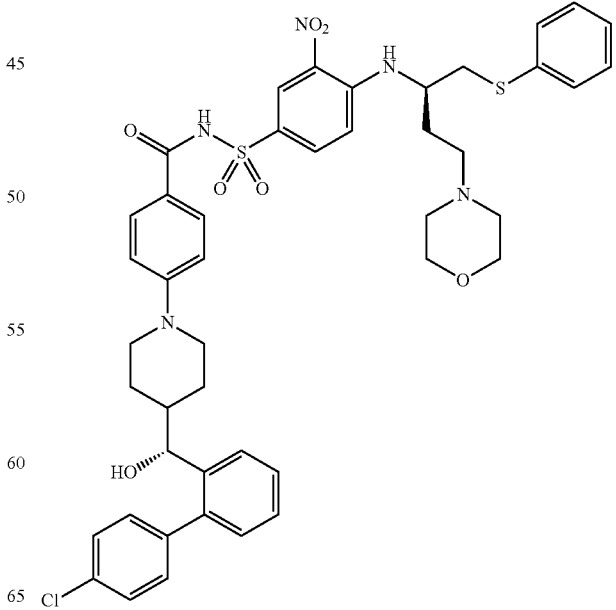

4-(4-((R)-(tert-butyldimethylsilyloxy)(4'-chlorobiphenyl-2-yl)methyl)piperidin-1-yl)-N-(4-((R)-4-morpholino-1-(phenylthio)butan-2-ylamino)-3-nitrophenylsulfonyl)benzamide (INTERMEDIATE 75, 329.0 mg, 0.33 mmol) was charged in a 100 ml flask under nitrogen and treated with TBAF (10.0 ml, 1.0 M in THF, 10 mmol). The resulting solution was stirred at room temperature for 35 minutes whereupon the volatiles were removed under reduced pressure. The concentrate was diluted with DCM (100 ml) and washed with 1N aq. NaHSO$_4$ (100 ml), and saturated aq. NaHCO$_3$ (30 ml), then dried (Na$_2$SO$_4$), filtered, and evaporated under vacuum. The concentrate was purified by column chromatography (ISCO, 12 g silica gel column, eluting with 0→5% MeOH/DCM) followed by further purification by column chromatography (ISCO, 12 g silica gel column, eluting with 0→90% DCM/[10% of 2M NH$_3$ in MeOH/90% DCM]) to provide the title product (228 mg, yield: 78%)

$^1$H NMR (300 MHz, DMSO-d$_6$) δ ppm 0.84 (br. s., 1 H) 1.01 (d, 2 H) 1.56-1.72 (m, 1 H) 1.88 (m, 2 H) 1.94-2.09 (m, 1 H) 3.36 (d, 2 H) 3.45-3.59 (m, 4 H) 3.64 (m, 1 H) 3.75-3.87 (m, 1 H) 4.07-4.21 (m, 1 H) 4.30 (dd, 1 H) 5.20 (d, 1 H) 6.78 (d, 2 H) 7.05 (d, 1 H) 7.10-7.25 (m, 4 H) 7.25-7.38 (m, 5 H) 7.38-7.52 (m, 3 H) 7.58 (d, 1 H) 7.67 (d, Hz, 2 H) 7.75-7.84 (m, 1 H) 8.38 (d, 1 H) 8.50 (d, 1 H).

LCMS: (ESI) m/z 870 [M+H]$^+$.

Example 17

4-(4-((R)-(4'-chlorobiphenyl-2-yl)(cyano)methyl)piperidin-1-yl)-N-(4-((R)-4-morpholino-1-(phenylthio)butan-2-ylamino)-3-(trifluoromethylsulfonyl)phenylsulfonyl)benzamide and 4-(4-((S)-(4'-chlorobiphenyl-2-yl)(cyano)methyl)piperidin-1-yl)-N-(4-((R)-4-morpholino-1-(phenylthio)butan-2-ylamino)-3-(trifluoromethylsulfonyl)phenylsulfonyl)benzamide, mixture of diastereomers

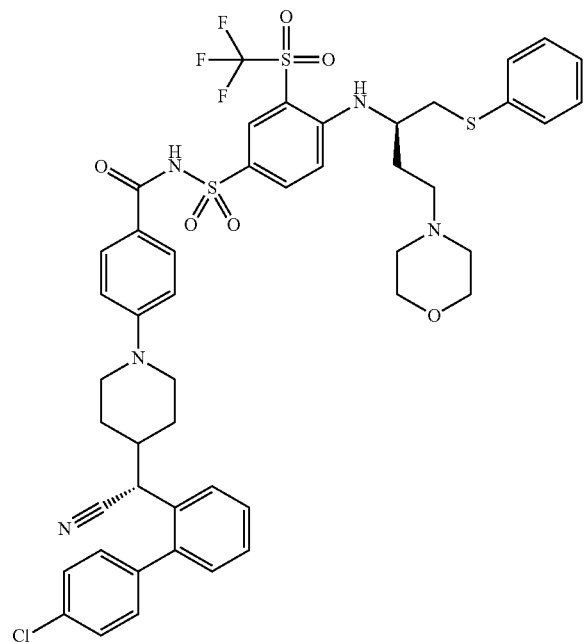 [SMILES: N#C[C@@H](c1ccccc1-c1ccc(Cl)cc1)C1CCN(c2ccc(C(=O)NS(=O)(=O)c3ccc(N[C@H](CCN4CCOCC4)CSc4ccccc4)c(S(=O)(=O)C(F)(F)F)c3)cc2)CC1]

-continued

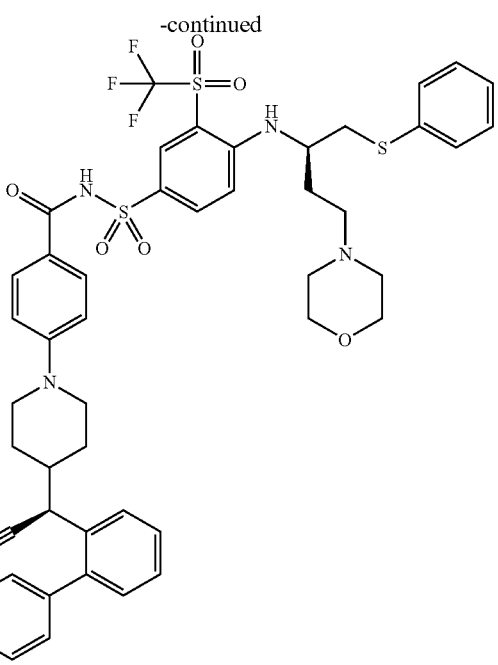

(R)-4-(4-((4'-chlorobiphenyl-2-yl)(cyano)methyl)piperidin-1-yl)benzoic acid and (S)-4-(4-((4'-chlorobiphenyl-2-yl)(cyano)methyl)piperidin-1-yl)benzoic acid hydrochloride salts (INTERMEDIATE 83, 67.8 mg, 0.15 mmol), (R)-4-(4-morpholino-1-(phenylthio)butan-2-ylamino)-3-(trifluoromethylsulfonyl)benzenesulfonamide (INTERMEDIATE 69, 81.4 mg, 0.15 mmol), DMAP (38.1 mg, 0.31 mmol), and EDC (59.0 mg, 0.31 mmol) were combined and sealed in a microwave tube. The tube was purged with nitrogen, and DCM (3.0 ml) and DIPEA (0.05 ml, 0.29 mmol) were added. The reaction mixture was stirred at room temperature for 4 days and was then diluted with water (5 ml) and extracted with DCM (2×5 ml). The combined extracts were dried (MgSO$_4$), filtered, and evaporated under reduced pressure. The residue was purified by column chromatography (ISCO, 4 g silica gel column, eluting with first with 0→10% MeOH/DCM and then with 0→100% EtOAc/hexanes). The fractions corresponding to product were collected and evaporated to dryness to give a gummy residue. The material was dissolved in a trace of DCM and diethyl ether was added, resulting in a precipitate. The slurry was evaporated under reduced pressure to provide the title product (60.4 mg, yield: 44%) as a mixture of diastereomers.

$^1$H NMR (400 MHz, DICHLOROMETHANE-d$_2$) δ ppm 1.05 (qd, 1 H), 1.30-1.45 (m, 2 H), 1.60-1.71 (m, 1 H), 1.81-1.93 (m, 1 H), 1.95-2.12 (m, 2 H), 2.19-2.45 (m, 6 H), 2.62 (td, 1 H), 2.75 (td, 1 H), 3.05-3.16 (m, 2 H), 3.53-3.65 (m, 4 H), 3.67-3.75 (m, 1 H), 3.78 (d, 1 H), 3.83-3.91 (m, 1 H), 3.93-4.03 (m, 1 H), 6.67-6.74 (m, 1 H), 6.78 (d, 2 H), 7.04 (d, 1 H), 7.20-7.34 (m, 6 H), 7.34-7.40 (m, 2 H), 7.40-7.51 (m, 4 H), 7.55-7.60 (m, 1 H), 7.62 (d, 2 H), 8.03 (dd, 1 H), 8.33 (d, 1 H).

LCMS: (ESI) m/z 966 [M+H]$^+$.

Example 18

4-(4-((R)-(4'-chlorobiphenyl-2-yl)(cyano)methyl)piperidin-1-yl)-N-(4-((R)-4-morpholino-1-(phenylthio)butan-2-ylamino)-3-(trifluoromethylsulfonyl)phenylsulfonyl)benzamide

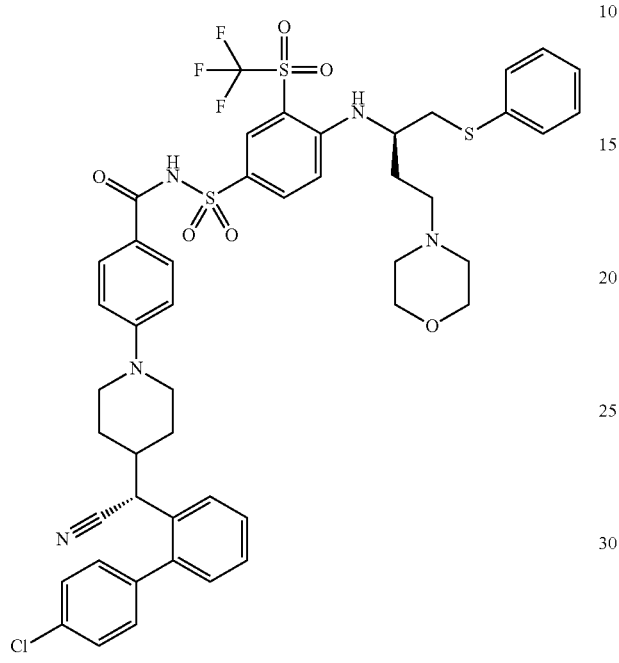

The title product (19.8 mg, yield: 20%) was prepared using a procedure similar to the one described for the synthesis of EXAMPLE 14. (R)-4-(4-((4'-Chlorobiphenyl-2-yl)(cyano)methyl)piperidin-1-yl)benzoic acid, hydrochloride salt (INTERMEDIATE 84, 44.9 mg, 0.1 mmol) and (R)-4-(4-morpholino-1-(phenylthio)butan-2-ylamino)-3-(trifluoromethylsulfonyl)benzenesulfonamide (INTERMEDIATE 69, 54.4 mg, 0.1 mmol) were used as starting materials. The resulting product was purified by column chromatography (ISCO, 4 g silica gel column, eluting with 0→5% MeOH/DCM) followed by further purification by column chromatography (ISCO, 4 g silica gel column, eluting first with 0→100% EtOAc/hexanes and then with 0→5% MeOH/DCM), providing the title product.

$^1$H NMR (400 MHz, DICHLOROMETHANE-$d_2$) δ ppm 0.98-1.11 (m, 1 H), 1.29-1.45 (m, 3 H), 1.61 (br. s., 1 H), 1.81-2.05 (m, 3 H), 2.21-2.37 (m, 1 H), 2.49-2.87 (m, 6 H), 3.14 (d, 2 H), 3.66-3.98 (m, 7 H), 4.07 (br. s., 1 H), 6.73-6.84 (m, 3 H), 7.02 (d, 1 H), 7.20-7.33 (m, 6 H), 7.35-7.51 (m, 6 H), 7.57 (dd, 1 H), 7.62 (d, 2 H), 8.06 (dd, 1 H), 8.36 (d, 1 H).

LCMS: (ESI) m/z 966 [M+H]$^+$.

Example 19

4-(4-((S)-(4'-chlorobiphenyl-2-yl)(cyano)methyl)piperidin-1-yl)-N-(4-((R)-4-morpholino-1-(phenylthio)butan-2-ylamino)-3-(trifluoromethylsulfonyl)phenylsulfonyl)benzamide

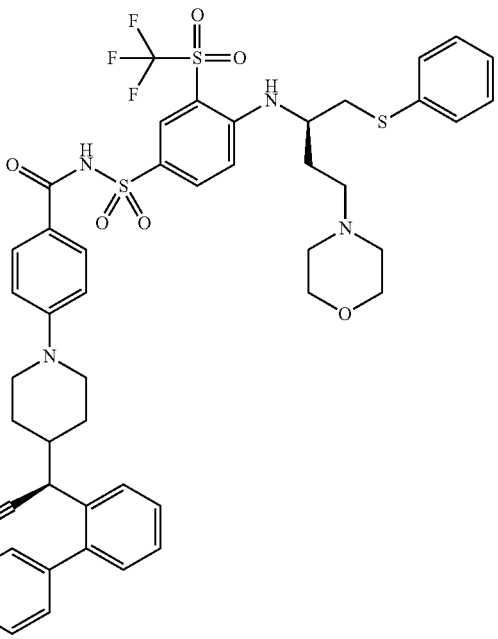

The title product (10.7 mg, yield: 11%) was prepared using a procedure similar to the one described for the synthesis of EXAMPLE 14. (S)-4-(4-((4'-Chlorobiphenyl-2-yl)(cyano)methyl)piperidin-1-yl)benzoic acid, HCl salt (INTERMEDIATE 85, 49.5 mg 0.11 mmol) and (R)-4-(4-morpholino-1-(phenylthio)butan-2-ylamino)-3-(trifluoromethylsulfonyl)benzenesulfonamide (INTERMEDIATE 69, 58.6 mg 0.11 mmol) were used as starting materials. The resulting product was purified by column chromatography (ISCO, 4 g silica gel column, eluting with 0→5% MeOH/DCM) followed by further purification by column chromatography (ISCO, 4 g silica gel column, eluting first with 0→100% EtOAc/hexanes and then with 0→3.5% MeOH/DCM), providing the title product.

$^1$H NMR (400 MHz, DICHLOROMETHANE-$d_2$) δ ppm 1.04 (qd, 1 H), 1.30-1.45 (m, 3 H), 1.61-1.72 (m, 1 H), 1.82-1.94 (m, 1 H), 2.21-2.47 (m, 6 H), 2.63 (td, 1 H), 2.76 (td, 1 H), 3.11 (d, 2 H), 3.53-3.66 (m, 4 H), 3.68-3.76 (m, 1 H), 3.78 (d, 1 H), 3.84-3.92 (m, 1 H), 3.94-4.05 (m, 1 H), 6.72 (d, 1 H), 6.78 (d, 2 H), 7.06 (d, 1 H), 7.20-7.34 (m, 6 H), 7.34-7.52 (m, 6 H), 7.55-7.65 (m, 3 H), 8.03 (dd, 1 H), 8.34 (d, 1 H).

LCMS: (ESI) m/z 966 [M+H]$^+$.

Example 20

4-(4-((R)-(4'-chlorobiphenyl-2-yl)(hydroxy)methyl)piperidin-1-yl)-N-(4-((R)-4-((S)-3-((diethylamino)methyl)morpholino)-1-(phenylthio)butan-2-ylamino)-3-(trifluoromethylsulfonyl)phenylsulfonyl)benzamide

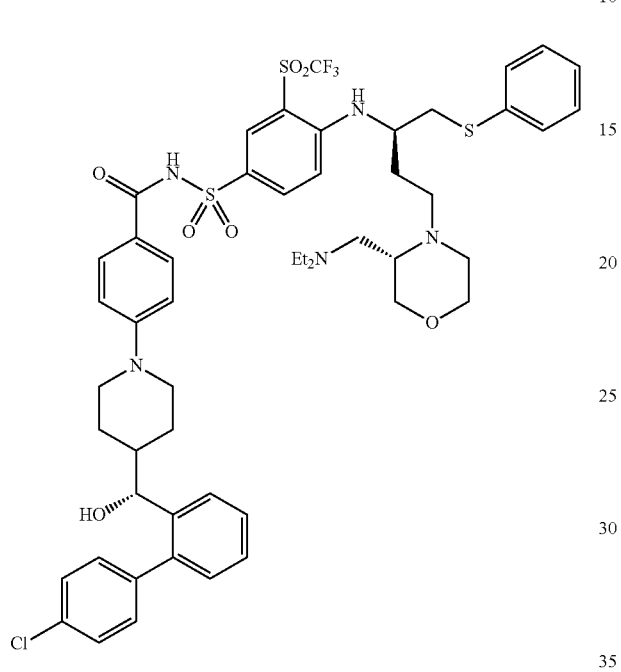

A solution of 4-(4-((R)-(tert-butyldimethylsilyloxy)(4'-chlorobiphenyl-2-yl)methyl)piperidin-1-yl)-N-(4-((R)-4-((S)-3-((diethylamino)methyl)morpholino)-1-(phenylthio)butan-2-ylamino)-3-(trifluoromethyl sulfonyl)phenylsulfonyl)benzamide, (INTERMEDIATE 89, 100 mg, 0.09 mmol) and TBAF (3.5 ml 3.46 mmol, 1 M in THF) was stirred for 45 minutes at room temperature. The solvent was removed under reduced pressure and the residue was taken up in DCM (50 ml). The organic layer was washed successively with 50 ml of water (50 ml) and saturated aqueous sodium bicarbonate (50 ml). The organic phase was dried over sodium sulfate, filtered, and concentrated under reduced pressure. The concentrate was purified by column chromatography (ISCO, eluting with 0→100% DCM/[10% 2N ammonia in MeOH in DCM] over 19 minutes and then eluting with 0→20% MeOH/DCM) to give the title product (43.0 mg, yield: 48%).

$^1$H NMR (400 MHz, DICHLOROMETHANE-$d_2$) δ ppm 0.68-1.28 (m, 11 H) 1.43-1.77 (m, 2 H) 1.79-2.04 (m, 2 H) 2.04-2.74 (m, 13 H) 2.86-3.07 (m, 2 H) 3.18-3.32 (m, 1 H) 3.35-3.89 (m, 6H) 4.39 (d, 1 H) 6.60 (d, 4 H) 7.03-7.39 (m, 12 H) 7.50 (d, 1 H) 7.66 (d, 2 H) 7.86-8.03 (m, 1 H) 8.16 (br. s., 1 H).

LCMS: (ESI) m/z 1042 [M+H]$^+$.

Example 21

4-(4-((R)-(4'-chlorobiphenyl-2-yl)(hydroxy)methyl)piperidin-1-yl)-N-(4-((R)-4-((R)-3-((diethylamino)methyl)morpholino)-1-(phenylthio)butan-2-ylamino)-3-(trifluoromethylsulfonyl)phenylsulfonyl)benzamide

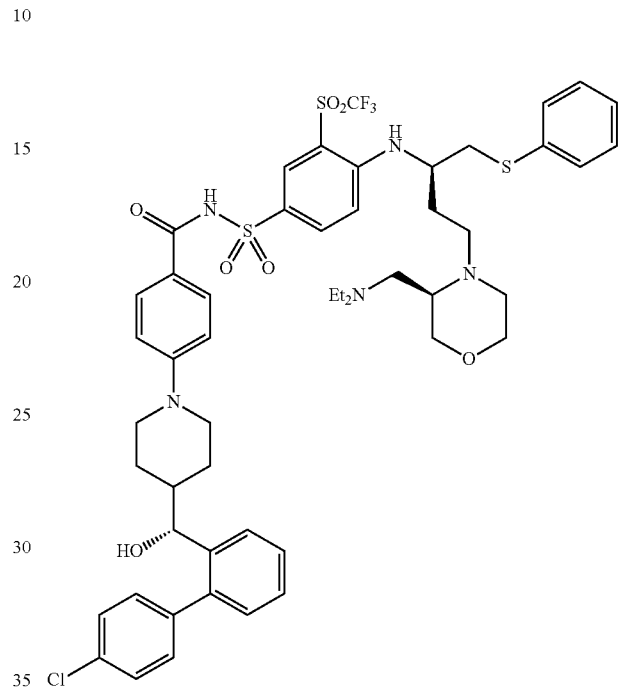

The title product (50 mg, yield: 55%) was prepared using a procedure similar to the one described for the synthesis of EXAMPLE 16. 4-(4-((R)-(tert-butyldimethylsilyloxy)(4'-chlorobiphenyl-2-yl)methyl)piperidin-1-yl)-N-(4-((R)-4-((R)-3-((diethylamino)methyl)morpholino)-1-(phenylthio)butan-2-ylamino)-3-(trifluoromethylsulfonyl)phenylsulfonyl)benzamide (INTERMEDIATE 93, 100 mg, 0.09 mmol) was used as starting material. The resulting product was purified by column chromatography (ISCO, eluting with 0→100% DCM/[10% 2N ammonia in MeOH in DCM] over 19 minutes and then eluting with 0→20% MeOH/DCM), providing the title product.

$^1$H NMR (400 MHz, DICHLOROMETHANE-$d_2$) δ ppm 0.85-1.30 (m, 10 H) 1.46-1.76 (m, 2 H) 1.78-2.02 (m, 2 H) 2.07-2.78 (m, 14 H) 2.86-3.11 (m, 2 H) 3.28-3.57 (m, 5 H) 3.68 (d, 1 H) 3.84 (br. s., 1 H) 4.38 (d, 1 H) 6.35-6.77 (m, 4 H) 6.97-7.40 (m, 12 H) 7.50 (dd, 1 H) 7.66 (d, 2 H) 7.91 (d, 1 H) 8.13 (br. s., 1 H).

LCMS: (ESI) m/z 1042 [M+H]$^+$.

Example 22

4-(4-((R)-(4'-chlorobiphenyl-2-yl)(hydroxy)methyl)piperidin-1-yl)-N-(4-((R)-4-((R)-2-(hydroxymethyl)morpholino)-1-(phenylthio)butan-2-ylamino)-3-(trifluoromethylsulfonyl)phenylsulfonyl)benzamide, formic acid salt

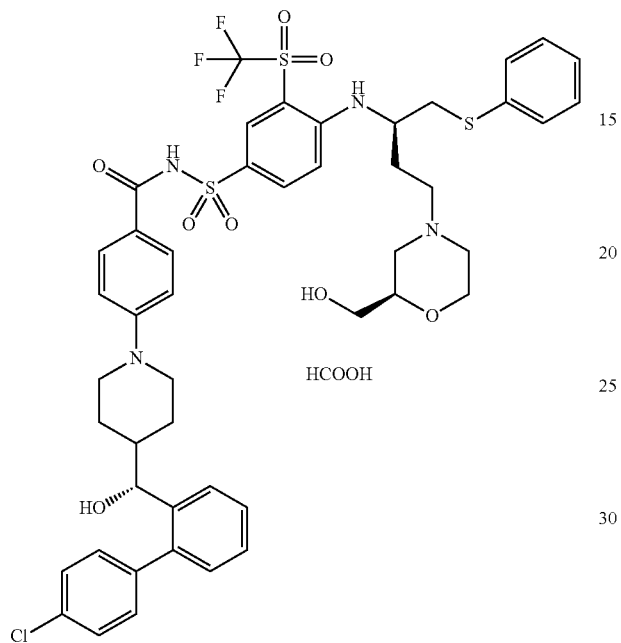

HCOOH

A solution of TBAF (115 μl, 0.11 mmol, 1M in THF) was added dropwise to a solution of 4-(4-((R)-(tert-butyldimethylsilyloxy)(4'-chlorobiphenyl-2-yl)methyl)piperidin-1-yl)-N-(4-((R)-4-((R)-2-((tert-butyldiphenylsilyloxy)methyl)morpholino)-1-(phenylthio)butan-2-ylamino)-3-(trifluoromethylsulfonyl)phenylsulfonyl)benzamide INTERMEDIATE 100, 77 mg, 0.06 mmol) in THF (420 μl) and the resulting mixture was stirred at room temperature overnight. HCl (4 M in dioxane, 39.9 μl, 1.15 mmol) was then added and the mixture was stirred at room temperature for 1 hr. The reaction mixture was diluted with EtOAc and the organic phase washed with H₂O (2×), dried (Na₂SO₄), filtered and concentrated under reduced pressure. The concentrate was purified by reverse phase HPLC (Gilson column, eluting with 15→70% H₂O/MeCN with 1% formic acid for 14 minutes) to provide the title product (31.0 mg, yield: 52%).

$^1$H NMR (300 MHz, METHANOL-d4) δ ppm 0.88-1.09 (m, 2 H) 1.10-1.35 (m, 3 H) 1.73-1.87 (m, 2 H) 1.91-2.20 (m, 5 H) 2.43-2.64 (m, 3 H) 2.68-2.85 (m, 3 H) 3.24 (dd, 2 H) 3.44-3.65 (m, 5 H) 3.70 (d, 1 H) 3.88 (d, 2 H) 4.06 (br. s., 1 H) 4.44 (d, 1 H) 6.81-6.90 (m, 3 H) 7.14-7.28 (m, 4 H) 7.28-7.48 (m, 9 H) 7.62 (d, 1 H) 7.73 (d, 2 H) 8.03 (d, 1 H) 8.29 (s, 1 H).

LCMS: (ESI) m/z 987.3 [M+H]⁺.

Optical Rotation:
Concentration: 0.1 g/dL
Lamp: Sodium
Wavelength: 589 nm
Temperature: 20° C.
Path length: 10 cm
Cell volume: 1 ml
Solvent: Methanol
[α]=+4

Example 23

4-(4-((R)-(4'-chlorobiphenyl-2-yl)(hydroxy)methyl)piperidin-1-yl)-N-(4-((R)-4-4S)-2-(hydroxymethyl)morpholino)-1-(phenylthio)butan-2-ylamino)-3-(trifluoromethylsulfonyl)phenylsulfonyl)benzamide, formic acid salt

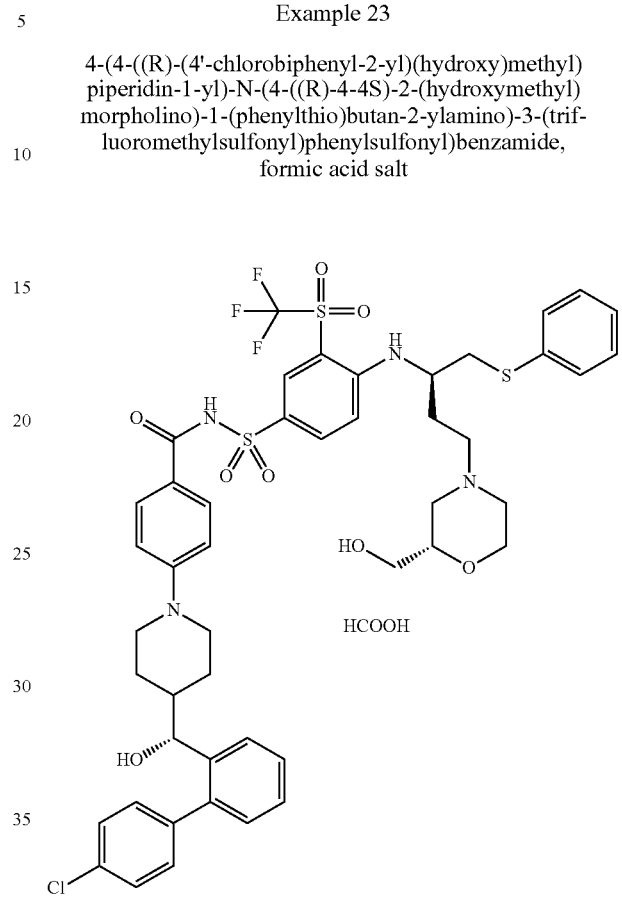

HCOOH

The title product (37 mg, yield: 62%) was prepared using a procedure similar to the one described for the synthesis of EXAMPLE 22. 4-(4-((R)-(tert-butyldimethylsilyloxy)(4'-chlorobiphenyl-2-yl)methyl)piperidin-1-yl)-N-(4-((R)-4-((S)-2-((tert-butyldiphenylsilyloxy)methyl)morpholino)-1-(phenylthio)butan-2-ylamino)-3-(trifluoromethylsulfonyl)phenylsulfonyl)benzamide (INTERMEDIATE 101, 77 mg, 0.06 mmol) was used as starting material. The resulting product was purified by reverse phase HPLC (Gilson, eluting with 15→70% H₂O/MeCN with 1% formic acid for 14 minutes), providing the title product.

$^1$H NMR (300 MHz, METHANOL-d4) δ ppm 0.87-1.05 (m, 1 H) 1.08-1.33 (m, 2 H) 1.81 (dd, 2 H) 1.90-2.16 (m, 3 H) 2.16-2.28 (m, 1 H) 2.42-2.66 (m, 4 H) 2.69-2.81 (m, 1 H) 2.93 (d, 1 H) 3.14-3.29 (m, 2 H) 3.47-3.65 (m, 4 H) 3.71 (d, 1 H) 3.79-3.93 (m, 2 H) 4.08 (dd, 1 H) 4.44 (d, 1 H) 6.82-6.89 (m, 3 H) 7.14-7.28 (m, 4 H) 7.29-7.47 (m, 8 H) 7.60-7.64 (m, 1 H) 7.72 (d, 2 H) 8.02 (dd, 1 H) 8.29 (d, 1 H).

LCMS: (ESI) m/z 987 [M+H]⁺.

Optical Rotation:
Concentration: 0.1 g/dL
Lamp: Sodium
Wavelength: 589 nm
Temperature: 20° C.
Path length: 10 cm
Cell volume: 1 ml
Solvent: Methanol
[α]=+10

Example 24

4-(4-((R)-(4'-chlorobiphenyl-2-yl)(hydroxy)methyl)piperidin-1-yl)-N-(4-((R)-4-((R)-3-(hydroxymethyl)morpholino)-1-(phenylthio)butan-2-ylamino)-3-(trifluoromethylsulfonyl)phenylsulfonyl)benzamide, formic acid salt

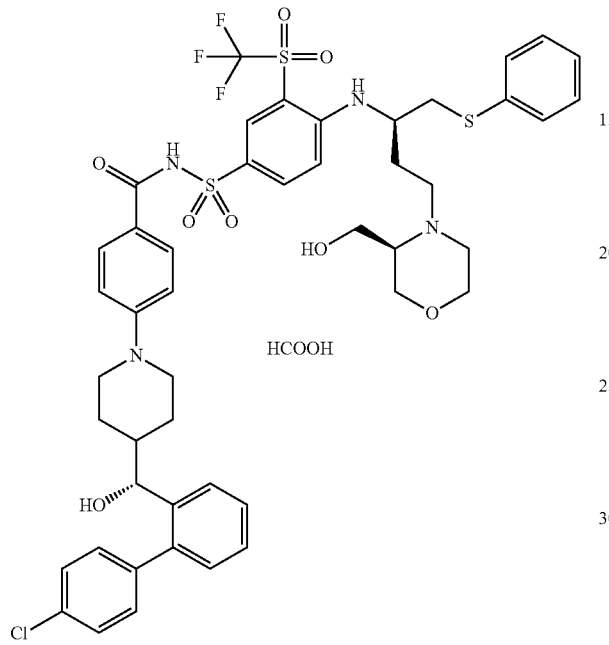

Step 1: To a solution of (R)-4-(4-(((tert-butyldimethylsilyloxy)(4'-chlorobiphenyl-2-yl)methyl)piperidin-1-yl)benzoic acid (INTERMEDIATE 13, 183 mg, 0.34 mmol) in DCM (3 ml) were added sequentially DMAP (125 mg, 1.02 mmol), 4-((R)-4-((S)-3-((tert-butyldiphenylsilyloxy)methyl)morpholino)-1-(phenylthio)butan-2-ylamino)-3-(trifluoromethylsulfonyl)benzenesulfonamide (INTERMEDIATE 105, 280 mg, 0.34 mmol) and EDC (131 mg, 0.68 mmol). The resulting solution was stirred at room temperature overnight. Evaporation of the volatiles under reduced pressure gave a residue which was purified by column chromatography (ISCO, 27 g silica gel column, eluting with 0→20% EtOAc/hexanes) to give 4-(4-((R)-(tert-butyldimethylsilyloxy)(4'-chlorobiphenyl-2-yl)methyl)piperidin-1-yl)-N-(4-((R)-4-((S)-3-((tert-butyldiphenylsilyloxy)methyl)morpholino)-1-(phenylthio)butan-2-ylamino)-3-(trifluoromethylsulfonyl)phenylsulfonyl)benzamide (EXAMPLE 24, STEP 1, 153 mg) which was used in the preparation of EXAMPLE 24, STEP 2 without further purification.

Step 2: To a solution of 4-(4-((R)-(tert-butyldimethylsilyloxy)(4'-chlorobiphenyl-2-yl)methyl)piperidin-1-yl)-N-(4-((R)-4-((S)-3-((tert-butyldiphenylsilyloxy)methyl)morpholino)-1-(phenylthio)butan-2-ylamino)-3-(trifluoromethyl sulfonyl)phenylsulfonyl)benzamide (EXAMPLE 24, STEP 1, 135 mg) in THF (2 ml) was added TBAF (0.54 ml, 0.54 mmol, 1M in THF). The resulting mixture was stirred at room temperature overnight whereupon HCl (2 ml, 4N in dioxane) was added and the mixture stirred for 30 minutes at ambient temperature. The volatiles were evaporated under reduced pressure to give a residue which was purified by reverse phase HPLC (Gilson column, eluting with 10→70% MeCN with 0.1% formic acid/water), to give the title product (92 mg, yield: 27%).

$^1$H NMR (DMSO-d6, 300Mz) 8.18 (s, 1H) 8.01 (d, 1H) 7.68 (d, 2 H) 7.58 (d, 1H) 7.49 (d, 2H) 7.43 (t, 1H) 7.27-7.37 (m, 5H) 7.20-7.26 (m, 2H) 7.12-7.18 (m, 2H) 6.99 (d, 1H) 6.84 (d, 2H) 4.30 (d, 1H) 4.12-4.23 (m, 2H) 3.80-4.06 (m, 9H) 3.62-3.75 (m, 2H) 3.55-3.61 (m, 1H) 3.44-3.64 (m, 2H) 3.25-3.42 (m, 2H) 1.83-1.93 (m, 1H) 1.64-1.74 (m, 1H) 0.99-1.36 (m, 3H) 0.83-0.92 (m, 2H).

LCMS: (ESI) m/z 987 [M+H]$^+$.

Example 25

4-(4-((R)-(4'-chlorobiphenyl-2-yl)(hydroxy)methyl)piperidin-1-yl)-N-(4-((R)-4-4S)-3-(hydroxymethyl)morpholino)-1-(phenylthio)butan-2-ylamino)-3-(trifluoromethylsulfonyl)phenylsulfonyl)benzamide, hydrochloride salt

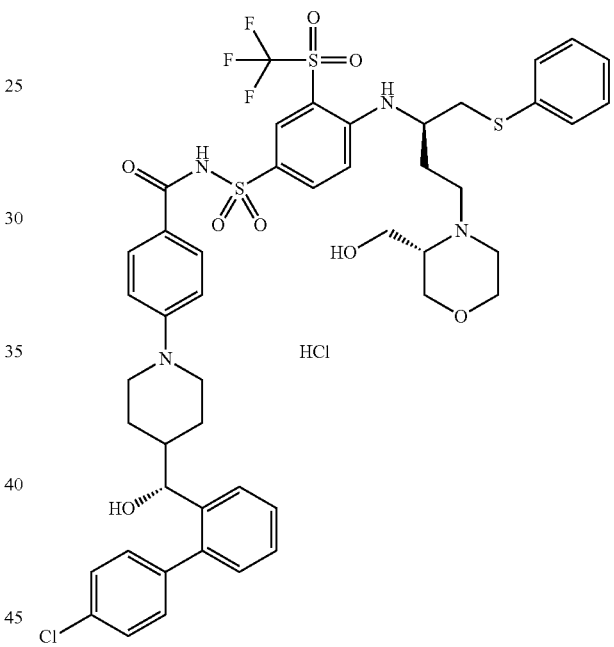

To a solution of 4-(4-((R)-(tert-butyldimethylsilyloxy)(4'-chlorobiphenyl-2-yl)methyl)piperidin-1-yl)-N-(4-((R)-4-((R)-3-((tert-butyldiphenylsilyloxy)methyl)morpholino)-1-(phenylthio)butan-2-ylamino)-3-(trifluoromethyl sulfonyl)phenylsulfonyl)benzamide (INTERMEDIATE 110, 134 mg, 0.10 mmol) in THF (2 ml) was added TBAF (0.2 ml, 0.2 mmol, 1M in THF). The resulting mixture was heated at 60° C. for 2 hours. The volatiles were evaporated under reduced pressure to give a residue which was purified by reverse phase HPLC (Gilson column, eluting with 5→70% MeCN with 0.1% TFA/water) to give the trifluoroacetate salt of 4-(4-((R)-(4'-chlorobiphenyl-2-yl)(hydroxy)methyl)piperidin-1-yl)-N-(4-((R)-4-((S)-3-(hydroxymethyl)morpholino)-1-(phenylthio)butan-2-ylamino)-3-(trifluoromethylsulfonyl)phenylsulfonyl)benzamide. The trifluoroacetate salt was dissolved in dioxane and treated with HCl in dioxane (4N in dioxane) and the resulting solution was stirred for 10 minutes at room temperature. Evaporation of the volatiles under reduced pressure gave the title product (72 mg, yield: 70%).

¹H NMR (DMSO-d6, 300Mz) 8.17 (d, 1H) 8.01 (d, 1H) 7.68 (d, 2 H) 7.59 (d, 1 H) 7.49 (d, 2H) 7.43 (t, 1 H) 7.28-7.37 (m, 5 H) 7.19-7.26 (m, 2 H) 7.13-7.18 (m, 2H) 6.98 (d, 1H) 6.84 (d, 2H) 4.30 (d, 1 H) 4.09-4.22 (m, 2 H) 3.52-4.08 (m, 12 H) 3.07-3.44 (m, 4 H) 1.81-1.93 (m, 1H) 1.64-1.74 (m, 1H) 0.98-1.36 (m, 3H) 0.79-0.92 (m, 2H).

LCMS: m/z 987 [M+H]⁺.

Example 26

4-(4-((R)-(4'-chlorobiphenyl-2-yl)(hydroxy)methyl) piperidin-1-yl)-N-(4-((2R)-4-(2-((diethylamino)methyl)morpholino)-1-(phenylthio)butan-2-ylamino)-3-(trifluoromethylsulfonyl)phenylsulfonyl)benzamide, single diastereomer

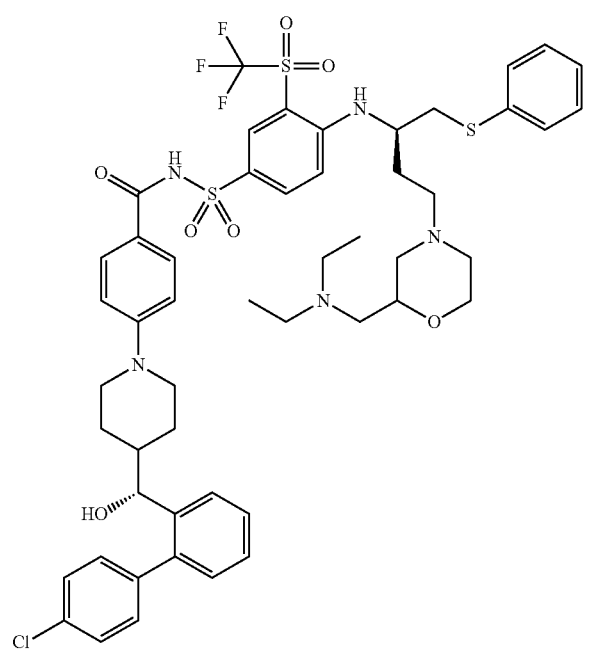 [SMILES: CCN(CC)CC1CN(CC[C@H](CSc2ccccc2)Nc2ccc(S(=O)(=O)NC(=O)c3ccc(N4CCC([C@@H](O)c5ccccc5-c5ccc(Cl)cc5)CC4)cc3)cc2S(=O)(=O)C(F)(F)F)CCO1]

To a solution of 4-(4-((R)-(tert-butyldimethylsilyloxy)(4'-chlorobiphenyl-2-yl)methyl)piperidin-1-yl)-N-(4-((2R)-4-(2-((diethylamino)methyl)morpholino)-1-(phenylthio)butan-2-ylamino)-3-(trifluoromethylsulfonyl)phenylsulfonyl) benzamide, single diastereomer (INTERMEDIATE 117, 199 mg, 0.17 mmol) in dioxane (2.027 ml) was added drop wise HCl (4M in dioxane, 0.430 ml, 1.72 mmol) and the reaction mixture was stirred at room temperature for 2 hours. The reaction mixture was neutralized with Et₃N (2 ml), diluted with DCM and filtered. The filtrate was concentrated under reduced pressure and purified by column chromatography (ISCO, eluting with 0→100% DCM to 10% MeOH/0.1% NH₃ in DCM) to provide the title product as a substantially separated diastereomer (0.06 g, 30%).

¹H NMR (400 MHz, DICHLOROMETHANE-d₂) δ ppm 8.06 (d, 1 H), 8.02 (d, 1H), 7.90 (d, 2H), 7.61 (m, 1H), 7.40-7.21 (m, 12 H), 6.82-6.76 (m, 3H), 6.46 (d, 1H), 4.49 (d, J=8.1 Hz, 1H), 4.02 (m, 1H), 3.82 (d, 1H), 3.66 (m, 2H), 3.48 (m, 1H), 3.33 (m, 1H), 3.17 (m, 1H), 3.09 (m, 4H), 2.83 (d, 1H), 2.73 (m, 2H), 2.55 (m, 2H), 2.32 (m, 1H), 2.20-2.01 (m, 3H), 1.86-1.69 (m, 4H), 1.50 (m, 1H), 1.40-1.28 (m, 4H), 1.12 (t, 6H).

LCMS: (ESI) m/z 1042 [M+H]⁺.

Example 27

Di-tert-butyl((R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)-phenyl)piperidin-4-yl)methoxy)methyl phosphate

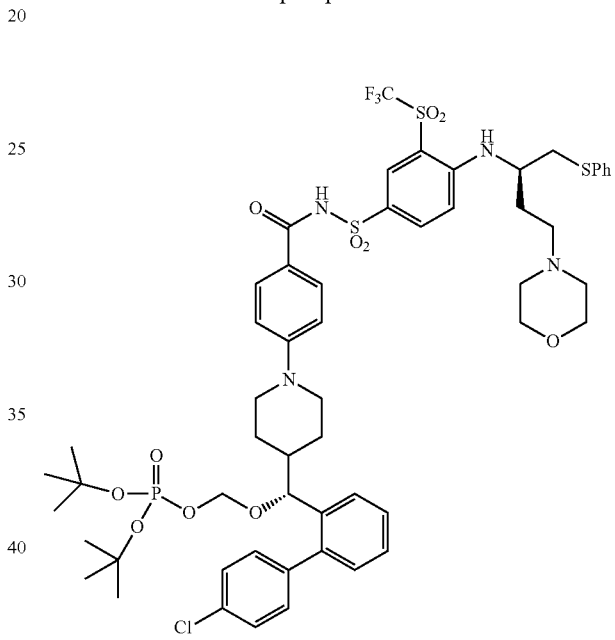

To a solution of (R)-4-(4-((4'-chlorobiphenyl-2-yl)(di-tert-butoxyphosphonooxymethoxy)methyl)piperidin-1-yl)benzoic acid (INTERMEDIATE 118, 73 mg, 0.11 mmol), EDC (43 mg, 0.23 mmol), and DMAP (28 mg, 0.23 mmol) in 3 ml of DCM was added (R)-4-(4-morpholino-1-(phenylthio)butan-2-ylamino)-3-(trifluoromethylsulfonyl)benzenesulfonamide (INTERMEDIATE 69, 69 mg, 0.12 mmol). The mixture was allowed to stir overnight at room temperature. The reaction mixture was diluted with DCM (20 ml) and washed with brine (5 ml). The collected organic layer was dried over Na₂SO₄ and concentrated in vacuo. The residue was purified by column chromatography (ISCO, eluting with 0→10% MeOH/EtOAc for 14 minutes) to provide the title product (58 mg, yield: 43%).

LCMS: m/z 1179 [M+H]⁺.

Example 28 tert-Butyl((R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methoxy)methyl hydrogen phosphate

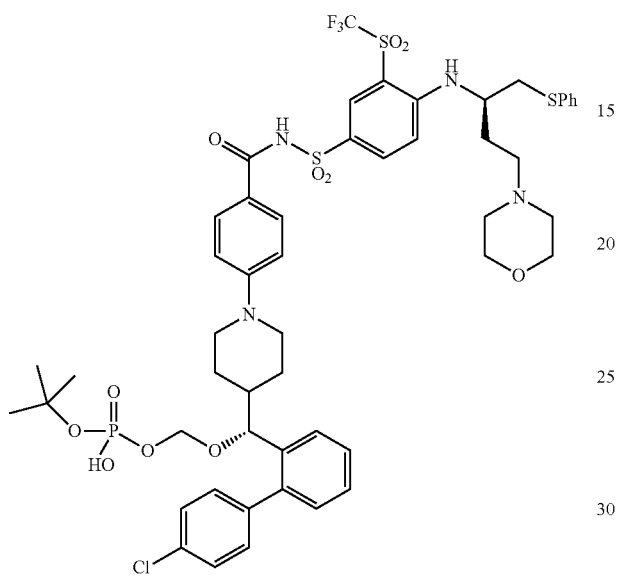

Nitrolotrimethanol (5.27 mg, 0.05 mmol) was added to a solution of di-tert-butyl((R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methoxy)methyl phosphate (EXAMPLE 27, 58.0 mg, 0.05 mmol) in acetone (1.8 ml) and 0.6 ml of pH7.2 buffer (Gibco, Dulbecco's Phosphate Buffered saline 1×). The resulting reaction mixture was stirred at 65° C. for 16 hours. Evaporation of the volatiles under reduced pressure gave a residue which was purified by reverse phase HPLC (Gilson column, eluting with 30→50% H$_2$O with 10 mM NH$_4$OAc/MeCN for 5 minutes) to provide the title product (0.017 g, yield: 19%).

$^1$H NMR (300 MHz, METHANOL-d$_4$) δ ppm 0.97-1.08 (m, 3 H) 1.14-1.21 (m, 3 H) 1.34 (s, 12 H) 1.51-1.65 (m, 1 H) 1.73-1.90 (m, 2 H) 1.95-2.15 (m, 1 H) 2.42-2.72 (m, 9 H) 3.57-3.66 (m, 5 H) 3.71-3.82 (m, 1 H) 3.90-4.01 (m, 1 H) 4.93-5.03 (m, 1 H) 6.66-6.75 (m, 2 H) 6.76-6.83 (m, 1 H) 7.00-7.16 (m, 3 H) 7.18-7.35 (m, 9 H) 7.39-7.46 (m, 1 H) 7.51-7.62 (m, 2 H) 7.85-7.97 (m, 1 H) 8.11-8.24 (m, 1 H).

LCMS: (ESI) m/z 1124 [M+H]$^+$.

Example 29

(R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methyl diethyl phosphate, hydrochloride salt

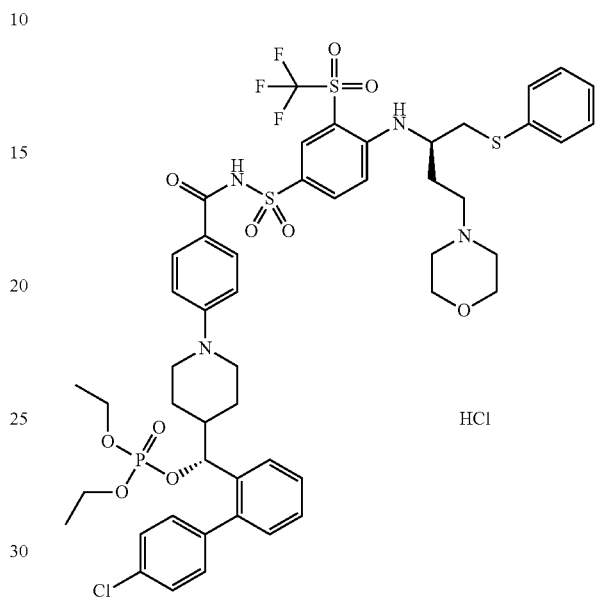

A mixture of (R)-4-(4-((4'-chlorobiphenyl-2-yl)(diethoxyphosphoryloxy)methyl)piperidin-1-yl)benzoic acid (INTERMEDIATE 120, 371 mg, 0.66 mmol), (R)-4-(4-morpholino-1-(phenylthio)butan-2-ylamino)-3-(trifluoromethylsulfonyl)benzenesulfonamide (INTERMEDIATE 69, 368 mg, 0.66 mmol), EDC (255 mg, 1.33 mmol), TEA (0.185 ml, 1.33 mmol), and DCE (5 ml) were stirred at r.t. for 2 hours. The mixture was diluted with DCM (15 ml) and adsorbed onto silica gel. Purification by column chromatography (ISCO, eluting with 0→10% MeOH/DCM over 19 minutes followed by elution with 0→10% 2M NH$_3$/MeOH/DCM over 24 minutes) gave a residue which was further purified by reverse phase HPLC, according to the conditions:

Column: Atlantis T3, OBD
Column dimensions: 30×100 mm, 5μ
Mobile phase A water with 0.1% TFA, pH 2
Mobile phase B 100% Acetonitrile
Flow rate (ml/min): 60 ml/min
Gradient: From A→B (60 to 80% in 10 minutes)

Like fractions were concentrated under reduced pressure. The concentrate was dissolved in DCM (5 ml) and treated with 4N HCl in dioxane (0.5 ml). Evaporation of the volatiles provided the title compound (60 mg, yield: 8%).

$^1$H NMR (400 MHz, DICHLOROMETHANE-d$_2$) δ ppm 0.60-0.85 (m, 2 H) 0.90-1.14 (m, 9 H) 1.32-1.44 (m, 1 H) 1.59 (br. s., 1 H) 1.70-2.46 (m, 4 H) 2.65-3.20 (m, 7 H) 3.21-3.48 (m, 4 H) 3.50-3.73 (m, 1 H) 3.75-4.33 (m, 8 H) 6.81-7.02 (m, 1 H) 7.04-7.67 (m, 15 H) 7.90 (br. s., 3 H) 8.28 (br. s., 1 H).

$^{31}$P NMR (121 MHz, DICHLOROMETHANE-d$_2$) δ ppm −2.73 (s, 1P).

LCMS: (ESI) m/z 1092 [M−H]$^+$.

Example 30

(R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methyl methyl hydrogen phosphate, hydrochloride salt

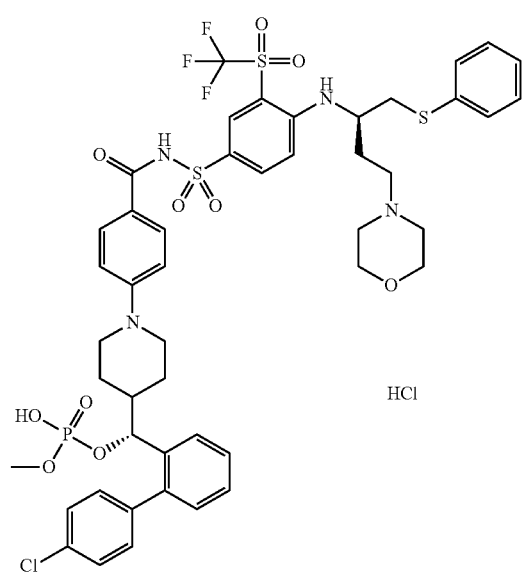 [SMILES: COP(=O)(O)O[C@@H](c1ccccc1-c1ccc(Cl)cc1)C1CCN(c2ccc(C(=O)NS(=O)(=O)c3ccc(N[C@H](CCN4CCOCC4)CSc4ccccc4)c(S(=O)(=O)C(F)(F)F)c3)cc2)CC1 ; Cl]

A mixture of (R)-4-(4-(((4'-chlorobiphenyl-2-yl)(dimethoxyphosphoryloxy)methyl)piperidin-1-yl)benzoic acid (INTERMEDIATE 122, 57.4 mg, 0.11 mmol), (R)-4-(4-morpholino-1-(phenylthio)butan-2-ylamino)-3-(trifluoromethylsulfonyl)benzenesulfonamide (INTERMEDIATE 69, 60 mg, 0.11 mmol), EDC (41.6 mg, 0.22 mmol), TEA (0.03 ml, 0.22 mmol), and DCE (2 ml) were stirred at r.t. for 4 days. The volatiles were removed under reduced pressure and the concentrate was purified by reverse phase HPLC according to the following conditions:

Column: Xbridge Sunfire
Column dimensions: 19×100 mm, 5μ
Mobile phase A: water with 0.1% TFA, pH 2
Mobile phase B: 100% Acetonitrile
Flow rate (ml/min): 20 ml/min
Gradient: A→B (From 40 to 60% in 10 minutes)

The like fractions were combined and the volatiles were removed under reduced pressure. The residue left was treated with HCl in dioxane (4N, 0.5 ml) and diluted with MeOH and the volatiles were subsequently removed under reduced pressure to give the title compound (34.0 mg, yield: 30%).

$^1$H NMR (400 MHz, METHANOL-$d_4$) δ ppm 1.37 (br. s., 2 H) 1.66 (br. s, 1 H) 1.86-2.40 (m, 4 H) 1.86-2.40 (m, 4 H) 3.04 (br. s, 5 H) 3.30-3.82 (m, 12 H) 3.87-4.25 (m, 3 H) 5.22 (br. s., 1 H) 6.99 (br. s., 1 H) 7.04-7.22 (m, 4 H) 7.23-7.71 (m, 11 H) 7.85 (br. s., 2 H) 8.02 (br. s., 1 H) 8.26 (s, 1 H). $^{31}$P NMR (121 MHz, METHANOL-$d_4$) δ ppm −0.37 (s, 1 P)

LCMS: m/z 1052 [M+H]$^+$.

Example 31

Di-tert-butyl(((R)-(4'-chlorobiphenyl-2-yl)(1-(4-(4-(((R)-4-((S)-3-((diethylamino)methyl)morpholino)-1-(phenylthio)butan-2-ylamino)-3-(trifluoromethylsulfonyl)phenylsulfonylcarbamoyl)phenyl)piperidin-4-yl)methoxy)methyl phosphate

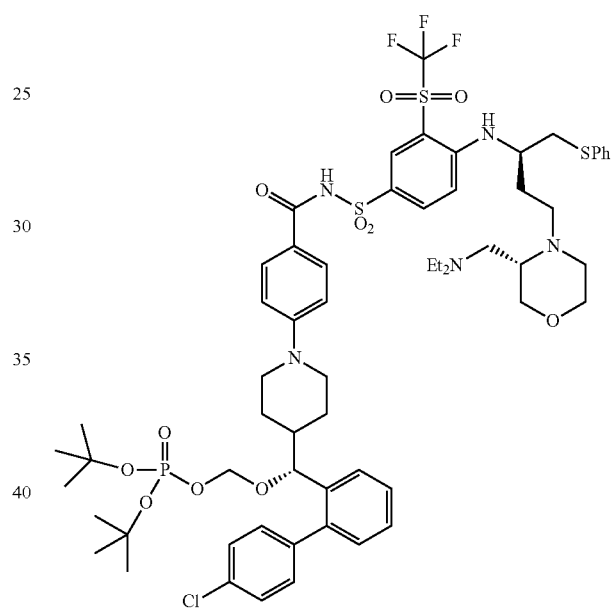

To a solution of (R)-4-(4-(((4'-chlorobiphenyl-2-yl)(di-tert-butoxyphosphonooxymethoxy)methyl)piperidin-1-yl)benzoic acid (INTERMEDIATE 118, 55.5 mg, 0.09 mmol), EDC (33 mg, 0.17 mmol), and DMAP (21 mg, 0.17 mmol) in DCM (3 ml) was added 4-((R)-4-((S)-3-((diethylamino)methyl)morpholino)-1-(phenylthio)butan-2-ylamino)-3-(trifluoromethylsulfonyl)benzenesulfonamide (INTERMEDIATE 88, 55 mg, 0.09 mmol). The resulting mixture was stirred overnight at room temperature. The reaction mixture was diluted with DCM (20 ml) and washed with brine (5 ml). The collected organic layer was dried over Na$_2$SO$_4$ and concentrated in vacuo. The residue was purified by column chromatography (ISCO, eluting with 0→10% MeOH/EtOAc for 14 minutes) to provide the title product (30 mg, 27%).

LCMS: (ESI) m/z 1263 [M−H]$^+$.

Example 32 tert-Butyl((R)-(4'-chlorobiphenyl-2-yl)(1-(4-(4-((R)-4-((S)-3-((diethylamino)methyl)morpholino)-1-(phenylthio)butan-2-ylamino)-3-(trifluoromethylsulfonyl)phenylsulfonylcarbamoyl)phenyl)piperidin-4-yl)methoxy)methyl hydrogen phosphate

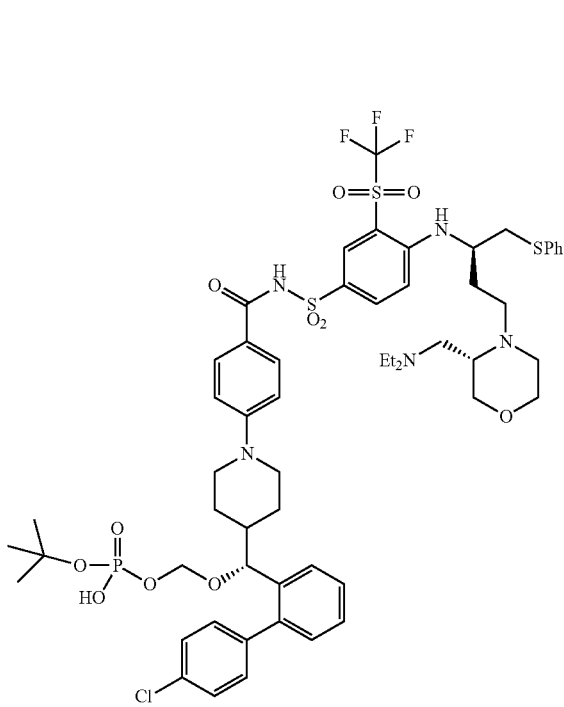

A similar procedure to that described for EXAMPLE 28 utilizing di-tert-butyl(R)-(4'-chlorobiphenyl-2-yl)(1-(4-(4-((R)-4-((S)-3-((diethylamino)methyl)morpholino)-1-(phenylthio)butan-2-ylamino)-3-(trifluoromethylsulfonyl)phenylsulfonylcarbamoyl)phenyl)piperidin-4-yl)methoxy)methyl phosphate (EXAMPLE 31, 110 mg, 0.09 mmol) as starting material was followed, with subsequent purification by reverse phase HPLC (Gilson column, eluting with 15→50% H$_2$O with 10 mM NH$_4$OAc/MeCN for 4 minutes) to provide the title product (0.027 g, yield: 27%).

$^1$H NMR (300 MHz, METHANOL-d$_4$) δ ppm 0.80-0.92 (m, 6 H) 0.95-1.06 (m, 5 H) 1.25 (s, 9 H) 1.52-1.87 (m, 4 H) 1.98-2.13 (m, 1 H) 2.20-2.34 (m, 1 H) 2.41-2.83 (m, 12 H) 2.85-2.99 (m, 2 H) 3.24-3.38 (m, 2 H) 3.50-3.65 (m, 2 H) 3.68-3.79 (m, 2 H) 3.85-4.00 (m, 1 H) 4.90-5.04 (m, 2 H) 6.57-6.75 (m, 3 H) 6.99-7.48 (m, 14 H) 7.59-7.71 (m, 2 H) 7.86-7.99 (m, 1 H) 8.13-8.25 (m, 1 H).

LCMS: (ESI) m/z 1208 [M−H]$^+$.

Example 33

4-(4-((R)-amino(4'-chlorobiphenyl-2-yl)methyl)piperidin-1-yl)-N-(4-((R)-4-morpholino-1-(phenylthio)butan-2-ylamino)-3-(trifluoromethylsulfonyl)phenylsulfonyl)benzamide, formic acid salt

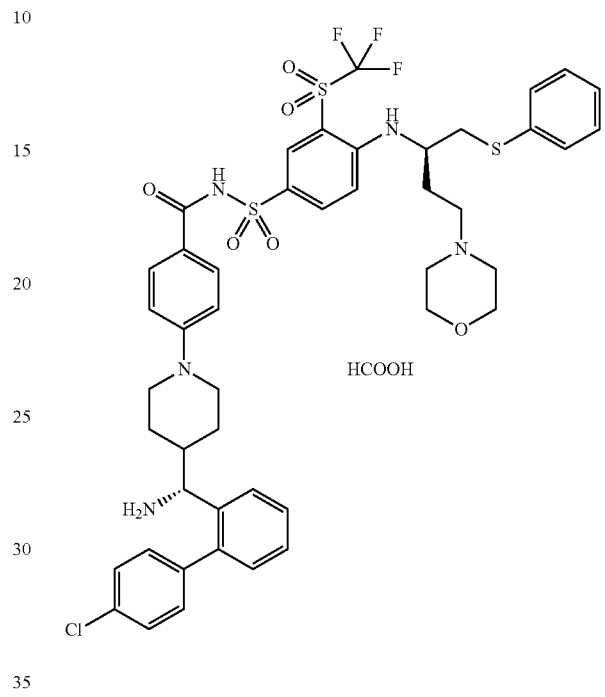

A solution of HCl (0.80 ml, 3.21 mmol, 4 M in dioxane) was added to a solution of 4-(4-((R)-(4'-chlorobiphenyl-2-yl)((S)-1,1-dimethylethylsulfinamido)methyl)piperidin-1-yl)-N-(4-((R)-4-morpholino-1-(phenylthio)butan-2-ylamino)-3-(trifluoromethylsulfonyl)phenylsulfonyl)benzamide (INTERMEDIATE 131, 0.17 g, 0.16 mmol) in MeOH (1.5 ml) and the reaction mixture was stirred at r.t for 2 hours. The reaction mixture was concentrated under reduced pressure to provide a residue which was purified by reverse phase HPLC (Gilson column, eluting with 20→50% H$_2$O/ACN with 0.1% formic acid for 10 minutes) to provide the title compound (0.10 g, yield: 60%).

$^1$H NMR (400 MHz, DMSO-d$_6$) δ ppm 8.05 (d, 1 H), 7.90 (dd, 1 H), 7.70-7.67 (m, 3H), 7.59-7.53 (m, 3H), 7.50-7.46 (m, 1H), 7.40-7.25 (m, 8H), 7.22-7.18 (m, 1 H), 6.81 (d, 1 H), 6.73 (d, 2 H), 6.68 (d, 1 H), 4.00 (m, 1H), 3.87-3.85 (m, 1H), 3.79-3.76 (m, 1H), 3.59-3.45 (m, 6H), 3.33-3.20 (m, 2H), 2.61-2.55 (m, 1H), 2.33-2.25 (m, 4H), 2.19-2.15 (m, 2H), 2.01-1.88 (m, 2 H), 1.84-1.81 (m, 1H), 1.73-1.66 (m, 1H), 1.17-1.08 (m, 2H), 0.83-0.75 (m, 1H).

LCMS: (ESI) m/z 956 [M+H]$^+$.

Example 34

4-(4-((R)-(4'-chlorobiphenyl-2-yl)(2-(methylamino)acetamido)methyl)piperidin-1-yl)-N-(4-((R)-4-morpholino-1-(phenylthio)butan-2-ylamino)-3-(trifluoromethylsulfonyl)phenylsulfonyl)benzamide, hydrochloride salt

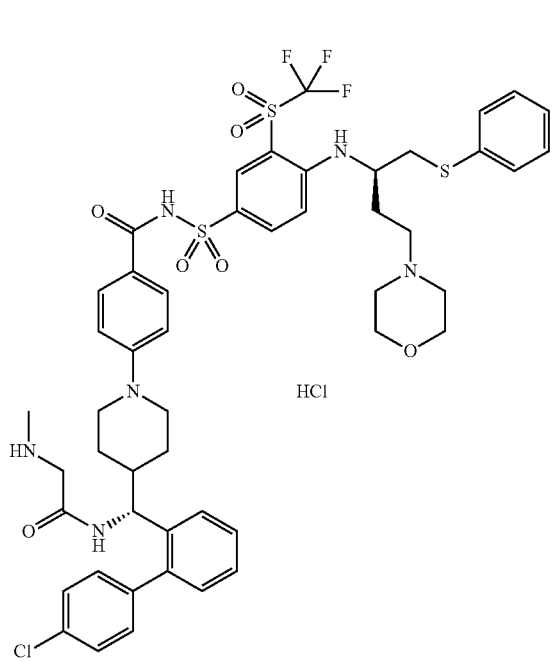 [SMILES: CNCC(=O)N[C@@H](c1ccccc1-c1ccc(Cl)cc1)C1CCN(c2ccc(C(=O)NS(=O)(=O)c3ccc(N[C@H](CCN4CCOCC4)CSc4ccccc4)c(S(=O)(=O)C(F)(F)F)c3)cc2)CC1 ; Cl]

A solution of HCl (0.42 ml, 1.67 mmol, 4 M in dioxane) was added to a solution of tert-butyl 2-(((R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methylamino)-2-oxoethyl (methyl)carbamate (INTERMEDIATE 132, 94 mg, 0.08 mmol) in MeOH (1.3 ml) and the reaction mixture was stirred at r.t for 3 hours. The reaction mixture was concentrated under reduced pressure to provide a residue which was purified by reverse phase HPLC (Gilson column, eluting with 20→50% H$_2$O/ACN with 0.1% formic acid for 10 minutes) to give a solid. The solid was dissolved in MeOH and the mixture was treated with a solution of HCl (2 N) in diethylether. Evaporation of the volatiles under reduced pressure provided the title compound (56 mg, yield: 61%).

$^1$H NMR (400 MHz, DMSO-d$_6$) δ ppm 8.18 (d, 1 H), 7.98 (dd, 1 H), 7.70-7.68 (m, 2H), 7.55-7.51 (m, 3H), 7.48-7.43 (m, 3H), 7.36-7.29 (m, 3 H), 7.25-7.21 (m, 3 H), 7.17-7.13 (m, 2H), 6.98 (d, 1 H), 6.85-6.83 (m, 2H), 4.79-4.75 (m, 1H), 4.22 (m, 1H), 3.95-3.65 (m, 6H), 3.41-3.32 (m, 4H), 3.17-2.90 (m, 5H), 2.74-2.62 (m, 1H), 2.57-2.53 (m, 4 H), 2.25-2.13 (m, 2H), 1.84-1.75 (m, 2H), 1.12-1.00 (m, 2H), 0.74-0.71 (m, 1H).

LCMS: (ESI) m/z 1027 [M+H]$^+$.

Example 35

4-(4-((R)-(2-aminoacetamido)(4'-chlorobiphenyl-2-yl)methyl)piperidin-1-yl)-N-(4-4R)-4-morpholino-1-(phenylthio)butan-2-ylamino)-3-(trifluoromethylsulfonyl)phenylsulfonyl)benzamide hydrochloride salt

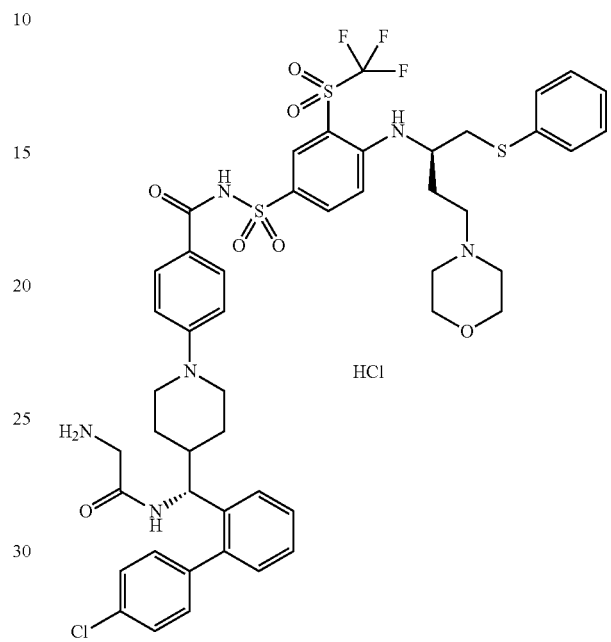

Step 1: DIPEA (0.08 ml, 0.46 mmol) was added to a solution of 4-(4-((R)-amino(4'-chlorobiphenyl-2-yl)methyl)piperidin-1-yl)-N-(4-((R)-4-morpholino-1-(phenylthio)butan-2-ylamino)-3-(trifluoromethylsulfonyl)phenylsulfonyl)benzamide, formic acid salt (EXAMPLE 33, 0.11 g, 0.11 mmol), 2-(tert-butoxycarbonylamino)acetic acid (20 mg, 0.11 mmol) and HATU (52 mg, 0.14 mmol) in DMF (2.2 ml) and the reaction mixture was stirred at r.t for 1 hour. The reaction mixture was concentrated under reduced pressure, diluted with DCM and washed with H$_2$O, 1N aq. NaHSO$_4$ and saturated aq. NaHCO$_3$. The organic layer was dried over Na$_2$SO$_4$, filtered and the filtrate was concentrated under reduced pressure a to provide tert-butyl 2-((R)-(4'-chlorobiphenyl-2-yl)(1-(4-(4-((R)-4-morpholino-1-(phenylthio)butan-2-yl amino)-3-(trifluoromethylsulfonyl)phenylsulfonylcarbamoyl)phenyl)piperidin-4-yl)methylamino)-2-oxoethylcarbamate (EXAMPLE 35, STEP 1, 0.13 g) which was used in the preparation of EXAMPLE 35, STEP 2 without further purification.

LCMS: (ESI) m/z 1113[M+H]$^+$.

Step 2: A solution of HCl (0.6 ml, 2.20 mmol, 4.0M in dioxane) was added to a solution of tert-butyl 2-((R)-(4'-chlorobiphenyl-2-yl)(1-(4-(4-((R)-4-morpholino-1-(phenylthio)butan-2-ylamino)-3-(trifluoromethylsulfonyl)phenylsulfonylcarbamoyl)phenyl)piperidin-4-yl)methylamino)-2-oxoethylcarbamate (EXAMPLE 35, STEP 1, 0.123 g, 0.11 mmol) in MeOH (1.7 ml) and the reaction mixture was stirred at r.t for 3 hours. The reaction mixture was concentrated under reduced pressure to provide a residue which was purified by reverse phase HPLC (Gilson column, eluting with 20→50% H$_2$O/ACN with 0.1% formic acid for 10 minutes) provided a solid. The solid was disolved in MeOH and the mixture treated with 2N HCl in diethyl ether. Evaporation of the volatiles under reduced pressure provided the title compound (64 mg, yield: 54% for 2 steps).

$^1$H NMR (400 MHz, DMSO-$d_6$) δ ppm 8.18 (d, 1 H), 7.98 (dd, 1 H), 7.70-7.68 (m, 2H), 7.56-7.53 (m, 3H), 7.48-7.43 (m, 3H), 7.36-7.29 (m, 3 H), 7.25-7.21 (m, 3 H), 7.17-7.13 (m, 2H), 6.98 (d, 1 H), 6.85-6.83 (m, 2H), 4.79-4.75 (m, 1H), 4.22 (m, 1H), 3.95-3.76 (m, 6H), 3.70-3.56 (m, 4H), 3.19-3.17 (m, 1H), 3.10-2.92 (m, 4H), 2.73-2.66 (m, 1H), 2.59-2.54 (m, 1 H), 2.23-2.15 (m, 2H), 1.86-1.83 (m, 1H), 1.75-1.73 (m, 1H), 1.12-1.00 (m, 2H), 0.74-0.71 (m, 1H).

LCMS: (ESI) m/z 1013[M+H]$^+$.

Example 36

4-(4-((R)-(4'-chlorobiphenyl-2-yl)(dimethylamino) methyl)piperidin-1-yl)-N-(4-((R)-4-morpholino-1- (phenylthio)butan-2-ylamino)-3-(trifluoromethylsul- fonyl)phenylsulfonyl)benzamide, hydrochloride salt

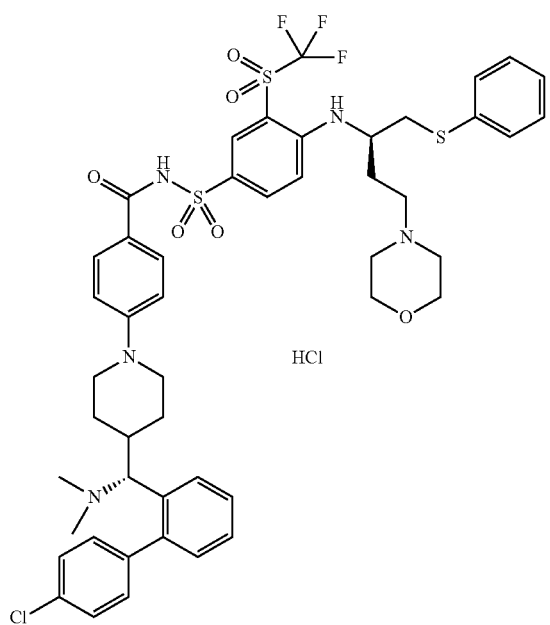 [SMILES: CN(C)[C@@H](c1ccccc1-c1ccc(Cl)cc1)C1CCN(c2ccc(C(=O)NS(=O)(=O)c3ccc(N[C@H](CCN4CCOCC4)CSc4ccccc4)c(S(=O)(=O)C(F)(F)F)c3)cc2)CC1 ; Cl]

Step 1: To a solution of (R)-ethyl 4-(4-((4'-chlorobiphenyl-2-yl)(dimethylamino)methyl)piperidin-1-yl)benzoate (INTERMEDIATE 133, 0.11 g, 0.23 mmol) in THF (1.4 ml) was added MeOH (0.5 ml) and a solution of LiOH (28 mg, 1.15 mmol) in water (0.5 ml) and the reaction mixture was stirred at 40° C. overnight. The reaction mixture was cooled to r.t, concentrated under reduced pressure, and the residue dried in a vacuum oven overnight to provide (R)-4-(4-((4'-chlorobiphenyl-2-yl)(dimethylamino)methyl)piperidin-1-yl)ben- zoate, lithium salt (EXAMPLE 36 STEP 1, 0.12 g), which was used in the preparation of EXAMPLE 36, STEP 2 without further purification.

LCMS: (ESI) m/z 449[M+H]$^+$.

Step 2: (R)-4-(4-((4'-chlorobiphenyl-2-yl)(dimethylamino)methyl)piperidin-1-yl)benzoate, lithium salt (EXAMPLE 36, STEP 1, 0.105 g, 0.23 mmol), DMAP (56 mg, 0.46 mmol), and EDC (0.176 g, 0.92 mmol) were placed in a 40 ml vial and flushed with nitrogen. DCM (4.5 ml) and DIPEA (0.08 ml, 0.46 mmol) were added, and the solution was stirred at r.t for 15 minutes. (R)-4-(4-morpholino-1-(phenylthio)butan-2-ylamino)-3-(trifluoromethylsulfonyl)benzenesulfonamide (INTERMEDIATE 69, 0.127 g, 0.23 mmol) was added to the solution and the reaction mixture was stirred at r.t overnight. The reaction mixture was diluted with DCM and washed with 1N sodium bisulfate (aq.) followed by saturated aq. sodium bicarbonate. The organic layer was dried (Na$_2$SO$_4$), filtered, and evaporated under reduced pressure to give a residue which was purified by reverse phase HPLC (Gilson column, eluting with 30→50% H$_2$O/ACN with 0.1% formic acid for 10 minutes) to provide a solid. The solid was dissolved in MeOH and the mixture was treated with 2N HCl in diethylether. Evaporation of the volatiles under reduced pressure provided the title compound (85 mg, yield: 35% for 2 steps).

$^1$H NMR (400 MHz, DMSO-$d_6$) δ ppm 8.18 (d, 1 H), 7.99 (dd, 1 H), 7.89-7.87 (m, 2H), 7.73-7.70 (m, 2H), 7.57-7.50 (m, 4H), 7.31-7.29 (m, 5H), 7.25-7.22 (m, 3H), 7.17-7.14 (m, 1H), 6.98 (d, 1 H), 6.92-6.89 (m, 2H), 4.23 (m, 1H), 3.95-3.90 (m, 5H), 3.81-3.75 (m, 2H), 3.42-3.32 (m, 4H), 3.19-3.16 (m, 1H), 3.10-2.92 (m, 4H), 2.80-2.72 (m, 2H), 2.67 (m, 3H), 2.57 (m, 3 H), 2.23-2.15 (m, 2H), 1.80-1.76 (m, 1H), 1.57-1.54 (m, 1H), 1.25-1.17 (m, 1H), 1.02-0.94 (m, 1H).

LCMS: (ESI) m/z 984[M+H]$^+$.

What is claimed is:

1. A compound of Formula (I):

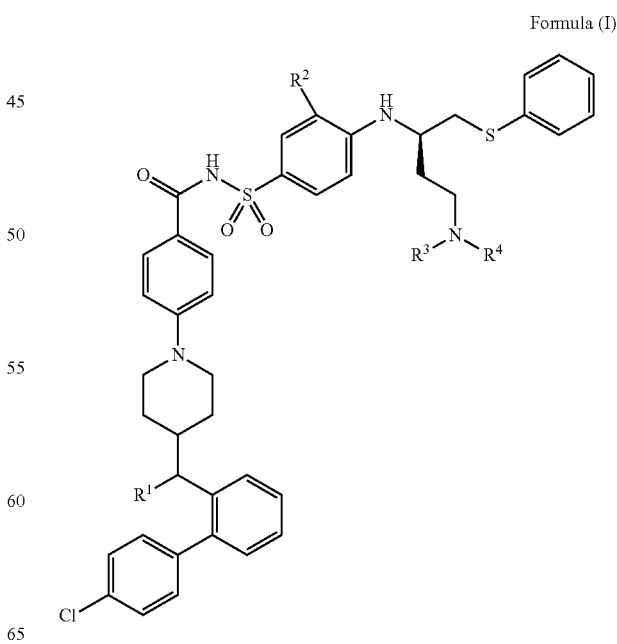

Formula (I)

or a pharmaceutically acceptable salt thereof, wherein:

$R^1$ is selected from —CN, —OR$^{1a}$, and —N(R$^{1a}$)$_2$;

$R^{1a}$ in each occurrence is independently selected from H, C$_{1-4}$alkyl, —C(O)CH$_2$NH$_2$, —C(O)CH$_2$NHCH$_3$, and when R$^1$ is —OR$^{1a}$, then R$^{1a}$ is additionally selected from —P(=O)(OH)(OCH$_3$), —P(=O)(OCH$_2$CH$_3$)$_2$, —CH$_2$OP(=O)(OH)[OC(CH$_3$)$_3$] and —CH$_2$OP(=O)[OC(CH$_3$)$_3$]$_2$;

$R^2$ is selected from —N(O)$_2$ and —S(O)$_2$CF$_3$;

$R^3$ is selected from H and C$_{1-4}$alkyl, wherein said C$_{1-4}$alkyl is optionally substituted with one or more R$^{40}$;

$R^4$ is selected from H and C$_{1-4}$alkyl, wherein said C$_{1-4}$alkyl is optionally substituted with one or more R$^{40}$;

or R$^3$ and R$^4$ together with the nitrogen to which they are attached form a 5-or 6-membered heterocyclic ring, wherein i) said 5-or 6-membered heterocyclic ring is optionally substituted on carbon with one or more R$^{40}$; and ii) if said 5-or 6-membered heterocyclic ring contains a nitrogen, that nitrogen is optionally substituted with R$^{40*}$ to form a tertiary amine;

$R^{40*}$ is selected from C$_{1-4}$alkyl and —(CH$_2$)$_2$OP(=O)(OH)$_2$, wherein said C$_{1-4}$alkyl is optionally substituted with one or more R$^a$;

$R^{40}$ in each occurrence is selected from —OR$^{40a}$, —N(R$^{40a}$)$_2$, —CH$_2$OR$^{5a}$, —CH$_2$N(R$^{5a}$)$_2$, —OP(=O)(OH)$_2$, and —OP(=O)[OC(CH$_3$)$_3$]$_2$;

$R^{5a}$ in each occurrence is selected from H and C$_{1-3}$alkyl;

$R^{40a}$ in each occurrence is independently selected from H and C$_{1-4}$alkyl; and $R^a$ is selected from halo, —OR$^m$, and —N(R$^m$)$_2$; and $R^m$ in each occurrence is independently selected from H and C$_{1-4}$alkyl.

2. The compound of Formula (I), or a pharmaceutically acceptable salt thereof, as claimed in claim 1, wherein, $R^1$ is —OH;

$R^2$ is —S(O)$_2$CF$_3$;

$R^3$ is C$_{1-2}$alkyl, wherein said C$_{1-2}$alkyl is optionally substituted with one or more R$^{40}$;

$R^4$ is C$_{1-2}$alkyl, wherein said C$_{1-2}$alkyl is optionally substituted with one or more R$^{40}$;

$R^{40}$ in each occurrence is selected from —OR$^{40a}$ and —OP(=O)(OH)$_2$; and $R^{40a}$ is H.

3. The compound of claim 1 wherein the compound has the following stereochemistry:

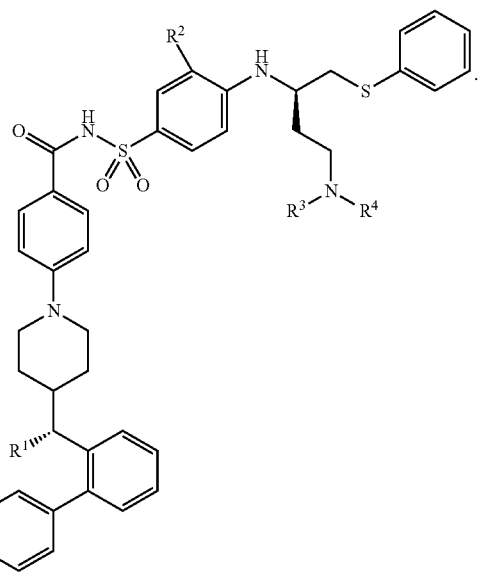

4. The compound of Formula (I), or a pharmaceutically acceptable salt thereof, as claimed in claim 3, wherein the compound is 4-(4-((R)-(4'-chlorobiphenyl-2-yl)(hydroxy)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide.

5. The compound of Formula (I), or a pharmaceutically acceptable salt thereof, as claimed in claim 3, wherein the compound is 2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethyl dihydrogen phosphate.

6. The compound of Formula (I), or a pharmaceutically acceptable salt thereof, as claimed in claim 3, wherein the compound is 4-(4-((R)-(4'-chlorobiphenyl-2-yl)(hydroxy)methyl)piperidin-1-yl)-N-(4-((R)-4-(ethyl(2-hydroxyethyl)amino)-1-(phenylthio)butan-2-ylamino)-3-(trifluoromethylsulfonyl)phenylsulfonyl)benzamide.

7. The compound of Formula (I), or a pharmaceutically acceptable salt thereof, as claimed in claim 3, wherein the compound is 2-(((R)-3-(4-(N-(4-(4-((R)-(4'-chlorobiphenyl-2-yl)(hydroxy)methyl)piperidin-1 -yl)benzoyl)sulfamoyl)-2-(trifluoromethylsulfonyl)phenylamino)-4-(phenylthio)butyl)(ethyl)amino)ethyl dihydrogen phosphate.

8. A pharmaceutical composition comprising a compound of Formula (I), or a pharmaceutically acceptable salt thereof, as claimed in claim 1, and at least one pharmaceutically acceptable carrier, diluent, or excipient.

* * * * *